US009085753B2

(12) United States Patent
Liu et al.

(10) Patent No.: US 9,085,753 B2
(45) Date of Patent: Jul. 21, 2015

(54) METHODS FOR CULTIVATING CELLS, PROPAGATING AND PURIFYING VIRUSES

(75) Inventors: Jonathan Liu, Milpitas, CA (US); Mark Thompson, Morgan Hill, CA (US); Luis J. Maranga, Santa Clara, CA (US); Floro Cataniag, Pittsburg, CA (US); Simon S. Hsu, Palo Alto, CA (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 0 days.

(21) Appl. No.: 13/473,494

(22) Filed: May 16, 2012

(65) Prior Publication Data

US 2012/0258136 A1  Oct. 11, 2012

Related U.S. Application Data

(62) Division of application No. 12/566,048, filed on Sep. 24, 2009, now Pat. No. 8,202,726.

(60) Provisional application No. 61/187,721, filed on Jun. 17, 2009, provisional application No. 61/104,933, filed on Oct. 13, 2008, provisional application No. 61/099,749, filed on Sep. 24, 2008.

(51) Int. Cl.
*C12N 7/02* (2006.01)
*A61K 39/145* (2006.01)

(52) U.S. Cl.
CPC .............. *C12N 7/02* (2013.01); *A61K 39/145* (2013.01); *C12N 2760/16051* (2013.01); *C12N 2760/16134* (2013.01); *C12N 2760/16151* (2013.01); *C12N 2760/16234* (2013.01); *C12N 2760/16251* (2013.01)

(58) Field of Classification Search
CPC ....... A61K 39/12; A61K 39/145; C12N 7/02; C12N 15/111; C12N 15/1131; C12N 2760/16022; C07K 2317/24; C07K 14/005; C07K 2317/92; C07K 16/065; C07K 1/18; C07K 16/1018; C07K 1/22
See application file for complete search history.

(56) References Cited

U.S. PATENT DOCUMENTS

| | | | |
|---|---|---|---|
| 5,824,536 A | 10/1998 | Webster et al. | |
| 5,948,410 A | 9/1999 | Van Scharrenburg et al. | |
| 6,194,191 B1 | 2/2001 | Zhang et al. | |
| 6,194,192 B1 | 2/2001 | Ueno et al. | |
| 6,245,549 B1 | 6/2001 | Ewasyshyn et al. | |
| 6,455,298 B1 | 9/2002 | Groner et al. | |
| 6,656,720 B2 | 12/2003 | Groner | |
| 6,726,907 B1 | 4/2004 | Zhang et al. | |
| 6,825,036 B2 | 11/2004 | Makizumi et al. | |
| 6,951,752 B2 | 10/2005 | Reiter et al. | |
| 7,262,045 B2 | 8/2007 | Schwartz et al. | |
| 7,553,665 B2 | 6/2009 | Aloni et al. | |
| 7,670,837 B2 | 3/2010 | Schwartz | |
| 8,119,388 B2 | 2/2012 | Schwartz | |
| 8,202,726 B2 | 6/2012 | Liu | |
| 8,357,376 B2 | 1/2013 | Liu | |
| 2004/0077086 A1 | 4/2004 | Reiter et al. | |
| 2004/0106184 A1* | 6/2004 | Senesac ........................ 435/239 |
| 2004/0171152 A1 | 9/2004 | Price | |
| 2004/0234947 A1 | 11/2004 | Huang | |
| 2005/0118698 A1 | 6/2005 | Vorlop et al. | |
| 2005/0186224 A1 | 8/2005 | Buchholz et al. | |
| 2006/0002862 A1 | 1/2006 | Truong-Le et al. | |
| 2006/0134138 A1 | 6/2006 | Kawaoka et al. | |
| 2006/0171955 A1 | 8/2006 | Alonso-Caplan et al. | |
| 2006/0188977 A1 | 8/2006 | Schwartz | |
| 2007/0202527 A1 | 8/2007 | Wallace et al. | |
| 2007/0249019 A1 | 10/2007 | Kang et al. | |
| 2008/0031895 A1 | 2/2008 | Galarza et al. | |
| 2008/0286850 A1 | 11/2008 | Liu | |
| 2010/0112000 A1 | 5/2010 | Schwartz | |
| 2010/0112669 A1 | 5/2010 | Liu | |

(Continued)

FOREIGN PATENT DOCUMENTS

| | | |
|---|---|---|
| AU | 2005322352 | 12/2011 |
| CN | 1326939 | 12/2011 |

(Continued)

OTHER PUBLICATIONS

Reimer et al., Purification of Large Quantities of Influenza Virus by Density Gradient Centrifugation, 1967, Journal of Virology, vol. 1, No. 6, pp. 1207-1216.*

Wickramasinghe et al., Tangential Flow Microfiltration and Ultrafiltration for Human Influenza A Virus Concentration and Purification, 2005, Biotechnology and Bioengineering, vol. 92, No. 2, pp. 199-208.*

Office Action mailed on: Jul. 23, 2013 in U.S. Appl. No. 13/595,879 filed on: Aug. 27, 2012 and published as: US 2013/0052717 on Feb. 28, 2013.

"Guidance for Industry: Characterization and Qualification of Cell Substrates and Other Biological Starting Materials used in the Production of Viral Vaccines for the Prevention and Treatment of Infectious Diseases." (2006) 25: 697-723.

(Continued)

*Primary Examiner* — Benjamin P Blumel
(74) *Attorney, Agent, or Firm* — Grant IP, Inc.

(57) ABSTRACT

The present invention provides novel serum-free cell culture medium and methods for cultivating MDCK cells. In particular, non-tumorigenic MDCK cells. The present invention also provides methods for producing influenza viruses (e.g., particularly cold-adapted, and/or temperature sensitive, and/or attenuated influenza viruses) that eliminate the need for a cell culture medium exchange step. The novel medium and methods are useful to grow influenza viruses, in cell culture to high titer. The present invention further provides purification methods for purifying influenza viruses with high overall recovery of live virus and result in levels of host cell DNA (HCD), host cell protein (HCP) and non-specific endonuclease (e.g., Benzonase), which are below the specifications required by regulatory agencies. The immunogenic compositions can be used to actively immunize subjects or to generate antibodies for a variety of uses, including passive immunization and diagnostic immunoassays.

13 Claims, 33 Drawing Sheets

(56) References Cited

U.S. PATENT DOCUMENTS

2012/0115206 A1 5/2012 Schwartz et al.
2013/0052717 A1 2/2013 Liu et al.

FOREIGN PATENT DOCUMENTS

| | | |
|---|---|---|
| EP | 0870508 | 10/1998 |
| EP | 0891420 | 2/2005 |
| EP | 1739167 | 1/2007 |
| EP | 1862537 | 12/2007 |
| JP | 2000-507448 | 6/2000 |
| JP | 2000-517188 | 12/2000 |
| JP | 2005-511051 | 4/2006 |
| RU | 1367487 | 10/1995 |
| RU | 2080124 | 5/1997 |
| RU | 2112543 | 6/1998 |
| SU | 1698288 | 12/1991 |
| WO | WO 98/22588 | 5/1998 |
| WO | WO 01/64846 | 9/2001 |
| WO | WO 02/12455 | 2/2002 |
| WO | WO 2004/110484 | 12/2004 |
| WO | WO 2005/026333 | 3/2005 |
| WO | WO 2005/113758 | 12/2005 |
| WO | WO 2006/071563 | 12/2006 |
| WO | WO 2008/105931 | 9/2008 |
| WO | WO 2008/125361 | 10/2008 |
| WO | WO 2010/036760 | 4/2010 |
| WO | WO 2010/036774 | 4/2010 |

OTHER PUBLICATIONS

Aggarwal, Kunal, Ab stract and Presentation—"Rational strategies for improving cell culture based production of Cold-Adapted Influenza Vaccine (CAIV) strains of FluMist®.", Cell Culture Engineering XI, Queensland, Australia. Apr. 13-18, 2008.
Aggarwal, Kunal, Abstract and Presentation—"Assessment of platform vaccine process development and improvement of vaccine productivity through bioprocess optimization", 236th American Chemical Society National Meeting. Philadelphia, P A. Aug. 17-21, 2008.
Aggarwal, Kunal, Poster—"Development of a cell culture production platform for Cold-Adapted Live Attenuated Influenza Vaccine (LAIV) strains: role of multiplicity of infection in improving bioreactor productivity", Biochemical Engineering XVI. Burlington, Vermont, Jul. 5-9, 2009.
American Type Culture Collection Cell Repository, et al. "Registry of Animal Cell Lines: Certified by the Cell Culture Collection Committee: MDCK." (1964) : 1-2.
Arthur, J. M. "The MDCK Cell Line is made Up of Populations of Cells with Diverse Resistive and Transport Properties." Tissue Cell (2000) 32: 446-50.
ATCC cell line database search accessed on Mar. 23, 2009 <http://www.atcc.org/ATCCAdvancedCatalogSearch/AllCollectionSearch/tabid/454/Default.aspx>.
Bashir, N., et al. "Phospholipids Regulate Growth and Function of MDCK Cells in Hormonally Defined Serum Free Medium." In Vitro Cell.Dev.Biol. (1992) 28A: 663-8.
Boerner, P., et al. "Characterization of Chemically and Virally Transformed Variants of Madin-Darby Canine Kidney (MDCK) Epithelial Cells." J.Cell.Physiol. (1985) 122: 299-307.
Boerner, P., et al. "Nutrient Transport and Growth Regulation in Kidney Epithelial Cells (MDCK) Cultured in a Defined Medium." Cold Spring Harbor Conferences on Cell Proliferation., 1982 555-565 Cold Spring Harbor Laboratory.
Brands, R., et al. "Influvac: A Safe Madin Darby Canine Kidney (MDCK) Cell Culture-Based Influenza Vaccine." Dev.Bio1.Stand. (1999) 98: 93,100; discussion 111.
Burteau et al., "Fortification of a protein-free cell culture medium with plant peptones improves cultivation and productivity of an interferon-gamma-producing CHO cell line," In Vitro Cell. Dev. Biol., vol. 39, No. 7, 291-296(2003).
Chiton Behring Gmbh. "Use of MDCK Cells for Manufacture of Inactivated Influenza Virus Vaccines. (Briefing Document)." FDA—Vaccines and Related Biological Products Advisory Committee. Bethesda, MD, Nov. 16, 2005. pp. 1-14 (as downloaded Dec. 12, 2008 from http://www.fda.gov/ohrms/dockets/ac/05/briefing/5-4188BI I8.pdf).
Coelingh, K., Presentation: "Next Generation Flu Vaccines: Taking a Crack at Vaccine Production using Cell Culture Technology." The Vaccine Discovery and Commercialization Meeting. Philadelphia, PA, USA, May 23, 2006. pp. 1-10.
Cortes, Bernadette, Abstract and Poster—"Modeling based scale-up strategy for bioreactor cell culture processes", Cell Culture Engineering XI, Queensland, Australia. Apr. 13-18, 2008.
Cortes, Bernadette, Poster—"The Utilization of Antifoam C Emulsion in Adherent Cell Culture Bioreactor Process: implications for process scale-up", Presented at BioProcess International Conference, Raleigh, NC. Oct. 12-16, 2009.
Dobbelaer, R. "ICH Guidelines and PhEur Monographs on Derivation and Characterization of Cell Substrates used for Production of biotechnological/biological Products. International Conference on Harmonization." Dev.Biol.Stand. (1999) 98: 159-65.
Dumitrescu, M. R., et al. "A Three Years Experience in using MDCK Cell Line for Influenza Virus Isolation (1979-1981)." Arch.Roum. Pathol.Exp.Microbiol. (1981) 40: 313-316.
Furminger,I. "Vaccine Production." Textbook of Influenza., 1998. Chapter 24: 324-32. Blackwell Oxford, UK.
Gaush, C. R., et al. "Characterization of an Established Line of Canine Kidney Cells (MDCK)." Proc.Soc.Exp.Biol.Med. (1966) 122: 931-5.
Genzel, Y., et al. "Metabolism of MDCK Cells during Cell Growth and Influenza Virus Production in Large-Scale Microcarrier Culture," Vaccine (2004) 22: 2202-8.
George, M., and et al., Abstract and Poster Presentation: "Development of a Fully Disposable Platform Process for Cell Culture Production of Cold-Adapted Live Attenuated Influenza Vaccine (CAIV) Strains of FluMist(R)." WillBio—Single-use BioProcessing Components and Systems. Concord, CA, USA, Jul. 16-18, 2007. pp. 1-5.
George, Meena Abstract and Poster—"Development of a cell culture production platform for Cold-Adapted live attenuated Influenza Vaccine (CAIV) strains of FluMist®: accelerated development of a fully disposable Phase I clinical manufacturing process", Vaccine Technology II. Albufeira, Portugal. Jun. 1-6, 2008.
George, Meena, Abstract and Poster—"Improving Vaccine Productivity through Medium Fortification and Process Intensification", Biopharmaceutical Manufacturing and Development Summit. San Francisco. Dec. 14-15, 2009.
George, Meena., et al.: "Production of cell culture (MDCK) derived live attenuated influenza vaccine (LAIV) in a fully disposable platform process.", Biotechnology and Bioengineering Aug. 15, 2010 LNKD—PUBMED:20589670, vol. 106, No. 6, Aug. 15, 2010, pp. 906-917, XP002622299, ISSN: 1097-0290.
Ghendon et al., "Further Development (MDCK of Live Cold-Adapted Influenza Cultivation of Vaccine Strains in Production Fermenters" VoprVirusol (2005) 50: 4-9.
Ghendon, et al. "Development of Cell Culture (MDCK) Live Cold-Adapted (CA) Attenuated Influenza Vaccine." Vaccine (2005) 23: 4678-84.
GIBCO BRL, A Guide to Serum-Free Cell Culture, on line catalog, published on 2003, Please see catalog of VP-SFM+ 11681-020.
Gritliths, E. "WHO Requirements for the use of Animal Cells as in Vitro Substrates for the Production of Biologicals: Application to Influenza Vaccine Production." Dev.Biol.Stand. (1999) 98: 153-7.
Halperin, S. A., et al., "Safety and Immunogenicity of a Trivalent, Inactivated, Mammalian Cell Culture-Derived Influenza Vaccine in Healthy Adults, Seniors, and Children." (2002) 20: 1240-7.
Hsu, S., "Affinity Purification of a Live Attenuated Influenza Virus from MDCK Cell Culture," presentation at: 4th Vaccine & ISV Annual Global Congress Oct. 3-5, 2010, Vienna, Austria.
Hsu, Simon, Presentation—"Challenges and Opportunities of Using Cell Culture for the Production of Live, Attenuated Influenza Vaccines (LAIV)", World Vaccine Congress. Lyon, France, Oct. 5-8, 2009.
Hsu,S. "Purification Development for a Live Attenuated Influenza Virus from MDCK Cell Culture" presentation at: The Immunotherapeutics and Vaccine Summit Aug. 17-19, 2010, Cambridge, MA.

(56) References Cited

OTHER PUBLICATIONS

Hussain, Althaf I., Poster—"Evaluation of High Yielding MDCK Clone for Commercial Production of Cold-Adapted (ca) Live Attenuated Influenza Virns Vaccines—Host Cell Susceptibility and Influenza Virns Replication in Permissive and Semi-Permissive Cells", New cells for new vaccines III. Wilmington, Delaware. Sep. 28-Oct. 1, 2008.

Hussain, Althaf, "Comparison of Egg and High Yielding MDCK Cell-derived Live Attenuated Influenza Virns for Commercial Production of Trivalent Influenza Vaccine: In-vitro Cell Susceptibility and Influenza Virus Replication kinetics in Permissive and Semi-Permissive Cells Vaccine", Vaccine (2010) 28:13848-13855.

Johnson, J. B., et al. "Tumorgenicity of Continuous Monkey Cell Lines in in Vivo and in Vitro Systems." Dev.Biol.Stand. (1981) 50: 27-35.

Kalbfuss, B., et al. "Harvesting and Concentration of Human Influenza A Virus Produced in Serum-Free Mammalian Cell Culture for the Production of Vaccines. " Biotechnol.Bioeng. (2007) 97: 73-85.

Kemble, G. Seminar: "Development ofLAIV Production in Cell Culture." Meeting with the World Health Organization. Geneva, Switzerland, Jun. 12, 2007, pp. I-5.

Kessler, N., et al. "Suitability of MDCK Cells Grown in a Serum-Free Medium for Influenza Virus Production." Dev.Biol. Stand. (1999) 98: 13,21; discussion 73-4.

Leighton, J., et al. "A Cell Line Derived from Normal Dog Kidney (MDCK) Exhibiting Qualities of Papillary Adenocarcinoma and of Renal Tubular Epithelium." Cancer (1970) 26:1 022-8.

Leighton, J., et al. "Clinical and Experimental Tumors of the Kidney in Tissue Culture and in the Chick Embryo." Eur.J.Cancer (1972) 8: 281-5.

Leighton, J., et al., "Secretory Activity and Oncogenicity of a Cell Line (MDCK) Derived from Canine Kidney." Science (1969) 163: 472-3.

Lewis, A. M.,Jr, et al. "A Defined-Risks Approach to the Regulatory Assessment of the use of Neoplastic Cells as Substrates for Viral Vaccine Manufacture." Dev.Biol.{Basen (2001) 106: 513-35.

Liu et al., Abstract and Presentation: "Development of a Process for Cell Culture Production of a Cold-Adapted Live Attenuated Influenza Vaccine (LAIV)." WillBio Meeting-BioProcess Technology. Amsterdam, Netherlands, Apr. 2-4, 2007. pp. 1-13.

Liu et al., Abstract and Presentation: "Selection and Characterization of a High Producing Host Cell Line for Influenza Vaccine Production." WillBio Meeting—Cell Engineering and Banking. Washington, DC, USA, Dec. 4-6, 2006. pp. 1-9.

Liu et al., "Developing highly productive bioprocesses to prepare for pandemic outbreaks," presentation at: IVTW (2010) International Vaccine Technology Workshop, Sep. 17-18, 2010, Hyderabad, India.

Liu et al., "Developing highly productive bioprocesses to prepare for pandemic outbreaks," published abstract from: IVTW (2010) International Vaccine Technology Workshop, Sep. 17-18, 2010, Hyderabad, India.

Liu et al., "Development of a highly productive cell culture-based influenza vaccine," presentation at: WCV (2011) BIT Life Sciences World Congress of Vaccine—3rd Annual Beijing China, Mar. 23, 2011.

Liu et al., "Development of a highly productive cell culture-based influenza vaccine," published abstract from: WCV (2011) BIT Life Sciences World Congress of Vaccine—3rd Annual Beijing China, Mar. 23, 2011.

Liu, Jonathan, "Cloning and assessment of tumorigenicity and oncogenicity of a Madin-Darby canine kidney (MDCK) cell line for influenza vaccine production", Vaccine (2010) 28:1285-1293.

Liu, Jonathan, "MDCK cells for manufacture oflive attenuated Influenza virus vaccines", World Vaccine Congress. Washington DC, Apr. 20-23 2009.

Liu, Jonathan, "Use of MDCK cells for production oflive attenuated influenza vaccine", Vaccine (2009) 27(46):6460-3.

Liu, Jonathan, Abstract and Presentation—"Cell culture-based vaccine: an alternative to egg derived influenza vaccine and its business and operational values", Session 21 of World Congress of Vaccine. Guangzhou, China. Dec. 1-5, 2008.

Liu, Jonathan, Abstract and Presentation—"Challenges and solutions for the next generation of vaccines: Development of cell culture-based live attenuated influenza vaccine", Vaccine Technology II. Albufeira, Portugal. Jun. 1-6, 2008.

Liu, Jonathan, Abstract and Presentation—"Development of a Process for Cell Culture Production of a Cold-Adapted Live Attenuated Influenza Vaccine (LAIV)", 4th Annual Meeting on BioProcess Technology—Europe. Amsterdam, Netherland. Apr. 2-4, 2007.

Liu, Jonathan, Abstract and Presentation—"Improvement of vaccine productivity with reduced manufacturing process development time", Session 59 World Congress of Vaccine. Guangzhou, China. Dec. 1-5, 2008.

Liu, Jonathan, Abstract and Presentation—"Selection and Characterization of a high producing host cell line for Influenza vaccine production" , The Williamsburg BioProcessing Foundation Cell Engineering and Banking, Washington, DC. Dec. 4-6, 2006.

Liu, Jonathan, Abstract and Presentation—Transitioning From Eggs to Cell Culture Production of FluMist®, a Live Attenuated Influenza Vaccine (LAIV), and Modeling Seasonal and Pandemic Vaccine Production, BioProcess Technology—Singapore. Singapore, Jul. 30-Aug. 1, 2007.

Liu, Jonathan, Presentation—"Overcome the Scale-up Hurdles and Produce Cell Culture Based Vaccine at Large Scale", Vaccines Europe, Brussels, Belgium, Nov. 17-18, 2009.

Liu, Yi, Abstract and Presentation—"Development of an Economic Production Platform for Live Attenuated Influenza Vaccines", The Immunotherapeutics and Vaccine Summit: Production and Manufacturing of Vaccines. Providence, Rhode Island. Aug. 17-18, 2009.

Lonardo et al.: 'Rapid methods for identification of poliovirus isolates and determination of polio neutralizing antibody titers in human sera.' J Virol Methods. vol. 101, No. 1-2, 2002, pp. 189-196.

Mabrouk, T., et al. "Influenza Vaccine Technologies and the use of the Cell-Culture Process (Cell-Culture Influenza Vaccine)." Dev.Biol. (Basel) (2002) 110: 125-34.

Madin, S. H., et al. "Established Kidney Cell Lines of Normal Adult Bovine and Ovine Origin." Proc.Soc.Exn.Biol.Med. (1958) 98: 574-6.

Mani, S., Abstract and Presentation: "Characterization of a Madin Darby Canine Kidney (MDCK) Cell Bank used in the Production of a Live Attenuated Influenza Vaccine (LAIV)." WillBio Meeting—Cell Engineering and Banking. Philadelphia, PA, USA, Dec. 3-5, 2007. pp. 1-8.

Maranga et al., Abstract and Poster: "Development of a Platform Process for Cell Culture Production of Cold-Adapted Live Attenuated Influenza (CAJV) Strains of FluMist(R)." 20th Meeting of the European Society for Animal Cell Technology (ESACT). Dresden, Germany, Jun. 17-20, 2007. pp. 1-6.

Maranga et al., Abstract and Presentation: "Development of a Platform Process for Cell Culture Production of Cold-Adapted Live Attenuated Influenza Vaccine." Biochemical Engineering XV. Quebec City, Canada, Jul. 15-19, 2007. pp. 1-7.

Maranga, Luis, Abstract—"Development of a Platform Process for Cell Culture Production of a Cold-Adapted Live Attenuated Influenza Vaccine (LAIV)", Presentation—"Development of a Platform Process for Cell Culture Production of Cold-adapted live Attenuated Influenza Vaccine (CAIV) strains of FluMist®". Biochemical Engineering XV. Quebec City, Canada. Jul. 15-19, 2007.

Maranga, Luis, Abstract and Poster—"Development of a Platform Process for Cell Culture Production of Cold-adapted live Attenuated Influenza Vaccine (CAIV) strains of FluMist®". 20th Meeting of the European Society for Animal Cell Technology. Dresden, Germany. Jun. 17-20, 2007.

Medema et al. "Safety Assessment of Mad in Darby Canine Kidney Cells as Vaccine Substrate." Dev.Biol.(Basel) (2006) 123: 243,50; discussion 265-270.

MedImmune, Briefing Document—"Use of Madin Darby Canine Kidney Cells for the Manufacture of Live, Attenuated Influenza Vaccines", FDA—Vaccines and Related Biological Products Advisory Committee. Silver Spring, MD, Sep. 25, 2008. pp. 1-51.

MedImmune, Presentation—"Live, Attenuated Influenza Vaccine Manufactured in MDCK Cells (VRBPAC Presentation)." FDA—

(56) References Cited

OTHER PUBLICATIONS

Vaccines and Related Biological Products Advisory Committee. Silver Spring, MD, Sep. 25, 2008. pp. 1-29.

MedImmune. "Use of MDCK Cells for Manufacture of Live, Attenuated Influenza Vaccines (VRBPAC Background Summary)." FDA—Vaccines and Related Biological Products Advisory Committee. Silver Spring, MD, Sep. 25, 2008. pp. 1-9.

Merten et al. "Production of Influenza Virus in Cell Cultures for Vaccine Preparation." Adv.Exn.Med.Bioi. (1996) 397: 141-51.

Merten et al. "Production of Influenza Virus in Serum-Free Mammalian Cell Cultures." Dev.Biol.Stand. (1999) 98: 23,37; discussion 73-4.

Nakazato, Y., et al. "Characterization of Subclones of Madin-Darby Canine Kidney Renal Epithelial Cell Line." Biochim.Bioohvs.Acta (1989) 1014: 57-65.

Pakes, S. P., et al. "Chromosome Analysis of 2 Canine Tumor Cell Lines." Am.J.Vet.Res. (1965) 26: 837-843.

Palache, A. M., et al. "immunogenicity and Reactogenicity of Influenza Subunit Vaccines Produced in MDCK Cells or Fertilized Chicken Eggs." The Journal of infectious diseases 176 Suppl 1 (1997): S20-3.

Palker, T., et al. "Protective Efficacy of Intranasal Cold-Adapted Influenza A/New Caledonia/20/99 (H1N1) Vaccines Comprised of Egg- or Cell Culture-Derived Reassortants." Virus Res. (2004) 105: 183-194.

Percheson et al. "A Phase I, Randomized Controlled Clinical Trial to Study the Reactogenicity and Immunogenicity of a New Split Influenza Vaccine Derived from a Non-Tumorigenic Cell Line." Dev.Biol. Stand. (1999) 98: 127-132; discussion 133-134.

Radaeva, I. F., et al. "Development and Certification of Libraries of the MDCK Continuous Cell Line for Production of Influenza Vaccine." Vopr.Virusol (2005) 50:43-46 Abstract with English language Translation.

Reh et al., Structural Basis for Stable DNA Complex Formation by the Caspase-activated DNase, 2005, The Journal of Biological Chemistry, vol. 280, No. 50, pp. 41707-41715.

Rindler, M. J., et al. "Retention of Differentiated Properties in an Established Dog Kidney Epithelial Cell Line (MDCK)." J.Cell Biol. (1979) 81: 635-48.

Saier et al. "Studies on Growth Regulation and the Mechanism of Transformation of the Kidney Epithelial Cell Line, MDCK: Importance of Transport Function to Growth." Prog.Clin.Biol.Res. (1982) 91: 569-97.

Saier, M. H.,Jr. "Growth and Differentiated Properties of a Kidney Epithelial Cell Line (MDCK)." Am.J.Physiol. (1981) 240: C106-9.

Schwartz, R., Abstract and Presentation: "Transitioning from Eggs to Cell Culture Production FluMist(R), a Live Attenuated Influeza Vaccine (LAIV), and Modeling Seasonal and Pandemic Vaccine Production." WillBio Meeting—BioProcess Technology. Singapore, Jul. 30-Aug. 1, 2007. pp. I-14.

Schwartz, Richard, Presentation—"Case Study: Establishing a Benchmark for Economic Vaccine Scale-up Strategies", European BioPharm Scale-Up Congress. Geneva, Switzerland. Sep. 17-19, 2008.

Schwartz, Richard, Presentation—"Developing a Cell Culture Based Influenza Vaccine Process", AICHE 46th Biotechnology Symposium South San Francisco, Apr. 29, 2008.

Solvay. "Madin Darby Canine Kidney Continuous Cell Line (Briefing Document)." FDA—Vaccines and Related Biological Products Advisory Committee. Bethesda, MD, Nov. 16, 2005. pp. 1-21 (as downloaded Dec. 12, 2008 from http://www.fda.gov/ohrms/dockets/ac/05/briefing/5-4188B1_19a.pdf).

Stiles, C. D., et al. "Growth Control of Heterologous Tissue Culture Cells in the Congenitally Athymic Nude Mouse." Cancer Res. (1976) 36: 1353-60.

Stiles, C. D., et al. "Relationship of Cell Growth Behavior in Vitro to Tumorigenicity in Athymic Nude Mice." Cancer Res. (1976) 36: 3300-5.

Subramanian et al., Abstract and Poster: "Developing a Cell Culture Process for Production of Live Attenuated Influenza Virus Vaccine in Madin Darby Canine Kidney Cells." WillBio Meeting—Viral Vectors and Vaccines. Amsterdam, Netherlands, May 25-27, 2005. pp. 1-6.

Subramanian et al., Presentation: "Developing a Cell Culture Process for Production of a Live Attenuated Influenza Virus Vaccine in Madin Darby Canine Kidney Cells." WillBio Meeting—Viral Vectors and Vaccines. Austin, Texas, USA, Nov. 14-16, 2005. pp. 1-5.

Taub, M., et al. "Alterations in Growth Requirements of Kidney Epithelial Cells in Defined Medium Associated with Malignant Transformation." J. Sunramol. Struct. Cell.Biochem. (1981) 15: 63-72.

Taub, M., et al. "An Established but Differentiated Kidney Epithelial Cell Line (MDCK)." Methods Enzymol. (1979) 58: 552-60.

Taub, M., et al. "Growth of Functional Primary Cultures of Kidney Epithelial Cells in Defined Medium." J.Cell.Physiol. (1980) 105: 369-78.

Taub, M., et al. "Growth of Madin-Darby Canine Kidney Epithelial Cell (MDCK) Line in Hormone-Supplemented, Serum-Free Medium." PNAS U.S.A. (1979) 76: 3338-3342.

Taub, N., et al. "The Development of Serum-Free Hormone-Supplemented Media for Primary Kidney Cultures and their use in Examining Renal Functions." Ann.N.Y.Acad.Sci. (1981) 372: 406-21.

Tree, et al., Comparison of large-scale mammalian cell culture system with egg culture for production of influenza virus A vaccine strains, Vaccine, May 2001, 19, 3444-3450.

Voeten, et al. "Characterization of High-Growth Reassortant Influenza A Viruses Generated in MDCK Cells Cultured in Serum-Free Medium." Vaccine (1999) 17: 1942-50.

Voeten, J. T., et al. "Generation and Characterization of Reassortant Influenza A Viruses Propagated in Serum-Free Cultured MDCK-SF1 Cells." Dev.Biol.Stand. (1999) 98: 77,87; discussion 89-90.

Youil, R., et al. "Comparative Study of Influenza Virus Replication in Vero and MDCK Cell Lines." J. Virol.Methods (2004) 120: 23-31.

Zhang et al., "Optimization of Downstream Production for Live Attenuated Influenza Vaccine to Improve Manufacturing Efficiency and Final Bulk Quality," poster presented at: BPI (2010) BioProcess International Conference & Exhibition Sep. 20-24, 2010.

Zhang et al., "Optimization of Downstream Production for Live Attenuated Influenza Vaccine to Improve Manufacturing Efficiency and Final Bulk Quality," published abstract from: BPI (2010) BioProcess International Conference & Exhibition Sep. 20-24, 2010.

Extended European Search Report dated Aug. 25, 2011 in European Application No. EP11004971 filed Dec. 16, 2011.

Supplementary European Search Report dated Feb. 24, 2009 in European Application No. EP05857088 filed on Dec. 16, 2005.

Supplementary European Search Report mailed on: Feb. 28, 2011 in European application No. EP07873787 filed on Sep. 14, 2007.

International Preliminary Report on Patentability. mailed on Jun. 26, 2007 for International Application No. PCT/US2005/45587 filed on: Dec. 16, 2005 and published as: WO 06/071563 on Jul. 6, 2006.

Written Opinion of the International Searching Authority mailed on Jul. 26, 2006 for International Application No. PCT/US2005/45587 filed on: Dec. 16, 2005 and published as: WO 06/071563 on Jul. 6, 2006.

International Search Report and Written Opinion mailed on: Nov. 25, 2009 in International Application No. PCT/US2009/58174 filed on: Sep. 24, 2009 and published as WO 10/036774 on: Apr. 1, 2010.

International Preliminary Report on Patentability mailed on: Mar. 29, 2011 in International Application No. PCT/US2009/58174 filed on: Sep. 24, 2009 and published as WO 10/036774 on: Apr. 1, 2010.

International Search Report and Written Opinion mailed on Feb. 3, 2010 in International Application No. PCT/US09/058157 filed on Sep. 24, 2007 and published as: WO 10/036760 on Apr. 1, 2010.

International Preliminary Report on Patentability mailed on Mar. 29, 2011 in International Application No. PCT/US09/058157 filed on Sep. 24, 2007 and published as: WO 10/036760 on Apr. 1, 2010.

International Preliminary Report on Patentability mailed on Mar. 17, 2009 in International Application No. PCT/US07/078527 filed on Sep. 14, 2007 and published as WO 08/105931 on Sep. 4, 2008.

International Search Report and Written Opinion mailed on Nov. 26, 2008 in International Application No. PCT/US07/078527 filed on Sep. 14, 2007 and published as WO 08/105931 on Sep. 4, 2008.

(56) References Cited

OTHER PUBLICATIONS

Office Action mailed on: Jun. 6, 2011 in U.S. Appl. No. 12/686,926, filed Jan. 13, 2010 and published as: US 2010/0112000 on May 6, 2010.

Office Action mailed on: Nov. 29, 2010 in U.S. Appl. No. 12/686,926, filed Jan. 13, 2010 and published as: US 2010/0112000 on May 6, 2010.

Office Action mailed on: Sep. 8, 2010 in U.S. Appl. No. 12/686,926, filed Jan. 13, 2010 and published as: US 2010/0112000 on May 6, 2010.

Extended European Search Report dated Jul. 27, 2012 in European Application No. EP09816835 filed: Sep. 24, 2009 based on International Application No. PCT/US2009/058174.

Decheme e.V. Press release, "Bioprocessing: Engineering know-how in greater demand than ever," ACHEMA 2006, 28th International Exhibition Congress on Chemical Engineering, Environmental Protection and Biochemistry, Trend Report No. 15:Bioprocessing, pp: 1-6.

Downing et al., "Active respiratory syncytical virus purified by ino-exchange chromatography: characterization of binding and elution requirements," Journal of Virological Methods, vol. 38, No. 2, Aug. 1, 1992, pp. 215-228.

Extended European Search Report dated Jul. 27, 2012 in European Application No. EP09816828 filed: Sep. 24, 2009 based on International Application No. PCT/US2009/058157.

Wolff et al., "Downstream Processing: From Egg to Cell Culture-Derived Influenza Virus Particles," Chemical Engineering & Technology, vol. 31. No. 6, Jun. 1, 2008, pp. 846-857.

Kalbfuss et al., "Purification of cell culture-derived human influenza A virus by size-exclusion and anion-exchange chromatography," vol. 96, Issue 5, pp. 932-944, Apr. 1, 2007.

Extended European Search Report dated: Jun. 11, 2013 in European Application No. EP13163566 filed: Sep. 24, 2006.

Office Action mailed on: Jun. 21, 2013 in U.S. Appl. No: 13/355,252, filed Jan. 20, 2012 and published as: US 2012/0115206 on May 10, 2012.

MOCK (NBI-2) (ATCC® CCl-34TM). ATCC®, retrieved on Jun. 5, 2013. Retrieved from the Internet <URL:atcc.org/Products/ All/ CCL-34. aspx#85786B46AA23451B94BC5045200673 F7>.

DMEM (ATCC® 30-2002™), ATCC®, retrieved on Jun. 5, 2013. Retrieved from the Internet <URl: atcc.org/products/all/30-2002. aspx>.

Office Action mailed on Jan. 28, 2014 in U.S. Appl. No. 13/355,252, filed Jan. 20, 2012 and published as US 2012-0115206 on May 10, 2012.

Office Action mailed on Feb. 13, 2014 in U.S. Appl. No. 13/595,897, filed Aug. 27, 2012 and published as US 2013-0052717 on Feb. 28, 2013.

Taub et al., "PGE1-independent MDCK cells have elevated intracellular cyclic AMP but retain the growth stimulatory effects of glucagon and epidermal growth factor in serum free medium" J. Cell. Physiol. (1984) 120:19-28.

Office Action mailed on May 27, 2014 in U.S. Appl. No. 13/595,897, filed Aug. 27, 2012 and published as US 2013-0052717 on Feb. 28, 2013.

Halperin et al., "Safety and immunogenicity of a new influenza vaccine grown in mammalian cell culture" Vaccine (1998) 16(3):1331-1335.

* cited by examiner

FIG. 7A
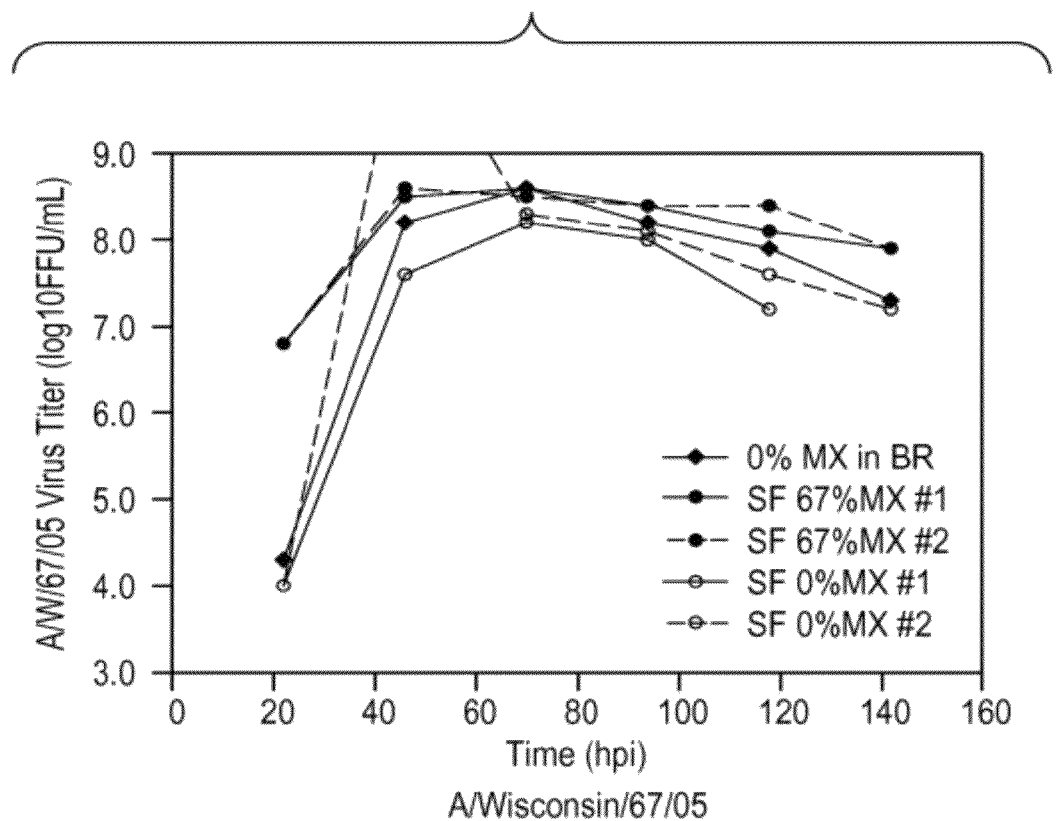
A/Wisconsin/67/05
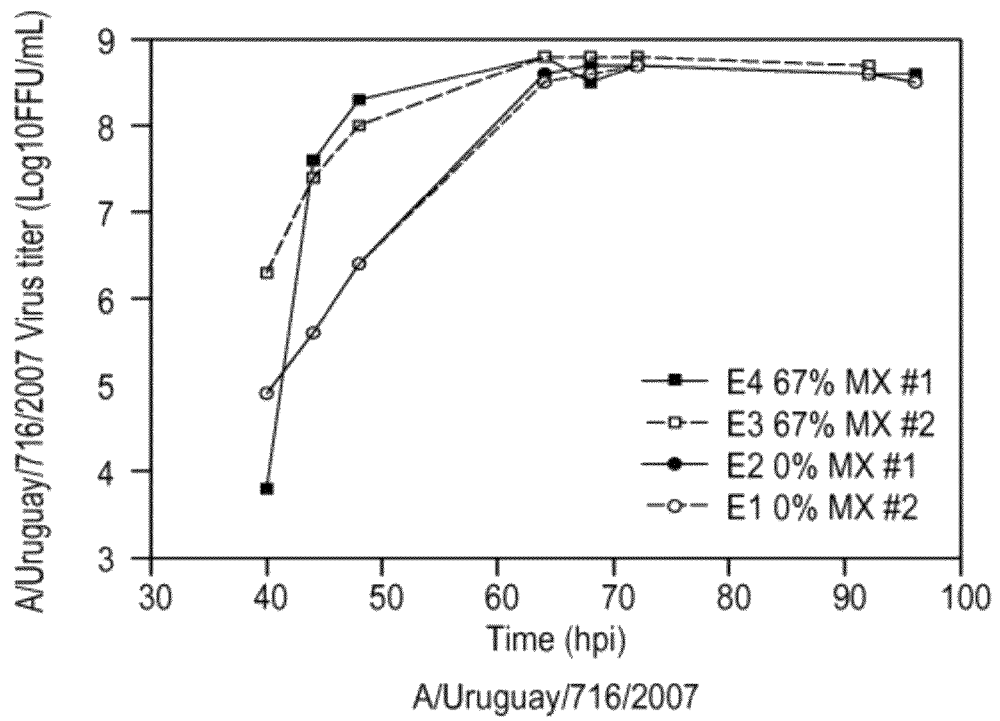
A/Uruguay/716/2007

FIG. 7B
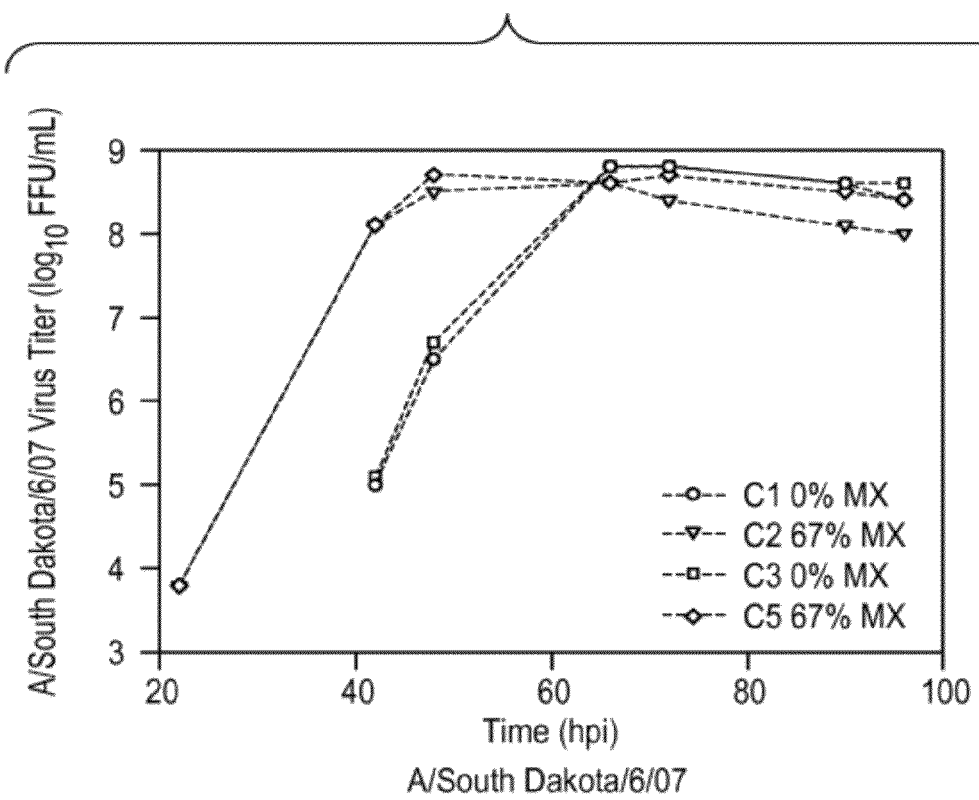
A/South Dakota/6/07
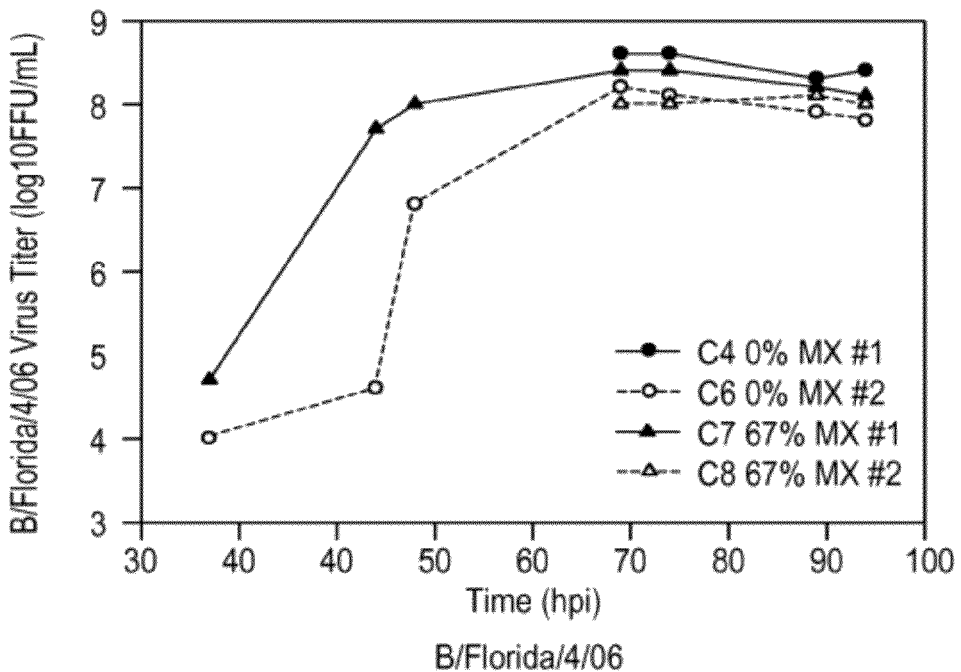
B/Florida/4/06

FIG. 9A
Direct Flow Filtration 1 (DFF1) Filter Rig Drawing
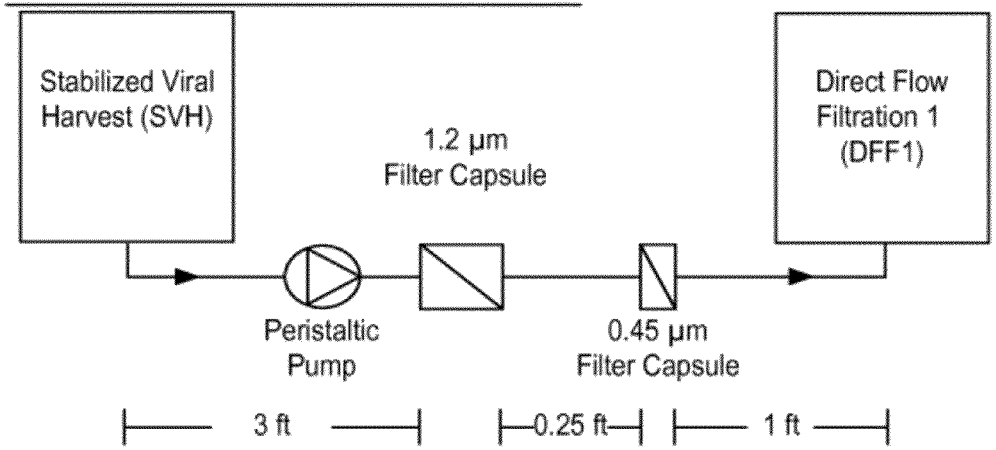
GE Healthcare Uniflux skid Tubing Rigs Drawings
UNIFLUX Sample/Buffer Feed Tubing Rig
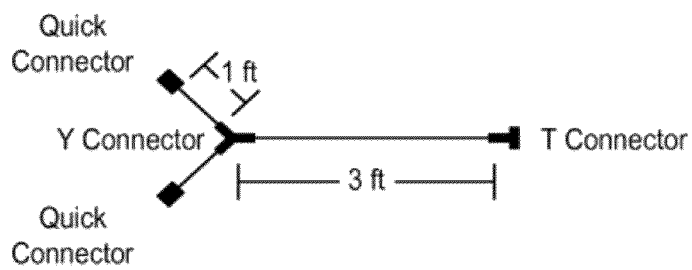
UNIFLUX Feed Drain Tubing Rig
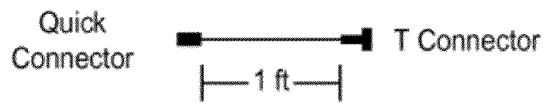
UNIFLUX Permeate Tubing Rig
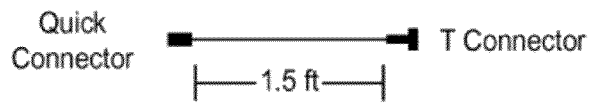
NOTE: All tubing rigs were prepared with 3/8" id silicone tubings.

FIG. 9B
GE Healthcare AKTA Process skid Tubing Rigs Drawings
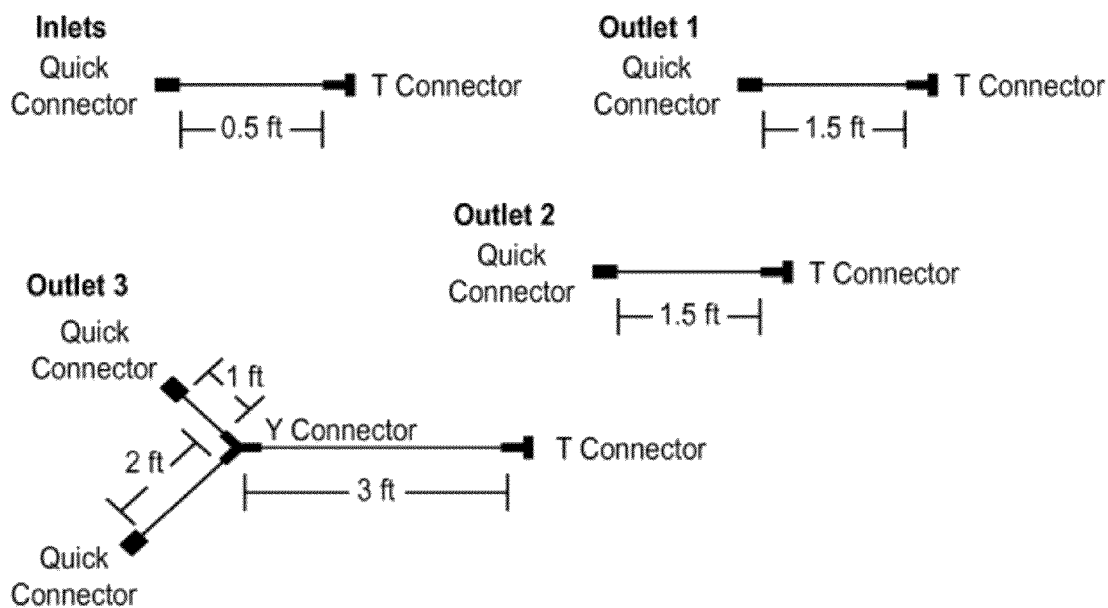
NOTE: All tubing rigs were prepared with 3/8" id silicone tubings.
Direct Flow Filtration 2 (DFF2) Filter Rig Drawing
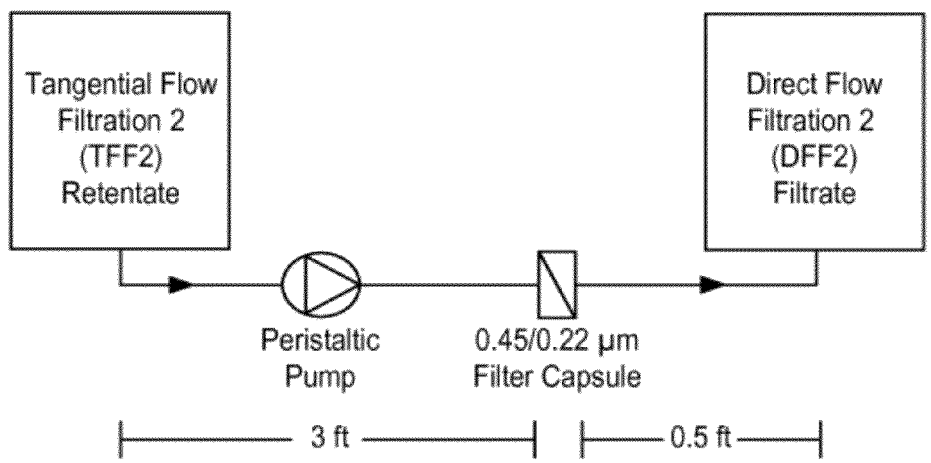

FIG. 16

Serial Propagation Titers Infected with A/Wisconsin/67/07

◆ EDTA Gibco　■ EDTA In house　▲ EDTA/TrypLE　□ Control

Serial Propagation Titers Infected with B/Malaysia/2506/04

◆ EDTA Gibco　■ EDTA In house　▲ EDTA/TrypLE　□ Control

FIG. 17B
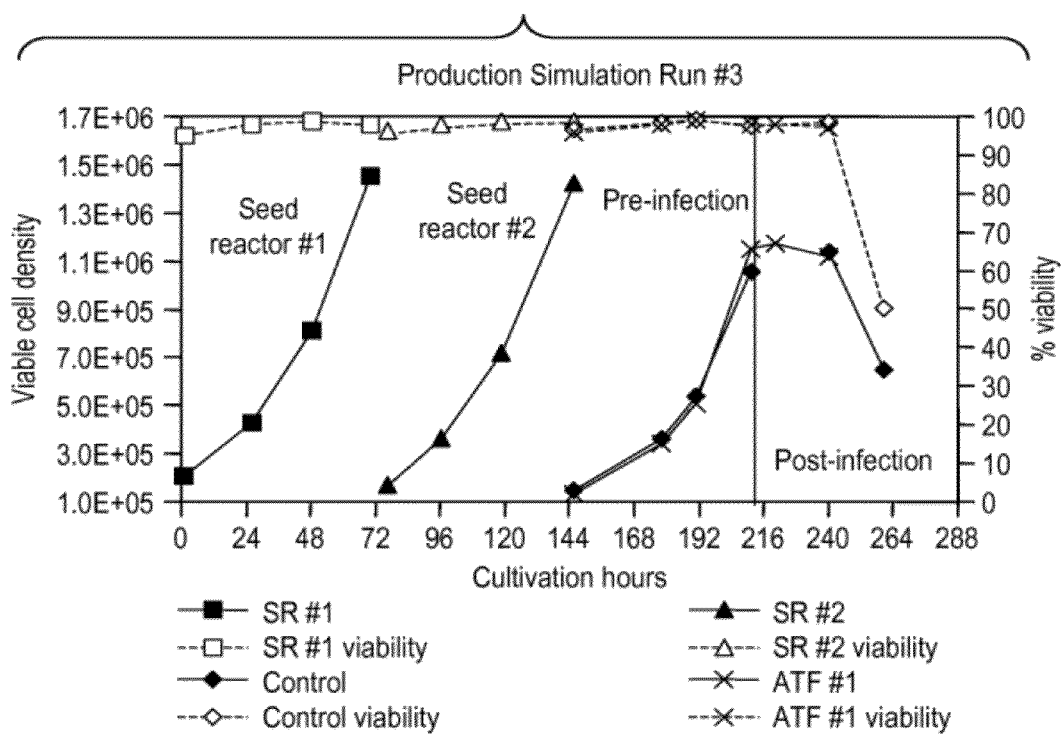
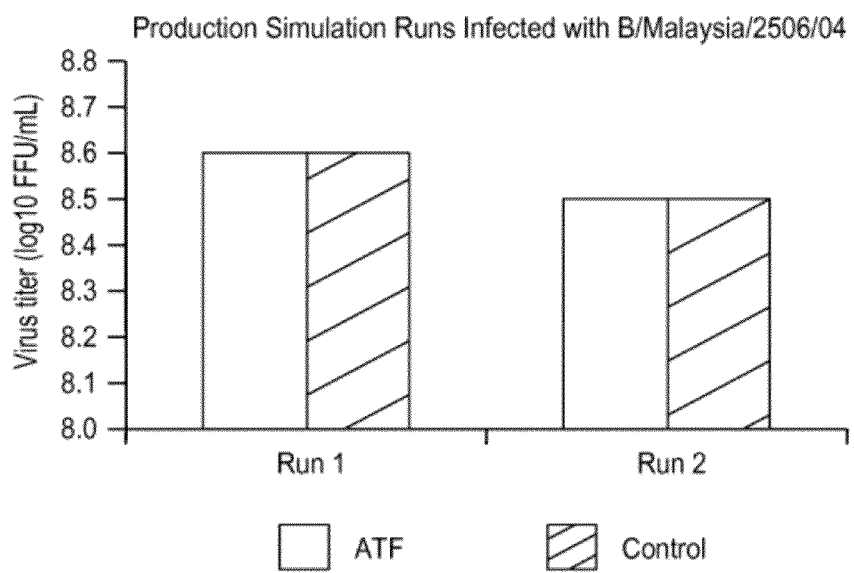

FIG. 18
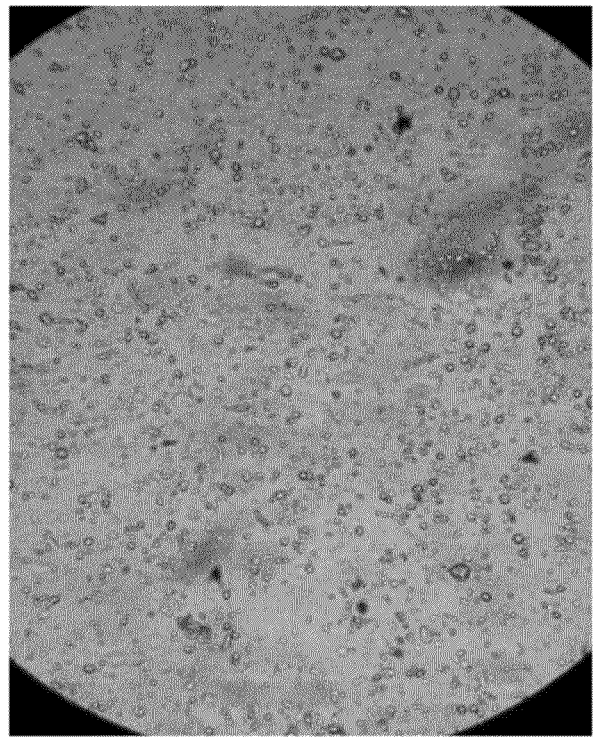
Absence of microcarrier after 66% media exchange using ATF
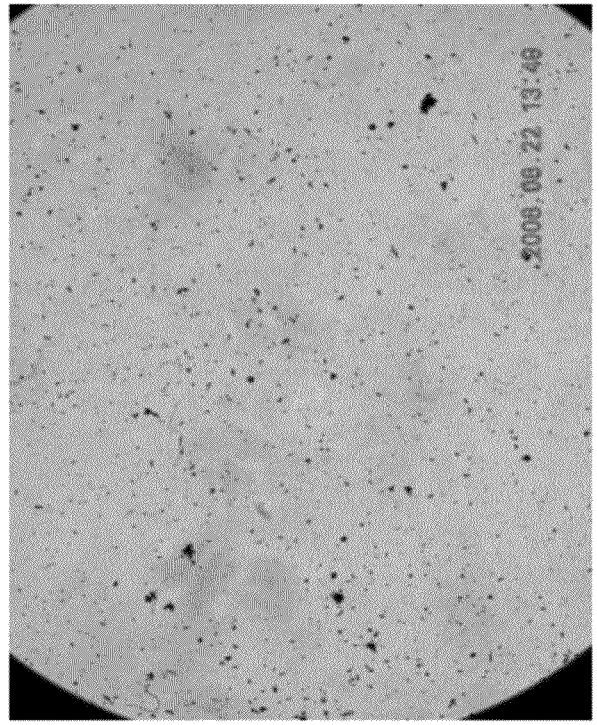
Absence of microcarriers in the waste bag after microcarrier sterilization using ATF

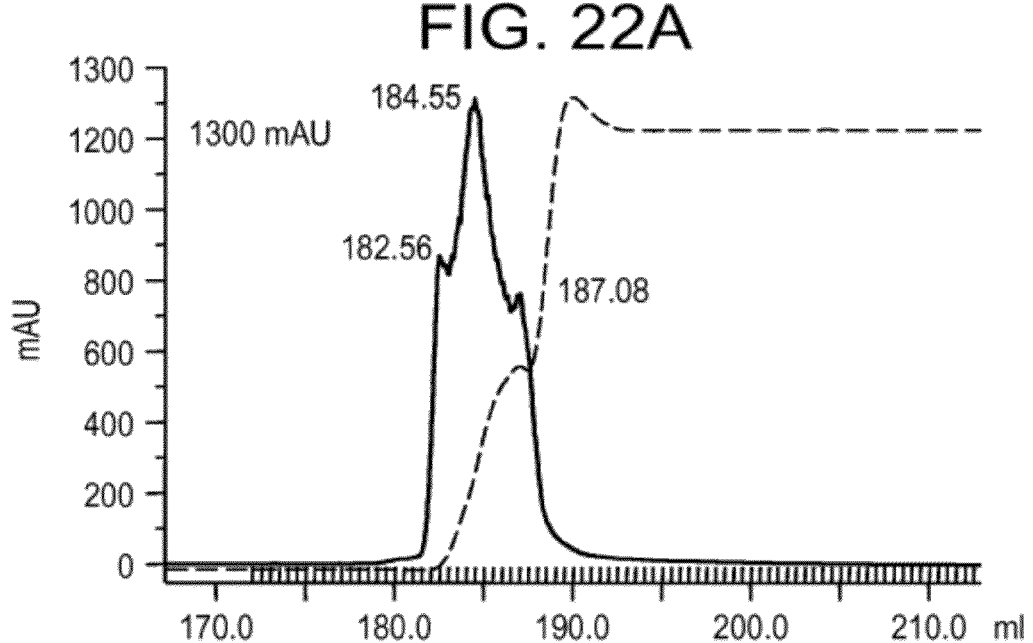
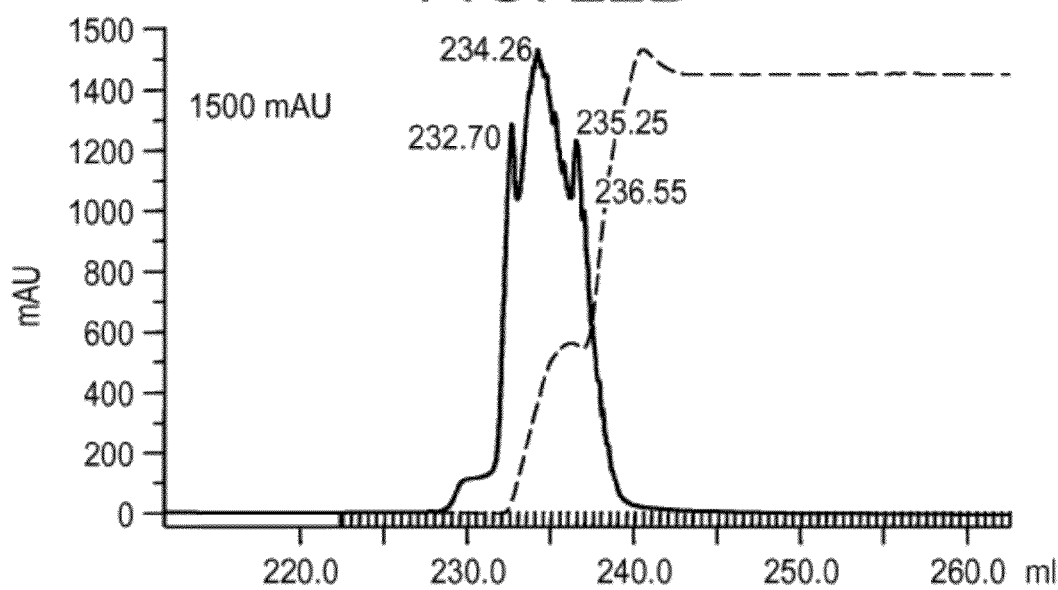

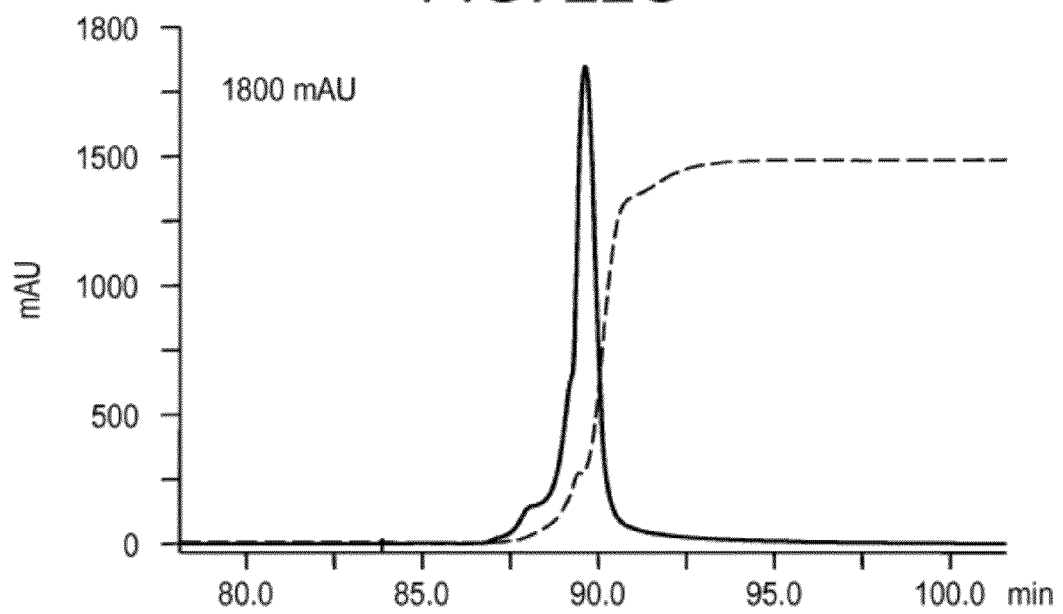

METHODS FOR CULTIVATING CELLS, PROPAGATING AND PURIFYING VIRUSES

1. CROSS REFERENCE TO RELATED APPLICATIONS

This application is a divisional of U.S. patent application Ser. No. 12/566,048, filed on Sep. 24, 2009, which claims the benefit under 35 U.S.C. §119(e) of the following U.S. Provisional Application Nos. 61/099,749 filed Sep. 24, 2008; 61/104,933 filed Oct. 13, 2008; 61/187,721 filed Jun. 17, 2009, each of the priority applications are incorporated by reference herein in their entirety for all purposes.

2. STATEMENT AS TO RIGHTS TO INVENTIONS MADE UNDER FEDERALLY SPONSORED RESEARCH AND DEVELOPMENT

One or more inventions described herein were made with Government support under Contract No. HHS0100200600010C awarded by Health and Human Services. Accordingly, the Government may have certain rights in such inventions.

3. FIELD OF THE INVENTION

The present invention relates to novel cell culture medium and methods for cultivating cells, in particular non-tumorigenic MDCK cells. The present invention further relates to methods for producing viruses (e.g., influenza, RSV) in cell culture. The present invention also provides methods for the purification of cell-associated viruses from adherent cells grown in a bioreactor for the development of vaccines.

4. BACKGROUND OF THE INVENTION

Vaccination is the most important public health measure for preventing disease caused by viral infection. The effective use of vaccines is dependent on being able to quickly produce large quantities of vaccine material (e.g., virus) from a stable and easy to cultivate source. The rapid development of vaccines and their abundant availability is critical in combating many human and animal diseases. Delays in producing vaccines and shortfalls in their quantity can cause problems in addressing outbreaks of disease. For example, recent studies suggest that there is cause for concern regarding the long lead times required to produce vaccines against pandemic influenza. See, for example, Wood, J. M., 2001, Philos. Trans. R. Soc. Lond. B. Biol. Sci., 356:1953. Accordingly, recent efforts to produce vaccines have focused on growth of viruses for vaccines in cell culture.

4.1 Influenza Virus

In particular, the use of Madin Darby Canine Kidney (MDCK) cells has been pursued by a number of groups. See, for example, U.S. Pat. No. 6,455,298; U.S. 2005/0118140; U.S. 2005/0118698; U.S. Pat. No. 6,825,306; WO2005/113758; and Radaeva, I. F., et al. Vopr. Virusol. (2005) 50: 43-6. However, many of the existing MDCK cell lines suffer from one or more defects including tumorigenicity, the requirement for animal serum in cell culture, and low yields of influenza viruses suitable for use in vaccines. Furthermore, many of the cell culture processes which have been developed for the production of vaccine material from these cell lines often require numerous manipulations including medium exchange steps and the use of large amounts of virus for inoculation. In addition, because of the continual emergence (or re-emergence) of different influenza strains, new influenza vaccines are generated each season based on the circulating influenza strains. Unfortunately, some influenza vaccine strains are more difficult to grow to high yields. The yield of each batch of cell culture derived material not only defines production capacity but also impacts the cost of manufacturing product thus improving viral yield (i.e., peak viral titer) is desirable.

Recently, novel serum-free medium and non-tumorigenic cell lines that can grow vaccine strains to very high titers and processes for the production of viral material in disposable bioreactors have been developed (see, U.S. 2006/0188977; and U.S. Ser. No. 11/855,769 filed Sep. 14, 2007). The instant invention expands this work and provides novel cell culture medium, highly reproducible efficient scalable processes for the production of large quantities of vaccine material in bioreactors from MDCK cells, in particular, non-tumorigenic cells lines, without the need for medium exchange, and robust downstream purification processes for the production of a highly purified live attenuated vaccine. The methods provided by the present invention are robust requiring minimal manipulation and are cost effective.

4.2 Respiratory Syncitial Virus (RSV)

Human respiratory syncytial virus (RSV) is the leading cause of severe lower respiratory tract infection (LRTI) in infants and young children and is responsible for considerable morbidity and mortality. A total of 18 million people are infected annually in the seven major markets (US, Japan, France, Germany, Italy, Spain, UK), including three million adults and almost 400,000 premature infants. Annually in the U.S. alone, it is estimated that 70,000-125,000 hospitalizations are attributed to RSV LRTI. Two antigenically diverse RSV subgroups A and B are present in human populations. RSV is also recognized as an important agent of infection in immuno-compromised adults and in the elderly. Due to the incomplete resistance to RSV reinfection induced by natural infection, RSV may infect multiple times during childhood and life. The goal of RSV immunoprophylaxis is to induce sufficient resistance to prevent the serious disease which may be associated with RSV infection. The current strategies for developing RSV vaccines principally revolve around the administration of purified viral antigen or the development of live attenuated RSV for intranasal administration. However, to date there have been no approved vaccines or for RSV.

The viral genomic RNA is not infectious as naked RNA. The RNA genome of RSV is tightly encapsidated with the major nucleocapsid (N) protein and is associated with the phosphoprotein (P) and the large (L) polymerase subunit. These proteins form the nucleoprotein core, which is recognized as the minimum unit of infectivity (Brown et al., 1967, J. Virol. 1: 368-373).

Despite decades of research, no commercially available safe and effective RSV vaccine has been developed for the prevention of severe morbidity and mortality associated with RSV infection. A formalin-inactivated virus vaccine has failed to provide protection against RSV infection and in fact lead to exacerbated symptoms during subsequent infection by the wild-type virus in infants (Kapikian et al., 1969, Am. J. Epidemiol. 89:405-21; Chin et al., 1969, Am. J. Epidemiol. 89:449-63). Efforts since have focused on developing live attenuated mutants obtained by recombinant methods, chemical mutagensis and cold passage of the wild type RSV for temperature-sensitive mutants (Gharpure et al., 1969, J. Virol. 3: 414-21; Crowe et al., 1994, Vaccine 12: 691-9).

However, purification of live attenuated virus from their cell-associated proteins, which would meet regulatory guidelines for efficacious prophylactic treatment of RSV infection, has proved elusive until now.

Similar to the influenza virus, RSV is grown in a stable cell line wherein the virus is closely associated with the host cell making it difficult to purify the virus from the cell-associated proteins while maintaining a minimum unit of infectivity. Adding to the complexity, RSV is fragile (e.g., shear sensitive). These factors, the virus being predominantly host cell associated and fragile, have made it difficult to purify the virus from host cell extract (e.g., DNA and proteins) while resulting in a clinically acceptable immunogenic composition comprising live attenuated virus. It is for these reasons, in part, why no vaccines are commercially available for RSV. Accordingly, there is a need for a purification process that can be used to purify RSV and other cell-associated viruses for preparation and formulation of immunogenic compositions.

5. SUMMARY OF THE INVENTION

The present invention provides serum-free cell culture medium and highly reproducible efficient scalable processes for the production of large quantities of vaccine material in bioreactors, including single use bioreactors and standard reusable bioreactors (e.g., stainless steel and glass vessel bioreactors).

In one aspect, the present invention provides an enriched serum-free cell culture medium that supports proliferation of MDCK cells (e.g., non-tumorigenic MDCK cells) to a high cell density and eliminates the need for a medium exchange step to obtain high viral titers.

In particular, the present invention provides methods for the replication of influenza viruses (e.g., cold-adapted, and/or temperature sensitive, and/or attenuated) in MDCK cells to high titer, e.g., a $\log_{in}$ TCID$_{50}$/mL and/or a $\log_{in}$ FFU/mL of at least about 7.4, or at least about 7.6, or at least about 7.8, or at least about 8.0, or at least about 9.0, or at least about 10.0 without a medium exchange step prior to infection.

In another aspect, the present invention provides improved methods for the propagation of non-tumorigenic cells on microcarriers including bead to bead transfer methods. In another aspect, the enriched serum-free cell culture medium of the invention maintains the non-tumorigenic characteristics of non-tumorigenic MDCK cells used for the initial inoculation. In other aspects, the enriched serum-free cell culture medium of the invention is used to establish and maintain non-tumorigenic MDCK cell lines.

In another aspect, the present invention provides methods for purifying live cell-associated viruses (e.g. influenza, RSV) from adherent cells grown in cell culture (e.g., MDCK Vero cell culture) that give an overall recovery of viruses of at least 30%, wherein the purified viruses comprise less than 0.1 ng HCD, and less than 0.3 μg HCP, and less than 0.0050 ng non-specific nuclease per 7.0±0.5 $\log_{10}$ FFU of virus.

6. BRIEF DESCRIPTION OF THE FIGURES

FIG. 1 is a plot of the viable cell density (VCD) and cell viability (V %) in 4×2 L bioreactors from day 0 to day 4 of cultivation. The bioreactors were cultured using the Seed Reactor (SR) process conditions detailed in Table 7. 2 dps data for SR 4 is not available.

FIG. 2 shows photographs (taken at 10× magnification) taken at intermediate sampling times between 0 and 40 minutes for 3×2 L seed reactors (SR) for experiment 1, 3 and 4 during B2B trypsinization. Trypsinization performed in bioreactors as per the bead to bead transfer protocol.

FIG. 3 is a plot of the viable cell density (VCD) and cell viability (V %) in 12×2 L final production reactors (FPR). The bioreactors of experiment 3 (FPR3.X.X) were infected on 5 dps (~120 hps) and those of other experiments infected on 4 dps. Post infection VCD and cell viability data for experiment 4 not available.

Figure 6:
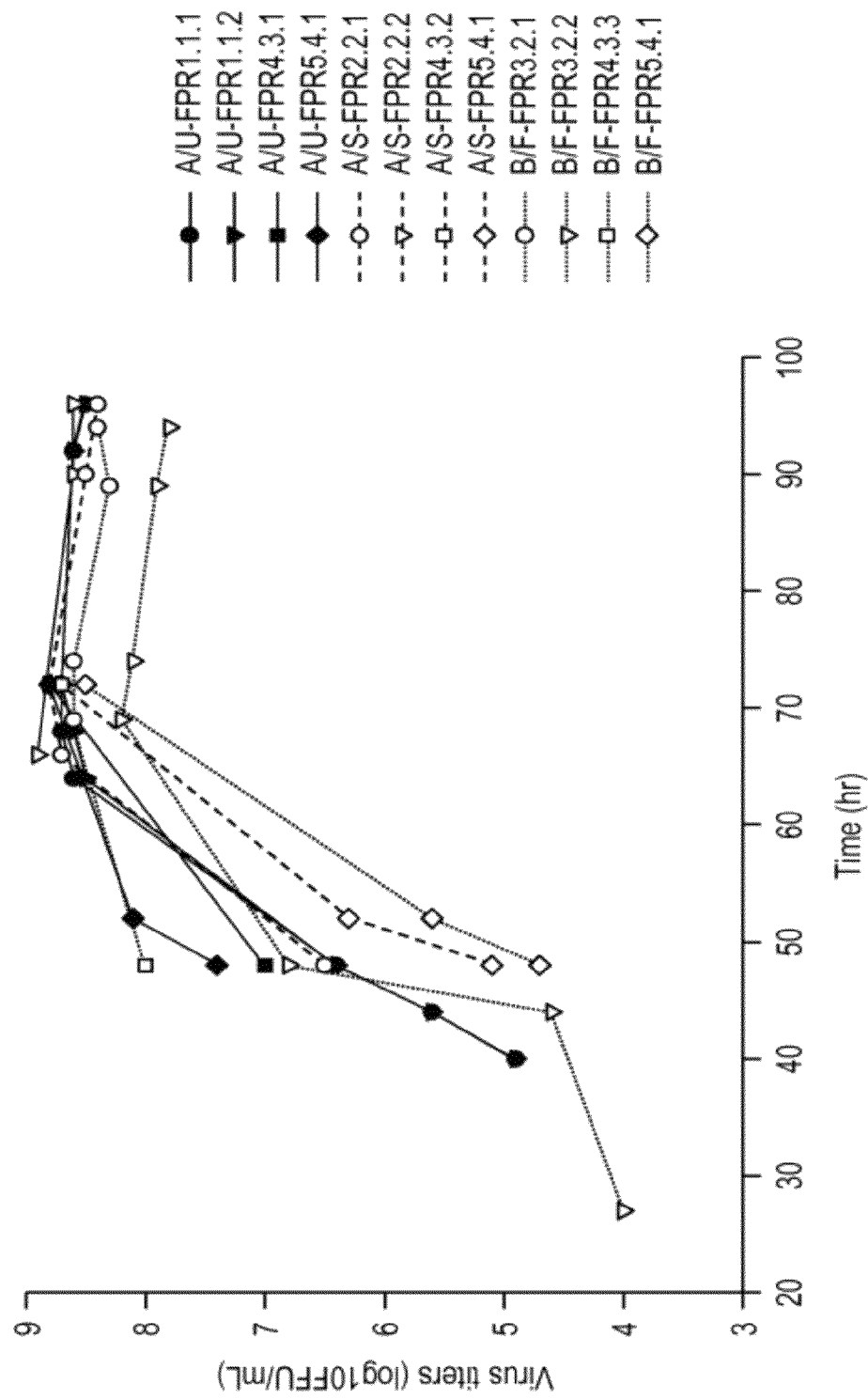

FIG. 6 shows a plot of ca A/Uruguay (A/U), ca A/South Dakota (A/S) and ca B/Florida (B/F) virus titers over time for the cells originally grown in 4×2 L seed reactors and then cultured followed by infecting in 12×2 L final production reactors (FPR) for all experiments. Note: each data point represents the average of three assay replicates. The virus titers below detection limit (<6.4 log 10 FFU/mL or <2.4 log 10 FFU/mL if diluted) are not recorded.

FIG. 7 shows virus production profiles over time for the strains produced using the 67% medium exchange process (67% MX) versus no medium exchange process (0% MX). Plots for strains ca A/Wisconsin/67/05 and ca A/Uruguay are shown in 8A, left and right panels, respectively, plots for ca A/South Dakota and ca B/Florida are shown in 8B, left and right panels, respectively.

Figure 8A:
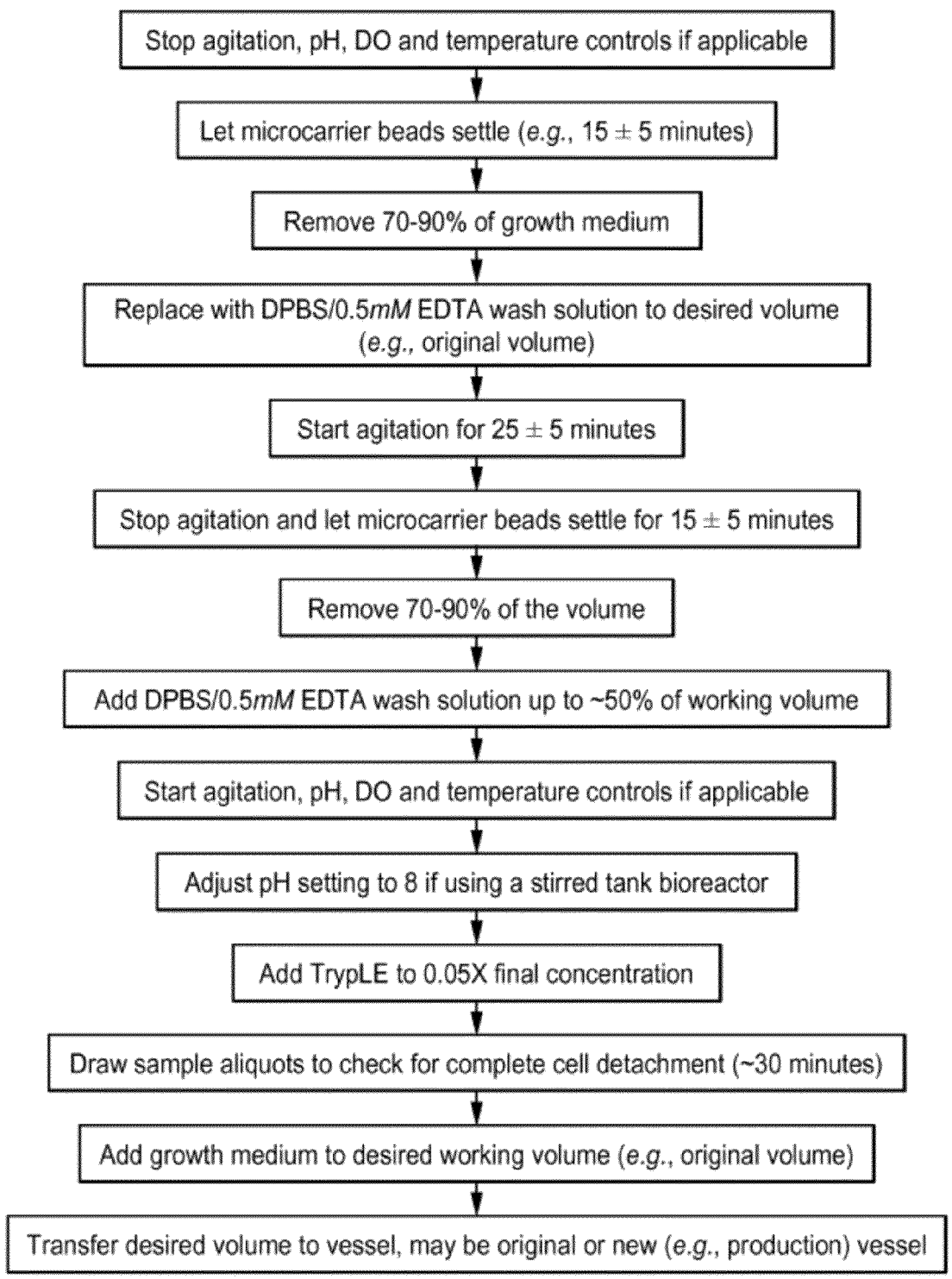
Figure 8B:
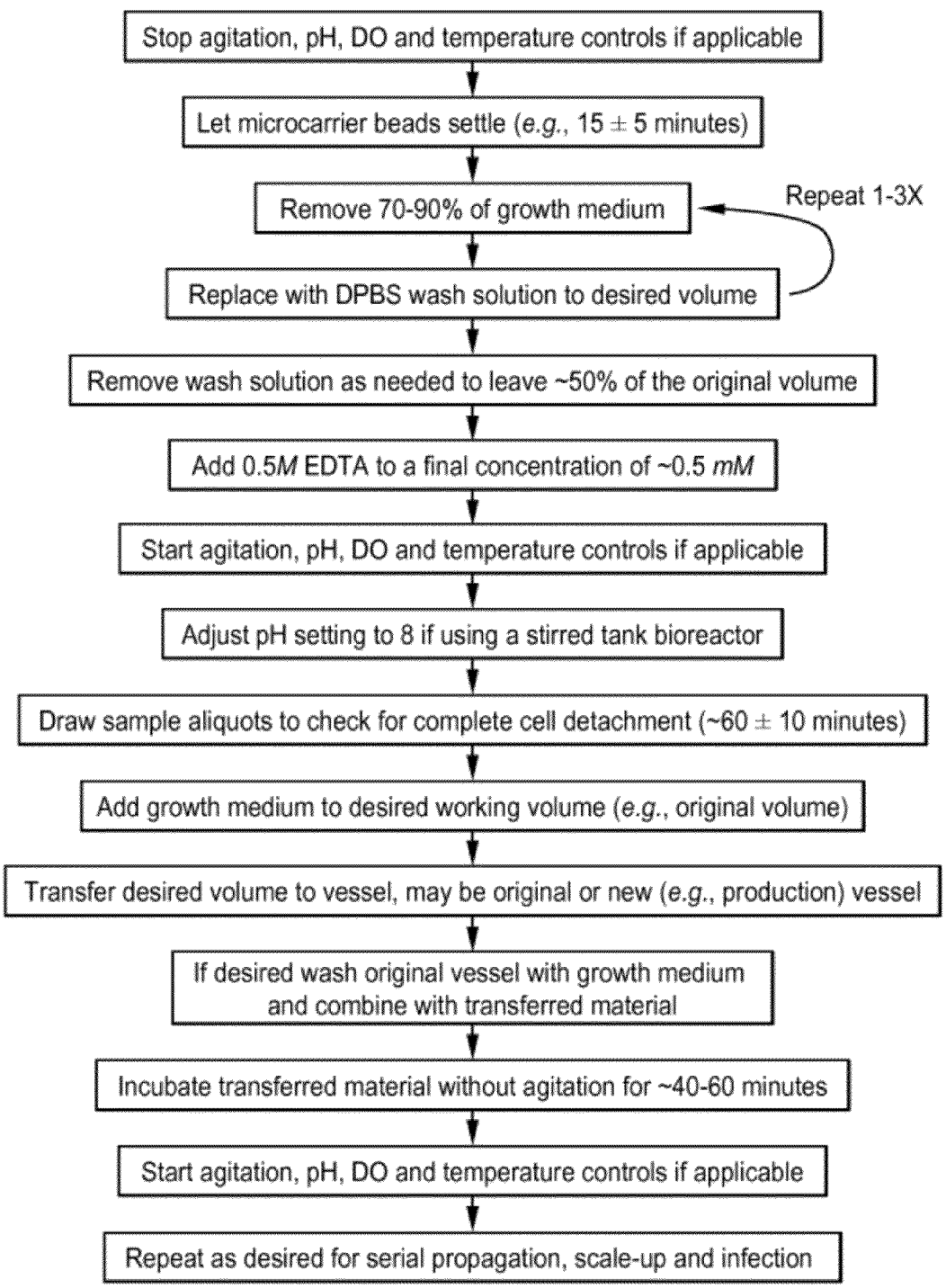

FIG. 8 presents flow charts of a bead to bead transfer processes. The process depicted in Panel A utilizes two wash steps each utilizing a buffered salt solution (DPBS) comprising a chelating agent (EDTA) and a protease (TrypLE™) at a final concentration of just 0.05× that effects cell detachment within ~30 minutes. The process depicted in Panel B utilizes 2-3 wash steps utilizing a buffered salt solution (DPBS) followed by incubation with a chelating agent (EDTA) at a final concentration of ~0.5 mM that effects cell detachment within ~60 minutes in the absence of any protease.

FIG. 9 presents drawings of the filter and tubing rigs used for the Direct Flow Filtration (DFF1) filter rig (Panel A, top), the GE Healthcare Uniflux skid tubing rigs (Panel A, bottom), the GE Healthcare AKTAprocess skid tubing rigs (Panel B, top), and the Direct Flow Filtration 2 (DIFF2) filter rig (Panel B, bottom).

Figure 10A:
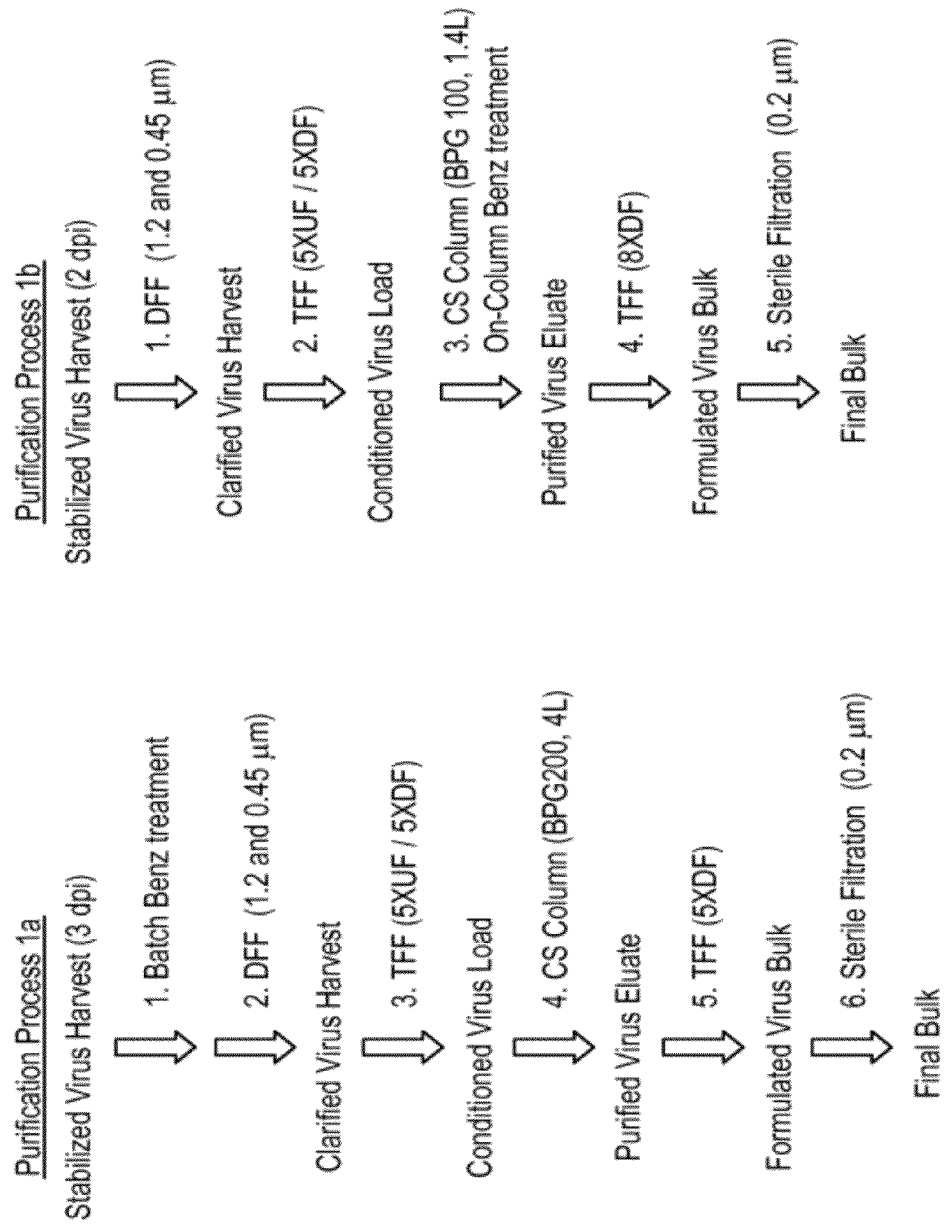

FIG. 10 presents the scheme of the initial purification process 1a in parallel with the improved purification process 1b in panel A. Additional modifications are detailed in the scheme presented in panel B. The details of each process are provided in Examples 3 and 4.

Figure 11:
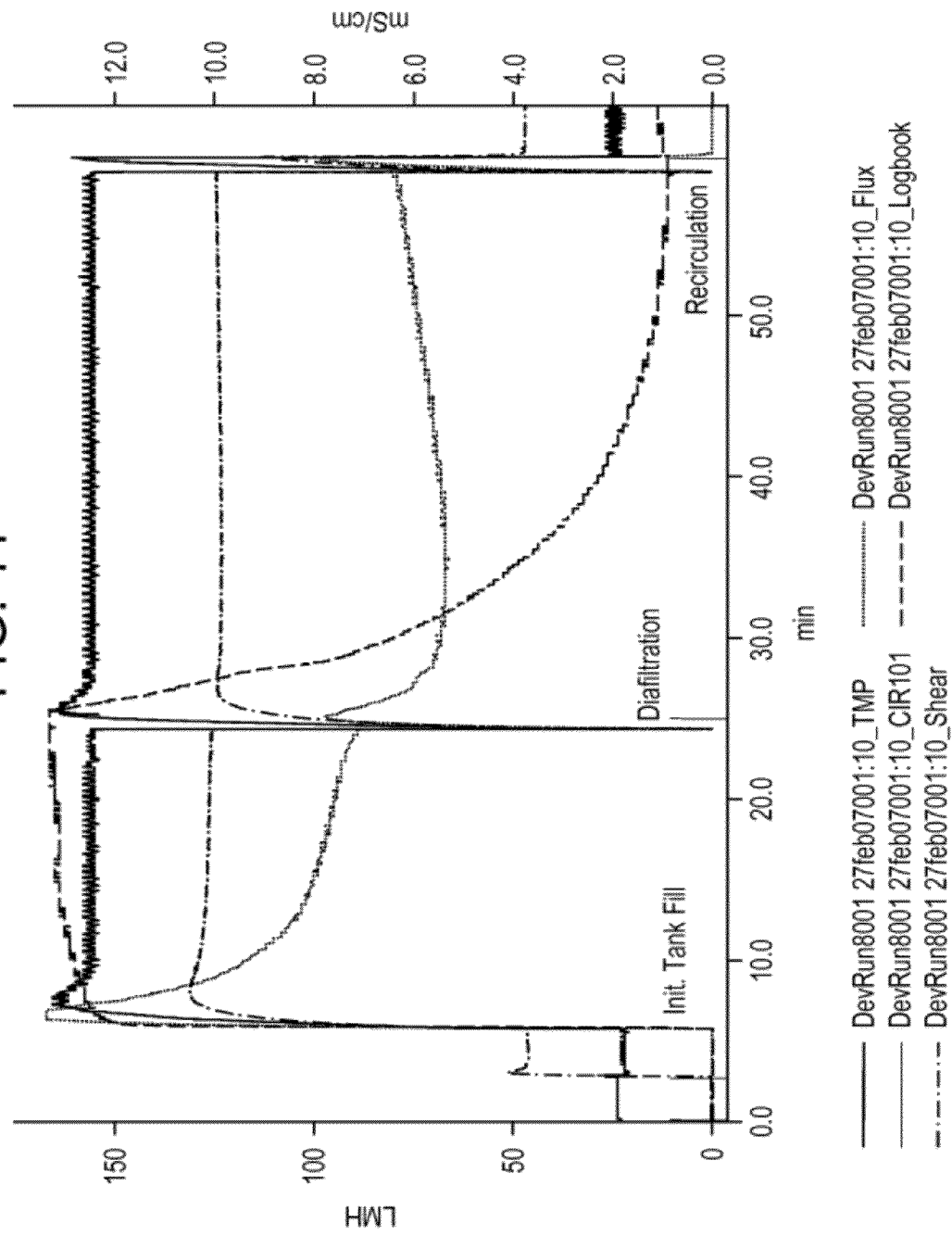

FIG. 11 presents the flux trace curve of TFF1 run #8.

Figure 12:
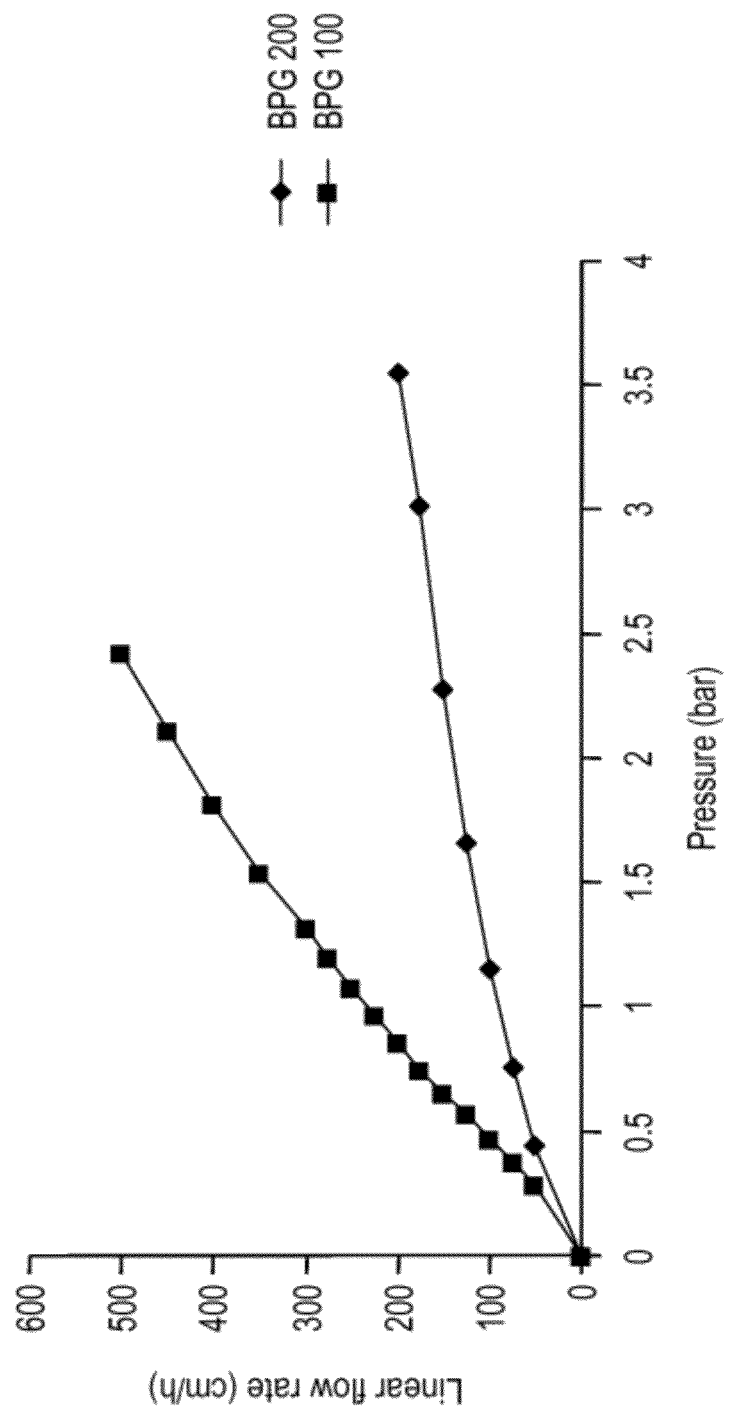

FIG. 12 presents the BPG 100 and BPG 200 CS column pressure flow characteristics.

Figure 13:
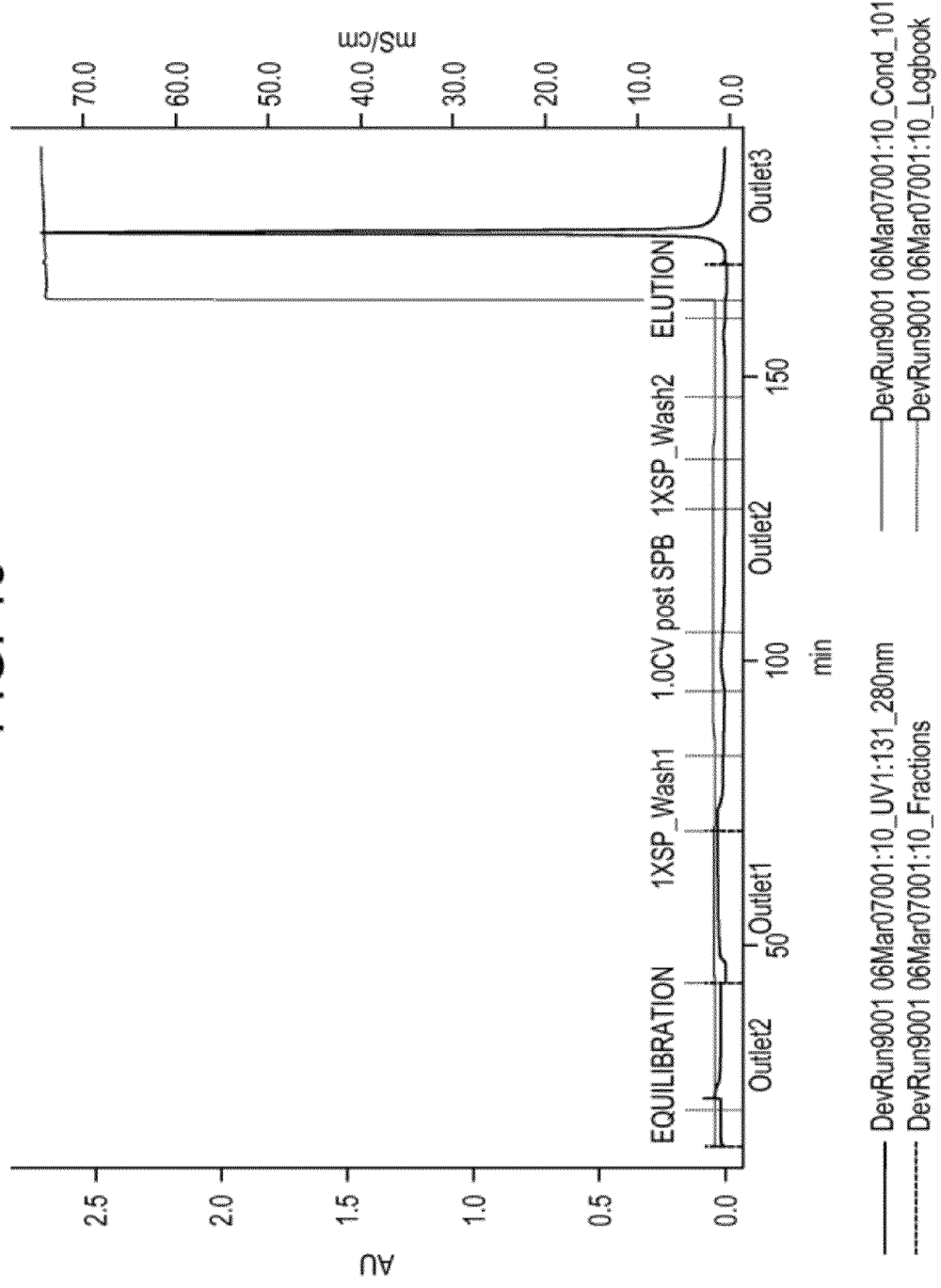

FIG. 13 presents the CS column elution chromatogram of run #9.

Figure 14:
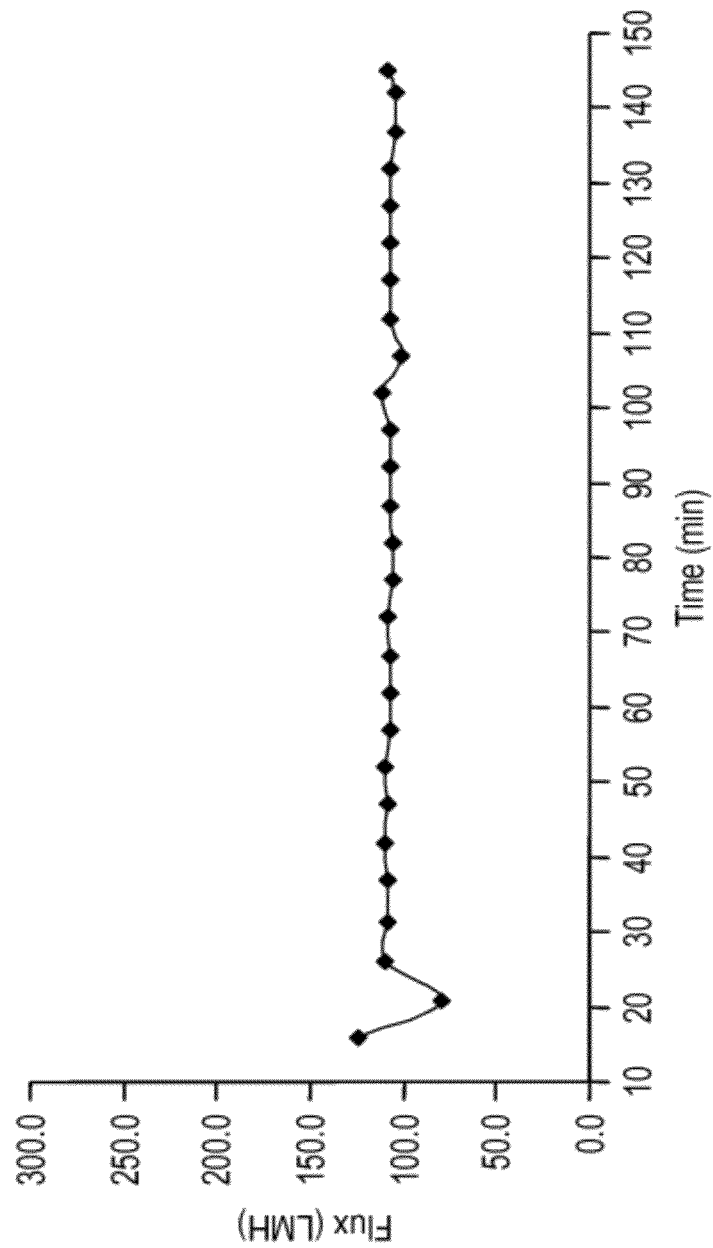

FIG. 14 presents the flux trace curve of run #8 TFF2 8XDF process.

Figure 15:
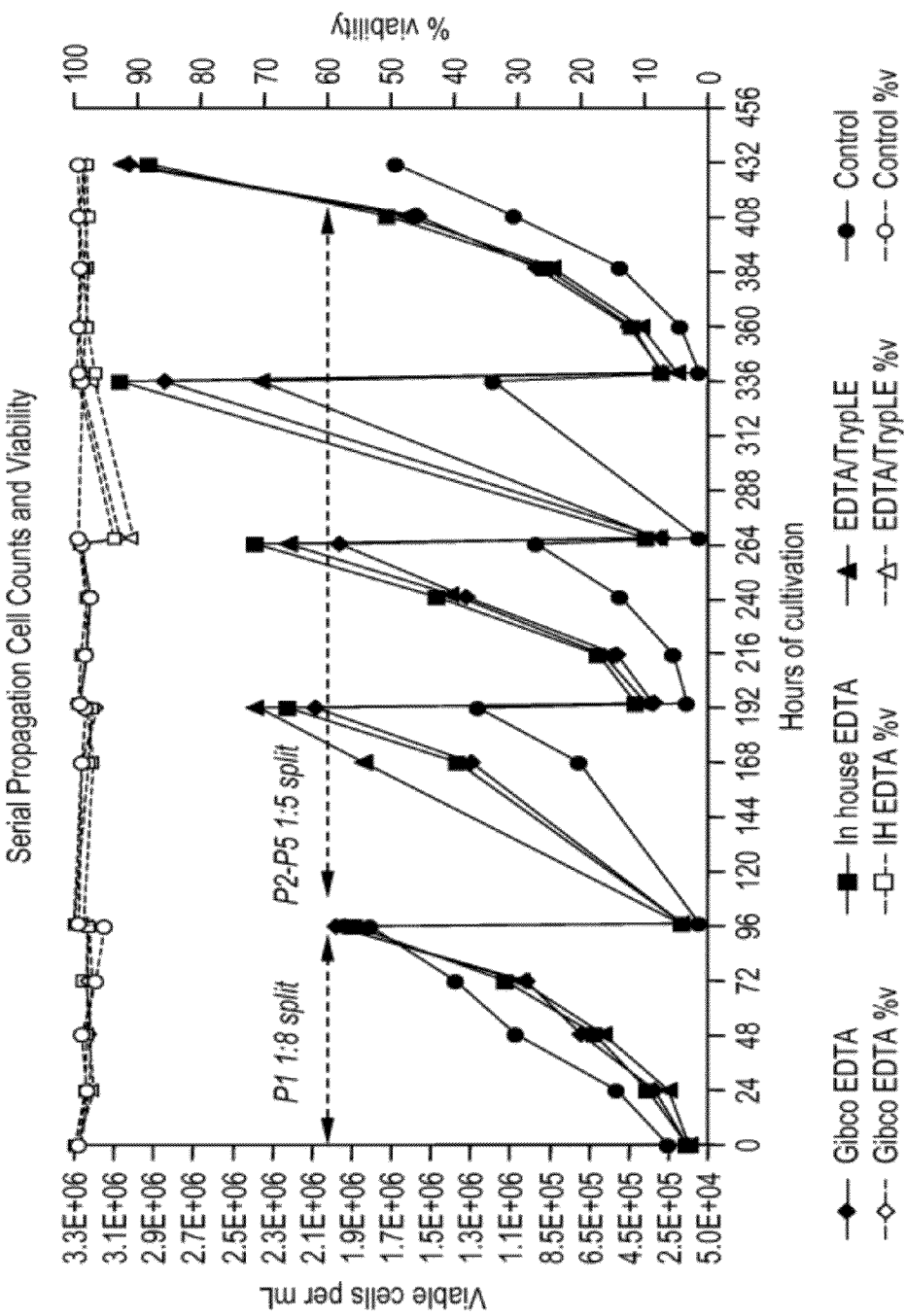

FIG. 15 presents a plot of the viable cells per mL (filled symbols/solid lines) and the percent viability (open symbols/dashed lines) over about 432 hours of cultivations for cells serially split and propogated in the absence of protease (diamonds and squares), cells serially split and propogated using EDTA/protease mix (triangles), and cells independently split and propagated using standard protease methods (circles).

FIG. 16 presents plots of the titers of ca A/Wisconsin/67/07 (top), ca B/Malaysia/2506/04 (bottom) obtained from each passage of cells serially split and propogated in the absence of protease (diamonds and squares), cells serially split and propogated using EDTA/protease mix (triangles), and cells independently split and propagated using standard protease methods (open squares). The plots show that titers of at least 8.0 log 10 FFU/mL are obtained using cells split and propagated by the no protease and the EDTA/protease process.

Figure 17A:
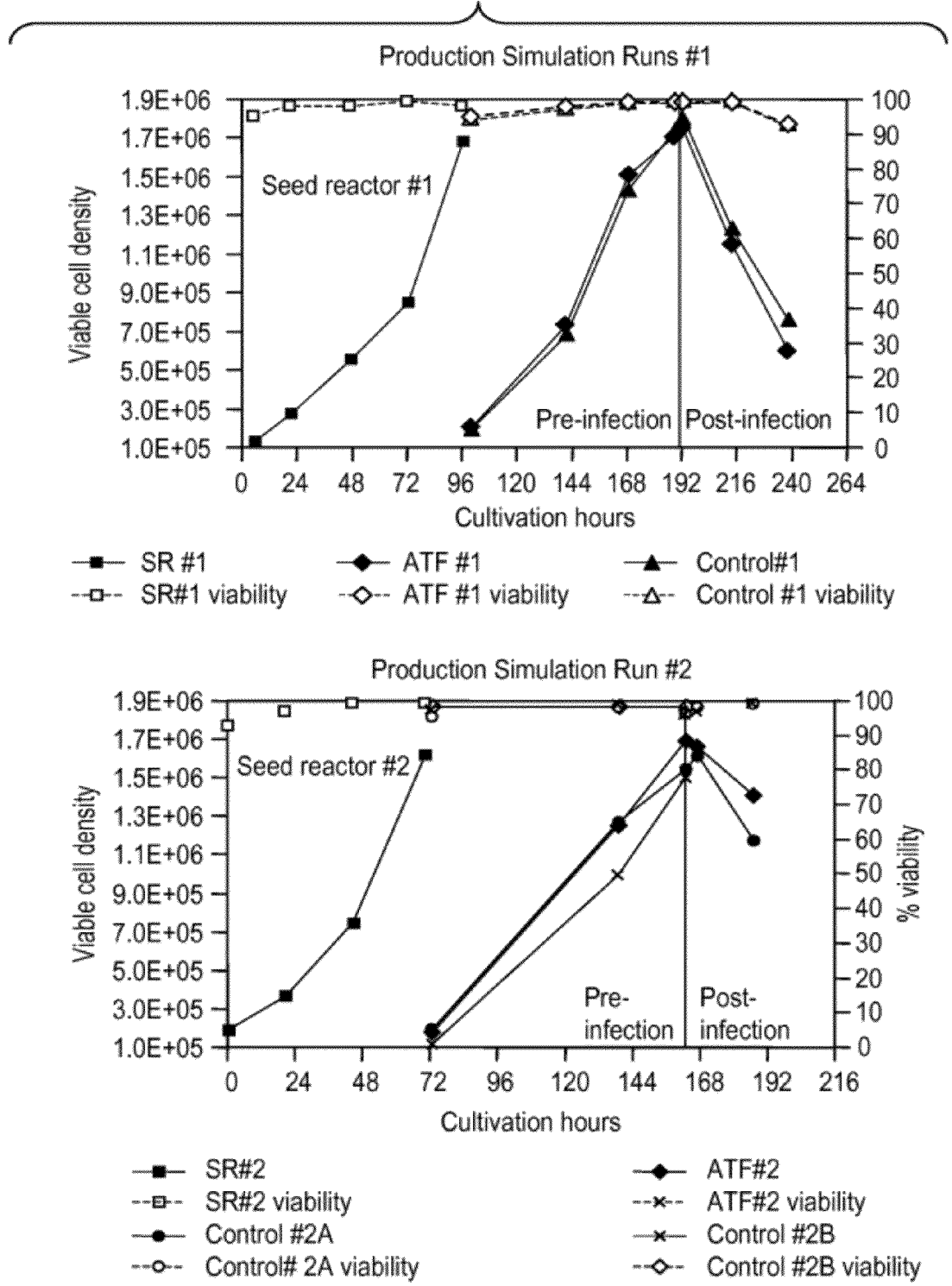
Figure 19A:
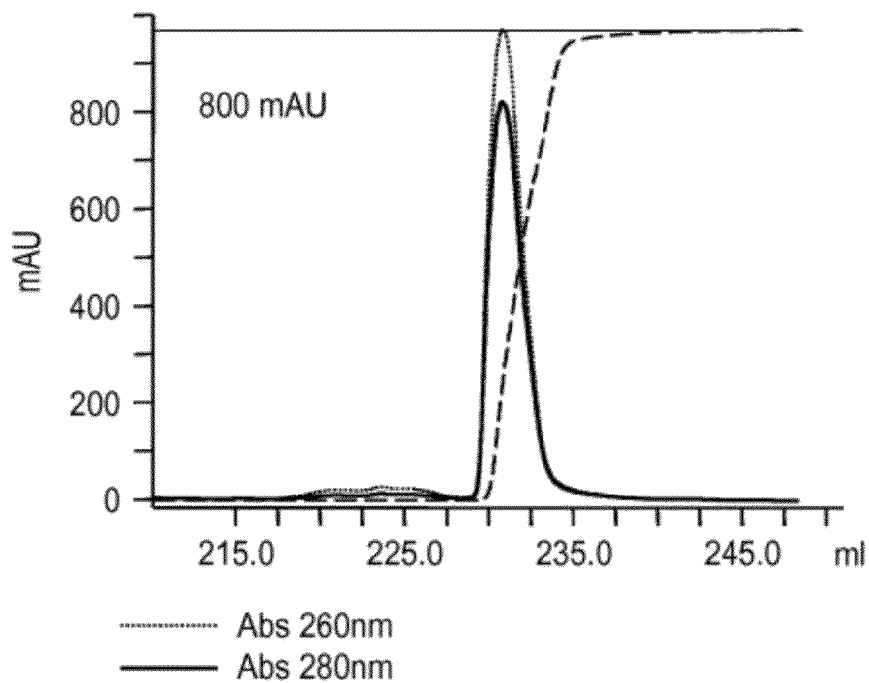
Figure 19B:
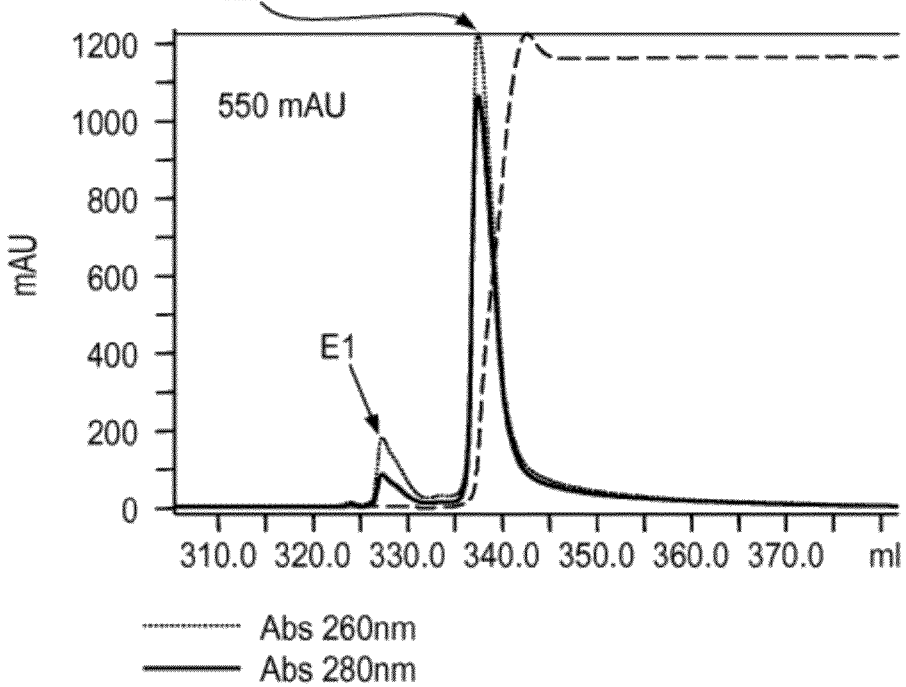
Figure 19C:
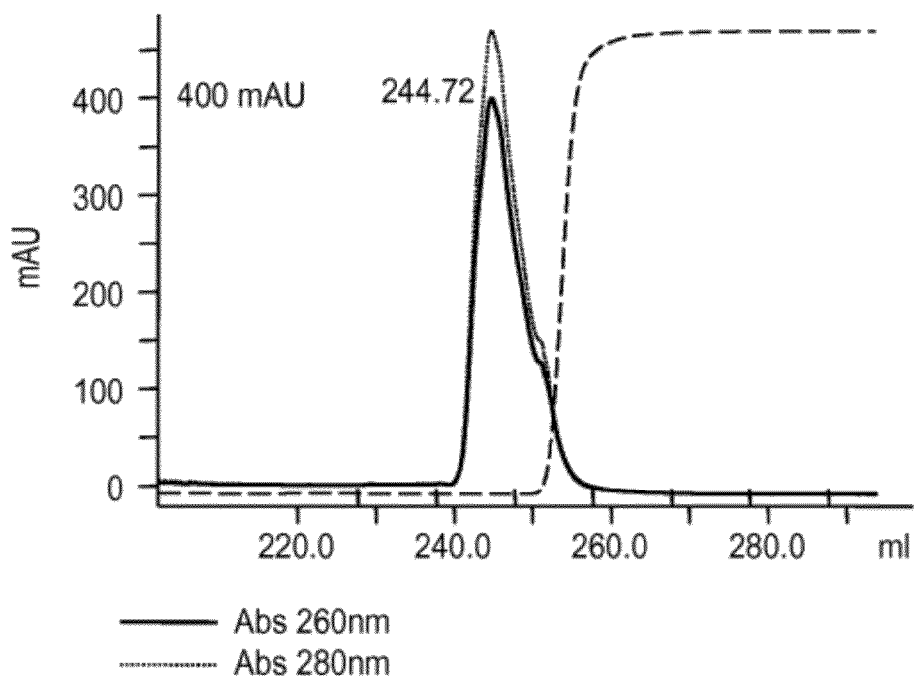
Figure 19D:
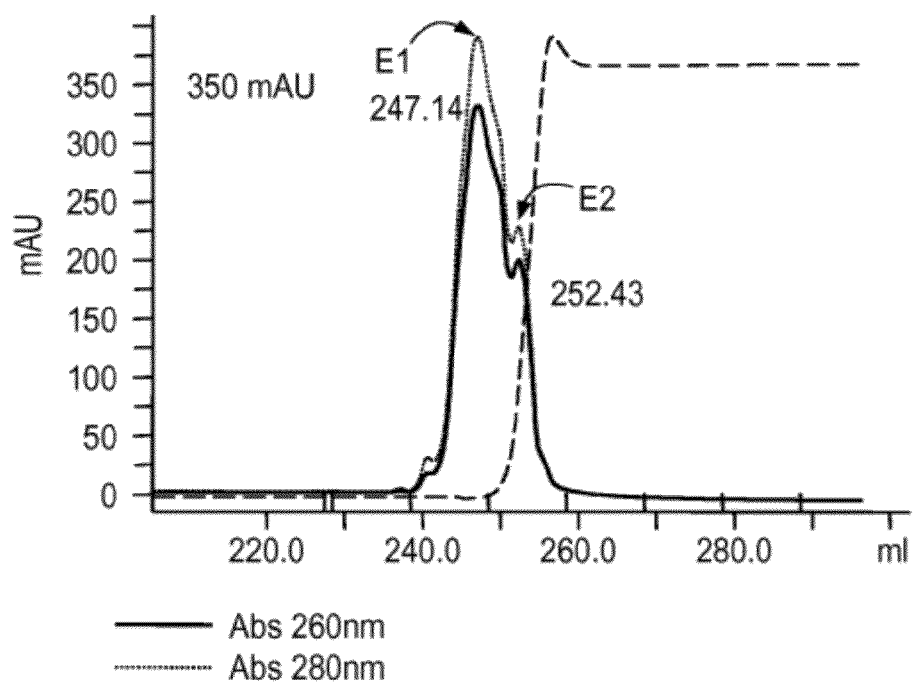

FIG. 17 presents plots of the viable cells per mL (filled symbols/solid lines) and the percent viability (open symbols/dashed lines) for three production simulation runs (Panel A and Panel B, top). Included in each plot is the seed reactor(s), simulation production reactor run(s) using ATF and control production run(s) not using ATF. Also presented in Panel B (bottom) is a plot of the titers of ca B/Malaysia/2506/04 obtained during two production simulation productions runs showing that the titers are comparable for runs performed using ATF and without ATF.

FIG. 18 presents photographs of fluids removed from bioreactors using the ATF process showing that they are free of microcarriers. The left panel shows the microcarrier wash removed using ATF during microcarrier sterilization, the right panel shows the media removed using ATF during the 66% media exchange step of MDCK cell culture.

FIG. 19 presents the elution chromatograms of Test Resin A-D column runs with 1 M NaCl elution (panels A-D, respectively). These chromatograms show that Test Resins A and B appeared to show separated multiple elution peaks having a smaller early peak (see arrow in panel B) while Test Resins C and D showed a single peak with peak shoulders and heterogeneous features (see arrow in panel D).

Figure 20A:
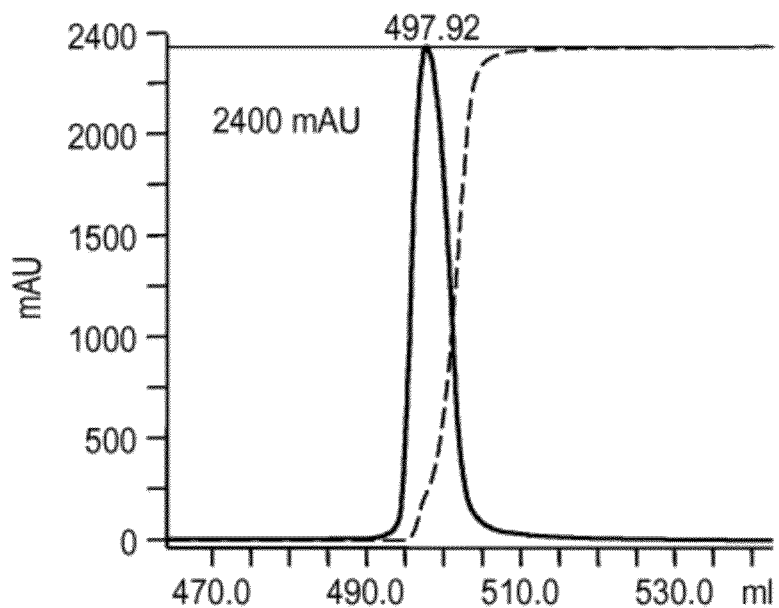
Figure 20B:
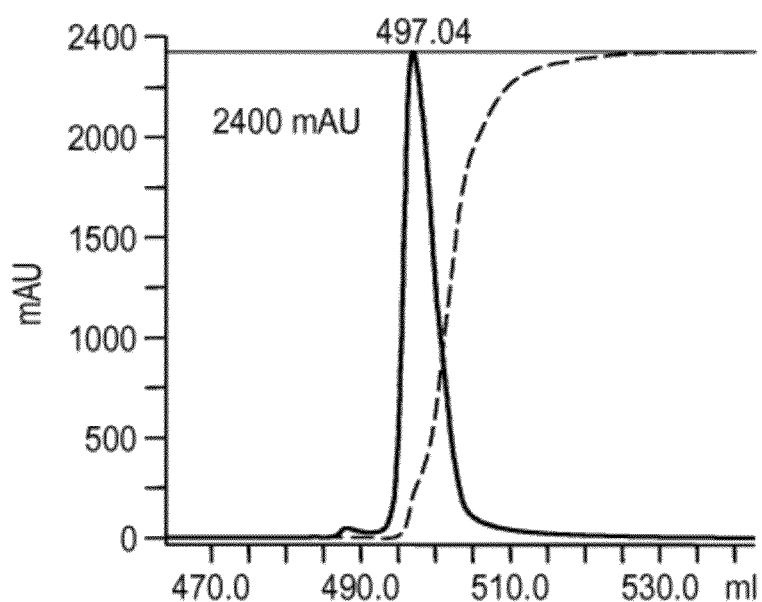

FIG. 20 presents the elution chromatograms of Test Resin C and D column runs with 2 M NaCl elution (panels A and B, respectively), showing that the elution peak was sharpened using a 2M NaCl elution.

Figure 21A:
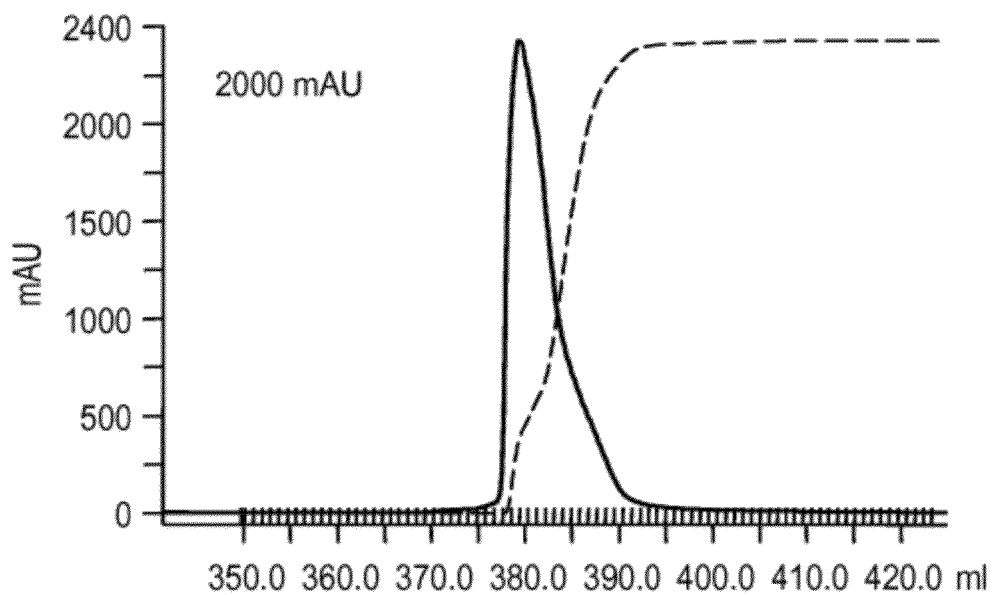
Figure 21B:
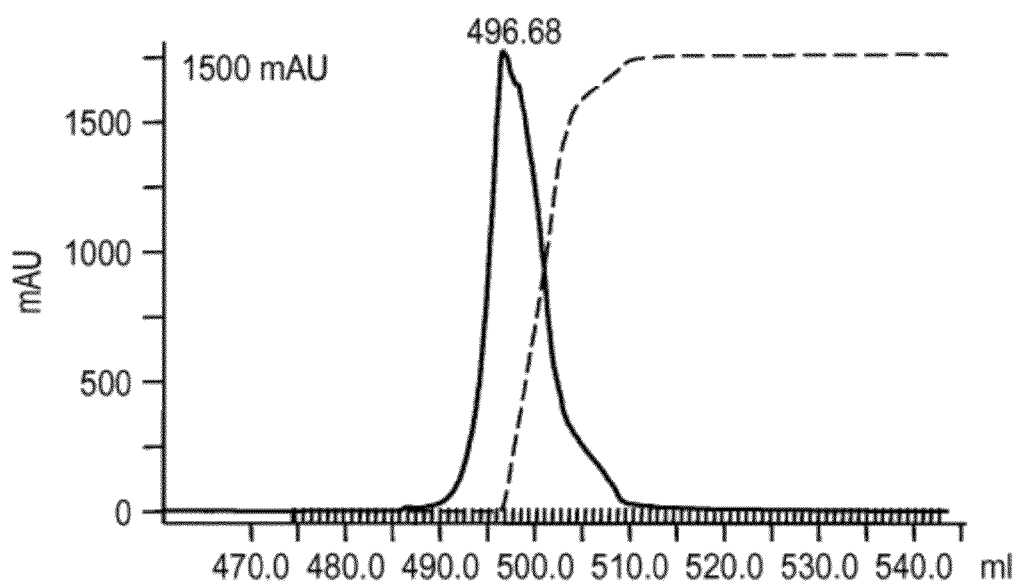

FIG. 21 presents the elution chromatograms of Test Resin C column runs for ca A/Wisconsin, ca A/Solomon Islands and ca B/Malaysia, Panels A, B, and C, respectively, showing that the peak profiles are similar and consistent.

FIG. 22 presents the elution chromatograms of column runs. Panels A and B show the elution for ca A/Wisconsin, and ca B/Malaysia respectively, for Test Resin D column showing that the peak profiles are similar and consistent. Panel C shows the elution peak chromatograms of Test Resin D at XK-50 column scale.

FIG. 23 presents pictures of cell cultures from A) untreated cells, and cells treated for 60 minutes with B) 0.5 mM EDTA, C) 1 mM EDTA, D) 2 mM EDTA, E) 5 mM EDTA, and F) 10 mM EDTA.

FIG. 24 presents pictures of cell cultures from cell pretreated with 2 mM EDTA, followed by treatment with 0.0125× TrypLE (Panels A and D), 0.025× TrypLE (Panels B and E) and 0.05× TrypLE (Panels C and F). Photographs were taken at 0 minutes after TrypLE addition (Panels A, B, and C) and again at 60 minutes after TrypLE addition (Panels D, E, and F).

Figure 25:
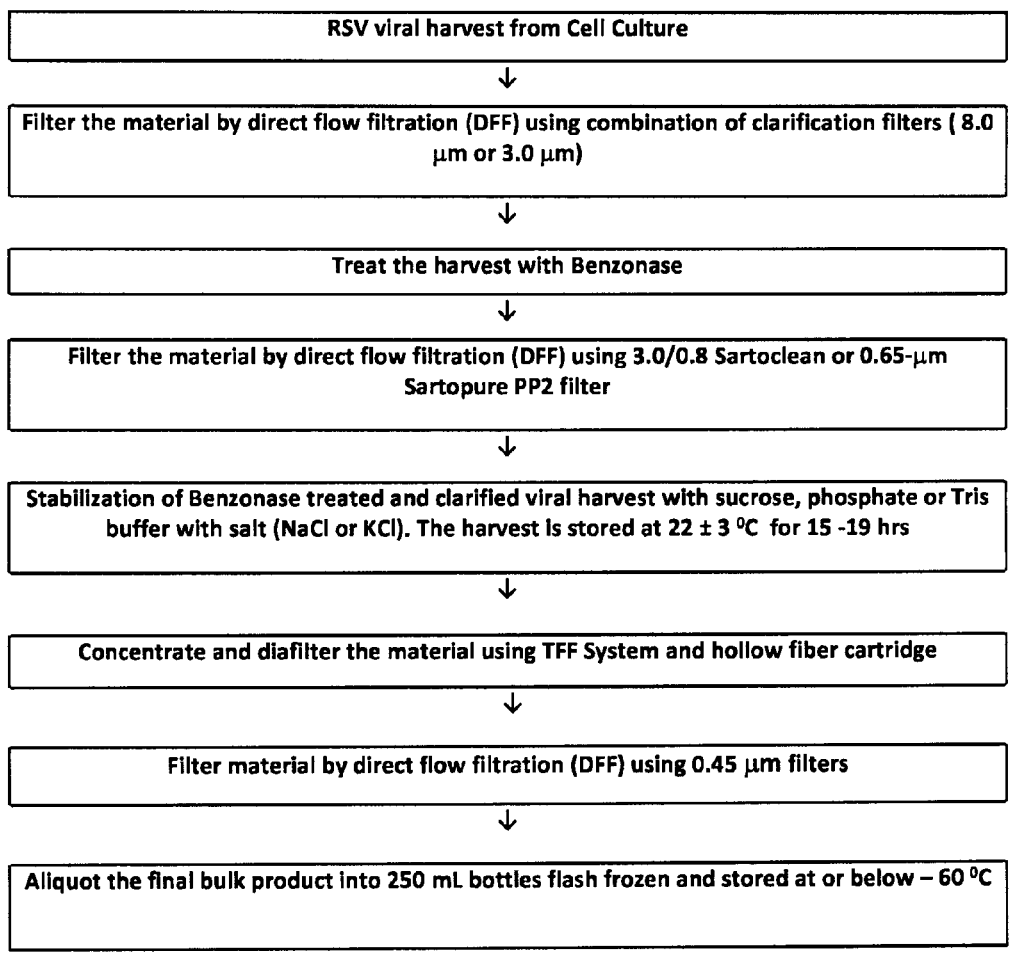

FIG. 25 presents an RSV Purification Process Description Flow Chart.

7. DETAILED DESCRIPTION

The present invention provides highly reproducible efficient scalable processes for the production of large quantities of virus (e.g., influenza virus or RSV) or viral antigen for prophylactic, diagnostic, immunotherapeutic or therapeutic use in bioreactors from adherent cells (e.g. MDCK cells, in particular, non-tumorigenic cell lines or Vero cells). In particular, the present invention provides robust methods for the production of cold-adapted, and/or temperature sensitive, and/or attenuated influenza or respiratory syncitial viruses, to high titer that do not require any medium exchange.

In addition, the present invention provides culture medium that support the cultivation of MDCK cells (e.g., non-tumorigenic MDCK cells) and support the replication of virus including, but not limited to influenza virus (e.g., cold-adapted, and/or temperature sensitive, and/or attenuated influenza viruses) to high titer without the need for any medium exchange.

In addition, the present invention also provides methods of preparing vaccine material (e.g., influenza virus) from MDCK cells (e.g., non-tumorigenic MDCK cells), and methods of preventing influenza infection utilizing vaccine materials produced in MDCK cells. Any cell-associated virus (e.g. influenza and RSV) may be purified by a process described herein and/or contained in an immunogenic composition described herein. As used herein, "a cell-associated virus" refers to a virus in which approximately 60% or more of the titer of the virus is found associated with virus-infected adherent cells as determined by any technique known to one of skill in the art. The methods of the invention are particularly useful for the production of cold adapted/temperature sensitive/attenuated (ca/ts/att) influenza strains (e.g., those in FluMist®) and RSV (e.g., rA2 cp248/404/1030ΔSH).

Viruses that can be grown in non-tumorigenic MDCK cells and/or Vero cells include but are not limited to negative strand RNA viruses, including but not limited to influenza, RSV, parainfluenza viruses 1, 2 and 3, and human metapneumovirus, as well as other viruses, including DNA viruses, retroviruses, positive strand RNA viruses, negative strand RNA viruses, double-stranded RNA viruses, including, but not limited to, papovavirus, vesicular stomatitis virus, vaccinia virus, Coxsackie virus, reovirus, parvovirus, adenovirus, poliomyeltitis virus, measles virus, rabies virus, and herpes virus.

7.1 Definitions

Tumorigenicity, as used herein, has the ordinary meaning attributed to this term by one skilled in the art. Tumorigenicity is, in one embodiment, determined by the adult nude mouse model (e.g., Stiles et al., 1976, Cancer Res, 36:1353, and Example 5 below). Tumorigenicity may also be tested by other assays, for example, by injection into a chick embryo and/or topical application to the chorioallantois (Leighton et al., 1970, Cancer, 26:1024).

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid. A recombinant virus may further incorporate one or more mutations introduced into the genome. A recombinant virus may also be a reassortant virus when it comprises components derived from more than one parental viral strain.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 54 minutes to 66 minutes.

The terms "temperature sensitive," "cold adapted" and "attenuated" are well known in the art. For example, the term "temperature sensitive" ("ts") indicates that the virus exhibits a 100 fold or greater reduction in titer at a higher temperature, e.g., 39° C. relative to a lower temperature, e.g., 33° C. for influenza A strains, and that the virus exhibits a 100 fold or greater reduction in titer at a higher temperature, e.g., 37° C. relative to a lower temperature, e.g., 33° C. for influenza B strains. For example, the term "cold adapted" ("ca") indicates that the virus exhibits a higher growth rate at a lower temperature, e.g., 25° C. within 100 fold of its growth at a higher temperature, e.g., 33° C. For example, the term "attenuated" ("att") indicates that the virus replicates in the upper airways of ferrets but is not detectable in lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses encompassed by the invention. Growth indicates viral quantity as indicated by titer, plaque size or morphology, particle density or other measures known to those of skill in the art.

7.2 Cells

The cell-associated viruses described herein can be propagated in any adherent cells that allow the viruses to grow to titers that permit use of the viruses. In one embodiment, the adherent cells allow the cell-associated viruses to grow to titers comparable to those determined for the corresponding wild-type viruses. In a specific embodiment, the cell-associated viruses described herein are propagated in cells that are susceptible to infection by the viruses.

In one embodiment, the cell-associated viruses described herein are propagated in mammalian cells. Representative mammalian cells that the cell-associated viruses described herein can be propagated in include, but are not limited to, Vero cells, CHO cells, Hep-2 cells, MBCK cells, MDCK cells, MRC-5 cells, HeLa cells and LLC-MK2 cells. In a specific embodiment, the cell-associated viruses described herein, including respiratory syncytial viruses, are propagated in Vero cells. In another specific embodiment, the cell-associated viruses, including influenza virus, are propagated in MDCK cells.

7.2.1 MDCK Cells

MDCK cells are known to support the isolation and replication of numerous viruses including but not limited to various viruses including but not limited to orthomyxoviruses, paramyxoviruses, rhabdoviruses and flaviviruses. In particular, MDCK cells are widely used for the production influenza viruses. However, as noted above, some MDCK cell lines are tumorigenic. If tumorigenicity is of regulatory concern the present invention provides methods to proliferate non-tumorigenic MDCK cells and use the same for the production of influenza viruses. Accordingly, in one embodiment, the methods of the invention utilize non-tumorigenic MDCK cells. In another embodiment, the method of the invention utilize MDCK cells regardless of tumorigencity.

Non-tumorigenic MDCK cell lines which may be utilized in the methods of the invention include but are not limited to, those which have been deposited with the American Type Culture Collection (10801 University Boulevard, Manassas, Va. 20110-2209) on deposited Jan. 5, 2005 and assigned ATCC Deposit Nos. PTA-6500 and PTA-6503 (designated MDCK-S and MDCK-SF103, respectively); those deposited on Oct. 5, 2006 and assigned ATCC Deposit Nos. PTA-7909 and PTA-7910, (designated subclones 1-A and 1-B, respectively).

Other MDCK cells which may be utilized include, but are not limited to, those which have been deposited with the American Type Culture Collection and assigned ATCC Deposit Nos. PTA-6501 and PTA-6502 (designated MDCK-SF101 and MDCK-SF102, respectively); those assigned ATCC Deposit No. CRL-12042 (designated MDCK.5F1); those assigned ATCC Deposit Nos. ATCC CCL34; CRL-2286; and CRL-2285.

In a specific embodiment, the non-tumorigenic MDCK cells used in the methods of the invention are non-tumorigenic in the adult nude mouse model (see, Stiles et al.). In another specific embodiment, the non-tumorigenic MDCK cells used in the methods of the invention are non-tumorigenic when injected into a chick embryo and/or topically applied to the chorioallantois (see, Leighton et al., Id). In still another embodiment, the non-tumorigenic MDCK cells used in the methods of the invention are non-tumorigenic in the adult nude mouse model but not when injected into a chick embryo and/or topically applied to the chorioallantois. In yet another embodiment, the non-tumorigenic MDCK cells used in the methods of the invention are non-tumorigenic in the adult nude mouse model and when injected into a chick embryo and/or topically applied to the chorioallantois. In still another embodiment, the non-tumorigenic MDCK cells used in the methods of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages. In still other embodiments, non-tumorigenic MDCK cells used in the methods of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a serum-free medium of the invention (e.g., MediV SFM 105+TE, MediV SFM 109, and MediV SFM 110).

Tumorigenicity may be quantified in numerous ways known to one of skill in the art. One method commonly utilized is to determine the "$TD_{50}$" value which is defined as the number of cells required to induce tumors in 50% of the animals tested (see, e.g., Hill R. The $TD_{50}$ assay for tumor cells. In: Potten C, Hendry J, editors. Cell clones. London: Churchill Livingstone; 1985. p. 223). In one embodiment, the non-tumorigenic MDCK cells used in the methods of the invention have a $TD_{50}$ value of between about $10^{10}$ to about $10^1$, or between about $10^8$ to about $10^3$, or between about $10^7$ to about $10^4$. In a specific embodiment, the non-tumorigenic MDCK cells used in the methods of the invention have a $TD_{50}$ value of more than about $10^{10}$, or of more than about $10^9$, or of more than about $10^8$, or of more than about $10^7$, or of more than about $10^6$, or of more than about $10^5$, or of more than about $10^4$, or of more than about $10^3$, or of more than about $10^2$, or of more than about $10^1$. In a specific embodiment, the non-tumorigenic MDCK cells used in the methods of the invention have a $TD_{50}$ value of $10^7$ or more.

It is further contemplated that the non-tumorigenic MDCK cells used in the method of the invention are also non-oncogenic. Methods for determining if cells are oncogenic generally involve the inoculation of cell lysates and/or DNA into newborn rodent species and evaluation of any tumor formation over time (see, for example, Nowinski and Hays, 1978, J. Virol., 27: 13-8; Peeper, et al., 2002, Nat Cell Biol., 4:148-53; Code of Federal Regulation (CFR), "Oncogenicity", Title 40, Vol. 8, Chapter 1, section 798.330, pp. 160-164). For example, cell lysates and/or DNA from at least $10^7$ cell equivalents are injected into newborn rodents (e.g., hamster, nude mice, rats) typically less then 4 days old which are then monitored for up to five months or more. Oncogenicity assays are routinely performed by commercial testing companies (e.g., BioReliance, see Protocols #001031 and #001030). In one embodiment, cell lysates and/or DNA from at least $10^5$, or at least $10^6$, or at least $10^7$ non-tumorigenic MDCK cells used in the methods of the invention do not induce tumor formation in 2 months, or in 3 months, or in 4 month, or in 5 months, or in 6 months, or longer, when injected into a newborn rodent species. In another embodiment, 0.01 mg, or 0.02 mg, or 0.03 mg, or 0.04 mg, or 0.05 mg, or 0.06 mg, or 0.07 mg, or 0.08 mg, or 0.09 mg, or 0.10 mg, or more, DNA from the non-tumorigenic MDCK cells used in the methods of the invention do not induce tumor formation in 2 months, or in 3 months, or in 4 month, or in 5 months, or in 6 months, or longer, when injected into a newborn rodent species.

It is contemplated that the MDCK cells (e.g., non-tumorigenic MDCK cells) used in the methods of the invention support the replication of viruses including but not limited to orthomyxoviruses (including influenza A and/or B strains), paramyxoviruses (including RSV A and/or B, human metapneumovirus and parainfluenza 1, 2 and/or 3), rhabdoviruses and flavoviruses.

In a specific embodiment, the MDCK cells (e.g., non-tumorigenic MDCK cells) used in the methods of the invention support the replication of cold adapted temperature sensitive, attenuated influenza viruses such as those found, for example, in FluMist® (Belshe et al., 1998, *N Engl J Med* 338:1405; Nichol et al., 1999, *JAMA* 282:137; Jackson et al., 1999, *Vaccine,* 17:1905) and/or reassortant viruses comprising the backbone (e.g., the remaining gene segments) of these viruses or comprising the backbone (or one or more vRNA segment(s)) of influenza viruses having one or more of the following characteristics: cold adapted, attenuated, and temperature sensitive.

One indication of the ability of a cell to support viral replication is the yield of infectious virus obtained from an infected cell culture. Viral yield can be determined by numerous assays designed to measure viral infection and/or growth. For example, viral yield can be quantified by determining the concentration of virus present in a sample according to a median tissue culture infectious dose ($TCID_{50}$) assay that measures infectious virions, a fluorescent focus assay (FFA) that detect virus antigens within infected cells in a cell culture monolayer (see, for example, U.S. Pat. No. 7,262,045). $TCID_{50}$ values are often reported as the $\log_{10} TCID_{50}/mL$ and the FFA values are often reported as $\log_{10} FFU/mL$ (fluorescent focus units/mL). Methods useful for the production of influenza viruses include, but are not limited to, those disclosed in Patent Publication WO 08/105,931 (see in particular Example 12).

In a specific embodiment, the MDCK cells (e.g., non-tumorigenic MDCK cells) used in the methods of the invention support the replication of influenza viruses ((e.g., ca/ts strains) to a $\log_{10} TCID_{50}/mL$ and/or a $\log_{10} FFU/mL$ of at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0. In another specific embodiment, the MDCK cells used in the methods of the invention support the replication of influenza viruses ((e.g., ca/ts strains) to a $\log_{10} TCID_{50}/mL$ and/or a $\log_{10} FFU/mL$ of at least about 7.6, at least 7.8, at least 8.0, at least 8.2, at least 8.4, at least 8.6, at least 8.8, at least 9.0, at least 9.2, at least 9.4, at least 9.6, at least 9.8, at least 10.0. In certain specific embodiments, the MDCK cells used in the methods of the invention are non-tumorigenic.

The wild-type influenza viruses used in preparation of the vaccine strains for annual vaccination against epidemic influenza are recommended annually by the Vaccines and Related Biological Products Advisory Committee to the Centers for Biologics Evaluation and Research (CBER) or the World Health Organization (WHO) and the European Medicines Evaluation Agency (EMEA), and are provided to manufacturers by the FDA or the Centers for Disease Control and Prevention (CDC). These strains may then used for the production of reassortant vaccine strains which generally combine the NA and/or HA genes of the wild-type viruses with the remaining gene segments derived from a donor virus (often referred to as a master donor virus or MDV) which will have certain desirable characteristics. For example, an MDV strain may be cold-adapted, and/or temperature sensitive, and/or attenuated, and/or have a high growth rate. The embodiments that follow immediately below relate to cold-adapted, and/or temperature sensitive, and/or attenuated versions of different influenza strains (e.g., wild type strains recommended by one or more health organization). Such cold-adapted, and/or temperature sensitive, and/or attenuated influenza viruses can be made by obtaining recombinant and/or reassortant influenza viruses that comprise the HA and NA gene segments from the strain of interest and the remaining gene segments from a suitable cold-adapted, and/or temperature sensitive, and/or attenuated influenza strain (also referred to herein as a "cold-adapted, temperature sensitive, attenuated backbone") such as, for example, the cold-adapted, temperature sensitive, attenuated influenza viruses found in FluMist® (ca A/Ann Arbor/6/60 and ca B/Ann Arbor/1/66). As used herein a recombinant and/or reassortant virus that comprises HA and NA gene segments from a wild type influenza virus strain and the remaining gene segments from a virus that is cold-adapted and/or temperature sensitive and/or attenuated influenza. Reassortant and/or recombinant virus are also referred to by the wild type strain designation preceded by one or more of the identifiers "ca", "att", "ts", for example a recombinant and/or reassortant virus that comprises HA and NA gene segments from A/New Calcdonia/20/99 and the remaining segments from a cold-adapted, temperature sensitive, attenuated influenza virus (e.g., A/Ann Arbor/6/60) may be designated simply "ca A/New Calcdonia/20/99."

In certain embodiments, the MDCK cells (e.g., non-tumorigenic MDCK cells) used in the methods of the invention support the replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10}$ TCID$_{50}$/mL and/or a $\log_{10}$ FFU/mL of at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0. In another specific embodiment, the MDCK cells (e.g., non-tumorigenic MDCK cells) used in the methods of the invention support the replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10}$ TCID$_{50}$/mL and/or a $\log_{10}$ FFU/mL of at least about 7.6, at least 7.8, at least 8.0, at least 8.2, at least 8.4, at least 8.6, at least 8.8, at least 9.0, at least 9.2, at least 9.4, at least 9.6, at least 9.8, at least 10.0. In certain specific embodiments, the MDCK cells used in the methods of the invention are non-tumorigenic.

In certain other embodiments, the MDCK cells (e.g., non-tumorigenic MDCK cells) used in the methods of the invention support the replication of a cold-adapted, and/or temperature sensitive, and/or attenuated version of at least one influenza A strain. It is contemplated that the influenza A strain may be of any subtype (e.g., $H_1N_1$, $H_3N_2$, $H_7N_7$, $H_5N_1$, $H_9N_2$, $H_1N_2$, $H_2N_2$). Presently at least 16 different HA and 9 different NA subtypes have been identified in influenza A viruses. Accordingly, the influenza A strain may comprise any combination of HA and NA subtypes currently known or identified in the future and/or may be a reassortant. In certain specific embodiments, the MDCK cells used in the methods of the invention are non-tumorigenic.

In certain other embodiments, the MDCK cells (e.g., non-tumorigenic MDCK cells) used in the methods of the invention support the replication of a cold-adapted, and/or temperature sensitive, and/or attenuated version of at least one influenza B strain. Influenza B viruses are not currently divided into subtypes based upon their hemagglutinin and neuraminidase proteins; rather they are classified by lineage. Presently, influenza B virus strains are divided into two lineages, the B/Yamagata and the B/Victoria lineages of which there are numerous sublineages. Accordingly, the influenza B strain may be derived from any lineage and/or sublineage currently known or identified in the future and/or may be a reassortant. In certain specific embodiments, the MDCK cells used in the methods of the invention are non-tumorigenic.

7.3 Cell Culture Medium and Methods

The present invention provides serum-free cell culture medium and highly reproducible efficient scalable processes for the production of large quantities of vaccine material in bioreactors, including single use bioreactors, standard reusable bioreactors (e.g., stainless steel and glass vessel bioreactors). In particular, the present invention provides methods for the replication of influenza viruses (e.g., cold-adapted, and/or temperature sensitive, and/or attenuated) to high titer, e.g., a $\log_{10}$ TCID$_{50}$/mL and/or a $\log_{10}$ FFU/mL of at least about 7.4, or at least about 7.6, or at least about 7.8, or at least about 8.0, or at least about 9.0, or at least about 10.0. In one aspect, the present invention provides an enriched serum-free cell culture medium that supports proliferation of MDCK cells (e.g., non-tumorigenic MDCK cells) to a high cell density and eliminates the need for a medium exchange step to obtain high viral titers. The elimination of a medium exchange step offers several advantages such as decrease in process time and usage of medium. Moreover, it reduces the number of operations required during manufacturing, which in turn decreases the chances of contamination. In another aspect, the present invention provides improved methods for the propagation of non-tumorigenic cells on microcarriers including bead to bead transfers methods. In another aspect, the enriched serum-free cell culture medium of the invention maintains the non-tumorigenic characteristics of non-tumorigenic MDCK cells.

7.3.1 Enriched Serum-Free Medium

It will be appreciated by one of skill in the art that the cell culture medium used to proliferate cells can impact one or more cell characteristics including but not limited to, being non-tumorigenic, being non-oncogenic, growing as adherent cells, growing as non-adherent cells, having an epithelial-like morphology, supporting the replication of various viruses when cultured, and supporting the replication of influenza virus to high titer as described herein. To reduce the risk of contamination by adventitious agents (e.g., mycoplasma, viruses, and prions) The use of serum or animal extracts in tissue culture applications for the production of therapeutic (e.g. vaccine) material should be minimized, or even eliminated. Furthermore, minimizing the number of manipulations required during a cell culture process can significantly decrease the chances of contamination. Accordingly, the present invention provides enriched serum-free culture medium useful for the proliferation of MDCK cells (e.g., non-tumorigenic MDCK cells) and production of vaccine material using batch culture methods. In particular the enriched serum-free culture medium of the invention (also referred to herein as "serum-free medium of the invention" and "medium of the invention") may be used in batch culture methods that do not utilize medium exchange, or supplementation. Accordingly, the development and use of the serum-free medium of the invention overcome one of the most challenging operational problems in cell culture-based production of vaccine material (e.g., influenza virus), the requirement for medium exchange/supplementation.

In one embodiment, serum-free medium of the invention support the proliferation of non-tumorigenic MDCK cells, wherein the cells remain non-tumorigenic after proliferation in the medium (i.e., after being passaged). In a specific embodiment, the MDCK cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a serum-free medium of the invention.

In another embodiment, serum-free medium of the invention support the proliferation of MDCK cells (e.g., non-tumorigenic MDCK cells) to high density. In a specific embodiment, serum-free medium of the invention support the proliferation of MDCK cells to a density of least $5 \times 10^5$ cells/mL, at least $6 \times 10^5$ cells/mL, at least $7 \times 10^5$ cells/mL, at least $8 \times 10^5$ cells/mL, at least $9 \times 10^5$ cells/mL, at least $1 \times 10^6$ cells/mL, at least $1.2 \times 10^6$ cells/mL, at least $1.4 \times 10^6$ cells/mL, at least $1.6 \times 10^6$ cells/mL, at least $1.8 \times 10^6$ cells/mL, at least $2.0 \times 10^6$ cells/mL, at least $2.5 \times 10^6$ cells/mL, at least $5 \times 10^6$ cells/mL, at least $7.5 \times 10^6$ cells/mL, or at least $1 \times 10^7$. In another specific embodiment, the serum-free medium of the invention support the proliferation of non-tumorigenic MDCK cells.

In still another embodiment, serum-free medium of the invention support the proliferation of MDCK (e.g., non-tumorigenic MDCK cells) cells to high density and subsequent replication of influenza virus to high titer without the need for a medium exchange step. In a specific embodiment, serum-free medium of the invention support the proliferation of MDCK cells to high density and subsequent replication of influenza virus (e.g., ca/ts strains) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8 or at least 10.0 without the need for a medium exchange step. In other specific embodiments, serum-free medium of the invention support the proliferation of non-tumorigenic MDCK cells to high density and subsequent replication of influenza virus including, but not limited to influenza viruses described supra.

In one embodiment, serum-free medium of the invention comprise a plant hydrolysate. Plant hydrolysates include but are not limited to, hydrolysates from one or more of the following: corn, cottonseed, pea, soy, malt, potato and wheat. Plant hydrolysates may be produced by enzymatic hydrolysis and generally contain a mix of peptides, free amino acids and growth factors. Plant hydrolysates are readily obtained from a number of commercial sources including, for example, Marcor Development, HyClone and Organo Technie. It is also contemplated that yeast hydrolysates my also be utilized instead of, or in combination with plant hydrolysates. Yeast hydrolysates are readily obtained from a number of commercial sources including, for example, Sigma-Aldrich, USB Corp, Gibco/BRL and others. In certain embodiments, synthetic hydrolysates can be used in addition or in place of plant or yeast hydrolysates. In certain embodiments, serum-free medium of the invention comprise a plant hydrolysate at a final concentration of between about 0.1 g/L to about 5.0 g/L, or between about 0.5 g/L to about 4.5 g/L, or between about 1.0 g/L to about 4.0 g/L, or between about 1.5 g/L to about 3.5 g/L, or between about 2.0 g/L to about 3.0 g/L. In a specific embodiment, serum-free medium of the invention comprise a plant hydrolysate at a final concentration of 2.5 g/L. In another specific embodiment, serum-free medium of the invention comprise a wheat hydrolysate at a final concentration of 2.5 g/L.

In another embodiment, serum-free medium of the invention comprise a lipid supplement. Lipids that may be used to supplement culture medium include but are not limited to chemically defined animal and plant derived lipid supplements as well as synthetically derived lipids. Lipids which may be present in a lipid supplement includes but is not limited to, cholesterol, saturated and/or unsaturated fatty acids (e.g., arachidonic, linoleic, linolenic, myristic, oleic, palmitic and stearic acids). Cholesterol may be present at concentrations between 0.10 mg/ml and 0.40 mg/ml in a 100× stock of lipid supplement. Fatty acids may be present in concentrations between 1 µg/ml and 20 µg/ml in a 100× stock of lipid supplement. Lipids suitable for medium formulations are readily obtained from a number of commercial sources including, for example HyClone, Gibco/BRL and Sigma-Aldrich. In certain embodiments, serum-free medium of the invention comprise a chemically defined lipid concentrate at a final concentration of between about 0.1× to about 2×, or between about 0.2× to about 1.8× or between about 0.3× to about 1.7×, or between about 0.4× to about 1.6×, or between about 0.5× to about 1.5×, or between about 0.6× to about 1.4×, or between about 0.7× to about 1.3×, or between about 0.8× and about 1.2×. In a specific embodiment, serum-free medium of the invention comprise a chemically defined lipid concentrate (CDCL) solution at a final concentration of 1×. In another specific embodiment, serum-free medium of the invention comprise the chemically defined lipid concentrate (CDCL) solution (Table 5) at a final concentration of 1×.

In another embodiment, serum-free medium of the invention comprise trace elements. Trace elements which may be used include but are not limited to, $CuSO_4.5H_2O$, $ZnSO_4.7H_2O$, Selenite.2Na, Ferric citrate, $MnSO_4.H_2O$, $Na_2SiO_3.9H_2O$, Molybdic acid-Ammonium salt, $NH_4VO_3$, $NiSO_4.6H_2O$, $SnCl_2$ (anhydrous), $AlCl_3.6H_2O$, $AgNO_3$, $Ba(C_2H_3O_2)_2$, KBr, $CdCl_2$, $CoCl_2.6H_2O$, $CrCl_3$ (anhydrous), NaF, $GeO_2$, KI, RbCl, $ZrOCl_2.8H_2O$. Concentrated stock solutions of trace elements are readily obtained from a number of commercial sources including, for example Cell Grow (see Catalog Nos. 99-182, 99-175 and 99-176). In certain embodiments, serum-free medium of the invention comprise Trace Element Solutions A, B and C (Table 4) at a final concentration of between about 0.1× to about 2×, or between about 0.2× to about 1.8× or between about 0.3× to about 1.7×, or between about 0.4× to about 1.6×, or between about 0.5× to about 1.5×, or between about 0.6× to about 1.4×, or between about 0.7× to about 1.3×, or between about 0.8× and about 1.2×. In a specific embodiment, serum-free medium of the invention comprise Trace Element Solutions A, B and C (Table 4) at a final concentration of 1×.

In another embodiment, serum-free medium of the invention comprise one or more hormone, growth factor and/or other biological molecules. Hormones include, but are not limited to triiodothyronine, insulin and hydrocortisone. Growth factors include but are not limited to Epidermal Growth Factor (EGF), Insulin Growth Factor (IGF), Transforming Growth Factor (TGF) and Fibroblast Growth Factor (FGF). In a particular embodiment, serum-free medium of the invention comprise Epidermal Growth Factor (EGF). Other biological molecules, include cytokines (e.g., Granulocyte-macrophage colony-stimulating factor (GM-CSF), interferons, interleukins, TNFs), chemokines (e.g., Rantes, eotaxins, macrophage inflammatory proteins (MIPs)) and prostaglandins (e.g., prostaglandins E1 and E2). In one embodiment, serum-free medium of the invention comprise a growth factor at a final concentration of between about 0.0001 to about 0.05 mg/L, or between about 0.0005 to about 0.025 mg/L, or between about 0.001 to about 0.01 mg/L, or between about 0.002 to about 0.008 mg/L, or between about 0.003 mg/L to about 0.006 mg/L. In a specific embodiment, serum-free medium of the invention comprise EGF at a final concentration of 0.005 mg/L. In a one embodiment, serum-free medium of the invention comprise triiodothyronine at a final concentration of between about $1\times10^{-12}$ M to about $10\times10^{-12}$ M, or between about $2\times10^{-12}$ M to about $9\times10^{-12}$ M, or between about $3\times10^{-12}$ M to about $7\times10^{-12}$ M, or between about $4\times10^{-12}$ M to about $6\times10^{-12}$ M. In a specific embodiment, serum-free medium of the invention comprise triiodothyronine at a final concentration of $5\times10^{-12}$ M. In one embodiment, serum-free medium of the invention comprise insulin at a final concentration of between about 1 mg/L to about 10 mg/L, or between about 2.0 to about 8.0 mg/L, or between about 3 mg/L to about 6 mg/L. In a specific embodiment, serum-free medium of the invention comprise insulin at a final concentration of 5 mg/L. In certain embodiments, serum-free medium of the invention comprise a prostaglandin at a final concentration of between about 0.001 mg/L to about 0.05 mg/L, or between about 0.005 mg/L to about 0.045 mg/L, or between about 0.01 mg/L to about 0.04 mg/L, or between about 0.015 mg/L to about 0.035 mg/L, or between about 0.02 mg/L to about 0.03 mg/L. In a specific embodiment, serum-free medium of the invention comprise a prostaglandin at a final concentration of 0.025 mg/L. In another specific embodiment, serum-free medium of the invention comprise prostaglandin E1 at a final concentration of 0.025 mg/L.

In still another embodiment, serum-free medium of the invention are fortified with one or more medium component selected from the group consisting of putrescine, amino acids, vitamins, fatty acids, and nucleosides. In specific embodiments, serum-free medium of the invention are fortified with one or more medium component such that the concentration of the medium component is about 1 fold, or about 2 fold, or about 3 fold, or about 4 fold, or about 5 fold higher or more than is typically found in a medium routinely used for propagating cell, such as, for example, Dulbecco's Modified Eagle's Medium/Ham's F12 medium (DMEM/F12). The standard composition of DMEM/F12 is provided for reference below in Table 1. In a specific embodiment, serum-free medium of the invention are fortified with putrescine. In another specific embodiment, serum-free medium of the invention are fortified with putrescine such that the concentration of putrescine is about 5 fold higher, or more, than is typically found in DMEM/F12.

Fatty acids which may be fortified include, unsaturated fatty acid, including but not limited to, linoleic acid and α-linolenic acid (also referred to as essential fatty acids) as well as, myristoleic acid, palmitoleic acid, oleic acid, arachidonic acid, eicosapentaenoic acid, erucic acid, docosahexaenoic acid; saturated fatty acids, including but not limited to, butanoic acid, hexanoic acid, octanoic acid, decanoic acid, dodecanoic acid, tetradecanoic acid, hexadecanoic acid, octadecanoic acid, eicosanoic acid, docosanoic acid, tetracosanoic acid and sulfur containing fatty acids including lipoic acid. In certain embodiments, the serum-free medium of the invention are fortified with extra fatty acids in addition to that provided by a lipid supplement as described supra. In a specific embodiment, serum-free medium of the invention are fortified with linoleic acid and linolenic acid. In another specific embodiment, serum-free medium of the invention are fortified with linoleic acid and linolenic acid such that the concentrations of linoleic acid and linolenic acid are about 5 fold higher, or more, than is typically found in DMEM/F12.

Amino acids which may be fortified in include the twenty standard amino acids (alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) as well as cystine and non-standard amino acids. In certain embodiments, one or more amino acids which are not synthesized by non-tumorigenic MDCK cells, commonly referred to as "essential amino acids", are fortified. For example, eight amino acids are generally regarded as essential for humans: phenylalanine, valine, threonine, tryptophan, isoleucine, methionine, leucine, and lysine. In a specific embodiment, serum-free medium of the invention are fortified with cystine and all the standard amino acids except glutamine (DMEM/F12 is often formulated without glutamine, which is added separately), such that the concentrations of cystine and the standard amino acids are about 5 fold higher, or more, than is typically found in DMEM/F12. In certain specific embodiment, serum-free medium of the invention comprise glutamine at a concentration of between about 146 mg/L to about 1022 mg/L, or between about 292 mg/L to about 876 mg/L, or between about 438 mg/L to about 730 mg/L. In another specific embodiment, serum-free medium of the invention comprise glutamine at a concentration of 584 mg/mL.

Vitamins which may be fortified include, but are not limited to, ascorbic acid (vit A), d-biotin (vit $B_7$ and vit H), D-calciumpantothenate, cholecalciferol (vit $D_3$), choline chloride, cyanocobalamin (vit $B_{12}$), ergocalciferol (vit $D_2$), folic acid (vit $B_9$), menaquinone (vit $K_2$), myo-inositol, niacinamide (vit $B_3$), p-amino benzoic acid, pantothenic acid (vit $B_5$), phylloquinone (vit $K_1$), pyridoxine (vit $B_6$), retinol (vit A), riboflavin (vit $B_2$), alpha-tocopherol (vit E) and thiamine (vit $B_1$). In a specific embodiment, serum-free medium of the invention are fortified with d-biotin, D-calcium, pantothenate, choline chloride, cyanocobalamin, folic acid, myo-inositol, niacinamide, pyridoxine, riboflavin, and thiamine such that the concentrations of the indicated vitamins are about 5 fold higher, or more, than is typically found in DMEM/F12.

Nucleosides which may be fortified include, but are not limited to, cytidine, uridine, adenosine, guanosine, thymidine, inosine, and hypoxanthine. In a specific embodiment, serum-free medium of the invention are fortified with hypoxanthine and thymidine such that the concentrations of hypoxanthine and thymidine are about 5 fold higher, or more, than is typically found in DMEM/F12.

Additional components that may be added to cell culture medium include, but are not limited to, sodium bicarbonate, a carbon source (e.g., glucose), and iron binding agents. In one embodiment, serum-free medium of the invention comprise sodium bicarbonate at a final concentration of between about 1200 mg/L to about 7200 mg/L, or between about 2400 mg/L and about 6000 mg/mL, or about 3600 mg/mL and about 4800 mg/mL. In a specific embodiment, serum-free medium of the invention comprise sodium bicarbonate at a final concentration of 4400 mg/mL. In one embodiment, serum-free medium of the invention comprise glucose as a carbon source. In another embodiment, serum-free medium of the invention comprise glucose at a final concentration of between about 1 g/L to about 10 g/L, or about 2 g/L to about 10 g/L, or about 3 g/L to about 8 g/L, or about 4 g/L to about 6 g/L, or about 4.5 g/L to about 9 g/L. In a specific embodiment, serum-free medium of the invention comprise glucose at a final concentration of 4.5 g/L. It is specifically contemplated that additional glucose may be added to a serum-free medium of the invention that is to be used for the proliferation of non-tumorigenic MDCK cells to high density and subsequent replication of influenza virus to avoid depletion of the carbon source. Accordingly, in certain embodiments, a serum free media of the present invention comprises an additional 1-5 g/L of glucose for a final glucose concentration of between about 5.5 g/L to about 10 g/L.

Iron binding agents which may be utilized include proteins such as transferrin and chemical compounds such as tropolone (see, e.g., U.S. Pat. Nos. 5,045,454; 5,118,513; 6,593,140; and PCT publication number WO 01/16294). In one embodiment, serum-free medium of the invention comprise tropolone (2-hydroxy-2,4,6-cyclohepatrien-1) and a source of iron (e.g., ferric ammonium citrate, ferric ammonium sulfate) instead of transferrin. For example, tropolone or a tropolone derivative will be present in an excess molar concentration to the iron present in the medium at a molar ratio of between about 5 to 1 and about 1 to 1. In certain embodiments, serum-free medium of the invention comprise tropolone or a tropolone derivative in an excess molar concentration to the iron present in the medium at a molar ratio of about 5 to 1, or about 3 to 1, or about 2 to 1, or about 1.75 to 1, or about 1.5 to 1, or about 1.25 to 1. In a specific embodiment, serum-free medium of the present invention comprises Tropolone at a final concentration of 0.25 mg/L and ferric ammonium citrate (FAC) at a final concentration of 0.20 mg/L and (see, e.g., Table 3).

The addition of components as described supra to a medium formulation can alter the osmolality. Accordingly, in certain embodiments, amount of one or more components typically found in DMEM/F12 is reduced to maintain a desired osmolality. In one embodiment, the concentration of sodium chloride (NaCl) is reduced in a serum-free medium of the invention. In another embodiment, the concentration of NaCl in a serum-free medium of the invention is about between about 10% to about 90%, or about 20% to about 80%, or about 30% to about 70%, or about 40% to about 60% of that typically found in DMEM/F12. In a specific embodiment, the final concentration of NaCl in a serum-free medium of the invention is 50% of that typically found in DMEM/F12. In another specific embodiment, the final the concentration of NaCl in a serum-free medium of the invention is 3500 mg/L.

In certain embodiments, the number of animal derived components present in serum-free medium of the invention are minimized or even eliminated. For example, commercially available recombinant proteins such as insulin and transferrin derived from non-animal sources (e.g., Biological Industries Cat. No. 01-818-1, and Millipore Cat. No. 9701, respectively) may be utilized instead proteins derived from an animal source. In a specific embodiment, all animal derived components are replaced by non-animal-derived products with the exception of cholesterol which may be a component of a chemically defined lipid mixture. To minimize the risks typically associated with animal derived products cholesterol may be from the wool of sheep located in regions not associated with adventitious agents including, but not limited to prions.

In a specific embodiment, serum-free medium of the invention comprise all the components of the MediV SFM 110 medium listed in Table 3, at the final concentrations indicated. In another specific embodiment, serum-free medium of the invention consist essentially of all the components of the MediV SFM 110 medium listed in Table 3, at the final concentrations indicated. In still another specific embodiment, MediV SFM 110 medium consisting of the components listed in Table 3 is a serum-free medium of the invention.

TABLE 1

DMEM/F12 Medium Formulation

| Component | mg/L |
|---|---|
| Salts | |
| Calcium Chloride, Anhydrous | 116.6 |
| Magnesium Chloride | 28.64 |
| Magnesium Sulfate, Anhydrous | 48.84 |
| Potassium Chloride | 311.8 |
| Sodium Chloride | 6999.5 |
| Sodium Phosphate, Monobasic, Monohydrate | 62.5 |
| Sodium Phosphate, Dibasic, Anhydrous | 71.02 |
| Trace Metals | |
| Cupric Sulfate, Pentahydrate | 0.0013 |
| Ferric Nitrate, Nonahydrate | 0.05 |
| Ferrous Sulfate, Heptahydrate | 0.417 |
| Zinc Sulfate, Heptahydrate | 0.432 |
| Other | |
| Putrescine, 2HCl | 0.081 |
| Sodium Bicarbonate | 2200 |
| Sodium Pyruvate | 55 |
| Vitamins | |
| d-Biotin (vit B7 and vit H) | 0.0035 |
| D-Calcium Pantothenate | 2.24 |
| Choline Chloride | 8.98 |
| Cyanocobalamin (vit B12) | 0.68 |
| Folic Acid | 2.65 |
| myo-Inositol | 12.6 |

TABLE 1-continued

DMEM/F12 Medium Formulation

| Component | mg/L |
|---|---|
| Niacinamide | 2.02 |
| Pyridoxine HCl (vit B6) | 2.031 |
| Riboflavin(vit B2) | 0.219 |
| Thiamine HCl (vit B1) | 2.17 |
| Amino Acids | |
| L-Alanine | 4.45 |
| L-Arginine HCl | 147.5 |
| L-Asparagine $H_2O$ | 7.5 |
| L-Aspartic Acid | 6.65 |
| L-Cysteine HCl $H_2O$ | 17.56 |
| L-Cystine 2HCl | 31.29 |
| L-Glutamic Acid | 7.35 |
| Glycine | 18.75 |
| L-Histidine HCl $H_2O$ | 31.48 |
| L-Isoleucine | 54.47 |
| L-Leucine | 59.05 |
| L-Lysine HCl | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine 2Na | 55.79 |
| L-Valine | 52.85 |
| Nucleosides | |
| Hypoxanthine, Na salt | 2.39 |
| Thymidine | 0.365 |
| Fatty Acids | |
| α Linoleic Acid | 0.042 |
| α DL--Lipoic Acid | 0.105 |

7.3.2 Bead to Bead Transfer

In one embodiment, non-tumorigenic MDCK cells are cultivated as adherent cells on a surface to which they attach. Adherent surfaces on which tissue culture cells can be grown on include but are not limited to, surface modified polystyrene plastics, protein coated surfaces (e.g., fibronectin and/or collagen coated glass/plastic) as well as a large variety of commercially available microcarriers (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor; Cytodex 1 and Cytodex 3, GE Healthcare Life Science). Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. The choice of adherent surface is determined by the methods utilized for the cultivation of the non-tumorigenic MDCK cells.

In one embodiment, the microcarrier is used at a concentration of between about 1 to about 4 g/L. In another embodiment, the microcarrier is used at a concentration of between about 2 to about 3 g/L. In certain embodiments the culture vessel (e.g. bioreactor) is seeded with the MDCK cells to be cultured at a seeding density of about 0.5 to about $2\times10^5$ cells/mL. In a specific embodiment, the seeding density is between about 0.7 to about $1.8\times10^5$ cells/mL, or between about 0.8 to about $1.6\times10^5$ cells/mL, or between about 0.9 to about $1.4\times10^5$ cells/mL, or between about 1.0 to about $1.2\times10^5$ cells/mL. Alternatively, the seeding density can be calculated on a per microcarrier basis. Accordingly, in certain embodiments the culture vessel (e.g. bioreactor) is seeded with the MDCK cells to be cultured at a seeding density of about 10 to about 40 cells/microcarrier, or of about 12 to about 38 cells/microcarrier, cells/microcarrier, or of about 14 to about 36 cells/microcarrier, or of about 16 to about 34 cells/microcarrier, or of about 18 to about 32 cells/microcarrier, or of about 20 to about 30 cells/microcarrier.

During the process of subculturing adherent cells (i.e., proliferating the cells, expanding the cell culture) the cells must be transferred from a confluent support surface (e.g., flask surface, microcarrier, etc) onto a new support surface. A number of methods can be utilized to effect such cell transfer. For example, proteases, including trypsin, TrypLE and collagenase, may be used to remove cells from flasks or microcarriers the cells are then, washed if desired, and diluted into a larger flask or into a larger volume of microcarrier containing medium for expansion. This process is commonly referred to a "splitting" the culture and may be quantified as the ratio of the original culture to the final culture. For example a split ratio of 1:8 indicates that 1 part of the original (e.g., 10 mL) culture is added to 7 parts fresh culture medium (e.g., 70 mL) to yield 80 mL. Alternatively, the number of cells in the original culture is determined and the dilution is calculated based on the desired seeding density and volume of the final culture. It is preferable to use a non-animal derived protease for such applications such as, TrypLE (Invitrogen, Carlsbad, Calif.). Alternatively, in microcarrier cultures, after the cells have detached fresh medium and/or microcarrier beads may then be added to the culture. In some embodiments, the protease treated culture is transferred to a larger culture vessel before, during or after the addition of fresh medium and/or microcarriers.

In a specific embodiment, a cell culture of MDCK cells (e.g., non-tumorigenic MDCK cells) growing as adherent cells on microcarriers are treated with a protease (e.g., TrypLE). The protease may be inactivated (e.g., by the addition of a protease inhibitor such as lima bean trypsin inhibitor) as needed, and fresh medium and/or microcarrier beads may then be added to the culture. In some embodiments, the protease treated culture is transferred to a larger culture vessel before, during or after the addition of fresh medium and/or microcarriers.

The use of proteases in bead to bead transfer methods can result in poor cell spreading and low cell counts. Accordingly, the present invention also provides methods of effecting bead to bead transfer which minimize or even eliminate the amount of protease needed to facilitate bead to bead transfer including but not limited to the method exemplified in the Examples at Section 9.3, which is also utilized in the Examples in Section 9.1. In particular, the inventors have determined that the amount of protease needed to release the cells from microcarriers can be reduced by at least 20 fold by pre-treatment with a chelating agent, in particular by pre-treatment at a pH higher than that used for the proliferation of the cells.

In some embodiments, bead to bead transfer is facilitated by pre-treating the cells with a chelating agent prior to the addition of a protease (e.g., TrypLE). In other embodiments, bead to bead transfer is facilitated by the addition of a chelating agent (e.g., EDTA) and incubation at a pH above that used for cell proliferation. In a specific embodiment, a cell culture of non-tumorigenic MDCK cells growing as adherent cells on microcarriers is treated with a chelating agent (e.g., EDTA) at a higher pH than used during proliferation of the cells prior to the addition of a protease. In certain embodiments, the pH is monitored and adjusted as need to facilitate detachment of the cells from the microcarrier substrate. After the cells have detached fresh medium and/or microcarrier beads may then be added to the culture. In some embodiments, the culture, with or without the original microcarriers is transferred to a larger culture vessel before, during or after the addition of fresh medium and/or microcarriers.

In certain embodiments, the cells are washed with a wash medium (e.g., a buffered salt solution) prior to being detached. Medium useful for washing cells include, but are not limited to, Hepes-Buffered solutions, Phosphate-Buffered Saline, Dulbecco's Phosphate-Buffered Saline, Hank's Balanced Salt Solution, Earle's Balanced Salt Solution. The process of washing the cells involves replacing a portion or all of the medium (growth and/or wash medium) with fresh wash medium (i.e., buffered salt solution). The process may be repeated multiple times. Generally, the microcarrier beads are allowed to settle for a time (e.g., 10 to 40 minutes) and the growth medium is removed from the vessel. Optionally, the removal of medium from a cell culture can be performed utilizing an alternating low shear tangential flow device, see for example U.S. Pat. No. 6,544,424. In certain embodiments, between about 50% to about 90% of the medium (growth and/or wash medium) is removed during the wash step. In certain embodiments, the medium is replaced with a volume of wash medium (i.e., buffered salt solution) that is less than, the same, or greater than, the volume of medium that was removed. In one embodiment, wash medium is added such that the resulting volume of cell culture is between about 25% to about 100% of the original working volume of the cell culture. In a specific embodiment, a wash medium is added to about 40% to about 60% of the original working volume of the cell culture. In another specific embodiment, a wash medium is added to about 90% to about 100% of the original working volume of the cell culture. In certain embodiments, the cells are washed two or more times.

In certain embodiments, the wash medium comprises a chelating agent. Chelating agents which can be utilized include but are not limited to, ethylenediaminetetraacetic acid (EDTA), Diethylenetriaminepentaacetate (DTPA), Ethylenebis (oxyethylene-trinitrilo)tetraacetic acid (EGTA). In a specific embodiment, the chelating agent is EDTA. In certain embodiments, the wash medium comprises the chelating agent at a concentration of between about 0.25 mM to about 0.75 mM. In certain other embodiments, the wash medium comprises the chelating agent at a concentration of between about 0.4 mM to about 0.6 mM. In a specific embodiment, the wash medium comprises the chelating agent concentration of about 0.5 mM.

In one embodiment, the pH of the wash medium comprising the chelating agent is between about 7.6 and about 8.4. In a specific embodiment, the pH of the wash medium comprising the chelating agent is between about 7.8 and about 8.2. In another specific embodiment, the pH of the wash medium comprising the chelating agent is between about 7.9 and about 8.1. The addition of a wash medium comprising a chelating agent to a cell culture may alter the pH of the resulting cell culture in wash medium. Accordingly, in certain embodiments, the pH of a cell culture being washed with a wash medium comprising a chelating agent is adjusted to between about 7.6 and about 8.4, as needed, after addition of the wash medium to the cell culture. In a specific embodiment, the pH of a cell culture being washed with a wash medium comprising a chelating agent is adjusted to between about 7.8 and about 8.2, as needed, after addition of the wash medium to the cell culture. In another specific embodiment, the pH of a cell culture being washed with a wash medium comprising a chelating agent is adjusted to between about 7.9 and about 8.1, as needed, after addition of the wash medium to the cell culture.

In certain embodiments, the cell culture is agitated after the addition of the wash medium comprising the chelating agent and prior to an additional wash step and/or the addition of a protease. Agitation of the culture may take place using means well known in the art, including but not limit to, stirring, shaking, rotating, and the like. The rate and duration of agitation is determined by the volume of the culture, the components of the wash medium, and the type of cells in the cell culture. In certain embodiments, the cell culture is agitated at a similar rate as that used for propagation of the cells. In other embodiments, the cell culture is agitated at a higher rate than that used for propagation of the cells. When a higher agitation rate is used the rate is increased between about 10% to about 90%, or between about 20% to about 80%, or between about 30% to about 70%, or between about 40% to about 65%. In a specific embodiment, the agitation rate used is between about 40% to about 65%. In some embodiments the cell culture is incubated with the chelating agent prior to the addition of protease with sufficient agitation to keep the majority of the microcarriers from settling to the bottom of the culture vessel. In certain embodiments, the cell culture is agitated for between about 5 minutes to about 60 minutes. In a specific embodiment, the cell culture is agitated for about 20 to about 40 minutes.

In certain embodiments, a protease (e.g., serine protease) is added to the cell culture during a wash but after any agitation. In a specific embodiment, the cells are washed two or more times and the protease is added during the last wash after any agitation. The protease is, in certain aspects of the invention, a serine protease, or a cysteine protease, or an asparagine protease. In a specific embodiment the protease is a serine protease (e.g., trypsin, TrypLE, etc). In another embodiment, the protease from *Streptomyces griseus* described in U.S. application Ser. No. 11/455,818 is used. The trypsin can be from an animal source, or, more preferably, is from a recombinant source. The amount of protease added to effect detachment under these conditions will be at least 5× less than that needed if the cells had not be pre-treated with a chelating agent and will be determined by the volume of the volume of the culture and the concentration of the protease. By way of example, the commercially available TrypLE™ Express provided as a 10× stock, would generally be used at a final concentration of about 1× (see, for example, Invitrogen™ TrypLE Select Product News) to detach highly adherent cells, such as MDCK cells. As demonstrated herein (see, Section 9.3) the final concentration of TrypLE™ required to detach cells from microcarriers is 0.05×, a 20 fold reduction. Accordingly, in certain embodiments, the final concentration of protease added to the cell culture is between about 0.1× to about 0.0125×, or between about 0.1× to about 0.0125×, or between about 0.1× to about 0.025, or between about 0.1× to about 0.05×, or between about 0.1× to about 0.075×, or between about 0.075× to about 0.0125×, or between about 0.05× to about 0.0125×, or between about 0.025× to about 0.0125×, or between about 0.075× to about 0.025× or about 0.5×, or about 0.1×, or about 0.09×, or about 0.08×, or about 0.07×, or about 0.06× or about 0.05×, or about 0.04× or about 0.02×, where 1× represents the final concentration of protease needed to detach cells which have not be pre-treated with a chelating agent under identical dissociation conditions. It will also be understood that 1× may also represent the final working concentration after dilution of a concentrated stock of protease (e.g., a protease supplied as a 10× stock) and that this working stock can be further diluted to obtain concentrations of less than 1×.

Reproducible bead to bead transfer in large scale manufacturing generally employs the use of multiple wash steps for example to ensure the pre-protease treated cell culture contains minimum protease inhibitors or as described above to minimize and/or eliminate the need for a protease. However, for large scale commercial processes these washing procedures can be costly to implement and may result in contaminations contributing to failures in productions runs, non-robustness in manufacturing processes and reductions in productivity. Accordingly, the present invention provides new methods to overcome these shortcomings by eliminating cell culture washing steps during bead to bead transfer. Methods of effecting bead to bead transfer which reduce or even eliminate the need for washing procedures include but are not limited to the method exemplified in the Examples at Section 9.5. In particular, the inventors have determined that pretreatment with a chelating agent (e.g., EDTA) prior to protease treatment can eliminate the need to remove the growth media and wash the cells. In addition, by supplementing the fresh media with additional media components (e.g., divalent cations and/or trace elements) there is no need to wash the cells post protease treatment.

In some embodiments, bead to bead transfer is facilitated by the addition of a chelating agent directly to the cell culture (i.e., without washing the cells) prior to the addition a protease (e.g., TrypLE). Chelating agents which can be utilized in the methods have been described above. In one embodiment the chelating agent is capable of chelating divalent cations (e.g., $Ca^{2+}$ and $Mg^{2+}$). In a specific embodiment, the chelating agent is EDTA. In some embodiments the chelating agent is added to the cell culture at a final concentration of between 0.5 mM to 5 mM, or between about 0.5 mM to about 4 mM, or between about 0.5 mM to about 3 mM, or between about 0.5 mM to about 2 mM, or between about 0.5 mM to about 1.5 mM, or between about 0.5 mM to about 1 mM, or between about 1 mM to about 5 mM, or between about 1.5 mM to about 5 mM, or between about 2.0 mM to about 5 mM, or between about 3.0 mM to about 5 mM, or between about 4.0 mM to about 5 mM, or between about 1 mM to about 2 mM. In a specific embodiment, the chelating agent is added to the cell culture at a final concentration of about 2 mM. After the addition of the chelating agent the cell culture may then be incubated for a period of time prior to the addition of protease. In some embodiments the cell culture is incubated with the chelating agent for between about 0 min to about 120 min, or between about 0 min to about 90 min, or between about 0 min to about 60 min, or between about 0 min to about 30 min, or between about 30 min to about 120 min, or between about 60 min to about 120 min, or between about 90 min to about 120 min, or between about 30 min to about 90 min, or about 60 min prior to the addition of protease. In certain embodiments, the cell culture is agitated after the addition of the chelating agent and prior to the addition of a protease. Means, rates and duration of agitation, have been described above and may be optimized by one of skill in the art without undue experimentation. In a specific embodiment the cell culture is incubated with the chelating agent prior to the addition of protease with sufficient agitation to keep the majority of the microcarriers from settling to the bottom of the culture vessel.

Prior to the addition of the protease the pH of the chelated cell culture may adjusted, for example, to the optimum pH for the protease. In a specific embodiment the pH is adjusted to between about 7.8 and about 8.2. Proteases which may be utilized after pretreatment with a chelating agent have been detailed above. In some embodiments, the final concentration of protease added to the cell culture after pre-treatment with a chelating agent is between about 0.1× to about 0.0125×, or between about 0.1× to about 0.0125×, or between about 0.1× to about 0.025, or between about 0.1× to about 0.05×, or between about 0.1× to about 0.075×, or between about 0.075× to about 0.0125×, or between about 0.05× to about 0.0125×, or between about 0.025× to about 0.0125×, or between about 0.075× to about 0.025×. In other embodiments, the final concentration of protease added to the cell culture after pre-treatment with a chelating agent is about 0.09×, or about 0.08×, or about 0.07×, or about 0.06× or about 0.05×, or about 0.04× or about 0.02×, where 1× represents the final working concentration after dilution of a concentrated stock of protease (e.g., a protease supplied as a 10× stock). The duration of protease treatment can be determined by monitoring cell detachment and may vary depending on the concentration of protease used. Methods for monitoring cell detachment are known in the art and include microscopic examination of the cell culture. Once the cells have detached the protease may be inactivated (e.g., by the addition of a protease inhibitor such as lima bean trypsin inhibitor) as needed, and fresh medium and/or microcarrier beads may then be added to the culture. In some embodiments, the protease treated culture is transferred to a larger culture vessel before, during or after the addition of fresh medium and/or microcarriers.

To facilitate reattachment and cell growth after protease treatment the fresh medium that is added to the cell culture is supplemented with one or more media component including, but not limited to, $CaCl_2$, $MgCl_2$, $MgSO_4$, trace elements A, B, and C. Additional microcarrier beads are also be added to the culture. Exemplary concentrations $CaCl_2$, $MgCl_2$ and $MgSO_4$, where 90% or more of the cells reattach to microcarriers are shown in Table 25. Exemplary concentrations of $CaCl_2$, $MgCl_2$, $MgSO_4$, trace elements A, B, and C, where the cells counts four day post seeding were at least 1.0E6 cells/mL are shown in Table 26. In certain embodiments the media is supplemented with between about 1.25 mM to about 1.5 mM $CaCl_2$, between about 0.1 mM to about 0.2 mM $MgCl_2$, and between about 0.1 to about 0.8 mM $MgSO_4$. In other embodiments, the media is further supplemented with about 2× of trace elements A, B, and C. In some embodiments, the culture, with or without the original microcarriers, is transferred to a larger culture vessel before, during or after the addition of fresh supplemented medium and microcarriers.

In one embodiment, MDCK cells are cultivated as adherent cells in a culture system. Culture systems which may be utilized to cultivate MDCK cells include for example, batch culture systems and fed batch culture systems where additional nutrients (e.g., carbon source, amino acids, etc) are added as they are depleted from the starting medium to facilitate growth to high cell densities. Alternatively or optional a perfusion culture systems (e.g., using cell retention systems, such as, for example, centrifugation, filtration, spin filters and the like) may be used to facilitate medium exchange and/or supplementation of depleted nutrients. In a specific embodiment, non-tumorigenic MDCK cells are cultivated as adherent cells in a batch culture system without medium exchange/supplementation (e.g., feeding or perfusion) using a serum-free medium of the invention (e.g., MediV SFM 110). Additional guidance regarding culture of MDCK cells (e.g., non-tumorigenic MDCK cells) as adherent cells may be found, for example, in US Patent Application Publication Nos. 2003/0108860; 2005/0118140; and PCT Publication WO 2008/105931. Commonly used culture systems useful for cultivation of MDCK cells include stirred vessel bioreactors.

7.3.3 Influenza Virus Culture Conditions

The present invention provides methods for the cultivation of MDCK cells (e.g., non-tumorigenic MDCK cells) and other animal cells in serum-free media formulations as set forth above. It is specifically contemplated that additional culture conditions may play a role in the maintenance of the properties of the MDCK cells, including being non-tumorigenic, being non-oncogenic, growing as adherent cells, growing as non-adherent cells, having an epithelial-like morphology, supporting the replication of various viruses, and supporting the growth of influenza viruses (e.g., cold-adapted, and/or temperature sensitive, and/or attenuated) to high titer, e.g., a $\log_{10}$ $TCID_{50}$/mL and/or a $\log_{10}$ FFU/mL of at least about 7.8, or at least about 8.0, or at least about 9.0. These culture conditions include, but are not limited to, the choice of adherent surface, cell density, temperature, $CO_2$ concentration, method of cultivation, agitation rates, dissolved oxygen content and pH.

It is specifically contemplated that the culture conditions may be adapted in a number of ways to optimize the growth of MDCK cells (e.g., non-tumorigenic MDCK cells). Such adaptations may also result in a increase in the production of viral material (e.g., virus), as described, for example, in US Patent Application Publication No. 2005/0118698. Alternatively, the culture conditions may be adapted to optimize the production of vaccine material from MDCK cells without regard for the growth of the cells. These culture conditions include but are not limited to adherent surface, cell density, temperature, $CO_2$ concentration, method of cultivation, dissolved oxygen content and pH.

In one embodiment, MDCK cells (e.g., non-tumorigenic MDCK cells) are cultivated at a $CO_2$ concentration of at least 1%, or of at least 2%, or of at least 3%, or of at least 4%, or of at least 5%, or of at least 6%, or of at least 7%, or of at least 8%, or of at least 9%, or of at least 10%, or of at least 20%.

In one embodiment the dissolved oxygen (DO) concentration ($pO_2$ value) is advantageously regulated during the cultivation of MDCK and is in the range from 5% and 100% (based on the air saturation), or between 10% and 60%. In a specific embodiment the dissolved oxygen (DO) concentration ($pO_2$ value) is at least 10%, or at least 20%, or at least 30%, or at least 50%, or at least 60%. In a specific embodiment, the DO concentration is maintained at 50%. In a particular embodiment, the DO is flowed down to 50% and then maintained at that level. Methods for maintaining DO levels include, for example, sparging with pure oxygen.

As agitation of cell cultures generally, and sparging in particular may resulting in foaming, in certain embodiments, an anti-foaming agent is added to a cell culture to reduce foaming. Anti-foaming agents useful for mammalian cell culture are readily obtained from a number of commercial sources including, for example, Invitrogen, Dow Corning, Sigma, and others. Specific antifoaming agents include but are not limited to, Antifoam C Emulsion, and, FoamAway™. In a specific embodiment, Antifoam C Emulsion is added to the culture at between about 10 ppm to about 1000 ppm, or at between about 25 ppm to about 750 ppm, or between about 50 ppm to about 500 ppm, or between about 75 ppm to about 250 ppm, or between about 50 ppm to about 150 ppm. In certain embodiments the antiforming agent is added to the cell culture twice a day, or once a day, or every other day. In other embodiments, the anti-foaming agent is added to the culture medium prior to the addition of MDCK cells.

In another embodiment, the pH of the culture medium used for the cultivation of the non-tumorigenic MDCK cells is regulated during culturing and is in the range from pH 6.4 to pH 8.0, or in the range from pH 6.8 to pH 7.4. In a specific embodiment, the pH of the culture medium is at about 6.4, or at about 6.6, or at about 6.8, or at about 7.0, or at about 7.2, or at about 7.4, or at about 7.6, or at about 7.8, or at least 8.0. In a particular embodiment the pH of the culture medium is about 7.4.

In a further embodiment, MDCK cells are cultured in a serum free medium of the invention at a temperature of 25° C. to 39° C. It is specifically contemplated that the culture temperature may be varied depending on the process desired. For example, the non-tumorigenic MDCK cells may be grown at 37±2° C. for proliferation of the cells and at a lower temperature (e.g., 25° C. to 35° C.) of for the production of vaccine material (e.g., virus). In another embodiment, the cells are cultured at a temperature of less than 30° C., or of less than 31° C., or of less than 32° C., or of less than 33° C., or of less than 34° C. for the production of vaccine material. In another embodiment, the cells are cultured at a temperature of 30° C., or 31° C., or 32° C., or 33° C., or 34° C. for the production of vaccine material. In a specific embodiment, the cells are cultured at a temperature of 33±2° C. for the production of vaccine material.

In certain embodiments, MDCK cells are cultured in a serum-free medium of the invention in a stirred-vessel bioreactor (e.g., plastic single use, glass or stainless steel reusable bioreactors) and one or more parameters selected from the group consisting of temperature, agitation rate, pH, dissolved oxygen (DO), $O_2$ and $CO_2$ flow rate, are monitored and/or controlled. In one embodiment, the temperature is maintained at between about 30° C. to about 42° C., or between about 33° C. to about 39° C., or between about 35° C. to about 38° C. In a specific embodiment, the temperature is maintained at about between about 36° C. to about 38° C. In one embodiment, the agitation rate is maintained at between about 100 to 200 rpm. In a specific embodiment a single use bioreactor is utilized and the rate of agitation is maintained at between about 80 to about 120 rpm, or between about 90 to about 100 rpm. In another specific embodiment a reusable bioreactor is utilized and the rate of agitation is maintained at between about 150 to about 200 rpm, or between about 160 to about 180 rpm. Agitation rates are controlled by means well known in the art. The type and size of bioreactor utilized as well as the type and number of impeller(s) used may require the agitation rate to be adjusted to maximize cell growth and/or minimize cell damage.

In another embodiment, the pH of the MDCK cell culture is maintained at between about 6.4 to pH 8.0. In a specific embodiment the pH of the starting culture is between about 6.8 to about 7.6 and the pH of the culture is maintained at about 7.0 to about 7.5 during the culture process. The initial pH may be lower or higher then the desired range and that the pH may be allowed to increase or decrease to the desired level (e.g., 7.4) where it is maintained. In a particular embodiment the pH is maintained at about 7.4. The pH may be controlled by sparging $CO_2$ and/or by adding acid (e.g., HCL) or base (e.g., NaOH, $NaHCO_3$, $Na_2CO_3$) as needed.

In still another embodiment the acceptable range for the DO is between about 100 to about 35%. In a specific embodiment, the DO of the MDCK cell culture is maintained at between about 35% to about 50%, or at about 50%. In another specific embodiment, the DO should not drop below about 35%. In certain embodiments, the initial DO may be 100% and the DO may be allowed to drop down to a predetermined level (e.g., 50%) where it is maintained. The DO is maintained, for example, by sparging $O_2$. In certain embodiments, the $O_2$ flow rate is maintained at less then about 2.0 L/min. In certain embodiments, the $CO_2$ flow rate is maintained at less then about 0.4 L/min. In still other embodiments, a constant total flow rate is maintained (e.g., 40 mL/min) and $N_2$ gas is supplied to maintain the flow rate. Accordingly, the supply of $N_2$ gas can be calculated from $O_2$ and $CO_2$ gases used to maintain the DO and pH.

The content of glucose, glutamine, lactate, other medium components, as well as the pH and $pO_2$ value in the medium and other parameters, such as agitation, may be readily manipulated during culture of the non-tumorigenic MDCK cells such that the cell density and/or virus production is optimized.

7.3.4 Respiratory Syncitial Virus Culture Conditions

In a specific embodiment, cells are cultured before infection with a cell-associated virus described herein to achieve a certain total viable cell count. For example, Vero cells may be cultured in VP-SFM supplemented with 4 mM L-glutamine and 1% CDLC) at approximately 37° C. and total viable cell counts and cell viability is measured. In a specific embodiment, cells are infected with cell-associated virus when a certain average viable cell count is achieved. For example, an average viable cell count of approximately $1.5 \times 10^8$ cells/tissue culture vessel or more may be achieved before the cells are infected with a cell-associated virus described herein, such as RSV. In one embodiment, an average viable cell count of approximately $1 \times 10^6$ cells/tissue culture vessel to approximately $1 \times 10^{14}$ cells/tissue culture vessel as measured using, e.g., a Vi-cell counter, is achieved before cells are infected with a cell-associated virus described herein. In another embodiment, an average viable cell count of approximately $1 \times 10^6$ cells/tissue culture vessel, approximately $5 \times 10^6$ cells/tissue culture vessel, approximately $1 \times 10^7$ cells/tissue culture vessel, or approximately $5 \times 10^7$ cells/tissue culture vessel as measured using, e.g., a Vi-cell counter, is achieved before cells are infected with a cell-associated virus described herein. In another embodiment, an average viable cell count of approximately $1 \times 10^8$ cells/tissue culture vessel, approximately $5 \times 10^8$ cells/tissue culture vessel, approximately $1 \times 10^9$ cells/tissue culture vessel, approximately $5 \times 10^9$ cells/tissue culture vessel, or approximately $1 \times 10^{10}$ cells/tissue culture vessel as measured using, e.g., a Vi-cell counter, is achieved before cells are infected with a cell-associated virus described herein.

A multiplicity of infection (MOI) that is determined to be optimal for the chosen cells is used to infect cells. In a specific embodiment, a MOI of approximately 0.0001 to approximately 1 or approximately 0.0005 to 0.005 is used to infect the cells described herein. In another embodiment, a MOI of approximately 0.0001, approximately 0.0005 or approximately 0.00075 is used to infect the cells described herein. In another embodiment, a MOI of approximately 0.001, approximately 0.005, approximately 0.0075 or approximately 0.01 is used to infect the cells described herein. In yet another embodiment, a MOI of approximately 0.05, approximately 0.075, approximately 0.1 or approximately 0.5 is used to infect the cells described herein. In a specific embodiment, a MOI of approximately 0.01 of rA2 cp248/404/1030ΔSH is used to infect Vero cells.

Cell-associated virus-infected cells may be incubated for a period of time in media and under conditions (e.g., temperature, $CO_2$ conditions, and pH) that are appropriate for the cell line chosen and result in optimal yields of virus titer. For example, Vero cells infected with a RSV, such as rA2 cp248/ 404/1030ΔSH, may be incubated in SF4 MegaVir medium (Invitrogen Corp., Carlsbad Calif.) supplemented with 4 mM L-glutamine and incubated at approximately 30° C. for approximately 10 days without $CO_2$ before the virus is harvested. In some embodiments, RSV-infected cells (e.g., RSV-infected Vero cells) are incubated for approximately 8 to 14 days before the virus is harvested. In specific embodiments, RSV-infected cells are incubated for approximately 8 days, preferably approximately 9 days, approximately 10 days, approximately 11 days, or approximately 12 days before the virus is harvested.

Cell-associated virus-infected cells described herein can be cultured in any tissue culture vessel known to one of skill in the art. In some embodiments, the cell-associated virus-infected cells are cultured in T-75 flasks or T-225 flasks. In other embodiments, the cell-associated virus-infected cells are cultured in 1 liter, 2 liter, 3 liter, 4 liter or 5 liter tissue culture vessels. In a specific embodiment, the cell-associated virus-infected cells are cultured in at least 40 500 ml working volume roller bottles. In a specific embodiment, the cell-associated virus-infected cells are cultured in a 4 liter tissue culture vessel, such as a roller bottle. In other embodiments, the cell-associated virus-infected cells are cultured in 10 liter, 15 liter, 20 liter or 25 liter tissue culture vessels. In other embodiments, the cell-associated virus-infected cells are cultured in 50 liter, 75 liter or 100 liter tissue culture vessels. In other embodiments, the cell-associated virus-infected cells are cultured in 250 liter, 500 liter or 1000 liter tissue culture vessels. The tissue culture vessels that may be used include flasks, roller bottles, bioreactors and any other tissue culture vessels known to one of skill in the art.

7.4 Production of Vaccine Material

The present invention provides robust methods for the production of viruses in cell culture in which MDCK cells (e.g., non-tumorigenic MDCK cells) are used to produce viruses. In particular, the present invention provides methods for the production of influenza viruses to high titers, without medium exchange or supplementation.

In one embodiment the method for producing influenza viruses comprises the following steps:
(a) proliferating MDCK cells in a serum-free culture medium, while maintaining one or more culture conditions selected from the group consisting of an agitation rate of between about 100 and 200 rpm, a pH of between about 6.0 to about 7.8, a temperature of between about 33° C. and about 42° C., and dissolved oxygen (DO) between about 35% to about 100%;
(b) infecting the proliferated MDCK cells with an influenza virus without exchanging the culture medium; and
(c) incubating the infected proliferated MDCK cells under conditions that permit replication of the influenza virus.

Influenza viruses which may be produced by the methods of the invention are described here (see, for example, Sections 7.2 and 7.7), and include but are not limited to, reassortant viruses that incorporate selected hemagglutinin and/or neuraminidase antigens in the context of an attenuated, temperature sensitive, cold adapted (ca/ts/att) master donor viruses. For example, viruses can comprise the backbones (or one or more vRNA segment) of master donor virus that are one or more of, e.g., temperature-sensitive (ts), cold-adapted (ca), or an attenuated (att) (e.g., A/Ann Arbor/6/60, B/Ann Arbor/1/66, PR8, B/Leningrad/14/17/55, B/14/5/1, B/USSR/60/69, B/Leningrad/179/86, B/Leningrad/14/55, B/England/2608/76 etc.). Methods for the production of reassortant influenza vaccine strains in either eggs or cell lines include, for example, those disclosed in Kilbourne, E. D. in Vaccines ($2^{nd}$ Edition), ed. Plotkin and Mortimer, WB Saunders Co. (1988) and those disclosed in PCT Application PCT Patent Publication Nos. WO 05/062820 and WO 03/091401, and in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770. Other influenza viruses which may be produced by the methods of the invention include recombinant influenza viruses which may express a heterologous gene product, see for example, U.S. Patent Publication Nos. 2004/0241139 and 2004/0253273. In certain embodiments, the method is used to produce cold-adapted, and/or temperature sensitive, and/or attenuated influenza viruses.

In a specific embodiment, the influenza viruses are produced to a peak viral titer $\log_{10}$ $TCID_{50}$/mL and/or $\log_{10}$ FFU/mL of at least about 8.0. In other embodiments, the influenza viruses are produced to a peak viral titer $\log_{10}$ $TCID_{50}$/mL and/or $\log_{10}$ FFU/mL of at least about 8.1, or of at least 8.2, or of at least 8.3, or of at least 8.4, or of at least 8.5, or of at least 8.6, or of at least 8.7, or of at least 8.8, or of at least 8.9, or of at least 9.0.

In certain embodiments, the MDCK cells are proliferated as adherent cells. In a specific embodiment the MDCK cells are non-tumorigenic MDCK cells and are proliferated as adherent cells. In another specific embodiment, the MDCK cells are selected from the group consisting of ATCC Deposit Nos. PTA-6500, PTA-6501, PTA-6502, PTA-6503, PTA-7909 and PTA-7910), and are proliferated as adherent cells. Bioreactors and methods useful for proliferating adherent cells have been described supra (see Sections 7.3.2 and 7.3.3). In other embodiments, the MDCK cells are proliferated as non-adherent cells. Methods for proliferating non-adherent MDCK cells are known in the art, see for example U.S. Pat. No. 6,455,298. Additional culture conditions such as, for example, temperature, agitation rate, pH, $pO_2$, $CO_2$ concentration, and cell seeding density are described in detail supra (see Sections 7.3.2 and 7.3.3).

In a specific embodiment, the MDCK cells are proliferated as adherent cells in a stirred vessel bioreactor. In certain embodiments of the method the temperature, agitation rate, pH, $pO_2$ value, $CO_2$ concentration and other parameters of the culture medium to culture the cells are regulated during culturing as described supra (see Sections 7.3.2 and 7.3.3). In certain embodiments the MDCK cells are proliferated to a cell density of between about $5 \times 10^5$ to about $3 \times 10^6$. Alternatively, or optionally the MDCK cells are proliferated for a set period of time. The initial seeding density, doubling time and desired final cell density will determine the time period for proliferation. In such embodiments, the cells can, for example, be proliferated for 1 to 10 days, or for 2 to 8 days, or for 3 to 7 days. In some embodiments, MDCK cells are proliferated for about 3 to about 5 days.

In certain embodiments, the serum-free medium is an enriched serum-free medium as described herein (see Section 7.3.1). In one embodiment, the serum-free medium comprises a plant hydrolysate, a lipid supplement, trace elements, and is fortified with one or more medium component selected from the group consisting of putrescine, amino acids, vitamins, fatty acids, and nucleosides. In another embodiment, the serum-free medium comprises all the components of the MediV SFM110 medium listed in Table 3. In a specific embodiment, the serum-free medium consists essentially of all the components of the MediV SFM 110 medium listed in Table 3. In another specific embodiment, the serum-free medium consists of the components listed in Table 3 at the final concentrations indicated. In certain embodiments the serum-free medium comprises glucose at a final concentration of about 4.5 g/L. In other embodiments the serum-free medium comprises glucose at a final concentration of about 9.0 g/L.

Influenza viruses which may be used to infect the cells (step (b)) include, but are not limited to, those that have been described herein (see, e.g., Sections 7.2 and 7.7). The amount of virus to be added to infect the cells (referred to herein as the "viral input") may be measured as the number of virus added per cell (also commonly referred to as the multiplicity of infection, or MOI). In some embodiments, the infection of the cells with virus is carried out using a viral input of about 0.00001 FFU/cell to about 10 FFU/cell, or about 0.00001 FFU/cell to about 1 FFU/cell, or about 0.00001 FFU/cell to about 0.1 FFU/cell, or about 0.00001 FFU/cell to about 0.001 FFU/cell. In one embodiment, the infection of cells with virus is carried out using a viral input of about 0.00001 FFU/cell to about 0.0001 FFU/cell, or about 0.00002 FFU/cell to about 0.0002 FFU/cell. In a specific embodiment, the infection of the cells with virus is carried out using a viral input of between 0.00001 FFU/cell to 0.00005 FFU/cell. In another specific embodiment, the infection of the cells with virus is carried out using a viral input of between 0.0001 FFU/cell to 0.0005 FFU/cell. The following formula may be used to determine the amount of virus to add:

Amount of virus in μL=Total cells×Viral input (FFU/cell)/$10^{Virus\ FFATiter}$ (FFU/mL)×1000.

Alternatively, the amount of virus used to infect the cells (i.e., viral imput) is determined by the final concentration of virus in the culture. For example, virus may be added at a final concentration of about $1\times10^3$ FFU/mL to about $0.001\times10^3$ FFU/mL, or about $0.1\times10^3$ FFU/mL to about $0.01\times10^3$ FFU/mL. The following formula may be used to determine the amount of virus to add to achieve the desired final concentration:

Amount of virus in μL=culture volume (mL)×final concentration (FFU/mL)/$10^{Virus\ FFATiter}$ (FFU/mL)×1000.

Optionally a protease can be added which brings about the cleavage of the precursor protein of hemagglutinin [$HA_0$] and thus the adsorption of the viruses on the cells. The addition of a protease can be carried out according to the invention shortly before, simultaneously to or shortly after the infection of the cells with influenza viruses. If the addition is carried out simultaneously to the infection, the protease can either be added directly to the cell culture to be infected or, for example, as a concentrate together with the virus inoculate. The protease is, in certain aspects of the invention, a serine protease, or a cysteine protease, or an asparagine protease. In one embodiment, trypsin is used. In a specific embodiment, TPCK-treated trypsin is used. In one embodiment, trypsin is added to the cell culture up to a final concentration of 1 to 5000 mU/ml, or 5 to 1000 mU/ml, or 100 to 500 mU/ml. In an alternative embodiment, trypsin is added to the cell culture up to a final concentration of 1 to 200 μg/ml, or 5 to 50 μg/ml, or 5 to 30 μg/ml in the culture medium.

The protease can be from an animal source, or, more preferably, is from a recombinant source. Recombinant proteases suitable for use are readily obtained from a number of commercial sources including, for example Invitrogen (TrypLE™) and Sigma-Aldrich (TrypZean™), as a stock solution (e.g., 1×-100×). In certain embodiments, a recombinant protease is used at a final concentration of between about 0.01× to about 1×, or between about 0.02× to about 0.8× or between about 0.03× to about 0.7×, or between about 0.04× to about 0.6×, or between about 0.05× to about 0.5×, or between about 0.06× to about 0.4×, or between about 0.07× to about 0.3×, or between about 0.8× and about 0.2×. In a specific embodiment, a recombinant protease is used at a final concentration of between about 0.02× and about 0.06×. In another embodiment, the protease is a recombinant trypsin-like protease, including but not limited to TrypLE™ (Invitrogen). In still another embodiment, the protease is from *Streptomyces griseus* as described in U.S. application Ser. No. 11/455,818.

After infection, the infected cell culture is cultured further to replicate the viruses, in particular until a maximum cytopathic effect or a maximum amount of virus or antigen can be detected. In one embodiment, after infection the cells are cultured at a temperature of between 30° C. and 37° C. In certain embodiments, after infection with viruses the cells are cultured at a temperature of less then 39° C., or less than 38° C., or less than 37° C., or less than 36° C., or less than 35° C., or less than 34° C., or less than 33° C., or less than 32° C., or less than 31° C., or less than 30° C. The culturing of the infected cells at temperatures below 33° C., in particular in the temperature ranges indicated above, leads to the production of higher yields of certain influenza viruses, such as, for example B strains (see, e.g., U.S. Patent Publication 2006/0153872). Furthermore, the culturing of the infected cells at temperatures below 35° C. is contemplated for the production of temperature sensitive, cold adapted (ts/ca) influenza virus. It is contemplated that ts/ca viruses may also be attenuated (att). In another embodiment, the cells are cultured at a temperature of less than 30° C., or of less than 31° C., or of less than 32° C., or of less than 33° C., or of less than 34° C. for the production of ts/ca influenza strains. In a specific embodiment, the cells are cultured at a temperature of 31° C., for the production of influenza virus B strains. In still another embodiment, after infection the cells are cultured at a temperature of 31±2° C.

In certain embodiments, the incubating of the cells (step (c)) is carried out for a sufficient period to produce suitable yields of virus, such as 2 to 10 days, or optionally 3 to 7 days, after infection. In one embodiment of the method, the incubating of the cells (step (c)) is carried out for 2 days, or 3 days, or 4 days, or 5 days, or after 6 days, or 7 days after infection. In other embodiments the incubating of the cells (step (c)) is carried out for 40 to 96 hours after infection. In a specific embodiment, the incubating of the cells (step (c)) is carried out for about 48 to about 72 hours after infection.

In certain embodiments of the method, the cells can, for example, be incubated after infection with viruses (step (b)) such that the agitation rate, pH, $pO_2$ value, $CO_2$ concentration and other parameters are maintained as described supra (see Sections 7.3.2 and 7.3.3).

In certain embodiments, the method further comprises, after step (c), the step of harvesting the culture medium containing the replicated virus (i.e., the culture medium in which infected cells have been grown). The harvested culture medium containing the replicated virus is also referred to herein as the "viral harvest".

In one embodiment any microcarriers utilized in the propagation of the MDCK cells are allowed to settle prior to harvesting the culture medium containing the replicated virus. Optionally, or alternatively, the culture medium containing the replicated virus can be harvested utilizing a alternating low shear tangential flow (ATF) device, see for example U.S. Pat. No. 6,544,424. The use of an ATF device can reduce or even eliminate the time needed to let microcarriers settle prior to harvest. In another embodiment, the viral harvest is stabilized with a suitable buffer.

In a specific embodiment, the viral harvest is stabilized by the addition of a concentrated buffer including but not limited to a sucrose phosphate (SP) buffer, which may be added to obtain a final concentration of about 218 mM sucrose, 11 mM phosphate buffer pH 7.0-7.4 in the stabilized viral harvest.

In another specific embodiment, step of harvesting the culture medium containing the replicated virus is coupled to the purification of the replicated viruses. For example, alternating tangential flow (ATF) may be used harvest the culture medium containing the replicated virus and the harvested material may be directly subjected one or more of the purification steps detailed infra.

7.5 Purification of Vaccine Material

The present invention provides robust methods for the purification of viruses, in particular live viruses for clinical use that have been replicated in cell culture. The purification methods of the invention may be used to purify viruses from cultures of mammalian cells including, but not limited to, human diploid lung fibroblast cell lines (e.g., MRC-5 and WI-38), human retinoblastoma cell lines, human kidney cell lines (e.g., PER.C6 and 293), fetal rhesus lung cell lines (e.g., FRhL2), African green monkey kidney cell lines (e.g., Vero), and canine kidney cell lines (e.g., MDCK). The purification methods of the invention give a high overall recovery of virus, in particular live virus and result in levels of host cell DNA (HCD), host cell protein (HCP) and non-specific endonuclease (e.g. Benzonase), which are below the specifications required by regulatory agencies.

Reducing the amount of HCD from virus preparations is particularly important for those viruses that are intended for clinical use in animals (including humans). Furthermore, it is contemplated that the size of any residual HCD should be smaller than the average size of an oncogene (1,925 base pairs) to reduce the oncogenic potential. Accordingly, in one aspect the present invention provides methods for the purification of influenza viruses or RSV that reduce the quantity and size of any residual HCD to levels below that acceptable for injectable vaccines (WHO recommendation is 10 ng per dose for parenterally administered vaccines; Griffiths, 1999, Dev Biol Stand. Basel, Karger, vol 98, pp 153-157.).

In certain embodiments, the purified viruses comprise less than about 10 ng HCD/dose, or less then about 9 ng HCD/dose, or less then about 8 ng HCD/dose, or less then about 7 ng HCD/dose, or less then about 6 ng HCD/dose, or less then about 5 ng HCD/dose, or less then about 4 ng HCD/dose, or less then about 3 ng HCD/dose, or less then about 2 ng HCD/dose, or less then about 1 ng HCD/dose, or less then about 0.8 ng HCD/dose, or less then about 0.6 ng HCD/dose, or less then about 0.4 ng HCD/dose, or less then about 0.2 ng HCD/dose. In a specific embodiment, the purified viruses comprise less than about 1 ng HCD/dose or less then about 0.8 ng HCD/dose, or less then about 0.6 ng HCD/dose, or less then about 0.4 ng HCD/dose, or less then about 0.2 ng HCD/dose.

In other embodiments, the purified viruses are influenza viruses and comprise less than about 10 ng HCD/7.0±0.5 $\log_{10}$ FFU, or less then about 9 ng HCD/7.0±0.5 $\log_{10}$ FFU, or less then about 8 ng HCD/7.0±0.5 $\log_{10}$ FFU, or less then about 7 ng HCD/7.0±0.5 $\log_{10}$ FFU, or less then about 6 ng HCD/7.0±0.5 $\log_{10}$ FFU, or less then about 5 ng HCD/7.0±0.5 $\log_{10}$ FFU, or less then about 4 ng HCD/7.0±0.5 $\log_{10}$ FFU, or less then about 3 ng HCD/7.0±0.5 $\log_{10}$ FFU, or less then about 2 ng HCD/7.0±0.5 $\log_{10}$ FFU, or less then about 1 ng HCD/7.0±0.5 $\log_{10}$ FFU, or less then about 0.8 ng HCD/7.0±0.5 $\log_{10}$ FFU, or less then about 0.6 ng HCD/7.0±0.5 $\log_{10}$ FFU, or less then about 0.4 ng HCD/7.0±0.5 $\log_{10}$ FFU, or less then about 0.2 ng HCD/7.0±0.5 $\log_{10}$ FFU. In a specific embodiment, the purified viruses comprise less than about 1 ng HCD/7.0±0.5 $\log_{10}$ FFU or less then about 0.8 ng HCD/7.0±0.5 $\log_{10}$ FFU, or less then about 0.6 ng HCD/7.0±0.5 $\log_{10}$ FFU, or less then about 0.4 ng HCD/7.0±0.5 $\log_{10}$ FFU, or less then about 0.2 ng HCD/7.0±0.5 $\log_{10}$ FFU.

In one embodiment, the amount of HCD is determined using a PicoGreen Assay. In another embodiment, the amount of HCD is determined using a real time polymerase chain reaction (rtPCR). These assays may be performed using methods exemplified in the Example provided in Section 0.

In certain embodiments, at least about 50%, or at least about 60%, or at least about 70%, or at least about 80% of the HCD present in the purified viruses is less than about 1000 base pairs (bp) in length. In a specific embodiment, at least about 80% of the HCD present in the purified viruses is less than about 1000 bp in length. In another specific embodiment, about 90% of the HCD present in the purified viruses is less than about 1000 bp in length. In other embodiments, at least about 40%, or at least about 50%, or at least about 60%, or at least about 70%, or at least about 80% of the HCD present in the purified viruses is less than about 500 bp in length. In a specific embodiment, at least about 60% of the HCD present in the purified viruses is less than about 500 bp in length.

In some embodiments, the purified viruses and comprise less than about 10 μg HCP/dose, or less then about 9 μg HCP/dose, or less then about 8 μg HCP/dose, or less then about 7 μg HCP/dose, or less then about 6 μg HCP/dose, or less then about 5 μg HCP/dose, or less then about 4 μg HCP/dose, or less then about 3 μg HCP/dose, or less then about 2 μg HCP/dose, or less then about 1 μg HCP/dose, or less then about 0.8 μg HCP/dose, or less then about 0.6 μg HCP/dose, or less then about 0.4 μg HCP/dose, or less then about 0.2 μg HCP/dose. In a specific embodiment, the purified viruses comprise less than about 1 ng HCP/dose, or less then about 0.8 μg HCP/dose or less then about 0.6 μg HCP/dose, or less then about 0.4 μg HCP/dose, or less then about 0.2 μg HCP/dose.

In other embodiments, the purified viruses the purified viruses are influenza viruses and comprise less than about 10 μg HCP/7.0±0.5 $\log_{10}$ FFU, or less then about 9 μg HCP/7.0±0.5 $\log_{10}$ FFU, or less then about 8 μg HCP/7.0±0.5 $\log_{10}$ FFU, or less then about 7 μg HCP/7.0±0.5 $\log_{10}$ FFU, or less then about 6 μg HCP/7.0±0.5 $\log_{10}$ FFU, or less then about 5 μg HCP/7.0±0.5 $\log_{10}$ FFU, or less then about 4 μg HCP/7.0±0.5 $\log_{10}$ FFU, or less then about 3 μg HCP/7.0±0.5 $\log_{10}$ FFU, or less then about 2 μg HCP/7.0±0.5 $\log_{10}$ FFU, or less then about 1 μg HCP/7.0±0.5 $\log_{10}$ FFU, or less then about 0.8 μg HCP/7.0±0.5 $\log_{10}$ FFU, or less then about 0.6 μg HCP/7.0±0.5 $\log_{10}$ FFU, or less then about 0.4 μg HCP/7.0±0.5 $\log_{10}$ FFU, or less then about 0.2 μg HCP/7.0±0.5 $\log_{10}$ FFU. In a specific embodiment, the purified viruses comprise less than about 1 μg HCP/7.0±0.5 $\log_{10}$ FFU, or less then about 0.8 μg HCP/7.0±0.5 $\log_{10}$ FFU or less then about 0.6 μg HCP/7.0±0.5 $\log_{10}$ FFU, or less then about 0.4 μg HCP/7.0±0.5 $\log_{10}$ FFU, or less then about 0.2 μg HCP/7.0±0.5 $\log_{10}$ FFU.

In one embodiment, the amount of HCP is determined by an Enzyme-Linked Immunosorbent Assay (ELISA) using an antibody against HCP for detection. This assay may be performed using methods exemplified in the Example provided in Section 0.

Methods for the preparation of inactive/disintegrated virus particles for vaccine compositions are well known in the art and have been utilized for over 40 years. However, these methods incorporate harsh steps, such as treatment with detergents of formaldehyde, which cannot be utilized for the preparation of intact virus particles generally, and live attenuated viruses in particular. Accordingly, the present invention provides methods for the purification of live intact viruses (e.g., influenza viruses or RSV) utilizing membranes and conditions to adequately separate HCD and HCP from the viral harvest. The methods of the present invention give a high overall recovery of live virus. In one embodiment, the overall recovery of purified viruses is at least 15%, or at least 20%, or at least 25%, or at least 30%, or at least 40%, or at least 50%, or at least 60%, or at least 70%. Methods to monitor the recovery of purified live virus include assays designed to measure viral infection and/or growth. For example, Focal Fluorescent Assays and Median Tissue Culture Infectious Dose ($TCID_{50}$) Assays can be used to monitor the recovery of purified live influenza virus. In certain embodiments, the method of purification of viruses of the instant invention gives an overall recovery of viruses of at least 30%, wherein the purified viruses comprise less than 0.1 ng HCD, and less than 0.3 µg HCP, and less than 0.0050 ng non-specific nuclease per 7.0±0.5 $\log_{10}$ FFU of virus.

The purification of virus harvest contains multiple steps, which can be optimized depending on the virus and purification conditions. In certain embodiments, the purification process may comprise anyone of the following, alone or in combination, a) clarification of viral harvest; b) concentration and/or buffer exchange; c) purification by chromatography and d) sterile filtration. These steps may comprise further steps such as treatment with a non-specific endonuclease and stabilization of the viral harvest or viral load. These steps may be performed multiple times in the purification process and in an order that maximizes the viral recovery while adequately removing HCP and HCD, as described above.

Methods useful for the clarification of a viral harvest include, but are not limited to, centrifugation, dialysis, and membrane filtration, which includes, but is not limited to, methods such as single pass, dead-end, direct flow filtration (DFF) in which liquid flows directly through the filter medium, and crossflow or tangential flow filtration (TFF) in which liquid flows tangential to (along) the surface of the membrane. TFF systems may be run so as to maintain a constant Filtrate Flux rate (often referred as simply "Flux" and which may be measured as liters of permeate per square meter of membrane per hour (LMH)) or to maintain a constant transmembrane pressure (abbreviated as "TMP" which may be measured as pounds per square inch (psi)). However, either constant Flux and the TMP may be regulated to prevent membrane fouling. Membranes for use in filtration applications are available from commercial sources.

Within the art, there are four commonly accepted categories of membranes defined by the size of the material they remove from the carrier liquid. They are, from the smallest to largest pore size are reverse osmosis membranes, nanofiltration membranes, ultrafiltration membranes, and microfiltration membranes. Filtration with the above-mentioned membranes separates molecules according to their molecular weight by using membranes with specific pore sizes. For example, separation with reverse osmosis membranes that have pore sizes less than 0.001 micrometers is intended to separate molecules that have a molecular weight less than 200 Daltons. Filtration with nanofiltration membranes that have pore sizes from 0.001-0.008 micrometers, inclusive, is intended to separate molecules that have a molecular weight from 200 Daltons to 15 kilodaltons (kDa) inclusive. Filtration with ultrafiltration membranes that have pore sizes from 0.005-0.1 micrometers, inclusive, is intended to separate molecules that have a molecular weight from 5 kDa-300 kDa, inclusive. Filtration with microfiltration membranes that have pore sizes from 0.05-3.0 micrometers, inclusive, is intended to separate molecules that have a molecular weight from 100 kDa-3000 kDa and larger. Accordingly, membrane-filtration can separate molecules of interest (e.g., viruses) from other cellular components based on size exclusion by utilizing membranes that have a particular Molecular Weight Cut-Off (MWCO) that is determined by the pore size of the membrane. The MWCO, also called Nominal Molecular Weight Limit (NMWL) or Nominal Molecular Weight Cut-Off (NM-WCO), is the kilodalton size designation for the filtration by membranes. The MWCO is defined as the molecular weight of the molecule that is 90% retained by the membrane. Because, for example, molecules of the same molecular weight can have significantly different shapes, the MWCO is not an exact metric, but is nevertheless a useful metric and is commonly employed by filter manufacturers. Membranes may be used as flat sheets or in a spirally wound configuration. Hollow fibers may also be used depending on the type of filtration method. Any number of potential membrane materials may be used including, but not limited to, regenerated cellulose, polyether sulfone (which may or may not be modified to alter its inherent hydrophobicity), polyvinylidene fluoride (PVDF), and ceramic and metal oxide aggregates, as well as polycarbonate, polypropylene, polyethylene and PTFE (TEFLON®). It is contemplated that combinations of filtration methods and membrane types may be used in separation and that the capacity of the filters, columns, etc., comprising separation membranes will be adjusted depending on the volume and/or concentration of material being processed.

Methods useful for concentrating and/or buffer exchange include, but are not limited to, dialysis, ultrafiltration (UF) and diafiltration (DF). TFF can incorporate both UF, which can be used to concentrate, and DF, which can be used to exchange buffers. Furthermore, the use of UF and/or DF may result in additional purification by the fractionation process that washes smaller molecules, which may be contaminants, through a membrane and leaves larger molecules of interest in the retentate. Accordingly, TFF, incorporating UF and/or DF may be used to concentrate and/or exchange buffers and/or purify. The choice of membranes for use in filtration applications has been described supra. According to the invention, DF can be either discontinuous or continuous DF. In discontinuous DF, the solution is concentrated, and the lost volume is replaced by a new buffer. In continuous DF, the solution volume is maintained by the inflow of new buffer solution while the old buffer solution is removed.

In certain embodiments, the clarified virus is concentrated about 2×, or about 3×, or about 4×, or about 5×, or about 6×, or about 7×, or about 8×, or about 9×, or about 10×, or more, wherein "×" equals the Total starting volume added to the operation/final retentate volume. In a specific embodiment, the clarified virus is concentrated between about 3× to about 5×. In another specific embodiment, the clarified virus is concentrated about 4×, wherein "×" equals the Total starting volume added to the operation/final retentate volume. In certain embodiments, the clarified virus is concentrated about 10× or more to increase the loading of all subsequent purification steps. In certain embodiments, following concentration about 1 diavolume, or about 2 diavolumes, or about 3 diavolumes, or about 4 diavolumes, or about 5 diavolumes, or about 6 diavolumes, or about 7 diavolumes, or about 8 diavolumes, or about 9 diavolumes or about 10 diavolumes, or more diavolumes of buffer are exchanged by DF, wherein a diavolume is the total buffer volume introduced to the operation during DF/retentate volume. In a specific embodiment, between about 4 diavolumes to about 6 diavolumes of buffer are exchanged wherein a diavolume is the total buffer volume introduced to the operation during DF/retentate volume. In another specific embodiment, about 5 diavolumes of buffer are exchanged, wherein a diavolume is the total buffer volume introduced to the operation during DF/retentate volume.

In certain embodiments, the retentate, comprising viruses (e.g., influenza, RSV), is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "conditioned viral load" or as the "#XUF #XDF" where "#" indicates either the fold concentration or the number of diavolumes of buffer exchanged for the UF and DF processes, respectively. In a specific embodiment, a membrane with a 500 kDa MWCO is used for the concentration and buffer exchange. In some embodiments, the membrane may be cleaned post process and reused. In other embodiments, a new membrane is used for each batch of clarified virus. In another specific embodiment, the clarified harvest is concentrated and the buffer exchanged as exemplified in the Examples provided in Sections 0 and 9.6.3.

Types of chromatography useful for the purification of viruses (e.g., influenza or RSV) include, but are not limited to, affinity chromatography as well as ion-exchange chromatography and/or hydroxyapatite chromatography. In certain embodiments, ion exchange chromatography is used. In one embodiment, cation exchange chromatography is used. In another embodiment, cation exchange chromatography is performed at high pH. In one embodiment, anion exchange chromatography is used. In a specific embodiment, a strong quaternary ammonium (Q) anion exchanger is used (e.g. Capto™ Q, GE Healthcare) In another embodiment, anion exchange chromatography is performed at low pH. Anion media useful for ion exchange chromatography include, but are not limited to, anion membrane adsorbers (e.g., Sartobind® Q15, D15) and cation membrane adsorbers (e.g., Sartobind® S15 and C15). In another embodiment, negative chromatography is used wherein the impurities are bound by anion or cation-exchange and virus is subsequently separated or purified from the impurities such as host cell protein and/or nucleic acid. It is contemplated that the chromatography can be performed in a batch process or alternatively utilizing a column process. In certain embodiments, the conditioned viral load is purified by column chromatography.

Methods useful for the efficient removal of contaminating HCD include, along with the other steps of the purification process, treatment with a non-specific endonuclease (e.g., Benzonase®). However, for those viruses that are intended for clinical use in animals (including humans) it is desirable that the amount of non-specific endonuclease in the final purified viruses be minimal. Accordingly, in another aspect the present invention provides methods for the purification of viruses that reduce the quantity any residual non-specific endonuclease used in the method to levels below that acceptable for injectable vaccines.

In one embodiment, the purified viruses comprise less than about 0.0060 ng, or less then about 0.0055 ng, or less then about 0.0050 ng, or less then about 0.0045 ng, or less then about 0.0040 ng, or less then about 0.0035 ng, or less then about 0.0030 ng, or less then about 0.0025 ng, or less then about 0.0020 ng, or less then about 0.0015 ng, or less then about 0.0010 ng, or less of non-specific endonuclease per dose. In a specific embodiment, the purified viruses comprise less than about 0.0040 ng, or less then about 0.0035 ng, or less then about 0.0030 ng, or less then about 0.0025 ng of non-specific endonuclease per dose.

In other embodiments, the purified viruses the purified viruses are influenza viruses or RSV and comprise less than about 0.0060 ng, or less then about 0.0055 ng, or less then about 0.0050 ng, or less then about 0.0045 ng, or less then about 0.0040 ng, or less then about 0.0035 ng, or less then about 0.0030 ng, or less then about 0.0025 ng, or less then about 0.0020 ng, or less then about 0.0015 ng, or less then about 0.0010 ng, or less of non-specific endonuclease per $7.0\pm0.5$ $\log_{10}$ FFU. In a specific embodiment, the purified viruses are influenza viruses or RSV and comprise less than about 0.0040 ng, or less then about 0.0035 ng, or less then about 0.0030 ng, or less then about 0.0025 ng of non-specific endonuclease per $7.0\pm0.5$ $\log_{10}$ FFU. In another specific embodiment, the purified viruses are RSV and comprise less than about 0.0040 ng, or less then about 0.0035 ng, or less then about 0.0030 ng, or less then about 0.0025 ng of non-specific endonuclease per $5.0\pm0.5$ $\log_{10}$ FFU. In yet another specific embodiment, the non-specific endonuclease is Benzonase®.

Sterility is of particular importance for those viruses and/or viral components that are intended for clinical use in animals (including humans). Accordingly, the methods for the purification of viruses (e.g., influenza or RSV) of the present invention incorporate sterilization, which can be performed as a terminal filtration step (e.g., RSV) or using know sterilization methods (e.g., Influenza virus). Methods useful for the sterilization of vaccine components (e.g., viruses, delivery devices, etc.) include, but are not limited to, irradiation, filtration, chemical treatment, and other suitable procedures. In one embodiment, the formulated virus bulk is sterilized by filtration. Filtration methods useful for sterilization include, but are not limited to, single pass, dead-end, direct flow filtration (DFF) and tangential flow filtration (TFF), which have been described supra. However, due to the fragile nature of RSV the virus can not be sterilized using a sterilization grade filter. Thus, in one embodiment, RSV is sterilized as part of a terminal filtration step during the purification process described herein.

Herein are provided specific methods for purifying influenza virus and RSV for vaccine formulation.

7.5.1 Purification of Influenza Viruses

In certain embodiments, the viruses to be purified are influenza viruses (e.g., cold-adapted, and/or temperature sensitive, and/or attenuated).

In one embodiment the method of purifying viruses from cell culture comprises the following steps:
(a) clarification of a viral harvest;
(b) concentration and/or buffer exchange following step (a);
(c) purification by chromatography following step (b);
(d) concentration and/or buffer exchange following step (c); and
(e) sterilization following step (d).

In one embodiment, the viruses are influenza viruses. In a specific embodiment, the influenza viruses are cold-adapted, and/or temperature sensitive, and/or attenuated influenza viruses.

In a specific embodiment, steps (a), (b), (d) and (e) are performed by membrane filtration. In another specific embodiment, steps (b) and (d) are performed by tangential flow filtration. In still another specific embodiment, steps (a) and (e) are performed by direct flow filtration. In yet another specific embodiment, step (b) includes both concentration by ultrafiltration and buffer exchange by diafiltration. In still another specific embodiment, step (d) includes only concentration. Additional embodiments of the method of purifying viruses are detailed infra.

In one specific embodiment, step (c) is performed by affinity column chromatography. In another specific embodiment, step (c) further incorporates treatment with a non-specific nuclease.

As described supra, viruses obtained from cell culture may be stabilized (e.g., by the addition of a sucrose phosphate (SP)), after harvest. Accordingly, the purification methods of the present invention encompass the clarification of a stabilized viral harvest. Alternatively, the steps of harvesting and clarification may be coupled. For example, ATF may be used to harvest cell culture replicated virus and pump the viral harvest directly to the media and/or device used for clarification of the virus.

For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a semi-permeable membrane of a defined range of pore sizes large enough to allow passage of the virus while retaining intact cells and other large particulate matter.

In one embodiment, the viral harvest is clarified by DFF and/or TFF using a MF membrane having a pore size large enough for the virus to pass through but small enough to retain intact cells and cellular debris. In one embodiment, the viral harvest is clarified by DFF and/or TFF through at least one membrane having a pore size of about 1.2 micrometers or less. In a specific embodiment, the viral harvest is clarified by DFF through at least one membrane having a pore size of between about 1.2 micrometers to about 0.45 micrometers. In another specific embodiment, the viral harvest is clarified by DFF through a first membrane have a pore size of 1.2 micrometers and a second membrane having a pore size of 0.45 micrometers. In certain embodiments, polypropylene and/or PVDF membranes are used. In still another specific embodiment, the viral harvest is clarified by DFF as exemplified in the Example provided in Section 0. In yet another specific embodiment, the harvesting of the cell culture replicated virus is coupled to the DFF step. For example, the cell culture replicated virus is harvested and applied directly to the media and device used for DFF. The coupling of the harvest and clarification steps reduces the number of manipulations, avoids the need for a harvest tank and reduces overall processing time.

In one embodiment, the clarified harvest is concentrated and/or the buffer is exchanged. In one embodiment, concentration and/or buffer exchange is performed by UF and DF. In another embodiment, TFF is used for both the UF and DF. In yet another embodiment, the harvesting of the cell culture replicated virus is coupled to the DFF step which is coupled to the TFF step. The coupling of the harvest, clarification and concentration/buffer exchange steps reduces the number of manipulations, and reduces overall processing time. In certain embodiments, the TFF is run so as to maintain a constant Filtrate Flux rate. In other embodiments, the TFF is run so as to maintain a constant TMP. In certain embodiments, the clarified virus is first concentrated by UF and then the buffer is exchanged by DF. In certain embodiments, the clarified virus is concentrated about 2×, or about 3×, or about 4×, or about 5×, or about 6×, or about 7×, or about 8×, or about 9×, or about 10×, or more, wherein "×" equals the Total starting volume added to the operation/final retentate volume. In a specific embodiment, the clarified virus is concentrated between about 3× to about 5×. In another specific embodiment, the clarified virus is concentrated about 4×, wherein "×" equals the Total starting volume added to the operation/final retentate volume. In certain embodiments, the clarified virus is concentrated about 10× or more to increase the loading of all subsequent purification steps. In certain embodiments, following concentration about 1 diavolume, or about 2 diavolumes, or about 3 diavolumes, or about 4 diavolumes, or about 5 diavolumes, or about 6 diavolumes, or about 7 diavolumes, or about 8 diavolumes, or about 9 diavolumes or about 10 diavolumes, or more diavolumes of buffer are exchanged by DF, wherein a diavolume is the total buffer volume introduced to the operation during DF/retentate volume. In a specific embodiment, between about 4 diavolumes to about 6 diavolumes of buffer are exchanged wherein a diavolume is the total buffer volume introduced to the operation during DF/retentate volume. In another specific embodiment, about 5 diavolumes of buffer are exchanged, wherein a diavolume is the total buffer volume introduced to the operation during DF/retentate volume. It is contemplated that the exchange buffer may be the same or different from that present in the viral harvest. In one embodiment, the exchange buffer is an SP buffer at a neutral pH. In a specific embodiment, the exchange buffer comprises (within 10% variation of one or more component) 218 mM sucrose, 11 mM phosphate buffer pH 7.0-7.4. In another specific embodiment, the exchange buffer consists (within 10% variation of one or more component) of 218 mM sucrose, 11 mM phosphate buffer, pH 7.0-7.4. In certain embodiments, the retentate, comprising viruses (e.g., influenza), is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "conditioned viral load" or as the "#XUF #XDF" where "#" indicates either the fold concentration or the number of diavolumes of buffer exchanged for the UF and DF processes, respectively. In a specific embodiment, a membrane with a 500 kDa MWCO is used for the concentration and buffer exchange. In some embodiments, the membrane may be cleaned post process and reused. In other embodiments, a new membrane is used for each batch of clarified virus. In another specific embodiment, the clarified harvest is concentrated and the buffer exchanged as exemplified in the Examples provided in Sections 0 and 9.6.3.

In certain embodiments, the conditioned viral load is purified by chromatography. In certain embodiments, the conditioned viral load is purified by column chromatography. In some embodiments, the conditioned viral load is purified by affinity chromatography. A variety of affinity chromatography media are available with similar separation properties, for example numerous affinity chromatography media are available for the concentration and purification of a number of viruses and viral proteins, including, but not limited to N(p-Aminophenyl)oxamic acid agarose, Cellufine™ Sulfate. Methods useful for evaluating the performace of affinity ligands are exemplified in Example 9.7. In a specific embodiment, Cellufine™ Sulfate (Chisso Corp.) affinity media is utilized for affinity chromatography. In another embodiment, FluSelect™ is utilized for affinity chromatography. In still another embodiment, the binding ligand of the affinity media comprises a sulfate moiety. In certain embodiments, the conditioned viral load is loaded directly onto an affinity media. In certain embodiments the unbound material may be passed over the affinity media to facilitate the binding of additional viruses.

In one embodiment, between about $10^{9.0}$ to about $10^{11}$, or between about $10^{9.2}$ to about $10^{9.8}$, or between about $10^{9.4}$ to about $10^{9.6}$ virus particles, are loaded per ml of affinity media. In another embodiment, at least about $10^{9.0}$, or at least about $10^{9.1}$, or at least about $10^{9.2}$, or at least about $10^{9.3}$, or at least about $10^{9.4}$, or at least about $10^{9.5}$, or at least about $10^{9.6}$, or at least about $10^{9.7}$, or at least about $10^{9.8}$, or at least about $10^{9.9}$, or at least about $10^{10}$, or at least about $10^{10.2}$, or at least about $10^{10.4}$, or at least about $10^{10.6}$, or at least about $10^{10.8}$, or at least about $10^{11}$, virus particles are loaded per mL of affinity media. In certain embodiments, the virus particles are live viruses. Methods for determining the number of lives virus in a sample are described herein.

In another embodiment, between about 9.0 $\log_{10}$ FFU to about 11 $\log_{10}$ FFU, or between about 9.2 $\log_{10}$ FFU to about 9.8 $\log_{10}$ FFU, or between about 9.4 $\log_{10}$ FFU to about 9.6 $\log_{10}$ FFU of virus, are loaded per mL of affinity media. In another embodiment, at least about 9.0 $\log_{10}$ FFU, or at least about 9.1 $\log_{10}$ FFU, or at least about 9.2 $\log_{10}$ FFU, or at least about 9.3 $\log_{10}$ FFU, or at least about 9.4 $\log_{10}$ FFU, or at least about 9.5 $\log_{10}$ FFU, or at least about 9.6 $\log_{10}$ FFU, or at least about 9.7 $\log_{10}$ FFU, or at least about 9.8 $\log_{10}$ FFU, or at least about 9.9 $\log_{10}$ FFU, or at least about 10 $\log_{10}$ FFU, or at least about 10.1 $\log_{10}$ FFU, or at least about 10.2 $\log_{10}$ FFU, or at least about 10.3 $\log_{10}$ FFU, or at least about 10.4 $\log_{10}$ FFU, or at least about 10.5 $\log_{10}$ FFU, or at least about 10.6 $\log_{10}$ FFU, or at least about 10.7 $\log_{10}$ FFU, or at least about 10.8 $\log_{10}$ FFU, or at least about 10.9 $\log_{10}$ FFU, or at least about 11 $\log_{10}$ FFU of virus are loaded per mL of affinity media. In a specific embodiment, Cellufine™ Sulfate (Chisso Corp.) affinity media is utilized and between 9.2 $\log_{10}$ FFU to 9.8 $\log_{10}$ FFU of virus are loaded per mL of Cellufine™ Sulfate. In another specific embodiment, Cellufine™ Sulfate (Chisso Corp.) affinity media is utilized and between 9.4 $\log_{10}$ FFU to 9.6 $\log_{10}$ FFU of virus are loaded per mL of Cellufine™ Sulfate. Instill another specific embodiment, Cellufine™ Sulfate (Chisso Corp.) affinity media is utilized and at least about 9.4 $\log_{10}$ FFU, or at least about 9.5 $\log_{10}$ FFU, or at least about 9.6 $\log_{10}$ FFU, or at least about 9.7 $\log_{10}$ FFU of virus are loaded per mL of Cellufine™ Sulfate.

In one embodiment the affinity media is washed, with a sufficient volume of buffer in which the viruses will remain bound to the affinity media (e.g., an SP buffer), to remove unbound and weakly bound contaminates from the affinity media. In certain embodiments, the wash buffer comprises (within 10% variation of one or more component) 218 mM sucrose, 11 mM phosphate buffer pH 7.0-7.4. In another specific embodiment, the wash buffer consists of (within 10% variation of one or more component) 218 mM sucrose, 11 mM phosphate buffer pH 7.0-7.4. In certain embodiments, the viruses are eluted from the affinity media after washing, using a sufficient volume of a buffer in which the viruses will not bind to the affinity resin to elute the virus without releasing any contaminants bound to the column, and collected. In certain embodiments, the elution buffer comprises salt. Salts useful for the elution of viruses (e.g., influenza) from affinity columns include sodium chloride, potassium chloride, ammonium chloride, magnesium chloride, and calcium chloride. Generally, the elution buffer is applied to the resin as either a gradient or step in the 0 to 1.0M concentration range. The effectiveness of the cation and anion used as the salts in the elution buffer correlate with the Hofmeister series, where the order of displacement for commonly used cations is: $Ca^{2+} > Mg^{2+} > Na^+ > K^+ > NH_4^+$ and the order of displacement effectiveness for commonly used anions: $PO_4^{3-} > SO_4^{2-} > COO^- > Cl^-$. In one embodiment, the elution buffer comprises (within 10% variation) sodium chloride at a final concentration of 1M. In another embodiment, the elution buffer comprises (within 10% variation of one or more component) 1 M sodium chloride, 218 mM sucrose, and 11 mM phosphate buffer pH 7.0-7.4. The collected eluted virus is also referred to herein as the "purified virus eluate." The elution of the viruses can be monitored by monitoring ultraviolet (UV) absorbance, in particular by monitoring the absorbance at 280 nanometers. In some embodiments, the conditioned viral load is purified by column chromatography, wherein the elution of the viruses is monitored and specific fractions comprises viruses are collected. Such an approach can be useful when it is desirable to minimize the volume of the eluted virus. In another specific embodiment, the conditioned viral load is purified by chromatography as exemplified in the Example provided in Section 0.

In certain embodiments, the method of purifying viruses (e.g., influenza) includes treatment with a non-specific endonuclease (e.g., Benzonase). In certain embodiments, the non-specific endonuclease treatment occurs early in the purification of viruses. In one embodiment, non-specific endonuclease treatment occurs after step (a) but before step (b). In another embodiment, non-specific endonuclease treatment occurs after step (b) but before step (c). Alternatively, the virus is treated with a non-specific endonuclease during step (c). The advantages of this approach are exemplified in the Example provided in Section 0. In a specific embodiment, the conditioned viral load is bound to an affinity media and then is exposed to a buffer comprising a non-specific endonuclease. In some embodiments the non-specific endonuclease is present in the buffer at a concentration of between about 10 U/mL and about 100 U/mL. In other embodiments, the non-specific endonuclease is present in the buffer at a concentration of between about 40 U/mL to about 60 U/mL. In one embodiment, the non-specific endonuclease is present in a buffer comprising sucrose. In a specific embodiment, the non-specific endonuclease is present in a buffer comprising 218 mM sucrose, 11 mM phosphate buffer pH 7.0-7.4. In another specific embodiment, the specific endonuclease is present, at a final concentration of between about 40 U/mL to about 60 U/mL, in a buffer consisting of (within 10% variation of one or more component) 218 mM sucrose, 11 mM phosphate buffer pH 7.0-7.4. In certain embodiments, the loading and wash conditions are adjusted to ensure that the bound virus will be exposed to the non-specific endonuclease for between about 10 minutes to about 120 minutes. In one embodiment, the loading and wash conditions are adjusted to ensure that the bound virus will be exposed to the non-specific endonuclease for between about 40 minutes to about 80 minutes. In still other embodiments, the loading and wash conditions are adjusted to ensure that the bound virus will be exposed to the non-specific endonuclease for at least 10 minutes, or at least 20 minutes, or at least 30 minutes, or at least 40 minutes, or at least 50 minutes, or at least 60 minutes, or at least 70 minutes, or at least 80 minutes, or at least 90 minutes, or at least 100 minutes, or at least minutes, or at least 110 minutes, or at least 120 minutes. In certain aspects of the invention, the time of exposure to the non-specific endonuclease, the concentration of the non-specific endonuclease and the volume of non-specific endonuclease containing buffer can be adjusted. For example, to minimize the time needed to cleave DNA contaminates the concentration of non-specific endonuclease may be increased; alternatively to minimize the amount of non-specific endonuclease utilized the time of exposure may be increased. Following treatment with a non-specific endonuclease it may be desirable to wash the affinity media with a sufficient volume of buffer in which the viruses will remain bound to the affinity media (e.g., an SP buffer) to remove any residue digested DNA contaminates. Accordingly, in certain embodiments, the affinity resin is washed as described supra before and/or after treatment with a non-specific endonuclease. In another specific embodiment, the non-specific endonuclease is Benzonase®. In still another specific embodiment, the conditioned viral load is treated with Benzonase® at the same time as purification by affinity chromatography as exemplified in the Example provided in Section 0.

In one embodiment, the purified influenza viruses comprise less than about 0.0060 ng, or less then about 0.0055 ng, or less then about 0.0050 ng, or less then about 0.0045 ng, or less then about 0.0040 ng, or less then about 0.0035 ng, or less then about 0.0030 ng, or less then about 0.0025 ng, or less then about 0.0020 ng, or less then about 0.0015 ng, or less then about 0.0010 ng, or less of non-specific endonuclease per $7.0\pm0.5 \log_{10}$ FFU. In a specific embodiment, the purified influenza viruses comprise less than about 0.0040 ng, or less then about 0.0035 ng, or less then about 0.0030 ng, or less then about 0.0025 ng of non-specific endonuclease per $7.0\pm0.5 \log_{10}$ FFU. In another specific embodiment, the non-specific endonuclease is Benzonase®. In certain aspects of the invention, following purification by chromatography the purified virus eluate is concentrated and/or the buffer is exchanged. Methods useful for concentrating and/or buffer exchange have been described supra. In certain embodiments, the buffer of the purified virus eluate is exchanged using DF. In one embodiment, more than about 5 diavolumes of buffer are exchanged by DF, wherein a diavolume is the total buffer volume introduced to the operation during DF/retentate volume. The advantages of exchanging more than about 5 diavolumes are detailed in the Example provided in Section 0. In another embodiment, about 6 diavolumes, or about 7 diavolumes, or about 8 diavolumes, or about 9 diavolumes or about 10 diavolumes, or more diavolumes of buffer are exchanged by DF, wherein a diavolume is the total buffer volume introduced to the operation during DF/retentate volume. In a specific embodiment, about 8 diavolumes, or more diavolumes of buffer are exchanged by DF, wherein a diavolume is the total buffer volume introduced to the operation during DF/retentate volume. In a specific embodiment, the exchange buffer comprises (within 10% variation of one or more component) 200 mM sucrose, 100 mM phosphate buffer pH 7.0-7.4. In another specific embodiment, the exchange buffer consists (within 10% variation of one or more components) of 200 mM sucrose, 100 mM phosphate buffer, pH 7.0-7.4. In certain embodiments, the retentate, comprising viruses, is collected after the desired volume of buffer is exchanged. After collection of the retentate some virus may remain weakly bound to the membrane. Accordingly, in some embodiments, the membrane is rinsed with additional exchange buffer which is added to the collected retentate. The collected retentate is also referred to herein as "formulated virus bulk" or as the "#XDF," where "#" indicates number of diavolumes of buffer exchanged during a DF process, respectively. In a specific embodiment, a membrane with a 500 kDa MWCO is used for the concentration and/or buffer exchange. In some embodiments, the membrane may be cleaned post process and reused. In other embodiments, a new membrane is used for each batch of purified virus eluate. In another specific embodiment, the buffer of the purified virus eluate is exchanged as exemplified in the Example provided in Section 0. In still other embodiments, the clarified virus is concentrated by UF and the buffer is exchanged by DF as described supra. The incorporation of an UF step will decrease the volume of the resulting formulated virus bulk. In certain embodiments, the virus eluate is concentrated about 2×, or about 3×, or about 4×, or about 5×, or more, wherein "x" equals the Total starting volume added to the operation/final retentate volume. In other embodiments, the virus eluate is concentrated between 2× and 4×. In a specific embodiment, the virus eluate is concentrated about 2× and then the buffer is exchanged by DF as described supra. In a specific embodiment, the buffer of the purified virus eluate is concentrated and the buffer exchange as exemplified in the Example provided in Section 9.6.3.

In one embodiment, the formulated virus bulk is sterilized by DFF and/or TFF. In another embodiment, the formulated virus bulk is sterilized using a MF membrane having a pore size large enough for the virus to pass through but small enough to retain other contaminants. In one embodiment, the formulated virus bulk is sterilized by DFF and/or TFF through at least one membrane having a pore size of about 0.45 micrometers. In certain embodiments, polypropylene and/or PVDF membranes are used. In one embodiment, additional components are added to the formulated virus bulk prior to sterilization. In certain embodiments, at least one component selected from the group consisting of amino acid excipients (e.g., glutamate, arginine), protein hydrolysate (e.g., collagen, gelatin), chelating agents (e.g., EDTA) and preservatives is added to the formulated virus bulk prior to sterilization. In a specific embodiment, glutamate, arginine and gelatin are added to the formulated virus bulk prior to sterilization. In another specific embodiment, cGAG (200 mM sucrose, 100 mM phosphate, 12.1% w/v arginine, 10% gelatin and 54 mM or 0.9% glutamate) is added to the purified virus bulk in a ratio of 1:9 v/v. In another specific embodiment, monosodium glutamate, arginine and gelatin are added to the formulated virus bulk prior to sterilization at a final concentration (within 10% variation) of 5.4 mM or 0.09%, 1.21% w/v, and 1.% w/v, respectively. In still another specific embodiment, the formulated virus bulk is sterilized by DFF as exemplified in the Example provided in Section 0.

In a specific embodiment, the method of purifying influenza viruses from cell culture comprises the following steps:
 (a) clarification of a viral harvest by direct flow filtration (DFF) through at least one membrane having a pore size of between about 1.2 micrometers to about 0.45 micrometers;
 (b) concentration by tangential flow ultrafiltration (UF) and buffer exchange by diafiltration (DF) following step (a) using a membrane having 500 kDa molecular weight cut off (MWCO);
 (c) purification by affinity column chromatography following step (b);
 (d) buffer exchange by DF following step (c) using a membrane having 500 kDa molecular weight cut off (MWCO); and
 (e) sterilization following step (d) by DFF through at least one membrane having a pore size of between about 0.45 micrometers to about 0.22 micrometers,
 wherein overall recovery of purified viruses of at least 30%, and wherein the purified viruses comprise less than 0.1 ng HCD, and less than 0.3 µg HCP per $7.0\pm0.5 \log_{10}$ FFU of virus.

In certain embodiments, step (c) further incorporates treatment with a non-specific nuclease.

Additional parameters that may be incorporated in the method of purifying viruses from cell culture, in particular influenza viruses are exemplified in the Example provided in Section 0 below.

7.5.2 Purification of RSV

In a specific embodiment, the viruses to be purified are respiratory syncitial viruses (RSV) (e.g., rA2 cp248/404/1030ΔSH).

In one embodiment the method of purifying viruses from cell culture comprises the following steps:
(a) clarification of a viral harvest;
(b) stabilization and/or buffer exchange following step (a);
(c) concentration and/or buffer exchange following step (b);
(d) purification by chromatography following step (c); and
(e) terminal filtration following step (d).

In a specific embodiment, step (a) includes multiple filtration steps. In another specific embodiment, step (a) further incorporates treatment with a non-specific nuclease. In another specific embodiment, steps (a) and (c) are performed by direct flow filtration. In another specific embodiment, step (c) is performed by tangential flow filtration. In yet another specific embodiment, step (c) includes both concentration by tangential flow filtration and buffer exchange by diafiltration. In one specific embodiment, step (d) is performed by ion exchange chromatograph (e.g. cation-exchange). In still another embodiment, step (c) includes only concentration. Additional embodiments of the method of purifying viruses (e.g., RSV) are detailed infra.

The purification methods of the present invention encompass the clarification of a viral harvest. The crude medium from infected cultures can first be clarified by centrifugation at, e.g., 1000-2000×g for a time sufficient to remove cell debris and other large particulate matter, e.g., between 10 and 30 minutes. Alternatively, the supernatant containing the virus is filtered through a series of semi-permeable membranes of a defined range of pore sizes large enough to allow passage of the virus while retaining intact cells and other large particulate matter. This clarification step in the purification process may include the treatment with a non-specific endonuclease (e.g. Benzonase) to degrade cell host DNA wherein the viral harvest is a) filtered by direct flow filtration (DFF); b) treated with a non-specific endonuclease; and c) filtered again by DFF.

In one embodiment, the viral harvest is clarified by DFF and/or TFF using a MF membrane having a pore size large enough for the virus to pass through but small enough to retain intact cells and cellular debris. In certain embodiments, the viral harvest is clarified by DFF in combination with treatment of a non-specific endonuclease. In a specific embodiment the viral harvest is filtered through at least one membrane having a pore size of about 10 micrometers or less, followed by treatment with a non-specific endonuclease and then filtered again through at least one membrane having a pore size of about 3.0 micrometers or less. In a specific embodiment, the first filter step in the clarification process is through at least one membrane having a pore size of between about 5.0 micrometers to about 1.0 micrometers. In a specific embodiment, the second filter step in the clarification process is through at least one membrane having a pore size of between about 3.0 micrometers to about 0.45 micrometers. In certain embodiments the first or second filter step, alone or in combination, use a dual membrane filter, wherein two filters of different sizes are stacked to prevent the clogging of the filter with the smaller pore size. In one embodiment this dual filter is about 3/0.8 micrometers in size, wherein the 3 micrometer filter acts as a prefilter to remove larger cellular debris. In another specific embodiment, the viral harvest is clarified by DFF through a first membrane having a pore size of about 3.0 micrometers and a second membrane having a pore size of about 3/0.8 or about 0.65 micrometers.

In certain embodiments, the method of purifying viruses (e.g., RSV) includes treatment with a non-specific endonuclease (e.g., Benzonase®) to degrade the host cell DNA (HCD). In certain embodiments, the non-specific endonuclease treatment occurs early in the purification of viruses. In one embodiment, the virus is treated with a non-specific endonuclease during step (a). In a specific embodiment, the filtered viral harvest is mixed with a buffer comprising a non-specific endonuclease. In some embodiments the non-specific endonuclease is present in the buffer at a concentration of between about 5 U/mL and about 100 U/mL. In other embodiments, the non-specific endonuclease is present in the buffer at a concentration of between about 40 U/mL to about 60 U/mL. In a specific embodiment the non-specific endonuclease is present at about 50 U/ml. In one embodiment, the non-specific endonuclease is present in a buffer comprising about 1.0 mM to about 10 mM MgCl. In a specific embodiment, the buffer comprises 50 U/ml of a non-specific endonuclease and 5 mM of MgCl. In another specific embodiment, the MgCl is present at 2 mM.

Following the first filter step in the clarification process, the non-specific endonuclease is incubated with the filtered viral harvest for about 1 hour to about 4 hours. In a specific embodiment the non-specific endonuclease is incubated with the viral harvest for about 3 hours. In still other embodiments, the non-specific endonuclease is incubated under conditions adjusted to ensure that the virus will be exposed to the non-specific endonuclease for at least 10 minutes, or at least 20 minutes, or at least 30 minutes, or at least 40 minutes, or at least 50 minutes, or at least 60 minutes, or at least 70 minutes, or at least 80 minutes, or at least 90 minutes, or at least 100 minutes, or at least minutes, or at least 110 minutes, or at least 120 minutes, or at least 150 minutes, or at least 180 minutes, or at least 210 minutes, or at least 240 minutes. In certain aspects of the invention, the time of exposure to the non-specific endonuclease, the concentration of the non-specific endonuclease and the volume of non-specific endonuclease containing buffer can be adjusted. For example, to minimize the time needed to cleave DNA contaminates the concentration of non-specific endonuclease may be increased; alternatively to minimize the amount of non-specific endonuclease utilized the time of exposure may be increased. In a specific embodiment, the non-specific endonuclease is Benzonase®. Following treatment with a non-specific endonuclease the treated filtered viral harvest is filtered again to remove any residue digested DNA contaminates and remaining host cell debris.

In certain embodiments the Benzonase treated clarified viral harvest is stabilized by the addition of a sucrose phosphate (SP), tris sucrose (TS) or sucrose phosphate glutamate (SPG) buffer. These buffers may further contain a salt such as sodium chloride or potassium chloride. In one embodiment the, TS buffer contains about 2.5 mM to about 75 mM, pH 7.2 TrisCl and about 250 mM to about 150 mM sucrose. In a specific embodiment, the stabilization buffer contains 50 mM, pH 7.2 TrisCl and 218 mM sucrose. The TS buffers may further contain, alone or in combination, NaCl, KCl, $KH_2PO_4$ or $K_2HPO_4$. In one embodiment the concentration of NaCl or KCl is about 125 mM to about 175 mM. In a specific embodiment the stabilization buffer contains 5 mM, pH 7.2 TrisCl, 175 mM sucrose and 150 mM NaCl or 150 mM KCl. In another specific embodiment, the stabilization buffer contains 36 mM pH 7.2 TrisCl, 214 mM sucrose and 150 mM NaCl or KCl. In one embodiment the $KH_2PO_4$ or $K_2HPO_4$ is present at about 10 mM to about 2.5 mM. In a specific embodiment the stabilization buffer contains 5 mM, pH 7.2 TrisCl, 175 mM sucrose, 150 mM NaCl and 5 mM $KH_2PO_4$. In another embodiment, the stabilization buffer is SPG, wherein the buffer contains 218 mM sucrose, 3.8 mM $KH_2PO_4$, 7.2 mM $K_2HPO_4$ and 5 mM Sodium Glutamate. One of skill in the art will recognize that the concentrations of the stabilization buffers can be altered depending on the virus, the viral harvest and purification conditions to obtain the highest yield of stabilized viral harvest.

In certain embodiments, the clarified harvest is concentrated and/or the buffer is exchanged. In one embodiment, concentration and/or buffer exchange is performed by UF and DF. In another embodiment, TFF is used for both the UF and DF. In certain embodiments, the TFF is run so as to maintain a constant Filtrate Flux rate. In other embodiments, the TFF is run so as to maintain a constant TMP. In a specific embodiment the UF step is performed using a 500 kDa hollow fiber cartridge (GE Healthcare) wherein the viral harvest is concentrated 5-fold using an operation TMP of 15 psi and a shear rate of 12000 sec$^{-1}$. These parameters can be altered depending on the virus and the purification conditions to maximize the ultimate virus yield for final vaccine formulation.

In certain embodiments, the clarified virus is first concentrated by UF and then the buffer is exchanged by DF. It is contemplated that the exchange buffer may be the same or different from that present in the viral harvest. In addition, the exchange buffer may be the same or different from the final formulation buffer depending on additional buffer exchange steps. In one embodiment, the exchange buffer is an SP, TS or a sucrose citrate buffer at a neutral pH. In a specific embodiment the exchange buffer comprises about 7-25% w/v sucrose, thus providing a low to high range of sucrose of about 100 mM to about 800 mM. In one embodiment, the exchange buffer comprises NaCl or KCl at a concentration of about 1 mM to about 150 mM. In another embodiment the exchange buffer comprises TrisCl at a concentration of about 2.5 mM to about 10 mM. In yet another embodiment, the exchange buffer comprises sodium or potassium citrate at a concentration of about 5.0 mM to about 50 mM. In one embodiment, the exchange buffer comprises potassium phosphate at a concentration of about 50 mM to about 150 mM. Examples of specific exchange buffers include, but are not limited to, 5 mM TrisCl; 7-25% w/v sucrose; 1 mM to 150 mM NaCl; 20 mM sodium or potassium citrate, 7-25% w/v sucrose, 150 mM NaCl or KCl; and 100 mM potassium phosphate, 7-25% w/v sucrose, 150 mM KCl. In a specific embodiment, the exchange buffer comprises 25% w/v sucrose, about 100 mM potassium phosphate buffer and about 150 mM KCl, pH 7.2. In another specific embodiment, the exchange buffer comprises 25% w/v sucrose, about 5 mM TrisCl and about 150 mM NaCl, pH 7.2. The exchange buffer components can be modified depending on the virus and the purification conditions to maximize viral yield of the chromatography step and the final filtration step.

In certain embodiments, the stabilized viral harvest is further purified by chromatography as described supra. In some embodiments, ion exchange chromatography is used (e.g., anion or cation). In a specific embodiment, following volume reduction by UF and buffer exchange by diafiltration of the treated clarified viral harvest the virus is further purified by ion-exchange chromatography. This chromatography step, or polishing step, is performed in one embodiment using negative chromatography. In this embodiment a surface (e.g., polymeric beads) is derivatized to bind HCD or HCP while excluding the binding of the virus particles thus allowing the virus to pass by the surface. This concept could also be applied to other surfaces such that the buffer comprising the virus particles can pass over or by the derivatized surface. The complete chromatography process is free of additives and easily scalable for use in large scale production of virus for vaccine formulation. It is contemplated that the chromatography can be performed in a batch process or alternatively utilizing a column process. In certain embodiments, the conditioned viral load is purified by column chromatography.

Following either the chromatography step, if performed, or the buffer exchange, the concentrated viral harvest is subjected to a sterilization step. In one embodiment, the sterilization step is a terminal filtration step. In one embodiment the termination filtration is DFF through at least one membrane having a pore size 3 micrometers or less. In a specific embodiment the filter is a dual 3/0.8 micrometer membrane. In another specific embodiment the filter is about 1 mM or less. In one aspect the filter is 0.8, 0.65 or 0.45 micrometers.

In a specific embodiment, the method of purifying respiratory syncitial virus from virus-infected cells comprises the following steps:
a. clarifying a viral harvest comprising;
   i. filtering the viral harvest by direct flow filtration (DFF) through at least one clarification filter having a pore size of between about 10 micrometers to about 3 micrometers;
   ii. treating the viral harvest with a non-specific endonuclease;
   iii. filtering the viral harvest by DFF through at least one clarification filter having a pore size of between about 3 micrometers to about 0.45 micrometers;
b. stabilizing the clarified viral harvest with sucrose, phosphate or Tris buffer with salt (NaCl or KCl);
c. concentrating the stabilized viral harvest by tangential flow filtration (TFF) and performing buffer exchange by diafiltration (DF) using a hollow fiber cartridge with the molecular weight cut off (MWCO) between 500 kDa-0.1 μm;
d. filtering the concentrated viral harvest by DFF through at least one clarification filter having a pore size of between about 0.8 micrometers to about 0.45 micrometers;
   whereby the respiratory syncitial virus is purified from the virus-infected cells and has a final viral infectivity titer of at least 5.7 $\log_{10}$ FFU/mL In another specific embodiment the purification method comprises a step of purification by cation-exchange chromatography following concentrating of the viral harvest and buffer exchange.

7.6 Vaccine Compositions and Methods of Use

The invention further relates to viruses (e.g., influenza or RSV) which are obtainable by a method of the invention. These viruses can be formulated by known methods to provide a vaccine for administration to humans or animals. The viruses can be present as intact virus particles (e.g., live attenuated viruses) or as inactive/disintegrated virus (e.g., treated with detergents of formaldehyde). Optionally, a defined viral component (e.g., protein) may be isolated from the viruses by methods know to the person skilled in the art, and used in the preparation of a vaccine. Methods for the generation and formulation of inactive/disintegrated virus particles for vaccine compositions are well known in the art and have been utilized for over 40 years.

7.6.1 Influenza Virus Vaccine

The formulation of intact virus particles (e.g., live attenuated viruses) may include buffers, amino acid excipients (e.g., glutamate, arginine), protein hydrolysate (e.g., collagen, gelatin), chelating agents (e.g., EDTA) and preservatives. Buffers useful for such a formulation may contain 200 mM sucrose and a phosphate or histidine buffer of pH 7.0-7.4. In certain embodiments, the formulation of intact virus particles comprises amino acid excipients such as glutamate and arginine. In certain other embodiments, the formulation of intact virus particles comprises stabilization protein hydrolysates such as collagen or gelatin (e.g., porcine, piscine, avian gelatin). In some embodiments, the formulation of intact virus particles can comprise live viruses that are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. For example, methods and compositions for formulating a refrigerator stable attenuated influenza vaccine are described in PCT Patent Publication No. WO/2006/041819; also see PCT Publication WO/2005/014862.

Thus, in certain embodiments, the invention provides a refrigerator stable vaccine formulation comprising one or more of the following (within 10% variation of one or more component) in the final formulations: 1-5% arginine; 1-4% gelatin; 5-10% sucrose (optionally in a phosphate buffer); 0.01-0.1% glutamic acid (monosodium, monohydrate); 10-150 mM potassium phosphate and 80-150 mM histidine.

In one specific embodiment, the vaccine formulation comprises one or more of the following (within 10% variation of one or more component); 1-2% arginine; 2% gelatin; 7-10% sucrose (optionally in a phosphate buffer); and 100 mM histidine. In another specific embodiment, the vaccine formulation comprises one or more of the following (within 10% variation of one or more component): 0.01-0.1% glutamic acid (monosodium, monohydrate); 1-2% arginine; 1% gelatin; and 7-10% sucrose in a phosphate buffer.

In certain other embodiments, the invention provides a refrigerator stable vaccine formulation comprising one or more of the following in the final formulations: sucrose: 6-8% weight/volume (w/v); arginine monohydrochloride 1-2% w/v; glutamic acid, monosodium monohydrate 0.05-0.1% w/v; gelatin hydrolysate, porcine Type A (or other sources such as piscine or avian) 0.5-2% w/v; potassium phosphate dibasic 1-2%; and potassium phosphate monobasic 0.25-1% w/v.

In one specific embodiment, the vaccine formulation comprises one or more of the following: sucrose: 6.84% weight/volume (w/v); arginine monohydrochloride 1.21% w/v; glutamic acid, monosodium monohydrate 0.094 w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following: sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 10% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 10% variation of one or more component): sucrose: 6.84% weight/volume (w/v); arginine monohydrochloride 1.21% w/v; gelatin hydrolysate, porcine Type A (or other sources) 1% w/v. In such embodiments, formulations are in buffer {e.g., a potassium phosphate buffer (pH 7.0-7.2)). In another specific embodiment, vaccine formulations comprise all of the following (within 20% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In yet another specific embodiment, the vaccine formulation comprises all of the following (within 30% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In still another specific embodiment, the vaccine formulation comprises all of the following (within 40% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 1% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 3% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In a specific embodiment, the vaccine formulation may contain, e.g., potassium phosphate (e.g., at least 50 mM, or at least 100 mM, or at least 200 mM, or at least 250 mM) as a buffer or alternatively, histidine (e.g., at least 50 mM, or at least 100 mM, or at least 200 mM, or at least 250 mM).

Optionally, spray drying, a rapid drying process whereby the formulation liquid feed is spray atomized into fine droplets under a stream of dry heated gas, may be utilized to extend storage time of a vaccine formulation. The evaporation of the fine droplets results in dry powders composed of the dissolved solutes (see, e.g., US Patent Publication No. 2004/0042972).

Generally, virus or viral components can be administered prophylactically in an appropriate carrier or excipient to stimulate an immune response specific for one or more strains of virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Optionally, the formulation for prophylactic administration of the viruses, or components thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, Bacille Calmette-Guerin (BCG), *Corynebacterium parvum*, and the synthetic adjuvants QS-21 and MF59.

Generally, vaccine formulations are administered in a quantity sufficient to stimulate an immune response specific for one or more strains of influenza virus. Preferably, administration of the viruses elicits a protective immune response. Dosages and methods for eliciting a protective immune response against one or more viral strain are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect. These methods can be adapted for any virus including but not limited to, orthomyxoviruses (including influenza A and B strains), paramyxoviruses (including RSV, human metapneumovirus and parainfluenza), rhabdoviruses and flavoviruses.

7.6.2 RSV Vaccines

In one embodiment, presented herein, are methods of eliciting an immune response in a subject, comprising administering to a subject in need thereof an effective amount of an immunogenic composition described herein that comprises a live attenuated purified virus (e.g., RSV). In some embodiments, the attenuated virus is a chimeric virus.

In a specific embodiment, presented herein are methods of eliciting an immune response in a mammal (e.g., a human), comprising administering to a mammal in need thereof an effective amount of an immunogenic composition described herein that comprises an attenuated RSV. In a particular embodiment, the attenuated RSV is rA2 cp248/404/1030ΔSH.

The immunogenic compositions described herein that comprise a live attenuated purified virus may be in the active immunization of a subject. In one embodiment, presented herein are methods of preventing a viral infection, comprising administering to a subject an effective amount of an immunogenic composition described herein that comprises a live attenuated purified virus, i.e., a vaccine. In some embodiments, a live attenuated virus is a chimeric virus.

In a specific embodiment, presented herein are methods for preventing a RSV infection, comprising administering to a mammal (e.g., a human) an effective amount of an immunogenic composition described herein that comprises a live attenuated purified RSV, i.e., a vaccine. In a particular embodiment, a live attenuated RSV is rA2 cp248/404/1030ΔSH.

The immunogenic compositions described herein that comprise a live attenuated purified virus may be used in the inhibition of viral infections. In one embodiment, presented herein are methods of inhibiting a viral infection, comprising administering to a subject in need thereof an effective amount of an immunogenic composition described herein that comprises a live attenuated purified virus. In some embodiments, the attenuated virus is a chimeric virus. In a specific embodiment, presented herein are methods for inhibiting a RSV infection, comprising administering to a mammal (e.g., a human) an effective amount of an immunogenic composition described herein that comprises a live attenuated purified RSV. In a particular embodiment, the attenuated RSV is rA2 cp248/404/1030ΔSH.

The immunogenic compositions described herein that comprise a live attenuated purified virus may be used to induce an immune response that results in a reduction in virus titer in a subject. In one embodiment, presented herein are methods of reducing the titer of a virus in a subject, comprising administering an immunogenic composition described herein that comprises a live attenuated cell-associated virus. In some embodiment, the attenuated virus is chimeric. In a specific embodiment, presented herein are methods for reducing RSV titer, comprising administering to a mammal (e.g., a human) an effective amount of an immunogenic composition described herein that comprises a live attenuated RSV. In a particular embodiment, the attenuated RSV is rA2 cp248/404/1030ΔSH.

In some embodiments, an effective amount of an immunogenic composition described herein reduces viral titer by approximately 2 fold, preferably approximately 5 fold or more, approximately 10 fold or more, or approximately 20 fold or more in a subject challenged by the virus relative to an untreated subject. In certain embodiments, an effective amount of an immunogenic compositions described herein reduces the duration and/or severity of one or more symptoms associated with a cell-associated virus infection in subjects subsequently infected with the cell-associated virus relative to untreated subjects. In some embodiments, an effective amount of an immunogenic composition described herein increases survival of subjects subsequently infected with the purified virus relative to untreated subjects.

The immunogenic compositions described herein that comprise a live attenuated purified virus may be administered to a naïve subject, i.e., a subject that has not been and is not currently infected with the virus of interest. In one embodiment, an immunogenic composition described herein that comprises a live attenuated cell-associated virus may be administered to a naïve subject that is at risk of developing a viral infection. In a specific embodiment, an immunogenic composition described herein that comprises a live attenuated RSV may be administered to a naïve subject that is at risk of developing a RSV infection. In a particular embodiment, the attenuated RSV is rA2 cp248/404/1030ΔSH.

The immunogenic compositions described herein that comprise a live attenuated purified virus may be administered to a subject that has previously been infected with a different group, subgroup or strain of the virus of interest. In one embodiment, an immunogenic composition is administered to a subject that has previously been infected with a virus of a different group, subgroup or strain than the virus of interest and is at risk of developing an infection with the virus of interest.

In one embodiment, an immunogenic composition described herein that comprises a live attenuated RSV (e.g., rA2 cp248/404/1030ΔSH) is administered a human infant or human infant born prematurely. In another embodiment, an immunogenic composition described herein that comprises a live attenuated RSV (e.g., rA2 cp248/404/1030ΔSH) is administered to a human with cystic fibrosis, bronchopulmonary dysplasia, congenital heard disease, congenital immunodeficiency or acquired immunodeficiency. In another embodiment, an immunogenic composition described herein that comprises a live attenuated RSV (e.g., rA2 cp248/404/1030ΔSH) is administered to a human toddler. In another embodiment, an immunogenic composition described herein that comprises a live attenuated RSV (e.g., rA2 cp248/404/1030ΔSH) is administered to a human child. In another embodiment, an immunogenic composition described herein that comprises a live attenuated RSV (e.g., rA2 cp248/404/1030ΔSH) is administered to a human child in school.

In a specific embodiment, an immunogenic composition described herein that comprises a live attenuated RSV (e.g., rA2 cp248/404/1030ΔSH) is administered to a human 1 to 24 months of age. In another embodiment, an immunogenic composition described herein that comprises a live attenuated RSV (e.g., rA2 cp248/404/1030ΔSH) is administered to a human 1 to 3 months of age. In another embodiment, an immunogenic composition described herein that comprises a live attenuated RSV (e.g., rA2 cp248/404/1030ΔSH) is administered to a human 6 to 24 months of age.

In another embodiment, an immunogenic composition described herein that comprises a live attenuated RSV (e.g., rA2 cp248/404/1030ΔSH) is administered a human who has had a bone marrow transplant. In another embodiment, an immunogenic composition described herein that comprises a live attenuated RSV (e.g., rA2 cp248/404/1030ΔSH) is administered to an elderly human. In another embodiment, an immunogenic composition described herein that comprises a live attenuated RSV (e.g., rA2 cp248/404/1030ΔSH) is administered to a human in a nursing home. In another embodiment, an immunogenic composition described herein that comprises a live attenuated RSV (e.g., rA2 cp248/404/1030ΔSH) is administered to a human that lives in a group home (i.e., a home in which 15 or more human subjects live).

In a specific embodiment, an immunogenic composition comprising a live attenuated RSV (e.g., rA2 cp248/404/1030ΔSH) is administered to a human subject (in a specific embodiment, the human subject is a human infant, a human infant born prematurely or a human toddler) before the RSV season, typically November through April in the northern hemisphere. In another embodiment, an immunogenic composition comprising a live attenuated RSV (e.g., rA2 cp248/404/1030ΔSH) is administered to a human subject (in a specific embodiment, the human subject is a human infant, a human infant born prematurely or a human toddler) during the RSV season, typically November through April in the northern hemisphere. In another embodiment, an immunogenic composition comprising a live attenuated RSV (e.g., rA2 cp248/404/1030ΔSH) is administered to a human subject (in a specific embodiment, the human subject is a human infant, a human infant born prematurely or a human toddler) before and during the RSV season, typically November through April in the northern hemisphere.

In certain embodiments, an immunogenic composition described herein that comprises a live attenuated purified virus does not result in complete protection from a viral infection, but results in a lower viral titer compared to an untreated subject when challenged with the virus. In certain embodiments, administration of an immunogenic composition described herein that comprises a live attenuated purified virus results in a 0.5 fold, 1 fold, 2 fold, 4 fold, 6 fold, 8 fold, 15 fold, 25 fold, 50 fold or greater reduction in the titer of the virus relative to an untreated subject when challenged with the virus. In some embodiments, administration of an immunogenic composition described herein that comprises a live attenuated virus results in a 10%, preferably a 25%, 50%, 75% or greater reduction in the titer of the virus relative to an untreated subject when challenged with the virus. Benefits of a reduction in the viral titer include, but are not limited to, less severe symptoms of a viral infection, fewer symptoms of a viral infection, and a reduction in the length of a viral infection.

The immunogenic compositions described herein comprising a live attenuated chimeric cell-associated virus may be used to induce an immune response to a non-viral antigen. The immunogenic composition described herein comprising a live attenuated chimeric cell-associated virus may be used to deliver a protein, polypeptide or peptide of interest to a subject to prevent and/or treat a disease.

Many methods may be used to introduce the immunogenic compositions, e.g., vaccine formulations, described herein, these include, but are not limited to, intranasal, intratracheal, oral, pulmonary, intradermal, intraperitoneal, and parenteral (e.g., intramuscular, intravenous, and subcutaneous) routes. In some embodiments, an immunogenic composition described herein that comprises a live attenuated cell-associated virus is administered via the natural route of infection of the virus. In a specific embodiment, an immunogenic composition comprising a live attenuated RSV (e.g., rA2 cp248/404/1030ΔSH) is administered intranasally.

In immunization procedures, the amount of an immunogenic composition to be used and the immunization schedule will be determined by a physician skilled in the art and will be administered by reference to the immune response and antibody titers of the subject. In a specific embodiment, a human infant, human infant born prematurely or a human toddler is administered a dose of an immunogenic composition comprising a live attenuated RSV (e.g., rA2 cp248/404/1030ΔSH), wherein the dose of the immunogenic composition comprises approximately 125 to 200 FFU of the attenuated RSV. In another embodiment, a human infant, human infant born prematurely or a human toddler is administered a dose of an immunogenic composition comprising a live attenuated RSV (e.g., rA2 cp248/404/1030ΔSH), wherein the dose of the immunogenic composition comprises approximately 125 FFU, approximately 150 FFU, approximately 175 FFU or approximately 200 FFU of the attenuated RSV.

In some embodiments, 2-6 doses of an immunogenic composition comprising approximately 125 to 200 FFU of a live attenuated RSV (e.g., rA2 cp248/404/1030ΔSH) is administered to a human infant, a human infant born prematurely or a human toddler. In some embodiments, the doses of the immunogenic composition are administered 1 to 6 months apart or 2 to 12 months apart. In a specific embodiment, 3 doses of an immunogenic composition comprising approximately 125 to 200 FFU of a live attenuated RSV (e.g., rA2 cp248/404/1030ΔSH) are administered to a human infant, a human infant born prematurely or a human toddler 2 months apart. For example, a first dose of an immunogenic composition comprising 150 FFU of a live attenuated RSV (e.g., rA2 cp248/ 404/1030ΔSH) is administered to an infant less than 1 month old, a second dose of the immunogenic composition comprising 150 FFU of the live attenuated RSV (e.g., rA2 cp248/404/ 1030ΔSH) is administered to the human infant at approximately 2 months old, and a third dose of the immunogenic composition comprising 150 FFU of the live attenuated RSV (e.g., rA2 cp248/404/1030ΔSH) is administered to the human infant at approximately 4 months old.

7.7 Viruses

A cell-associated virus may be a naturally occurring virus, a mutagenized virus (e.g., a virus mutated by exposure to UV irradiation, mutagens, and/or passaging), a reassortant (for cell-associated viruses with segmented genomes), and/or a genetically engineered virus. Non-limiting examples of cell-associated RNA viruses include respiratory syncytial virus (RSV), measles virus, influenza virus, human foamy virus, retroviruses such as HTLV, lentiviruses such as HIV and SIV, and reoviruses. Alternatively, a cell-associated virus is a DNA virus, such as a herpes virus. Non-limiting examples of cell-associated DNA viruses include herpes virus, EBV, CMV and Marek's disease virus. In certain embodiments, the cell-associated virus purified by a process described herein and/or contained in an immunogenic composition described herein is replication-defective. In a specific embodiment, one or more functions essential for viral genome replication and/or synthesis are defective in the replication-defective cell-associated virus. In another embodiment, one or more functions essential for assembly of viral particles are defective in the replication-defective cell-associated virus. In another embodiment, one or more functions essential for viral genome replication or synthesis and viral particle assembly are defective in the replication-defective cell-associated virus.

In a specific embodiment, the cell-associated virus purified by a process described herein and/or contained in an immunogenic composition described herein is an attenuated virus. In a particular embodiment, the cell-associated virus is a live attenuated virus. An attenuated cell-associated virus may have, e.g., a reduced ability to replicate its viral genome, a reduced ability to replicate in an intended host, a reduced ability to assemble infectious viral particles, and/or a reduced ability to infect a host cell relative to a wild-type cell-associated virus. The attenuation of the cell-associated viruses can be tested by any method known to one of skill in the art. See, e.g., U.S. application Ser. No. 10/831,780, Apr. 23, 2004 (published on Jan. 27, 2005 as U.S. Application Publication No. 2005/0019891) and in particular Section 5.7 entitled "Attenuation of Recombinant Viruses,". In some embodiments, the attenuated virus is produced using well-known mutagenesis techniques, such as cold passaging the virus or exposure to UV irradiation and/or mutagens. In other embodiments, the attenuated virus is genetically engineered.

A cell-associated virus may be a chimeric virus. In a specific embodiment, the chimeric virus is a replication-defective virus. In a particular embodiment, the chimeric virus is an attenuated virus.

7.7.1 Influenza Virus

The culture medium, methods, processes and compositions herein are particularly useful for the production and purification of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and M2. The smallest segment encodes two products, NS1 which is translated from the full length RNA, and NS2 which is translated from a spliced mRNA variant.

Reassortant viruses are produced to incorporate selected hemagglutinin and/or neuraminidase antigens from clinical isolates in the context of an approved master strain also called a master donor virus (MDV). FluMist®, for example, makes use of approved cold adapted, attenuated, temperature sensitive MDV strains (e.g., ca A/AnnArbor/6/60 and ca B/Ann Arbor/1/66). Other strains that may be used as a master donor virus include, but are not limited to, ca A/AnnArbor/6/60, ca B/Ann Arbor/1/66, ca A/Leningrad/134/17/57, A/PuertoRico/8/34 (PR8), ca B/Ann Arbor/1/94, B/Leningrad/14/17/55, B/USSR/60/69, and B/Leningrad/179/86.

A number of methods are useful for the generation of reassortant viruses including egg-based methods and more recently cell culture methods See, e.g., PCT Publications WO 03/091401; WO 05/062820 and U.S. Pat. Nos. 6,544,785; 6,649,372; 6,951,75, and U.S. patent application Ser. Nos. 11/455,818, 11/455,734, and 11/501,067. It is contemplated that the media and methods of the invention are useful for the production of influenza viruses including, but not limited to, the influenza strains disclosed herein and reassortant viruses comprising genes of a master donor virus (e.g., ca A/AnnArbor/6/60, ca B/AnnArbor/1/66, PR8, etc.). It is further contemplated that that the media and methods of the invention are useful for the production of influenza viruses, including reassortant viruses, having one or more of the following phenotypes, temperature sensitive, cold adapted, attenuated. Reassortants may be generated by classical reassortant techniques, for example by co-infection methods or optionally by plasmid rescue techniques (see, e.g., PCT Publications WO 03/091401 and WO 05/062820; U.S. Pat. Nos. 6,544,785, 6,649,372, 6,951,754, 6,887,699, 6,001,634, 5,854,037, 5,824,536, 5,840,520, 5,820,871, 5,786,199, and 5,166,057; U.S. Patent Application Publication Nos. 20060019350, 20050158342, 20050037487, 20050266026, 20050186563, 20050221489, 20050032043, 20040142003, 20030035814, and 20020164770; and Neumann et al. (1999) *Generation of* influenza A virus entirely from cloned cDNAs. *Proc Natl Acad Sci USA* 96:9345-9350; Fodor et al. (1999) *Rescue of influenza A virus from recombinant DNA. J. Virol* 73:9679-9682; Hoffmann et al. (2000) *A DNA transfection system for generation of influenza A virus from eight plasmids Proc Natl Acad Sci USA* 97:6108-6113; WO 01/83794; Hoffmann and Webster (2000), *Unidirectional RNA polymerase 1-polymerase II transcription system for the generation of influenza A virus from eight plasmids,* 81:2843-2847; and Hoffmann et al. (2002), *Rescue of influenza B viruses from* 8 plasmids, 99(17): 11411-11416. Recently, reassortants have been generated by plasmid rescue in MDCK cells (see, e.g., PCT publication WO 2007/124327; Wang and Duke; 2007 Oct. 23, J. Virol., 4:102).

7.7.2 Respiratory Syncitial Virus

The methods, processes and compositions herein are particularly useful for the production and purification of RSV for vaccines. Any group, subgroup or strain of RSV (e.g., group A or group B) may be purified by a process described herein and/or contained in an immunogenic composition described herein. See, e.g., Sato et al., 2005, Journal of Clinical Microbiology 43: 36-40 for a discussion of the groups and subgroups of RSV. In one embodiment, the RSV belongs to group A. In another embodiment, the RSV belongs to group B.

The RSV purified by a process described herein and/or contained in an immunogenic composition described herein may be a naturally occurring RSV strain, a mutagenized RSV (e.g., a virus mutated by exposure to UV irradiation, mutagens, and/or passaging), and/or a genetically engineered RSV. In one embodiment, the RSV genome comprises one or more mutations in one or more viral genes, such as the F, G, NS1, NS2, M1 (open reading frame ("ORF")1), M2(ORF2), SH2, N, P, or L genes. In some embodiments, a combination of substitutions, deletions and/or insertions are introduced into the RSV genome. In some embodiments, the RSV genome comprises one or more missense mutations in one or more viral genes, such as the F, G, NS1, NS2, M1(ORF1), M2(ORF2), SH2, N, P, or L genes. In some embodiments, the RSV genome comprises a deletion of one or more all or a portion of one or more viral genes, such as the NS1, NS2, M1(ORF1), M2(ORF2), SH2, N, P, or L genes.

In one embodiment, the RSV that may be purified by a process described herein and/or contained in an immunogenic composition described herein is replication-defective. In a specific embodiment, the RSV that may be purified by a process described herein and/or contained in an immunogenic composition described herein is attenuated. For non-limiting examples of mutations that may be introduced into the RSV genome to attenuate the virus see, e.g., U.S. application Ser. No. 10/831,780, Apr. 23, 2004 (published on Jan. 27, 2005 as U.S. Application Publication No. 2005/0019891) and U.S. application Ser. No. 11/389,618, filed Mar. 24, 2006 (published on Jul. 20, 2006 as U.S. Application Publication No. 2006/0160130). Attenuated RSVs include, but are not limited to, cold-passaged (cp) mutants (e.g., cpRSV described in, e.g., Kim et al., 1971, Pediatrics 48: 745-755, which is incorporated herein by reference in its entirety), temperature-sensitive (ts) mutants (e.g., RSV ts-1, RSV ts-2, ts1A, ts19A, and ts1C described in, e.g., Crowe et al., 1993, Vaccine 11:1395-1404; Crowe et al., 1995, Vaccine 13:847-855; Mills et al., 1971, J. Immunol. 107:123-130; and Pringle et al., Vaccine 1993 11:473-478), cold-passaged temperature sensitive (cpts) mutants (e.g., cpts248/404, cpts248/255, cpts 248/955 and cpts 530/1009; see, e.g., Karron et al., 1997, J Infect Dis. 176:1428-1436), and genetically engineered mutants (e.g., rA2 cp248/404ΔSH, rA2 cp248/404/1030ΔSH, rΔNS1, rΔM2-2, and r248ΔNS2 described in, e.g., Karron et al., J. of Infect. Diseases 191: 1093-1140; Whitehead et al., 1999, J. Virol. 73: 3438-3442; and Collins et al., 2005, Proc. Am. Thorac. Soc. 2: 166-173,).

In a specific embodiment, the RSV that may be purified by a process described herein and/or contained in an immunogenic composition described herein is rA2 cp248/404/1030ΔSH. This attenuated RSV contains multiple attenuating genetic elements that are responsible for its temperature sensitivity and attenuation properties including: (i) a set of 5 missense mutations in the N, F and L proteins that attenuate cold-passaged RSV; (ii) the 248 and 1030 modifications that are separate missense mutations in the L protein that lower the restrictive temperature and confer a temperature sensitive phenotype and attenuate the virus; (iii) the 404 modifications that are a combination of a nucleotide substitution in the gene-start transcription signal of the M2 gene and a missense mutation in the L protein that together confer additional temperature sensitivity; and (iv) ΔSH which is a deletion of the entire SH gene that confers an attenuated phenotype. See Table 2 below for the locations of the amino acid substitutions introduced into the RSV genome.

TABLE 2

Amino Acid Substitutions Introduced Into The RSV Genome

| Nucleotide Substitutions | Amino Acid Substitutions* | Gene | Phenotype |
|---|---|---|---|
| G1939A | V to I | N | Att |
| A5895C | E to A | F | Att |
| C6810T | T to I | F | Att |
| T7187C | T to C | M2 gene-start | Ts |
| G9035A, T9036C | C to Y | L | Att |
| C10570T, A10571T | Q to L | L | ts |
| T11628G | D to E | L | Ts |
| T12040A | Y to N | L | Ts |
| C13147T, T13149C | H to Y | L | Att |

*Amino acid substitutions relative to wild-type RSV A2

In some embodiments, the RSV that may be purified by a process described herein and/or contained in an immunogenic composition described herein is engineered to express one or more heterologous sequences (i.e., the RSV is a chimeric virus). The heterologous sequences may be introduced, e.g., into the F, G, NS1, NS1, M1 (ORF1), M2(ORF2), N, P, SH2 and/or L coding sequences. Non-limiting examples of heterologous sequences that a RSV may be engineered to express include antigens (e.g., viral antigens, bacterial antigens, tumor antigens (such as those described by Robbins and Kawakawi, 1996, Curr. Opin. Immunol. 8: 628-636), fungal antigens, and parasitic antigens), a marker or tag (e.g., a flag tag and a His tag), chimeric proteins (e.g., a hybrid of RSV G proteins from two different strains of RSV), and proteins, polypeptides or peptides possessing a desired biological property or activity (e.g., cytokines such as interferon (IFN)-α IFN-β, IFN-γ, IL-2, IL-7, IL-9, IL-15, and IL-22). In a specific embodiment, the chimeric RSV is attenuated. For non-limiting examples of chimeric RSVs see, e.g., U.S. application Ser. No. 10/831,780, Apr. 23, 2004 (published on Jan. 27, 2005 as U.S. Application Publication No. 2005/0019891) and U.S. application Ser. No. 11/389,618, filed Mar. 24, 2006 (published on Jul. 20, 2006 as U.S. Application Publication No. 2006/0160130).

In one embodiment, RSV is engineered to express one or more viral antigens from a virus belonging to a different group, subgroup, or strain of RSV than the RSV vector. For example and not by limitation, the RSV vector may be derived from a group B RSV and the heterologous sequence may be derived from a group A RSV.

In another embodiment, RSV is engineered to express one or more viral antigens obtained or derived from a virus other than RSV. Non-limiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment, the viral antigen is derived from a virus that results in respiratory disease, such as influenza antigens (e.g., hemagglutinin H5 and H7), metapneumovirus antigens, parainfluenza virus antigens, Newcastle disease virus antigens, Sendai virus antigens, and infectious Laryngotracheits virus antigens (ILV). In certain embodiments, the viral antigen is derived from human parainfluenza virus type 1, human parainfluenza virus type 2, human parainfluenza virus types 3, or from Sendai virus. In another embodiment, the viral antigen, is HIV gp120, HIV nef, influenza virus neuraminidase, influenza virus hemagglutinin, HTLV tax, herpes simplex virus glycoprotein (e.g., gB, gC, gD, and gE) or hepatitis B surface antigen, hepatitis C virus E protein or coronavirus spike protein.

In another embodiment, RSV is engineered to express one or more bacterial antigens (e.g., a bacterial coat protein or protective antigen associated with a bacteria). Non-limiting examples of bacterial antigens include antigens derived from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), Enterobacteriaceae family (e.g., *C itrobacter* species, *Edwardsiella, Enterobacter aerogenes, Erwinia species, Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus pyrogenes*), *Streptococcus* (e.g., *Streptococcus enteritidis, Streptococcus fasciae*, and *Streptococcus pneumoniae*), Vampirovibr Helicobacter family, Yersinia family, *Bacillus antracis* and Vampirovibrio family. In a specific embodiment, the bacterial antigen is derived from a bacteria that cause or are associated with a respiratory disease, such as *Pneumococcus* species, *Haemophilus influenzae, Streptococcus*, and *Chlamydia pneumoniae.*

In another embodiment, RSV is engineered to express one or more fungal antigens obtained or derived from a pathogenic fungus. Non-limiting examples of fungal antigens include antigens derived from *Cryptococcus neoformans; Blastomyces dermatitidis; Aiellomyces dermatitidis; Histoplasma capsulatum; Coccidioides immitis; Candida* species, including *C. albicans, C. tropicalis, C. parapsilosis, C. guilliermondii* and *C. krusei, Aspergillus* species, including *A. fumigatus, A. flavus* and *A. niger, Rhizopus* species; *Rhizomucor* species; *Cunninghammella* species; *Apophysomyces* species, including *A. saksenaea, A. mucor* and *A. absidia; Sporothrix schenckii, Paracoccidioides brasiliensis; Pseudallescheria boydii, Torulopsis glabrata; Trichophyton* species, *Microsporum* species and *Dermatophyres* species. In a specific embodiment, the fungal antigen is derived from a pathogenic fungus that cause or are associated with a respiratory disease.

In another embodiment, RSV is engineered to express one or more parasitic antigens. Non-limiting examples of parasitic antigens include antigens derived from members of the Apicomplexa phylum such as, for example, *Babesia, Toxoplasma, Plasmodium, Eimeria, Isospora, Atoxoplasma, Cystoisospora, Hammondia, Besniotia, Sarcocystis, Frenkelia, Haemoproteus, Leucocytozoon, Theileria, Perkinsus* and *Gregarina* spp.; *Pneumocystis carinii*; members of the Microspora phylum such as, for example, *Nosema, Enterocytozoon, Encephalitozoon, Septata, Mrazekia, Amblyospora, Arneson, Glugea, Pleistophora* and *Microsporidium* spp.; and members of the Ascetospora phylum such as, for example, *Haplosporidium* spp., as well as species including *Plasmodium falciparum, P. vivax, P. ovale, P. malaria; Toxoplasma gondii; Leishmania mexicana, L. tropica, L. major, L. aethiopica, L. donovani, Trypanosoma cruzi, T brucei, Schistosoma mansoni, S. haematobium, S. japonium; Trichinella spiralis; Wuchereria bancrofti; Brugia malayli; Entamoeba histolytica; Enterobius vermiculoarus; Taenia solium, T saginata, Trichomonas vaginatis, T hominis, T tenax; Giardia lamblia; Cryptosporidium parvum; Pneumocytis carinii, Babesia bovis, B. divergens, B. microti, Isospora belli, L hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineas, G. Viverini, Fasciola hepatica, Sarcoptes scabiei, Pediculus humanus; Phthirlus pubis*; and *Dermatobia hominis.*

8. SPECIFIC EMBODIMENTS

1. A method for producing influenza viruses in cell culture to a log 10 TCID50/mL of at least about 8.0 and/or to a log 10 FFU/mL of at least about 8.0, comprising:

(a) proliferating MDCK cells in a serum-free culture medium, while maintaining one or more culture conditions selected from the group consisting of: an agitation rate of between about 100 and 200 rpm; a pH of between about 6.0 to about 7.8; a temperature of between about 33° C. and about 42° C.; and dissolved oxygen (DO) of between about 35% to about 100%;

(b) infecting the proliferated MDCK cells with an influenza virus without exchanging the culture medium; and (c) incubating the infected proliferated MDCK cells under conditions that permit replication of the influenza virus.

2. The method of embodiment 1, wherein the culture medium is MediV SFM 110.

3. The method of embodiment 1 or 2, wherein the MediV SFM 110 comprises 9 g/L glucose.

4. The method of any one of the preceding embodiments, wherein the MDCK cells are proliferated as adherent cells on microcarriers 5. The method of embodiment 4, wherein the concentration of microcarriers is between 1 and 3 g/L.

6. The method of embodiment 4 or 5, wherein the MDCK cells are seeded onto microcarriers at a density of between 10 to 40 cells/microcarrier and proliferated for between 2 and 5 days.

7. The method of any one of the preceding embodiments, wherein the agitation rate is maintained between about 100 and 200 rpm; the pH is maintained between about 6.0 to about 7.8; the temperature is maintained between about 33° C. and about 42° C.; and the dissolved oxygen (DO) is maintained between about 35% to about 100%.

8. The method of any one of the preceding embodiments, wherein the MDCK cells are proliferated at an agitation rate of between 150 rpm to 200 rpm.

9. The method of any one of the preceding embodiments, wherein the MDCK cells are proliferated at a pH of between 7.0 and 7.8.

10. The method of embodiment 9, wherein the pH is 7.4±0.2.

11. The method of any one of the preceding embodiments, wherein the MDCK cells are proliferated at a temperature of 37±2° C.

12. The method of any one of the preceding embodiments, wherein the MDCK cells are from the cell line deposited as ATCC Accession No. PTA-7909 or PTA-7910.

13. The method of any one of the preceding embodiments, wherein the MDCK cells are proliferated to a cell density of between $5 \times 10^5$ to $3 \times 10^6$ cells/mL.

14. The method of any one of the preceding embodiments, wherein step (b) is carried out using a viral input of between $0.01 \times 10^3$ FFU/mL to $0.1 \times 10^3$ FFU/mL.

15. The method of embodiment 14, wherein step (b) is carried out using a viral input of between $0.01 \times 10^3$ FFU/mL to 0.05 FFU/mL.

16. The method of any one of the preceding embodiments, wherein step (b) is carried out using a viral input of between 0.00001 FFU/cell and 0.0001 FFU/cell.

17. The method of embodiment 16, wherein step (b) is carried out using a viral input of between 0.00001 FFU/cell and 0.00005 FFU/cell.

18. The method of any one of the preceding embodiments, wherein the influenza viruses are cold adapted.

19. The method of embodiment 18, wherein the influenza viruses are also attenuated and temperature sensitive.

20. The method of any one of the preceding embodiments, wherein the influenza virus is an influenza A virus.

21. The method of any one of the preceding embodiments, wherein the influenza virus is an influenza B virus.

22. The method of embodiment 20, wherein the influenza A virus comprises one or more gene segments of influenza strain ca A/Ann Arbor/6/60.

23. The method of any one of embodiment 21, wherein the influenza B virus comprises one or more gene segments of influenza strain ca B/Ann Arbor/1/66.

24. The method of any one of the preceding embodiments, wherein the MDCK cells are incubated at between 30° C. and 35° C. during the replication of the influenza virus in step (c).

25. The method of embodiment 24, wherein the MDCK cells are incubated at 33±2° C. during the replication of the influenza virus in step (c).

26. The method of any one of the preceding embodiments, wherein the MDCK cells are incubated at an agitation rate of between 150 rpm to 200 rpm during the replication of the influenza virus in step (c).

27. The method of any one of the preceding embodiments, wherein the MDCK cells are incubated at a pH of between about 7.0 and about 7.8 during the replication of the influenza virus in step (c).

28. The method of embodiment 27, wherein the pH is 7.4±0.2.

29. The method of any one of the preceding embodiments, wherein a protease is present during step (c).

30. The method of embodiment 29, wherein the protease is a serine protease.

31. The method of embodiment 29 or 30, wherein the protease is a recombinant animal free protease.

32. The method of embodiment 31, wherein the protease is present at a final concentration of 0.03×.

33. The method of any one of the preceding embodiments, further comprising the step of harvesting the culture medium after infection.

34. The method of embodiment 33, wherein the culture medium is harvested between 48 hours to 72 hours after infection.

35. A method of effecting bead to bead transfer of cells in a cell culture grown on microcarriers comprising:

(a) a first wash step in which all or a portion of the growth medium; is replaced with a wash medium comprising a chelating agent;

(b) incubation of the cell culture in the wash medium with or without agitation;

(c) addition of a protease to the cell culture in the wash medium;

(d) incubation of the cell culture with the protease with or without agitation; and (e) transfer to a new growth vessel.

36. The method of embodiment 35, further comprise a second wash step between steps (b) and (c) with a wash medium comprising a chelating agent.

37. The method of embodiment 35 or 36, wherein fresh growth medium and/or additional microcarriers are added after step (d).

38. The method of any one of embodiments 35 to 37, wherein the fresh growth medium and/or additional microcarriers are added prior to, during, or after step (e).

39. The method of any one of embodiments 35 to 38, wherein the concentration of the chelating agent is between 0.4 mM and 0.6 mM.

40. The method of any one of embodiments 35 to 39, wherein the pH of the wash medium is between 7.8 and 8.2.

41. The method of embodiment of any one of embodiments 35 to 40, wherein the protease is a recombinant animal free protease.

42. The method of embodiment 41, wherein the protease is added to a final concentration of between 0.04× and 0.06×.

43. The method of any one of embodiments 35 to 42, wherein the cell culture is agitated during step (b).

44. The method of any one of embodiments 35 to 43, wherein the cell culture is agitated during step (d).

45. The method of embodiment 43 or 44, wherein the cell culture is agitated at between 175 rpm and 275 rpm.

46. The method of embodiment 45, wherein the cell culture is agitated at 230±25 rpm.

47. The method of any one of embodiments 35 to 46, wherein the cell culture is incubated in steps (b) and (d) for between 15 and 60 minutes.

48. The method of any one of embodiments 35 to 47, wherein a protease inhibitor is added after step (d).

49. A method of effecting bead to bead transfer of cells in a cell culture grown on microcarriers comprising:
 (a) adding a chelating agent to the cell culture without washing the cells;
 (b) incubating the cell culture in the presence of the chelating agent with or without agitation;
 (c) addition of a protease to the cell culture in the presence of the chelating agent;
 (d) incubation of the cell culture with the protease with or without agitation; and
 (e) adding additional fresh media and supplementing the cell culture with one or more media components.

50. The method of embodiment 49, wherein the one or more media components are selected from the group consisting of CaCl2, MgCl2, MgSO4, trace elements A, trace elements B, and trace elements C.

51. The method of embodiment 49 or 50, wherein the one or more media components are between 1.25 mM to 1.5 mM $CaCl_2$, between 0.1 mM to 0.2 mM MgCl2, and between 0.1 to 0.8 mM MgSO4, 2× Trace Elements A, 2× Trace Elements B, and 2× Trace Elements C.

52. The method of any one of embodiments 49 to 51, wherein the cell culture is transferred to a new growth vessel prior to, during, or after step (e).

53. The method of any one of embodiments 49 to 52, wherein the concentration of the chelating agent is between 0.5 mM and 5 mM.

54. The method of embodiment 53, wherein the concentration of the chelating agent is about 2 mM.

55. The method of any one of embodiments 49 to 54, wherein the pH of the cell culture is adjusted as need to be between 7.8 and 8.2 prior to or during step (c).

56. The method of embodiment of any one of embodiments 49 to 55, wherein the protease is a recombinant animal free protease.

57. The method of any one of embodiments 49 to 56, wherein the protease is added to a final concentration of between 0.04× and 0.06×.

58. The method of any one of embodiments 49 to 57, wherein the cell culture is agitated during step (b).

59. The method of any one of embodiments 49 to 58, wherein the cell culture is agitated during step (d).

60. The method of embodiment 58 or 59, wherein the cell culture is agitated at between 175 rpm and 275 rpm.

61. The method of any one of embodiments 49 to 60, wherein the cell culture is incubated in steps (b) and (d) for between 15 and 90 minutes.

62. The method of any one of embodiments 49 to 61, wherein a protease inhibitor is added after step (d).

63. A method of purifying influenza viruses from cell culture comprising:
 (a) clarification of a viral harvest by direct flow filtration (DFF) through at least one membrane having a pore size of between about 1.2 micrometers to about 0.45 micrometers;
 (b) concentration by tangential flow ultrafiltration (UF) and buffer exchange by diafiltration (DF) following step (a) using a membrane having 500 kDa molecular weight cut off (MWCO);
 (c) purification by affinity column chromatography following step (b);
 (d) concentration by UF and/or buffer exchange by DF following step (c) using a membrane having 500 kDa molecular weight cut off (MWCO); and
 (e) sterilization following step (d) by DFF through at least one membrane having a pore size of between about 0.45 micrometers to about 0.22 micrometers,
 wherein the overall recovery of purified viruses is at least 30%, and wherein the purified viruses comprise less than 0.1 ng HCD, and less than 0.3 µg HCP per 7.0±0.5 $\log_{10}$ FFU of virus.

64. The method of embodiment 63, wherein sucrose and a phosphate buffer are added to the viral harvest to a final concentration, within 10% variation, of 218 mM sucrose, 11 mM phosphate buffer pH 7.0-7.4, prior to step (a).

65. The method of embodiment 63 or 64, wherein steps (a) and (b) are coupled.

66. The method of any one of embodiments 63 to 65, wherein step (b) is performed at a transmembrane pressure (TMP) of between about 10 psi to about 20 psi.

67. The method of any one of embodiments 63 to 66, wherein step (b) is performed at a flux rate of between about 35 liters per meter per hour (LMH) to about 50 LMH.

68. The method of any one of embodiments 63 to 67, wherein step (b) is performed at a shear rate of between about 12,000 $s^{-1}$ to about 16,000 $s^{-1}$.

69. The method of any one of embodiments 63 to 68, wherein step (b) results in a 5× concentration and least 5 diavolumes of buffer are exchanged.

70. The method of any one of embodiments 63 to 69, wherein the exchange buffer in step (b) comprises, within 10% variation, 218 mM sucrose, 11 mM phosphate buffer pH 7.0-7.4.

71. The method of any one of embodiments 63 to 70, wherein buffer exchanged by DF occurs in step (d).

72. The method of any one of embodiments 63 to 70, wherein concentration by UF and buffer exchange by DF occur in step (d).

73. The method of any one of embodiments 63 to 70 or 72 wherein step (d) results in at least a 2× concentration.

74. The method of any one of embodiments 63 to 73, wherein least 8 diavolumes of buffer are exchanged in step (d).

75. The method of any one of embodiments 63 to 74, wherein the exchange buffer in step (d) comprises, within 10% variation, 200 mM sucrose, 100 mM phosphate buffer pH 7.0-7.4.

76. The method of any one of embodiments 63 to 75, wherein between 8.0 $\log_{10}$ FFU to $\log_{10}$ FFU of influenza viruses are loaded per mL of affinity media.

77. The method of embodiment 76, wherein between 9.0 $\log_{10}$ FFU to 10.0 $\log_{10}$ FFU of influenza viruses are loaded per mL of affinity media.

78. The method of embodiment 76, wherein between 9.2 $\log_{10}$ FFU to 9.8 $\log_{10}$ FFU of influenza viruses are loaded per mL of affinity media.

79. The method of any one of embodiments 63 to 78, wherein after the virus are loaded the affinity media is washed 80. The method of any one of embodiments 63 to 79, wherein step (c) further incorporates exposure to a buffer comprising a non-specific endonuclease.

81. The method of embodiment 80, wherein the length of exposure to the buffer comprising the non-specific nuclease is between 30 and 90 minutes.

82. The method of embodiment 81, wherein the length of exposure to the buffer comprising the non-specific endonuclease is 50±10 minutes.

83. The method of any one of embodiments 80 to 82, wherein the non-specific endonuclease is Benzonase™.

84. The method of any one of embodiments 80 to 83, wherein the buffer comprising the non-specific endonuclease, comprises, within 10% variation, 218 mM sucrose, 11 mM phosphate buffer pH 7.0-7.4, and the non-specific endonuclease at a final concentration of between 40 U/mL to 60 U/mL.

85. The method of any one of embodiments 80 to 84, wherein after the treatment with the buffer comprising the non-specific endonuclease the affinity media is washed with a buffer comprising, within 10% variation, 218 mM sucrose, 11 mM phosphate buffer pH 7.0-7.4.

86. The method any one of embodiments 80 to 85, wherein the purified viruses comprise less than 0.0050 ng non-specific endonuclease per 7.0±0.5 $\log_{10}$ FFU of virus.

87. The method of any one of embodiments 63 to 86, wherein the affinity media is selected from the group consisting of Cellufine™ Sulfate and FluSelect™

88. The method of any one of embodiments 63 to 87, wherein the influenza viruses are eluted from the affinity media with a buffer comprising, within 10% variation, 1 M sodium chloride, 218 mM sucrose, and 11 mM phosphate buffer pH 7.0-7.4.

89. Influenza viruses produced by the method of any one of embodiments 1 to 34, or 63 to 88.

90. Purified influenza viruses comprising less than 0.1 ng HCD, and less than 0.3 μg HCP per 7.0±0.5 $\log_{10}$ FFU of virus, wherein the influenza viruses were purified from a culture of mammalian cells.

91. The purified influenza viruses of embodiment 90, wherein the mammalian cells are selected from the group consisting of human diploid lung fibroblast cells, human retinoblastoma cells, human kidney cells, fetal rhesus lung cells, African green monkey kidney cells, and canine kidney cells.

92. The purified influenza viruses of embodiment 90, wherein the mammalian cells are MDCK cells.

93. The purified influenza viruses of embodiment 90, wherein the mammalian cells are culture is a VERO cell culture.

94. An immunogenic composition comprising polypeptides of the influenza viruses of any one of embodiments 89 to 93.

9. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein. Of course, it will be appreciated that specific listing or description of particular equipment and reagents used, sizes, manufacturer, etc., is not to be considered limiting on the current invention unless specifically stated to be so. It with be further appreciated that other equipment and reagents which perform similarly may be readily substituted.

9.1 Medium and Cell Culture Processes

Serum-free medium formulations (e.g., MediV SFM 107, MediV SFM 105) useful for the proliferation of MDCK cells, in particular non-tumorigenic MDCK cells, to high density have been described (see, e.g., FL410US and G-FL414US). However, work using these serum-free medium formulations with non-tumorigenic MDCK cells adapted to serum-free medium (e.g., ATCC Accession No. PTA-7909 or PTA-7910) revealed that, while reasonable peak viral titers (generally measured as $\log_{10}$ FFU/mL) of reassortant influenza virus could be obtained without medium exchange, the peak titers were still lower that those obtained with medium exchange, in which a portion (e.g., ~67%) of the growth medium is removed and replaced with an infection medium after proliferation the cells and prior to (or at the same time as) infection. Furthermore additional protease (TrypLE) was required to obtain these peak titers. To overcome the need for medium exchange and/or the requirement for addition protease a fortified medium, MediV SFM 110, was developed. MediV SFM 110 comprises 5× the concentration of the vitamins, linoleic acid, lipoic acid, nucleosides, putrescine and nearly all the amino acids present in the previously described mediums (see Table 3). Use of MediV SFM 110 did not improve cell densities over those obtained with MediV SFM 105+TE (data not shown). However, using MediV SFM 110, 0% and 67% medium exchange showed similar viral titers.

The performance of twelve runs using a no medium exchange (MX) process and cells prepared by bead to bead transfer (see the Example provided in Section 9.2 below) from four seed reactors and grown in MediV SFM 110 media are described below. Three cold adapted (ca), temperature sensitive (ts), attenuated (att) reassortant influenza virus strains comprising the HA and NA from the wild type strains A/Uruguay/716/2007, A/South Dakota/6/2007, and B/Florida/4/2006 (referred to by the wild type strain designation preceded by the identifier "ca") were produced at 2 L scale and all the three strains produced viruses at a titer of at least 8.4 $\log_{10}$ FFU/mL. Proper detachment of cells in the seed reactors and attachment of cells in the final production reactors (FPRs) were observed after bead to bead transfer using 1×DPBS wash and trypsinization using TrypLE select and EDTA at pH8.0. Upon infection these cells were sampled periodically to determine the optimum harvest time. It was found that the peak virus titers were observed at 3 days post infection (dpi) for all virus types. Four runs for each of these strains were performed to verify reproducibility of results and the data were in-line to each other. ca A/Uruguay/716/2007 produced the highest titer at 8.7±0.05 $\log_{10}$ FFU/mL at 3 days post infection (dpi), while the peak titers for ca A/South Dakota/6/2007 and ca B/Florida/4/2006 were 8.8±0.0 $\log_{10}$ FFU/mL and 8.45±0.25 $\log_{10}$ FFU/mL respectively at 3 dpi.

The reproducibility of data from these runs indicates the no medium exchange process is a robust process. Thus, the fortified media maintained productivity without either exchanging or adding medium or components. Accordingly, development and use of the fortified medium has overcome one of the most challenging operational problems in cell culture-based influenza vaccine production, the requirement for medium exchange/supplementation.

9.1.1 Materials and Methods

Materials, Reagent and Equipments:
Other materials, equipment and reagents which perform similarly may be readily substituted.
1. Dulbecco's Modified Eagle's Medium (DMEM)/Ham F12 (Gibco, Grand Island, N.Y., Cat No. ME080012)
2. MilliQ or WFI Water
3. MediV SFM 110 base powder (Gibco, Grand Island, N.Y., Cat No. ME080045)
4. Glucose (Invitrogen, Carlsbad, Calif., Cat No. 15023-021)
5. Sodium Selenite (Sigma, St. Louis, Mo., Cat No. 6607-31)?
6. L-Glutamine (Gibco, Grand Island, N.Y., Cat No. 25030-081)
7. CD Lipids (100×) (Gibco, Grand Island, N.Y., Cat No. 11905-031)
8. Wheat Peptone (Organotechnie, SAS, La Courneuve, France, Cat No. 19559)
9. Insulin (Serological, Norcross, Ga., Cat No. 4506)
10. T3 (Sigma, St. Louis, Mo., Cat No. T5516)
11. Hydrocortisone (Mallinckrodt, Phillipsburg, N.Y., Cat No. 8830(-05))
12. Prostaglandin E1(Sigma, St. Louis, Mo., Cat No. P7527)
13. EGF (Sigma, St. Louis, Mo., Cat No. E9644)
14. Ferric Ammonium Citrate (J T Baker, Phillipsburg, N.J., Cat No. 1980-01)
15. Tropolone (Sigma, St. Louis, Mo., Cat No. T89702-5G)
16. Trace Element A (Cellgro/Mediatech, Manassas, Va., Cat No. 99-182-cl)
17. Trace Element B (Cellgro/Mediatech, Manassas, Va., Cat No. 99-175-cl)
18. Trace Element C (Cellgro/Mediatech, Manassas, Va., Cat No. 99-176-cl)
19. Sodium Biocarbonate (Invitrogen, Carlsbad, Calif., Cat. No. 91425/87-5067)
20. Dulbecco's phosphate buffered saline (DPBS) pH-7.4 (Invitrogen, Carlsbad, Calif., Cat No. 14190-367)
21. EDTA-DPBS solution Bag (Gibco Cat No. 14190-367)
22. 0.5M EDTA pH8 (Gibco, Grand Island, N.Y., Cat No. 15575-038)
23. 0.2 µm steri cup filter (Millipore, Bedford, Mass., Cat No. SCGPU05RE)
24. TrypLE Select (Gibco, Grand Island, N.Y., Cat No. 12563)
25. Lima Bean Inhibitor (Worthington, Lakewood, N.J., Cat No. LS002829)
26. Cytodex 3 (Amersham Biosciences, Piscataway, N.J., Cat No. 17-0485-03)
27. Sucrose Phosphate (Hyclone, Logan, Utah, Cat No. SH3A1578-01)
28. 10-20 L sterile bag (SAFC Biosciences JRH, Lenexa, Kans., 1329B)
29. Roller Bottles (Corning, Corning, N.Y., Cat No. 3907)
30. NaOH 1M solution (EMD, Darmstadt, Germany, Cat No. 1071)
31. 0.2 µm sterile filter (Corning, Corning, N.Y., Cat No. 430320, 430767)
32. 1 mL, 5 mL, 10 mL, 25 mL, 50 mL Pipettes (VWR, Brisbane, Calif., Cat. Nos. 53284-700, 53283-704, 708, 710, respectively)
33. 5 mL aspirating pipettes (VWR, Brisbane, Calif., Cat No. 53392-044)
34. 1.8 mL Eppendorf tubes (USA Scientific, Ocala Fla., Cat No. 1415-5510)
35. Micropipette tips (Art Molecular Bioproducts, San Diego Calif., Cat No. 20E, 200E and 1000E)
36. Sucrose Phosphate, 10× (Hyclone, Logan, Utah, Cat#SH3A1578-01)
37. Applikon Controller Units (Applikon Biotechnology, Foster City, Calif. Models: ADI 1010, ADI 1025)
38. 3 L glass vessel and headplate (Biotechnology, Foster City, Calif.)
39. 2.5" A310 impellers (Lightnin, Rochester, N.Y.)
40. 60 mm marine impeller (Applikon Biotechnology, Foster City, Calif.).
41. 45 mm marine impellers (Applikon Biotechnology, Foster City, Calif.).
42. Peristaltic pump (Watson Marlow Bredel Pump, Wilmington, Mass., Model 520S/R)
43. Biosafety cabinet (The Baker Company, Sanford, Me., SG-600)
44. Roller bottle incubator (Bellco Biotechnology, Vineland, N.J., Model 7630-80589)
45. Water bath (Boekel Grant, West Chester, Pa., PB-1400)
46. Nucleocounter (New Brunswick Scientific, Edison, N.J., M1293-0000)
47. Bioprofile 400 (Nova Biomedical, Waltham, Mass., Bioprofile 400)
48. Microscope (Zeiss, Thornwood, N.Y., Axiovert 25)
49. Digital Camera (Nikon, Melville, N.Y., Model E5400)
50. Micropipette (Labsystem, Boston, Mass., Model No. P2-20, P100, P200, P1000)
51. Pipette aid (Drummond, Broomall, Pa., Cat. No. 4-000-100)
52. $CO_2$ Shake flask incubator (ATR Biotech, Laurel, Md., Model AJ118)

Cell Source:

Serum-free MDCK clone ID 9B9-1E4 cells (ATCC accession number PTA-7910, see WO 08/105,931) derived from the Process Development Bank (PDB) were cultivated in roller bottles, using MediV SFM105 with trace elements A, B and C or MediV SFM109[4]. The composition of MediV SFM 105 with trace elements A, B and C is similar to MediV SFM 109 media, with the exception that MediV SFM 105 is made out of liquid and MediV SFM109 is made out of powder. Cells were routinely passaged every 3 to 4 days post-seeding as per SOP D0200[5], with the exception that the 2×DPBS wash was not performed.

Virus Seed:

This process was developed with the 2008/2009 FluMist® seasonal strains: ca A/Uruguay/716/2007 (Lot #nb3903 pg94, 141900675A), ca A/South ca Dakota/6/2007 (Lot #141900666), and ca B/Florida/4/2006 (141900641A). All these seeds were produced in eggs. Similar results have been obtained for seed viruses produced in cell culture using plasmid rescue methods (see, for example, Wang and Duke; 2007 Oct. 23, J. Virol., 4:102; Hoffmann, et al., 2000, PNAS, 97(11):6108-13; and Hoffmann, et al., 2002, PNAS, 99(17):11411-6)

Culture Medium:

For these runs MediV SFM 105 with 1× Trace Elements A, B and C and a total 4.5 g/L of D-glucose or MediV SFM 109 with a total 4.5 or 9.0 g/L of D-glucose were used in all routine cell passaging for roller bottles and seed reactors (SRs) runs, respectively. MediV SFM 110 medium with a total of 9.0 g/L of D-glucose was used for final production reactors (FPRs) runs. Depending on the seeding conditions and the anticipated he concentration of D-glucose may be adjusted between about 4.5 to about 9.0 g/L. The composition of each culture medium is detailed in Table 3.

TABLE 3

MediV SFM Medium Formulations

| Component[a] | MediV SFM 105 + TE[d] mg/L | MediV SFM 109 mg/L | MediV SFM 110 mg/L |
|---|---|---|---|
| Salts | | | |
| Calcium Chloride, Anhydrous | 116.6 | 116.6 | 116.6 |
| Magnesium Chloride | 28.64 | 28.64 | 28.64 |
| Magnesium Sulfate, Anhydrous | 48.84 | 48.84 | 48.84 |
| Potassium Chloride | 311.8 | 311.8 | 311.8 |
| Sodium Chloride[c] | 6999.5 | 6999.5 | 3500 |
| Sodium Phosphate, Monobasic, Monohydrate | 62.5 | 62.5 | 62.5 |
| Sodium Phosphate, Dibasic, Anhydrous | 71.02 | 71.02 | 71.02 |
| Trace Metals | | | |
| *$NH_4VO_3$* | *0.00065* | *0.00065* | *0.00065* |
| *$AgNO_3$* | *0.00017* | *0.00017* | *0.00017* |
| *Aluminum Chloride $6H_2O$* | *0.0012* | *0.0012* | *0.0012* |
| *$Ba(C_2H_3O_2)_2$* | *0.00255* | *0.00255* | *0.00255* |
| *Cadmium Chloride ($CdCl_2$)* | *0.00228* | *0.00228* | *0.00228* |
| *Chromium Chloride ($CrCl_3$, anhydrous)* | *0.00032* | *0.00032* | *0.00032* |
| *Cobalt Chloride $6H_2O$* | *0.00238* | *0.00238* | *0.00238* |
| *Cupric Sulfate, Pentahydrate* | *0.0029* | *0.0029* | *0.0029* |
| *Ferric Citrate* | *1.1551* | *1.1551* | *1.1551* |
| Ferric Nitrate, Nonahydrate | 0.05 | 0.05 | 0.05 |
| *Ferric Ammonium Citrate (FAC)* | *0.2* | *0.2* | *0.2* |
| Ferrous Sulfate, Heptahydrate | 0.417 | 0.417 | 0.417 |
| *$GeO_2$* | *0.00053* | *0.00053* | *0.00053* |
| *$MnSO_4 H_2O$* | *0.00017* | *0.00017* | *0.00017* |
| *Molybdic Acid ammonium Salt* | *0.00124* | *0.00124* | *0.00124* |
| *Nikelous Sulfate ($NiSO_4$ $6H_2O$)* | *0.00013* | *0.00013* | *0.00013* |
| *Potassium Bromide* | *0.00012* | *0.00012* | *0.00012* |
| *Potassium Iodide* | *0.00017* | *0.00017* | *0.00017* |
| *Rubidium Chloride* | *0.00121* | *0.00121* | *0.00121* |
| Sodium Selenite | 0.0173 | 0.0173 | 0.0173 |
| Sodium Selenite, Pentahydrate | 0.00263 | | |
| *Sodium Floride* | *0.0042* | *0.0042* | *0.0042* |
| *Sodium Meta-Silicate•$9H_2O$* | *0.14* | *0.14* | *0.14* |
| *Stannous Chloride(Tin Chloride-$SnCl2$)* | *0.00012* | *0.00012* | *0.00012* |
| *Zinc Sulfate, Heptahydrate* | *1.295* | *1.295* | *1.295* |
| *$ZrOCl_2$ $8H_2O$* | *0.00322* | *0.00322* | *0.00322* |
| Nucleosides[b] | | | |
| Hypoxanthine, Na salt | 2.39 | 2.39 | 11.95 |
| Thymidine | 0.365 | 0.365 | 1.825 |
| Amino Acids[b] | | | |
| L-Alanine | 4.45 | 4.45 | 22.25 |
| L-Arginine HCl | 147.5 | 147.5 | 737.5 |
| L-Asparagine $H_2O$ | 7.5 | 7.5 | 37.5 |
| L-Aspartic Acid | 6.65 | 6.65 | 33.25 |
| L-Cysteine HCl $H_2O$ | 17.56 | 17.56 | 87.8 |
| L-Cystine 2HCl | 31.29 | 31.29 | 156.45 |
| L-Glutamic Acid | 7.35 | 7.35 | 36.75 |
| *L-Glutamine* | *584* | *584* | *584* |
| Glycine | 18.75 | 18.75 | 93.75 |
| L-Histidine HCl $H_2O$ | 31.48 | 31.48 | 157.4 |
| L-Isoleucine | 54.47 | 54.47 | 272.35 |
| L-Leucine | 59.05 | 59.05 | 295.05 |
| L-Lysine HCl | 91.25 | 91.25 | 456.25 |
| L-Methionine | 17.24 | 17.24 | 86.2 |
| L-Phenylalanine | 35.48 | 35.48 | 177.4 |
| L-Proline | 17.25 | 17.25 | 86.25 |
| L-Serine | 26.25 | 26.25 | 131.25 |
| L-Threonine | 53.45 | 53.45 | 267.25 |
| L-Tryptophan | 9.02 | 9.02 | 45.1 |
| L-Tyrosine 2Na | 55.79 | 55.79 | 278.95 |
| L-Valine | 52.85 | 52.85 | 264.25 |
| Vitamins[b] | | | |
| d-Biotin (vit B7 and vit H) | 0.0035 | 0.0035 | 0.0175 |
| D-Calcium Pantothenate | 2.24 | 2.24 | 11.2 |
| Choline Chloride | 8.98 | 8.98 | 44.9 |
| Cyanocobalamin (vit B12) | 0.68 | 0.68 | 3.4 |
| Folic Acid | 2.65 | 2.65 | 13.25 |
| myo-Inositol | 12.6 | 12.6 | 63 |
| Niacinamide | 2.02 | 2.02 | 10.1 |
| Pyridoxine HCl (vit B6) | 2.031 | 2.031 | 10.155 |
| Riboflavin (vit B2) | 0.219 | 0.219 | 1.095 |
| Thiamine HCl (vit B1) | 2.17 | 2.17 | 10.85 |
| Fatty Acids[b] | | | |
| α Linoleic Acid | 0.042 | 0.042 | 0.21 |
| α DL--Lipoic Acid | 0.105 | 0.105 | 0.525 |
| Other | | | |
| Putrescine[b], 2HCl | 0.081 | 0.081 | 0.405 |
| Sodium Bicarbonate | 2200 | 2200 | 4400 |
| Sodium Pyruvate | 55 | 55 | 55 |
| *Tropolone* | *0.25* | *0.25* | *0.25* |
| *Glucose[e]* | *≥4500* | *≥4500* | *≥4500* |
| *Insulin* | *5* | *5* | *5* |
| *T3* | *0.000003367* | *0.000003367* | *3.367E−06* |
| *PGE1* | *0.025* | *0.025* | *0.025* |
| *Hydrocotisone* | *0.01812* | *0.01812* | *0.01812* |
| *EGF* | *0.005* | *0.005* | *0.005* |
| *Wheat peptone* | *2500* | *2500* | *2500* |
| *CDLC stock solution (components below)* | *1X* | *1X* | *1X* |
| *Arachidonic Acid* | *0.02* | *0.02* | *0.02* |
| *Cholesterol* | *2.2* | *2.2* | *2.2* |
| *DL-α-Tocopherol-Acetate* | *0.7* | *0.7* | *0.7* |
| *Linoleic Acid* | *0.1* | *0.1* | *0.1* |
| *Linolenic Acid* | *0.1* | *0.1* | *0.1* |
| *Myristic Acid* | *0.1* | *0.1* | *0.1* |
| *Oleic Acid* | *0.1* | *0.1* | *0.1* |
| *Palmitic Acid* | *0.1* | *0.1* | *0.1* |
| *Palmitoleic Acid* | *0.1* | *0.1* | *0.1* |
| *Pluronic F68* | *1000* | *1000* | *1000* |
| *Stearic Acid* | *0.1* | *0.1* | *0.1* |
| *Tween 80* | *22* | *22* | *22* |
| Final pH | | | 7.3 |

[a]Components not found in DMEM/F12 are shown in italics.
[b]Components found in DMEM/F12 and fortified in MediV SFM 110
[c]Reduced concentration in MediV SFM 110 to maintain osmolality
[d]Trace Elements A, B, and C
[e]Glucose is present at a final concentration of at least 4.5 g/L and may be supplemented up to a final concentration of about 9.0 g/L.

TABLE 4

1000X Trace Element Solutions A, B and C

| Components | mg/L |
|---|---|
| Trace Elements Soln. A | |
| $CuSO_4•5H_2O$ | 1.60 |
| $ZnSO_4•7H_2O$ | 863.00 |
| Selenite•2Na | 17.30 |
| Ferric citrate | 1155.10 |
| Trace Elements Soln. B | |
| $MnSO_4•H_2O$ | 0.17 |
| $Na_2SiO3•9H2O$ | 140.00 |
| $NH_4VO_3$ | 0.65 |

TABLE 4-continued

1000X Trace Element Solutions A, B and C

| Components | mg/L |
|---|---|
| $NiSO_4 \cdot 6H_2O$ | 0.13 |
| $SnCl_2$ (anhydrous) | 0.12 |
| Molybdic acid, Ammonium salt | 1.24 |
| Trace Elements Soln. C | |
| $AlCl_3 \cdot 6H_2O$ | 1.20 |
| $AgNO_3$ | 0.17 |
| $Ba(C_2H_3O_2)_2$ | 2.55 |
| KBr | 0.12 |
| $CdCl_2$ | 2.28 |
| $CoCl_2 \cdot 6H_2O$ | 2.38 |
| $CrCl_3$ (anhydrous) | 0.32 |
| NaF | 4.20 |
| $GeO_2$ | 0.53 |
| KI | 0.17 |
| RbCl | 1.21 |
| $ZrOCl_2 \cdot 8H_2O$ | 3.22 |

TABLE 5

100X Chemically Defined Lipid (CDCL) Solution

| Component | FW | mg/L |
|---|---|---|
| Arachidonic Acid | 304.5 | 2 |
| Cholesterol | 387 | 220 |
| DL-α-Tocopherol-Acetate | 473 | 70 |
| Linoleic Acid | 280 | 10 |
| Linolenic Acid | 278.43 | 10 |
| Myristic Acid | 228.37 | 10 |
| Oleic Acid | 282.46 | 10 |
| Palmitic Acid | 256.42 | 10 |
| Palmitoleic Acid | 254.41 | 10 |
| Pluronic F68 | | 100000 |
| Stearic Acid | 284.48 | 10 |
| Tween 80 | | 2200 |

Bioreactor Conditions and Methods:

For all the experiments, the FPRs were inoculated using 1:8 split contents from seed reactor (SR) and infected with reassortants of the 2008/2009 seasonal viruses, ca A/Uruguay, ca A/South Dakota and ca B/Florida. Several FPRs were run at identical conditions to ensure robustness of process and capture variability. First 3 experiments were performed to compare the medium exchange (MX) and no medium exchange (No-MX) processes side-by-side using one of 2008/2009 virus for each experiment. For each of the first 3 experiments, 2×2 L FPRs were run in replicates at identical conditions, where no medium exchange was performed at the time of infection and the reactors were infected with the same virus strains to capture process variability. Thus, a total of 6×2 L bioreactors were inoculated with 1:8 split cell culture contents from SRs and infected with all three 2008/2009 seasonal virus strains with no medium exchange process.

The last 2 experiments were performed to generate more data for the performance of no medium exchange process for the 08/09 strains. For the $4^{th}$ experiment, 3×2 L FPRs were inoculated from 1×2 L SR and were infected with all three seasonal virus reassortant types. Experiment 5 was a replicate of experiment 4 using identical conditions. The experiment was repeated in order to capture process variability in order to access performance of the no medium exchange process.

The virus strain used for infection and the source of cells used to inoculate FPRs in each experiment are described in Table 6.

TABLE 6

Virus strain and cell source used in Final Production Reactors (FPRs) infection

| Experiment | Cell Source (SRs) | FPRs | Infection virus |
|---|---|---|---|
| Experiment 1 | SR1 | FPR1.1.1 | ca A/Uruguay |
| | | FPR1.1.2 | ca A/Uruguay |
| Experiment 2 | SR2 | FPR2.2.1 | ca A/South Dakota |
| | | FPR2.2.2 | ca A/South Dakota |
| Experiment 3 | SR3 | FPR3.2.1 | ca B/Florida |
| | | FPR3.2.2 | ca B/Florida |
| Experiment 4 | SR4 | FPR4.3.1 | ca A/Uruguay |
| | | FPR4.3.2 | ca A/South Dakota |
| | | FPR4.3.3 | ca B/Florida |
| Experiment 5 | | FPR5.4.1 | ca A/Uruguay |
| | | FPR5.4.1 | ca A/South Dakota |
| | | FPR5.4.3 | ca B/Florida |

Seed Reactors (SRs):

For all the experiments, cells were grown in seed bioreactors at either 2 L or 5 L scale using 2 g/L of Cytodex 3 microcarriers in MediV SFM 105 medium containing Trace Elements A, B and C (MediV SFM 105+TE) or MediV SFM 109 media. The composition of MediV SFM 105 with trace elements A, B and C is nearly identical to MediV SFM 109 media, with the exception that MediV SFM 105 is made out of liquid and MediV SFM 109 is made out of powder and contains less sodium selenite. The glucose and glutamine concentrations were 9.0 g/L and 4 mM respectively. The vessels were inoculated at $1.35 \times 10^5$ cells/mL for experiments 1 to 3 and $1.8 \times 10^5$ cells/mL for experiments 4 and 5. The dissolved oxygen (D.O.) in SRs was maintained at 50% using a combination of pure oxygen and $N_2$ at a constant total flow of 0.02 vvm. The pH control was dual sided utilizing both $CO_2$ and 1N NaOH for all the SRs. Working volume for SRs for experiment 1 and experiment 2 were 2 L and 5 L respectively. Both were equipped with one marine impeller and agitated at 175 RPM. The working volume SRs for experiments 3 and 4 was 2 L. Both were equipped with 2 Lightnin impellers and agitated at 175 RPM. The impact of impeller and working volume on cell growth and metabolism is neglected for the scope of study. For the first 3 experiments, SRs were inoculated with 22.5 cells/MC. In order to achieve better cell growth, the SRs for experiment 4 and 5 were inoculated at 30 cells/MC. The experimental design describing each FPR with its respective SR is presented Table 6 and the process conditions are described in Table 7 for each SRs. After 4 days post seeding, the agitator, gas flow and D.O. and temperature controls of SRs were switch off to allow microcarriers to settle and cells were washed and trypsinized with one half of the working volume of bioreactor with addition of 10x TrypLE and pH8 essentially as detailed below in the Example provided in Section 9.2, below. The contents of SRs were trypsinized using B2B transfer protocol as specified in Table 8.

Final Production Reactors (FPRs):

The seed reactors contents were then pumped into feed bottles and 125 mL of this cell inoculum were used to inoculate the FPRs at the split of 1:8. The cells in the FPRs were grown in MediV SFM 110 medium containing 9.0 g/L glucose concentration. 2 L FPR glass vessels were equipped with 2 lightnin impellers and agitated at 175 RPM. The D.O. was controlled at 50% air saturation controlled with total flow strategy at 0.02 vvm, where constant total flow of 40 mL/min was maintained where supply of $N_2$ gas was calculated from $O_2$ and $CO_2$ gases ($N_2$=40-$O_2$—$CO_2$). The pH control was dual sided utilizing both $CO_2$ and 1N NaOH for all the FPRs.

The temperature during the growth and infection phase was controlled at 37° C. and 33° C. respectively. The virus strain for FPRs are listed in Table 6 and process conditions during growth and infection phase for the FPRs are listed in Table 9.

TABLE 7

Seed Reactor (SR) Process Conditions

| Parameter set-points | Controlled Quantity | | | |
|---|---|---|---|---|
| | SR1 | SR2 | SR3 | SR4 |
| Glucose (g/L) | 9.0 | 9.0 | 9.0 | 9.0 |
| Initial cells/micro-carriers (λ) | 22.5 | 22.5 | 30 | 30 |
| Final Working Volume (L) | 2 | 5 | 2 | 2 |
| Micro-carrier (MC) concentration (g/L) | 2 | 2 | 2 | 2 |
| Dissolved Oxygen | 50 | 50 | 50 | 50 |
| pH | 7.4 | 7.4 | 7.4 | 7.4 |
| Growth Temperature (° C.) | 37 | 37 | 37 | 37 |
| Impeller quantity/type | 1/marine | 1/marine | 2/lightnin | 2/lightnin |
| Agitation (RPM) | 175 | 175 | 175 | 175 |
| pH control | With 1N NaOH and $CO_2$ | With 1N NaOH and $CO_2$ | With 1N NaOH and $CO_2$ | With 1N NaOH and $CO_2$ |
| Total flow (constant throughout the run) (mL/min) | 40 | 40 | 40 | 40 |
| Media used | SFM105 with Trace elements A, B and C | SFM109 | SFM109 | SFM109 |

TABLE 8

Trypsinization conditions using bead to bead protocol

| Steps | Specifications and Set-points | Values | Units |
|---|---|---|---|
| 1. | Remove Media | 80 | % |
| 2. | Add 0.5 mM EDTA/DPBS wash solution to the original working volume | 80 | % |
| 3. | Start the agitation to original setting | 15 ± 5 | min |
| 4. | Stop agitation to allow MCs to settle down | 15 ± 5 | Min |
| 5. | Remove media and DBPS | 80 | % |
| 6. | Add 0.5 mM EDTA/DPBS wash solution to half of original working volume | 50 | % |
| 7. | Set agitator speed | 250 | RPM |
| 8. | Start the DO and temperature controls to original settings | 50, 37 | %, ° C. |
| 9. | Adjust the pH setting on controller | 8.0 | pH |
| 10. | Add 10x TrypLE Select (X of remaining volume) | 0.05 | X |
| 11. | Time for trypsinization | 50 ± 10 | Min |

TABLE 9

Final Production Reactor (FPR) Process Conditions

| Parameter set-points | FPRs |
|---|---|
| Final working volume (L) | 2 |
| Final microcarrier (MC) concentration (g/L) | 2 |
| Cell source | B2B SR |
| Split ratio | 1:8 |
| Volume of SR content post bead to bead transferred (mL)[#] | 125 |
| Dissolved oxygen | 50 |
| pH | 7.4 |
| pH control | With 1N NaOH and $CO_2$ |
| Agitation (RPM) | 175 |
| Final growth media glucose concentration (g/L) | 9.0 |
| Growth temperature (° C.) | 37 |
| Media | SFM110 |
| Infection temperature (° C.) | 33 |
| 10x TrypLE select concentration (X) | 0.03 |

[#]The cell content is concentrated 2X during the bead to bead transfer process. Accordingly, 125 mL post bead to bead is equivalent to 250 mL pre bead to bead.

Analytical Procedures:

Daily sampling of the vessels were performed. Cells were counted using the Nucleocounter, and photographs were taken using microscope at 10× magnification to examine cell morphology. pH, pO2, pCO2 and concentrations of glucose, lactate, glutamine and ammonium were monitored daily using a Nova Bioprofile 400 Analyzer. A pH re-calibration of the bioreactor was carried out when the difference between the online and offline values was higher than 0.03 pH units. Infected samples were stabilized with 10× Sucrose Phosphate (SP) and frozen at −80° C. until analyzed. The progression of the virus replication was analyzed by measuring the viral infectivity by Focal Fluorescent Assay (FFA) essentially as described below.

Focal Fluorescent Assay (FFA):

MDCK cells are grown in 96 well plates in MEM/EBSS+ 1× non-essential amino acids+2 mM glutamine+PEN/Strep (VGM) at 36±1° C. ° C., 5±2% $CO_2$, until confluent (~4 days). The VGM is then removed and the cells are washed with fresh VGM followed by infection with 100 μL of virus inoculum (e.g., ca A/Uruguay, ca A/South Dakota and ca B/Florida)) that is serially diluted (e.g., $10^{-1}$, $10^{-2}$ ... $10^{-7}$) in VGM and incubated for approximately 19-20 hrs at 33±1° C., 5±2% $CO_2$. Each virus dilution is inoculated to cells in three replicates. After incubation for approximately 19-20 hours at 33±1° C., 5±2% $CO_2$ the cells are immuno-stained with anti-influenza antibodies to determine the virus titer of the samples according to the following procedure. The cell culture medium containing the viruses is removed from each plate and the plates are washed with 200 μl/well of DPBS followed by fixation in 100 μL of cold 4% paraformadehyde for 15±3 minutes at room temperature. The plates are then washed twice with 250 μl/well of 1× Phosphate Buffered Saline+0.05% Tween 20 (TPBS) followed by incubation of the cells with primary antibody specific for either A strains or B strains. The primary antibodies are diluted to the desired dilution in 0.1% saponin, 1% BSA, and 0.1% sodium azide in 1×PBS (SBSA). After incubation for 60±5 minutes at 37±1° C., the primary antibody is removed, cells are washed thrice with 250 μL TPBS, and secondary antibody conjugated to a fluorescent dye (e.g., rabbit anti sheep labeled with FITC) prepared to the desired dilution in SBSA is added to the wells. After incubation for 60±5 minutes at 37±1° C., the secondary antibody is removed and the plates are washed twice as described above and twice with nano water followed by blot-drying with paper towels. The plates are then air dried with the lids off in the dark at room temperature for at least 10 minutes. The fluorescent signals are visualized using an inverted fluorescence microscope at 100× total magnification. Images may be taken using imaging software such as the SPOT program. Generally the central band of each well is examined and all foci are counted and only those wells which have a count of between 8 and 120 foci are counted. The $\log_{10}$ FFU/mL is calculated for each well counted and the mean and standard deviation of three wells are calculated.

9.1.2 Results and Discussion

Figure 1:
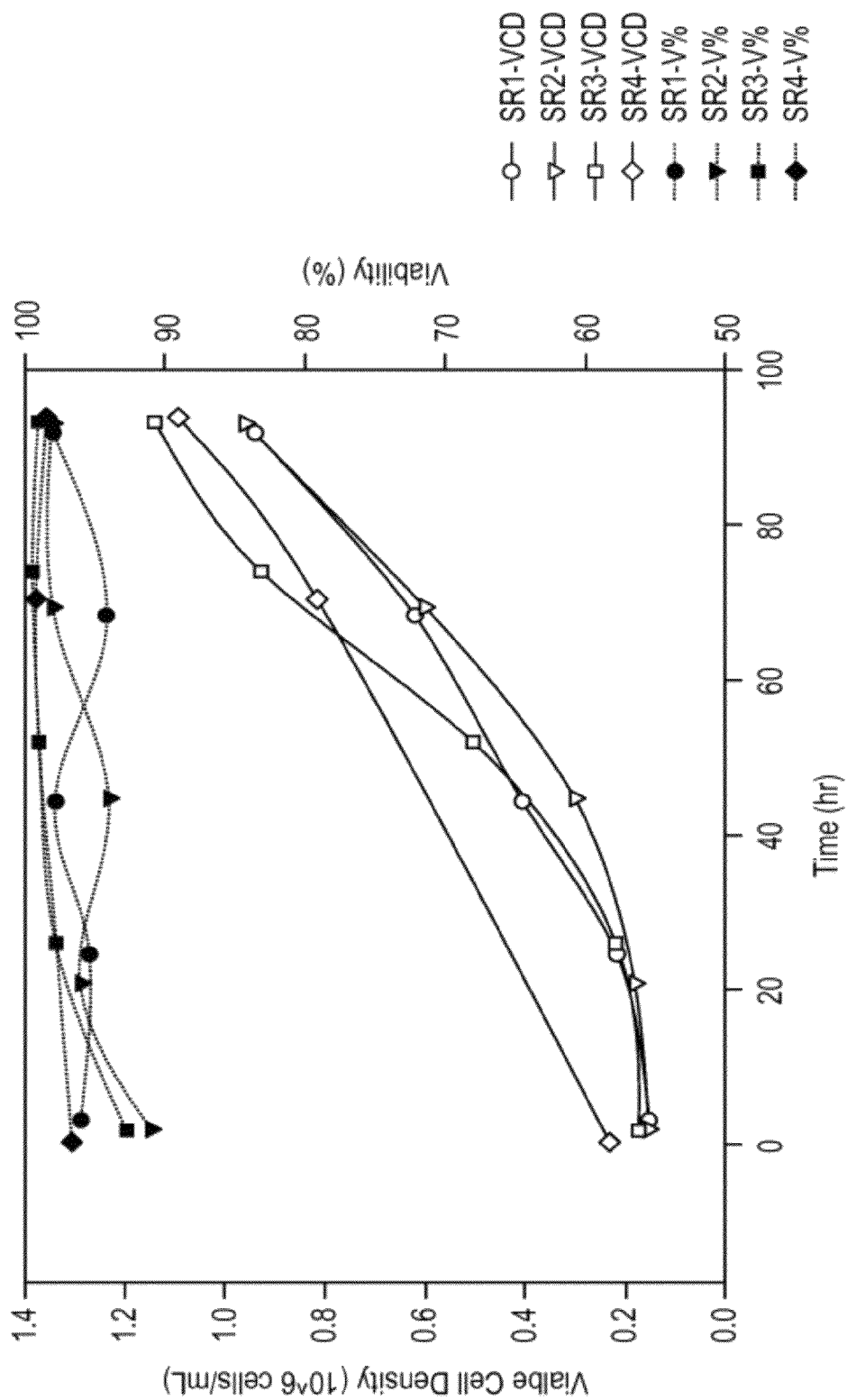
Figure 2:
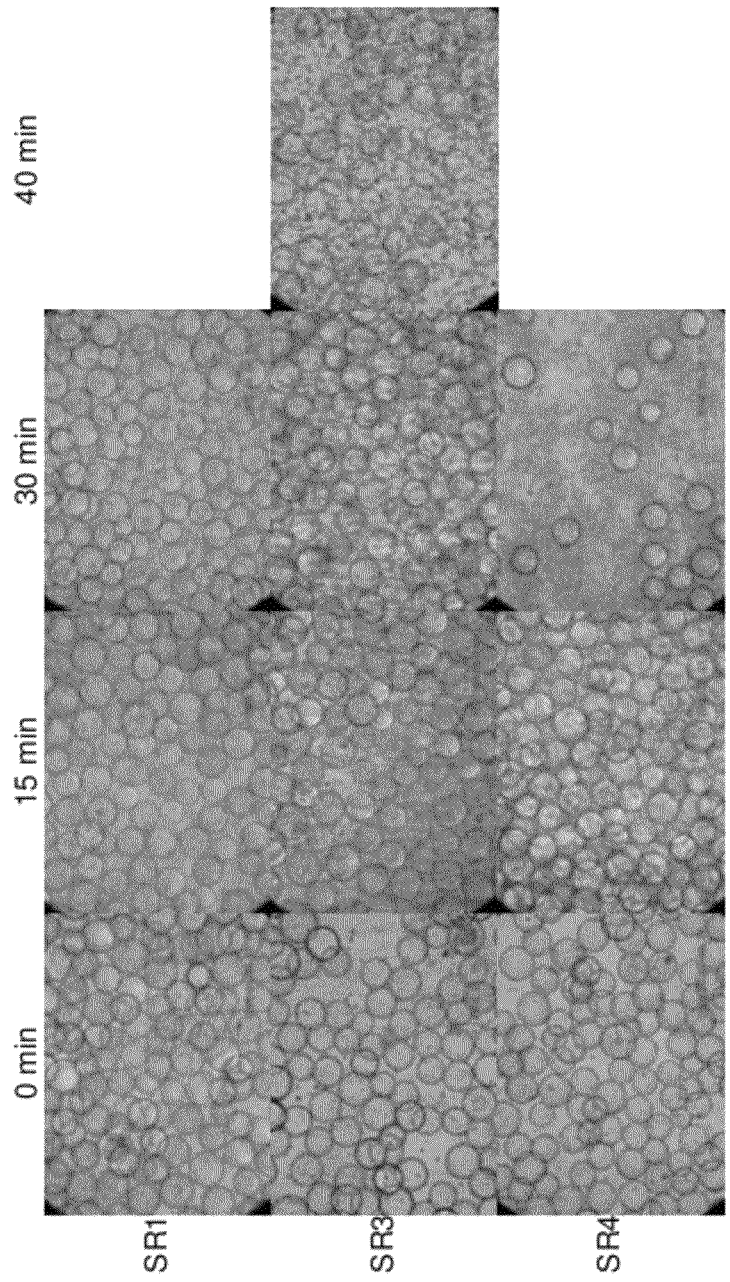
Figure 3:
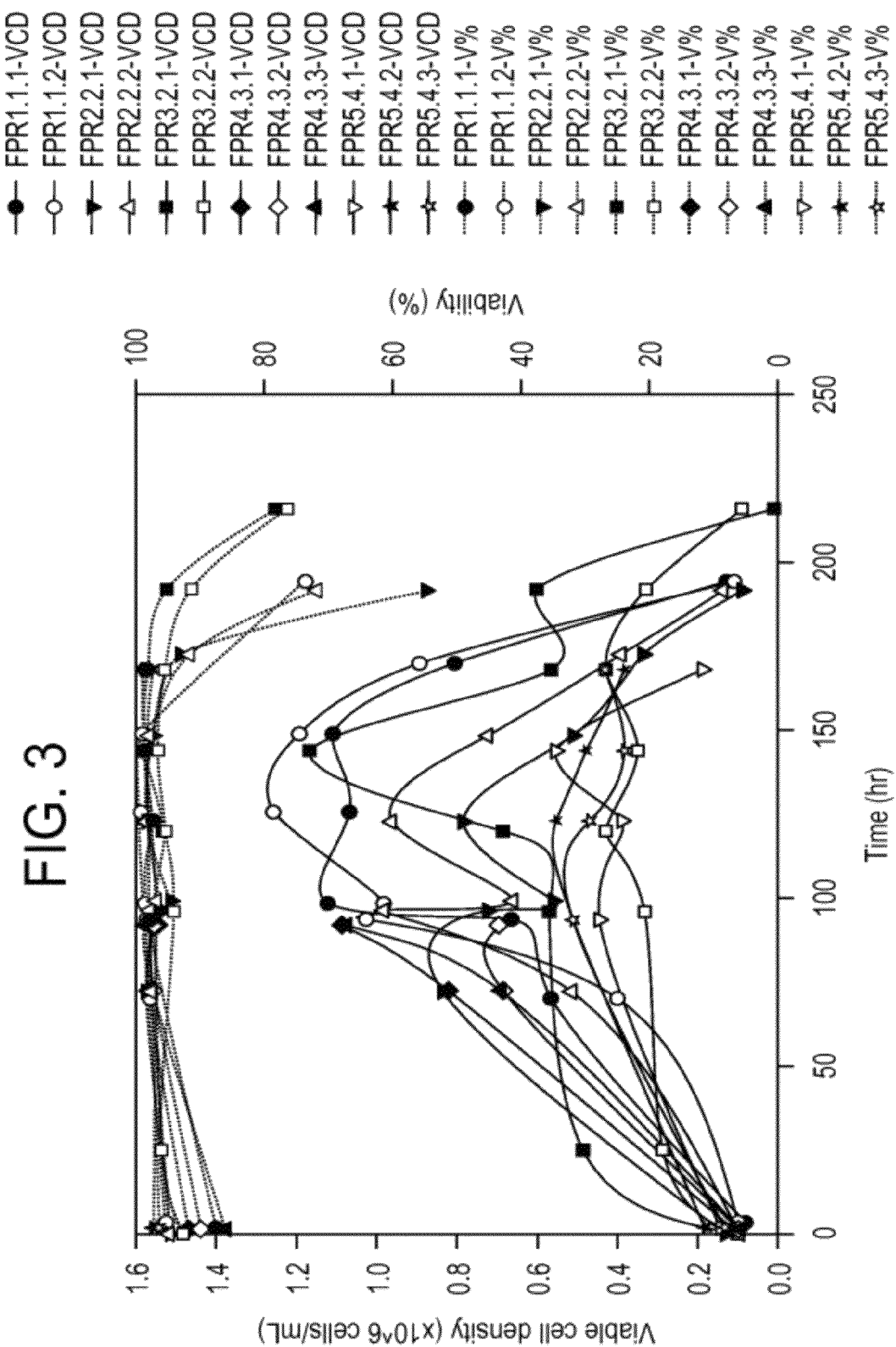

Cells were inoculated with 22.5 and 30 cells/microcarriers (MC) for the seed bioreactors for the first 3 experiments and last 2 experiments respectively. FIG. 1 plots the viable cell density (VCD) and cell viability (V %) for the SRs for all experiments. At 4 dps the cell densities for the seed reactors ranged from 0.94 to 1.14 million cells/mL. The difference in cell density was potentially due to the difference in inoculation cell concentration of 22.5 and 30 cells/MC. The cell density at 4 day post seeding (dps) in SRs inoculated with 22.5 and 30 cells/MC were 0.95±0.01 and 1.12±0.024 million cells/mL respectively. Cell viability for all bioreactors was above 90%. After 4 days of cultivation, bead to bead transfer with 1×0.5 mM EDTA-DPBS wash and 10× TrypLE select was performed in the seed reactors to trypsinize cells. The trypsinization lasted 30+/−10 minutes with intermittent sampling to observe cell detachment under the microscope. After about 30 to 40 minutes trypsinization, approximately 90% of cells were detached from MCs and seen as single cells as shown in FIG. 2. The trypsinized cells were used to inoculate the final bioreactors at a split ratio of 1:8 for all the experiments. The cell growth for all the FPRs was plotted in FIG. 3. Since the VCD for all the FPRs in experiment 2 were less than $0.6 \times 10^6$ cells/mL at 4 dps and the cell culture in these FPRs experienced longer lag phase, these cells were infected on 5 dps instead of 4 dps. In addition, the post infection VCD data were not available for FPRs in experiment 4. Finally, in spite of the low VCD of less than $0.5 \times 10^6$ cells/mL the FPRs were infected on 4 dps in experiment 5. The viability was above 90% for the FPRs during cell growth phase.

The cell density at the time of infection for all the FPRs are recorded in Table 10. Large variation in viable cell density was seen. It ranged from 0.44 to $1.12 \times 10^6$ cells/mL. This difference was related to cell counting error. The average VCD for both SRs and FPRs is recorded in Table 11. On 4 dps average VCD for SRs and FPRs is about $1.12 \times 10^6$ cells/mL and $0.73 \times 10^6$ cells/mL, respectively.

TABLE 10

Viable cell density at infection for all FPRs (unit: $\times 10^6$ cells/mL)

| Runs | VCD at infection ($\times 10^6$ cells/mL) | Days post seeding |
|---|---|---|
| FPR1.1.1 | 1.12 | 4 |
| FPR1.1.2 | 0.98 | 4 |
| FPR2.2.1 | 0.56 | 4 |
| FPR2.2.2 | 0.66 | 4 |
| FPR3.2.1 | 0.68 | 5 |
| FPR3.2.2 | 0.44 | 5 |
| FPR4.3.1 | 1.09 | 4 |
| FPR4.3.2 | 0.69 | 4 |
| FPR4.3.3 | 1.07 | 4 |
| FPR5.4.1 | 0.51 | 4 |
| FPR5.4.2 | 0.51 | 4 |
| FPR5.4.3 | 0.44 | 4 |

TABLE 11

Average viable cell density for all SRs and FPRs

| Average 4dps VCD ($\times 10^6$cells/mL) | SRs w/λ of 22.5 cells/MC | 0.95 ± 0.01 |
|---|---|---|
| | SRs w/λ of 30 cells/MC | 1.12 ± 0.024 |
| Average VCD at infection ($\times 10^6$ cells/mL) | FPRs with no MX process | 0.73 ± 0.026 |

Figure 4:
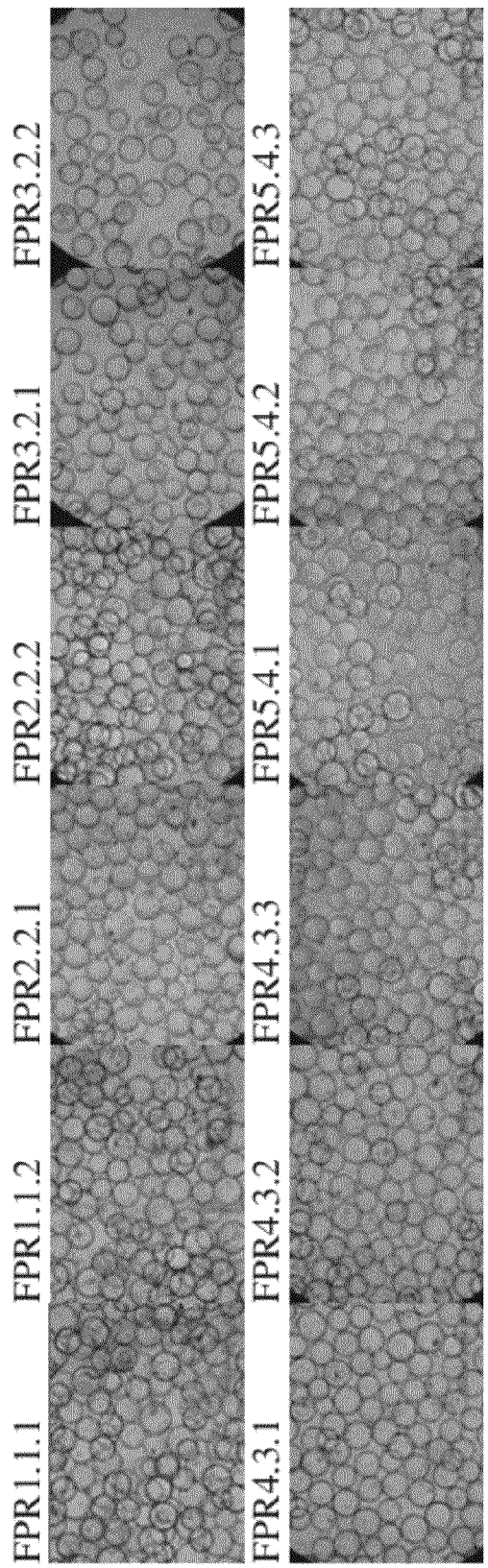
FIG. 4 shows photographs (taken at 100× magnification) taken on 4 dps for 12×2 L final production reactors for all experiments.
Figure 5:
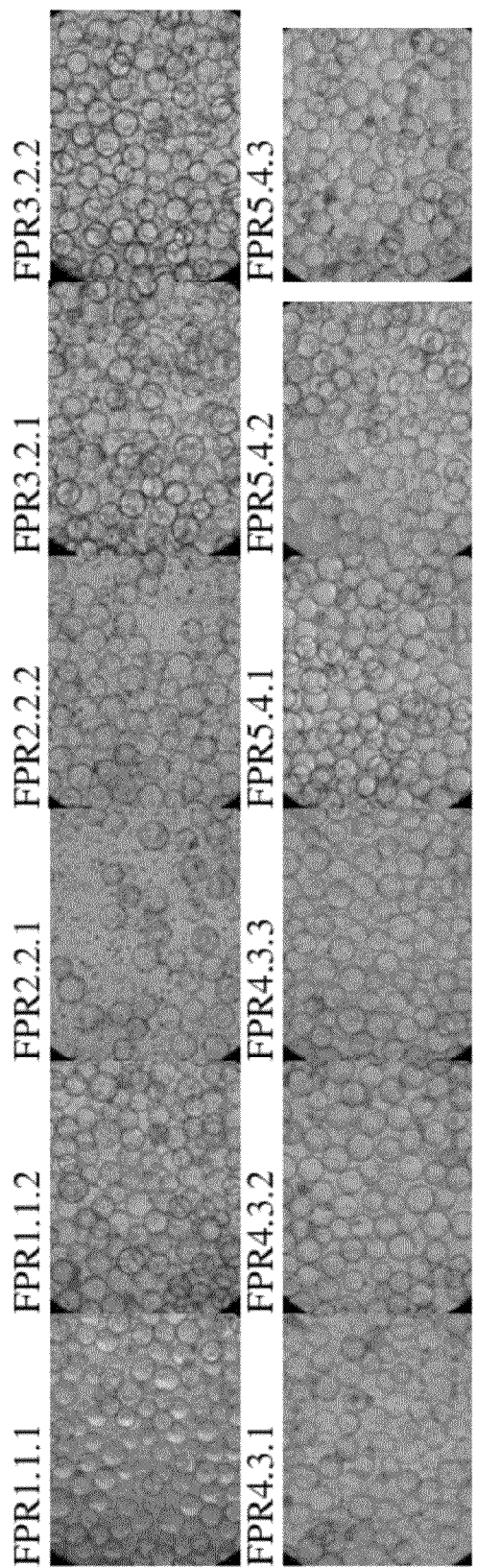
FIG. 5 shows photographs (taken at 100× magnification) taken on 3 dpi for 9×2 L final production reactors (FPR) for all experiments.

After trypsinization, the cells in FPRs attached to the microcarrier beads at 0 dps and then began to proliferate on the surface of the microcarrier beads. Most of the microcarriers were covered with cells and only some beads remained empty (no cells covering the beads) by 4 dps. Cell morphology was similar in all the experiments. Photographs showing typical cell morphology on 3 dps and 4 dpi are presented in FIG. 4 and FIG. 5, respectively.

On 4 or 5 dps, the FPRs in experiment 1, 2 and 3 were infected with ca A/Uruguay, ca A/South Dakota and ca B/Florida respectively. Prior to infection 0.03× of 10× TrpLE select was added to the cell culture medium. In experiment 4 and 5 individual FPR was infected with one of the three seasonal strains ca A/Uruguay, ca A/South Dakota and ca B/Florida at 20 FFU/mL. FIG. 6 shows that peak virus titers were reached between 68 and 74 hours post infection (hpi). Moreover, the virus titer remained high thereafter until 92 hpi.

The average virus titers for each virus strain types is summarized in Table 12 They were 8.7, 8.8 and 8.45 $\log_{10}$ FFU/mL for ca A/Uruguay, ca A/South Dakota and ca B/Florida, respectively. This is in line to or above what was observed for these viruses when 67% medium exchange was made.

Additional experiments were performed to compare viral titers for four strains (ca A/Wisconsin/67/05, A ca A/Uruguay, ca A/South Dakota and ca B/Florida) produced using the 67% medium exchange process (performed essentially as described in International Patent Publication WO 08/105, 931, see Example 12) versus no medium exchange process (performed essentially as described above). At least two runs were performed for each process and strain. It can be seen from FIG. 7 that the peak viral titers for each strain are comparable between the 67% medium exchange and the no medium exchange process.

TABLE 12

Average peak virus tiers for each virus strains for the FPRs.

| Virus strain | Average peak virus titer (log10FFU/mL) | Peak harvest day (dpi) | No. of FPRs |
|---|---|---|---|
| ca A/Uruguay/716/2007 | 8.7 ± 0.05 | 3 | 4x2L |
| ca A/SouthDakota/6/2007 | 8.8 ± 0.0 | 3 | 4x2L |
| ca B/Florida/4/2006 | 8.45 ± 0.25 | 3 | 4x2L |

Medium exchange is a major operational step in current cell culture-based influenza vaccine manufacturing process. Many efforts have been made to eliminate medium exchange prior to infection since without medium exchange the probability of microorganism contamination will be reduced and more operational friendly processes can be implemented. Through a series of twelve bioreactor runs without medium exchange the process performance data, more specifically, cell detachment/attachment, cell growth and virus titers were collected to assess the variability of a new vaccine production process and the feasibility of inoculating FPR with cells directly taken out of SR using a new bead to bead transfer procedure. Three virus strains namely, ca A/Uruguay, ca A/South Dakota and ca B/Florida were each produced four times with no medium exchange prior to infection. It was confirmed that VCD could be reached up to $1 \times 10^6$ cells/mL on 4 dps in SRs and B2B transfer with 1×DPBS, TrypLE Select and EDTA could be accomplished successfully with effective (>90%) cell detachment in seed reactors after 30 to 40 minutes of trypsinization. Cells in FPRs proliferated on the surface of microcarrier beads and reached average VCD of about $0.73 \times 10^6$ cells/mL at the time of infection. Peak virus titers for ca A/Uruguay, ca A/South Dakota and ca B/Florida for all the FPR runs with no MX process were 8.7±0.05, 8.8±0.0 and 8.45±0.25 $\log_{10}$ FFU/mL respectively at 3 dpi. This was better than or in-line with what was generally observed for the virus strains with the 67% medium exchange (see FIG. 8). The peak virus titer for all virus types was greater than 8.4 $\log_{10}$ FFU/mL. These results clearly demonstrated that the B2B transfer and no MX process described here is a very robust process. They minimize the use of costly medium reagents and can reduce the likelihood of contamination.

9.2 Alternating Tangential Flow (ATF) Process

To facilitate in situ fluid exchange in bioreactors we have developed a cell culture based manufacturing processes using ATF to: a) wash microcarriers in situ); b) exchange cell culture media in culture vessels; and c) separate the production cells from cell culture-produced biologicals, vaccines and other materials and harvest the bulk products in a much more efficient and controlled fashion. As shown in FIG. 18, no microcarries are present in the waste bag after microcarrier sterilization or after media exchange. Further more, as shown in Table 13, the use of ATF coupled with direct flow filtration during viral harvest does not result in any increase in host cell protein or host cell DNA present in the harvest or the final purified product.

TABLE 13

Host DNA and Protein In ATF Produced Material ca B/Malaysia
Lot: App07-60
12000s-1,
70LMH

| | DNA (ng/mL) by Picogreen | Total Protein (ug/mL) by BCA | Titer (log10FFU/mL) |
|---|---|---|---|
| Bioreactor VH | 6588.8 | 1277.04 | 8.7 |
| SP added to VH (SVH) | 4583.2 | 1108.77 | 8.6 |
| SVH 1 hr (ATF start) | 6278.4 | 1135.20 | 8.6 |
| ATF 0.25 h | 4755.7 | 1130.69 | 8.7 |
| ATF 0.5 h | 6776.8 | 1204.43 | 8.6 |
| ATF 0.75 h | 4505.1 | 1128.49 | 8.6 |
| ATF 1 h | 5239.3 | 1155.79 | 8.7 |
| TFF1 (5XUF 5XDF) (ATF/DFF/TFF coupling) | 5794.5 | 84.18 | 9.1 |

This example describes the processes and parameters used for several production simulation runs that utilized ATF and control runs which did not. Representative equipment and reagents that can be used in the process are detailed in Table 14 and Table 15. Of course, other equipment and reagents which perform similarly may be optionally substituted herein and specific mention of particular brands or types of equipment and reagents should not be construed as limiting unless specifically indicated to be so. The ATF system provides an efficient means for fractionating a mixture or suspension cells, molecules and other particulates. The ATF process provides the means for generating rapid, low shear, tangential flow. The ATF system provides the means for confining the process. Since the entire process is enclosed the ATF system can be used for pre and post-sterilization of microcarrier bead washes, pre-infection media exchange and during the harvest process. The filtration system consists of a housing assembly that can accept either a hollow fiber filtration module or a screened module for fractionation of larger particles such as microcarriers. The housing is positioned between the process vessel or a bioreactor at one end and a diaphragm pump at the other end. The vessel serves as a storage container for the content to be filtered. A filtrate pump is used for controlled removal of the filtered stream. The unfiltered material remains in the system. ATF is a pulsating, reversible, flow of fluid, back and forth, between process vessel and diaphragm pump. The pump is partitioned into two chambers with a flexible diaphragm. One of the pump chambers serves as a liquid reservoir that registers with the process vessel through the screen module. The second pump chamber is an air chamber that registers with pump flow control system. Typically, controlled addition of compressed air into the air chamber increases the pressure in this chamber relative to the process vessel. This expands the air chamber, inversely reducing the volume in the liquid chamber, in the process driving the liquid content from pump to process vessel through the screen module. The flow through the screen module lumens generates tangential flow in one direction. Inversely, with a slightly pressurized vessel or by attaching the air chamber to an exhaust or vacuum, the pressure in the air chamber is reduced relative to the process vessel and the liquid flow will be from the vessel to the liquid chamber of the pump generating tangential flow in the other direction. The cycle is repeated.

TABLE 14

Materials and Reagents

| Component | Suggested Vendor | Catalog (MEDI Material) # |
|---|---|---|
| MediV 105 SFM (final 9 g/L glucose) | N/A | See Table 2 above |
| NaOH pellet | EM | SX0583-3 |
| Lima Bean Trypsin Inhibitor | Worthington | LS002829 |
| SF non-tumorigenic MDCK Clone | N/A | ATCC accession number PTA-7910, see WO 08/105931 |
| TrypLE Select 1X | Invitrogen | 12563-011 |
| Cytodex 3 | Amersham Biosciences | 17-0485-03 |
| DPBS (without $Ca^{2+}$ and $Mg^{2+}$) | Invitrogen | 14190-136 |

TABLE 15

Equipment List

| Equipment | Manufacturer | Model |
|---|---|---|
| Bio Safety Cabinet (BSC) | Baker | SG-600 |
| Water Bath | VWR | 1235 |
| $CO_2$ Incubator | Thermo Forma | 3110 |
| −80° C. Freezer | Revco | ULT2586-9-A36 |
| Cedex Cell Counter | Innovatis | G007D00138 |
| NucleoCounter | ChemoMetec A/S | M1293-0000 |
| Tubing Welder | Terumo | SCD IIB 72721T |
| NucleoCassettes | ChemoMetec A/S | M1293-0100 |
| Roller Bottle Incubator | Bellco | 7630-80589 |
| Microscope | Zeiss | Axiovert 25/Nikon |
| 2 L Bioreactor | Applikon | Z611000010 |
| 7 L Bioreactor | Applikon | |
| Bioreactor DO probe | Applikon | Z01002352 |
| Bio console | Applikon | ADI 1035 |
| Bio Controller | Applikon | ADI 1030 |
| Bioreactor pH probe | Applikon | Z001023510 |
| Lipseal stirrer assembly | Applikon | Z5100002MO |
| Tubing Welder | Terumo | SCD IIB 72721T |
| Nova Bioprofile Analyzer | | Bioprofile 400 |
| Peristaltic Pump | Cole Parmer | 7553-70 |
| ATF2 with C26 controller | Refine Technology | ZZ:ATF2:MC-G1 |

Pre-Seeding Preparations:

ATF may be utilized for any process in which fluid is removed and/or exchanged from the bioreactor. For example, the ATF system can be used to remove the DPBS wash solution after hydrating the microcarrier beads prior to sterilization of the vessel and/or after the autoclaving steps the ATF system can be used to remove the DPBS wash solution and replaced with Complete Growth Media. Table 16 shows the ATF control settings utilized during fluid exchange in production simulation runs 1-3.

1. Prepare Cytodex 3 microcarrier and weigh desired amount of Cytodex 3 (4 g for 2 L bioreactor and 10 g for 5 L bioreactor) and transfer to cleaned sterile bioreactor and hydrate in 50~100 mL of 1×PBS per gram of beads no less than 3 hours or overnight and washing with fresh PBS. The washing steps can be done with the ATF using settings detailed in Table 16.
2. Attach tubing and filters to all free headplate ports.
3. Connect DO probe overnight prior to calibration to allow for polarization (Note: minimum of 6 hours).
4. Calibrate pH and DO probes according to the manufacturer's instructions and attach to the assembled bioreactor making sure that the tip of the probe is submerged within the DPBS already present in the reactor vessel. Add more DPBS to the reactor vessel if necessary.
5. Autoclave the entire unit at 121° C. for 30 minutes at 15 psi in the liquid cycle.
6. Once autoclaved and cool, connect the DO probe, the pH probe and the stirrer motor.
7. Aliquot 1N NaOH into small feed bottles, connect base line and prime to its respective reactor vessels.
8. Batch media a day before inoculation (seeding)
   a. Warm up desired amount of cell growth media (CGM), MediV 105 SFM, in the 37° C. waterbath.
   b. Drain out the DPBS from bioreactor from the drain port. Alternatively, use the ATF system to drain the DPBS wash solution and replace with CGM using settings detailed in Table 16.
   c. Wash beads once with fresh, warmed CGM with the following steps:
      i) Add desired volume of CGM after draining out of DPBS.
      ii) Turn on agitation control to 120 rpm for 10 minutes
      iii) Turn off agitation to allow the beads to settle and drain out the supernatant.
   d. Add desired volume of CGM to bioreactor.
9. Turn on aeration, temperature control and stirrer. Set points for cell expansion are as follows: pH=7.4, temperature=37° C., DO=50% air saturation, and stirrer=between about 135 to about 175 rpm (generally faster for smaller bioreactor).
10. Add glucose to final 9 g/L
11. Draw samples and measure by NOVA, perform DO calibration and pH correction (if needed).
12. Turn on bioreactor controller and run with a flow rate between 40 and 320 mL/min (for working volumes between 2 to 16 L).

Seeding and Growth:

Calculate the average viable cells per roller bottle or seed reactor and transfer the appropriate amount of cells into glass feed bottle with fresh, warmed media. A straight 1:8 split may be utilized for bead to bead transfer, or alternatively a seeding density of between about $1\times10^5$ to about $1.5\times10^5$ may be used. Note cells may be split using any of the bead to bead transfer methods described in Examples 9.3 or 9.4 below. The data shown in FIG. 17 were generated from cells split using the EDTA/Trypsin protocol (Example provided in Section 9.3). After inoculation, draw sample for post-inoculation Nova and nuclei count daily. Once the nuclei count reached the desired cell density in 3~4 days post culturing, perform virus infection. Set points for cell expansion are as follows: pH=7.4, temperature=37° C., DO=50% air saturation, and stirrer=between about 135 to about 175 rpm (for working volumes between 2 to 16 L).

Infection:

Prior to infection about 66% of the CGM is removed an replaced with complete infection medium (CIM, DMEM/F-12, 45% glucose, 200 mM L-glutamine, 1:330 dilution of 10× TrypLE) as follows: All control loops are turned off and the microcarrier beads are allowed to settle. The desired amount of media, equivalent to 66% is removed from the bioreactor and replaced with fresh, warmed CIM. The set points are adjusted and the controller loops are turned back on. Set points for infection are as follows: pH=7.4, temperature=33° C., DO=50% air saturation, and stirrer=between about 135 to about 175 rpm (for working volumes between 2 to 16 L). Table 16 shows the ATF control settings utilized during media exchange in production simulation runs 1-3. Using the control settings described in Table 16 the desired amount of media, equivalent to 66% is removed, using the ATF system with agitation and not allowing the microcarrier beads to settle, from the bioreactor and replaced with equal volume of fresh, warmed CIM. Once the set points are reached the desired amount of virus is added. If desired a nuclei count is performed prior to infection and the amount of virus need to infect the bio reactor is calculated, for example 20-200 MOI (FFU/mL) for seasonal strains or 2000 MOI (FFU/mL) for pandemic strains may be used. Alternatively, a set amount of virus at a known concentration (FFU/mL) is added based on the working volume of the reactor. See for example WO 08/105,931 (Example 12 in particular).

Harvest:

At the desired time (generally between 48-72 hours post infection) the control loops are turned off and the microcarrier beads are allowed to settle. An appropriate sterile bag container is attached to the bioreactor outlet port and the viral harvest is removed by peristalitc pump or ATF device. When using a peristalitic pump care must be exersized to not include the microcarrier beads. Once harvest is complete 10×SP buffer (2.18 M sucrose and 110 mM potassium phosphate, pH

TABLE 16

| ATF Control Settings | | | | |
|---|---|---|---|---|
| ATF Control Settings | Run #1 | Run #2 | Run #3 | Run #4 |
| Pressure set point | 0.6 psi | 0.6 psi | 1 psi | 1 psi |
| Pressure cycle flow | 3.1 L/min | 3.1 L/min | 4 L/min | 4 L/min |
| Exhaust cycle flow | 1.8 L/min | 1.8 L/min | 2 L/min | 2 L/min |
| Exhaust time | 3.8 sec | 3.8 sec | 2.7 sec | 2.7 sec |
| Filtrate flow rate (Media exchange) | 500 mL/min | 500 mL/min | 750 mL/min | 750 mL/min |
| Filtrate flow rate (harvest) | 160 mL/min | 160 mL/min | 160 mL/min | 160 mL/min |

7) may be added to the bag to a final concentration of 1×. When ATF is utilized the harvest step may be directly coupled to the direct flow filtration step as described in Example provided in Section 9.6.3, below. Table 16 shows the ATF control settings utilized during harvest in production simulation runs 1-4.

9.3 Rapid Bead to Bead Transfer Process with Low Concentration of Protease

This example describes the processes and parameters for rapid and efficient bead to bead transfer of MDCK cells using DPBS/0.5 mM EDTA pH8 wash solution and a low concentration of protease (e.g., 0.05× TrypLE) in spinner flask, shaker flask or stirred tank bioreactor. An overview of the process flow is provided in FIG. 8A. Representative equipment and reagents that can be used in the process are detailed in Table 17, Table 18, and Table 19. Of course, other equipment and reagents which perform similarly may be optionally substituted herein and specific mention of particular brands or types of equipment and reagents should not be construed as limiting unless specifically indicated to be so.

This process was utilized in the twelve runs described above. As noted, a proper cell detachment in the seed reactors and attachment for cells in FPRs was observed using the bead to bead transfer protocol using 1×DPBS wash with EDTA and trypsinization using TrypLE select at pH8. Thus, the bead to bead transfer process is rapid, efficient and robust.

TABLE 17

Equipment List

| Equipment | Manufacturer | Model |
| --- | --- | --- |
| Bio Safety Cabinet (BSC) | Baker | SG-600 |
| Controller/Console | Applikon | ADI1030/ADI1035 |
| Stirred tank bioreactors (5 L, 10 L; 15 L) | Applikon | Z611000010 |
| Microscope | Zeiss or Nikon | Axiovert25 |
| Cedex Cell Counter | Innovatis | G007D00138 |
| Peristaltic Pump | Cole Parmer | 7553-70 or equivalent |

TABLE 18

Materials and Reagents

| Component | Suggested Vendor | Catalog Number |
| --- | --- | --- |
| 10X TrypLE Select | Invitrogen | 04-0090DG |
| Ethylenediaminetetraacetic acid (EDTA, disodium salt dihydrate) FW | Sigma or equivalent | Cat #E5134-500G |
| 0.5M EDTA pH 8 | Gibco | 15575-038 |
| 0.5M EDTA pH 8 | In-House | NA |
| Dulbecco's Phosphate Buffered Saline (20 L bag); without $Ca^{2+}$ and $Mg^{2+}$ | Gibco or equivalent | 14190-367 |
| Dulbecco's Phosphate Buffered Saline powder 10X; without $Ca^{2+}$ and $Mg^{2+}$ | Gibco or equivalent | 21600-069 |

TABLE 19

DPBS/0.5 mM EDTA - pH 8 Wash Solution Preparation

| Component | Concentration | Volume (mL) |
| --- | --- | --- |
| DPBS | N/A | 1000 |
| 0.5M EDTA pH 8 (Gibco or In-house) | 0.5 mM | 1 |
| pH | 8.0 ± 0.1 | NA |

Preparation of 1× Liquid Medium DPBS from 10×DPBS Powder:

Add powdered medium to room temperature water with gentle stirring. (Do not heat water). Rinse out the inside of the container to remove all traces of powder. Dilute to a desired volume with water. Stir until dissolved. (Do not over-mix). Adjust pH of medium to 7.8±0.1 (final working pH is 8.0). pH units will usually rise 0.1-0.3 upon filtration. After pH has been adjusted keep container closed until medium is filtered. Sterilize immediately using 0.1 micron membrane.

Preparation of 0.5M Stock EDTA:

Add 186.1 g EDTA (disodium, dihydrate) to 800 mL of deionized water. Add about 20 g of NaOH pellets or 10N NaOH while stirring to bring pH to 8.0. Note: Add the last few grams slowly to avoid overshooting the pH. EDTA won't dissolve until the pH is around 8. Adjust volume to 1 L with deionized water. Filter with 0.1 micron filter. Aliquot into smaller volumes (200 mL each bottle) and store at room temperature.

Preparation of DPBS/0.5 M Stock EDTA:

Add 1 mL of 0.5M stock EDTA pH8 for every liter of DPBS. Adjust pH of medium to 7.8±0.1 (final working pH is 8.0) if necessary. Note: pH units will usually rise 0.1-0.3 upon filtration. Filter with 0.1 micron filter.

1×DPBS/0.5 mM EDTA-pH8.0 Wash Procedures:

Stop the agitation, pH, DO, temperature controls if applicable. Let microcarrier beads settle for 15±5 minutes. Remove through the outlet port 80±10% of spent growth medium. See Table 20. Note: this procedure could be done using alternating tangential flow (ATF). Replace with equal volume of 1×DPBS/0.5 mM EDTA-pH8.0 wash solution to the culture vessel. See Table 20. Start the agitation to original setting and wash cells for 25±5 minutes. Stop the agitation and let microcarrier beads settle for 15±5 minutes. Remove through the outlet port 80±10% of wash solution. See Table 21. Note: this procedure could be done using the ATF. Add 1×DPBS/0.5 mM EDTA-pH8.0 wash solution to the vessel up to 50% of working culture volume. See Table 20. Set agitator speed to desired rpm. See Table 21. Start the agitator, pH, DO and temperature controls. Adjust the pH setting to 8.0. See Table 21.

TABLE 20

DPBS/0.5 mM EDTA - pH 8.0 Wash Volume and Agitation speed

| | Bioreactor working volume | | | |
| --- | --- | --- | --- | --- |
| | 2 L | 5 L | 10 L | 15 L |
| Vol. to be removed (L) | 1.6 ± 0.2 | 4 ± 0.5 | 8 ± 1 | 12 ± 1.5 |
| Vol. to be added (L) | 1.6 ± 0.2 | 4 ± 0.5 | 8 ± 1 | 12 ± 1.5 |
| Agitation (rpm) | 175 | 175 | 134 | 134 |

TABLE 21

1X DPBS/0.5 mM EDTA pH 8.0 Wash Volume, Agitation speed, pH, Temp and DO settings

| | Bioreactor working volume | | | |
|---|---|---|---|---|
| | 2 L | 5 L | 10 L | 15 L |
| Vol. to be removed (L) | 1.6 ± 0.2 | 4 ± 0.5 | 8 ± 1 | 12 ± 1.5 |
| Vol. to be added (L) | 0.6 ± 0.2 | 1.5 ± 0.5 | 3.0 ± 1.0 | 4.5 ± 1.5 |
| Agitation (rpm) | 250 | 250 | 220 | 220 |
| pH | 8.0 ± 0.1 | 8.0 ± 0.1 | 8.0 ± 0.1 | 8.0 ± 0.1 |
| Temperature | 37 ± 0.1° C. | 37 ± 0.1° C. | 37 ± 0.1° C. | 37 ± 0.1° C. |
| DO | 50% | 50% | 50% | 50% |

Cell Detachment Procedure:

When the culture pH reached to 8±0.1, add calculated volume of 10× TrypLE to a final concentration of 0.05× through the injection port or through the medium port. See Table 22. Note: You can also perform 1:200 dilution of the 10× TrypLE relative to the desired working volume. Through the sampling port, take sample aliquots every 15±2 minutes until fully detached. Note: Cell detachment should be complete in <60 minutes. Add basal medium to the original working volume of the culture vessel. Stop all control loops except the agitator and pH controls.

Bead to Bead Procedure:

Transfer the desired volume of detached cells to final production reactor. See Table 23.

TABLE 22

10X TrypLE volumes

| | Bioreactor working volume | | | |
|---|---|---|---|---|
| | 2 L | 5 L | 10 L | 15 L |
| 10X TrypLE (mL) | 5 | 12.5 | 25 | 37.5 |

TABLE 23

Bead to Bead Process Transfer to Final Production Reactor

| | Bioreactor working volume | | | |
|---|---|---|---|---|
| 1:8 split | 2 L | 5 L | 10 L | 15 L |
| Vol. of trypsinized cells | 0.250 L | 0.625 L | 1.25 L | 1.875 L |
| Complete Growth medium | 1.725 L | 4.375 L | 8.75 L | 13.125 L |
| Cytodex3 microcarriers | 3.45 g | 8.75 g | 17.5 g | 26.25 g |

9.4 Protease-Free Bead to Bead Transfer Process and Use of ATF

One of the major challenges for producing vaccines, recombinant proteins and other bio therapeutics is to reproducibly detach the adherent production cells from the culture vessels and then reattach them to new culture vessels, a process normally known as sub-culturing of cells. This task becomes particularly difficult for microcarrier-based production in large scale manufacturing. To ensure the cells be properly sub-cultured trypsin or trypsin-like reagents (e.g., TrypLE) are commonly used. However, the trypsinization process can be hard to control and the risk of over- or under-trypsinization can have a negative impact on the robustness of manufacturing processes and even reduction in productivity. Here we describe a new method that allows mammalian cells, in particular highly adherent MDCK cells, to be serially passaged without using trypsin or trypsin-like reagents. This method makes use of EDTA to replace trypsin or trypsin-like reagents. This method may further be coupled with alternating tangential flow device (ATF) to facilitate in situ fluid exchange in the bioreactors.

With the newly developed protease-free process we have successfully passaged MDCK cells for more than 5 times consecutively and consistently reached high cell viability (>90%) and high cell density (>1×106 cells/mL) (see FIG. 15). We have also used the cells prepared by this method to produce high titer viruses including cold adapted live attenuated influenza viruses of several different subtypes. The virus titer was at least 8 log 10 FFU/mL for each of the three representative virus strains that compose the seasonal vaccine (A/H1, A/H3 and B strains)(FIG. 16, and data not shown). This process can be used for both vaccine and cell culture-based biological (monoclonal antibody, recombinant protein, etc.) production at large and small scale.

This example describes the processes and parameters for rapid and efficient bead to bead transfer of MDCK cells by washing the cells and incubating the cells with EDTA pH8 in spinner flask, shaker flask or stirred tank bioreactor in the absence of any protease. Representative equipment and reagents that can be used in the process are detailed in Table 17, Table 18, and Table 19 above. Of course, other equipment and reagents which perform similarly may be optionally substituted herein and specific mention of particular brands or types of equipment and reagents should not be construed as limiting unless specifically indicated to be so.

1×DPBS/0.5 mM EDTA-pH8.0 Wash and Incubation Procedures:

Stop the agitation, pH, DO, temperature controls if applicable. 1) Let microcarrier beads settle, 15±5 minutes is generally sufficient, and remove ~70-80% or more of spent growth medium. Note: this procedure could be done using alternating tangential flow (ATF). 2) Replace with desired volume of 1×DPBS wash solution to the culture vessel. Generally, an equal volume of wash buffer is suggested for efficient washing. 3) Repeat steps (1) and (2) as desired, generally a total of three washes is suggested. 4) Remove wash solution as needed to leave the desired volume (e.g., ~50% of the original volume) Note: this procedure could be done using the ATF. 5) Add 0.5 mM EDTA-pH 8.0 to a final concentration of 0.5 mM. 6) Start agitation as well as pH, DO and temperature controls if applicable Agitation will be generally be between 100 to 250 rpm depending on working volume and/or impeller. 100 rpm was utilized for small scale transfer of a few hundred milliliters or less. Also see, for example, Table 21 for agitator speeds that may be used for larger working volumes. 7) Incubate with agitation for 60±10 minutes. Sample aliquots may be drawn to check for complete cell detachment. Table 24 details the conditions utilized for small scale bead-to-bead transfers.

Once cells are detached the cells are then ready to split. Generally, growth added is added to desired working volume (e.g., original volume) and the desired volume of detached cells are transferred to a new vessel. Alternatively additional growth medium and/or microcarriers are added to the original vessel. For scale-up process a 1:5 to 1:8 split has been found to be useful, Table 23 provides the details for 1:8 splits for several final working volumes. Optionally, the original flask is rinsed with growth medium and combined with the transferred material, this volume should be accounted for when performing scale-ups so as not to dilute the cells too much. 8) Incubate the new flask at the appropriate temperature (here 37° C. was used) without any agitation for 40-60 minutes. 9) Start agitation as well as pH, DO and temperature controls if applicable for growth of cells. 10) Repeat steps (1)-(9) as needed for serial propagation and scale-up for infection.

Parallel cultures were serially propagated over five (5) passages using the protease-free method (EDTA from commercial or in-house preparations) essentially as detailed in Table 24 or ETDA/TrypLE essentially as detailed in the Example provided in Section 9.2. For the control cells new cells were trypsinized (cells are washed and incubated with 1× TrypLE for 15-20 min, fresh growth medium is added and the cells are centrifuged for 10 min 1000 rpm and resuspended in fresh growth medium) and used to seed spinner flasks for comparison of cell growth/viability and titer each passage. The cell counts and viability over time during cultivation are plotted in FIG. 15. As can be seen from the plots, the cell counts and viability of the cultures propagated using EDTA alone (protease free) and ETDA/TrypLE are comparable. Furthermore, both these methods were generally seen to produce a higher density culture then the control method. Cells from each passage of the parallel cultures were also used to produce influenza virus. The viral titers obtained for ca A/Wisconsin/67/07 and ca B/Malaysia/2506/04 (FIG. 16, top and bottom panels, respectively) were similar regardless of the propagation method used.

TABLE 24

Protease-free bead to bead transfer conditions

| Steps | Specifications and Set-points | Values | Units |
|---|---|---|---|
| 1. | Beads settle 15 minutes; remove media | 70-80 | % |
| 2. | Add DPBS wash solution to the original working volume | 80 | % |
| 3. | Repeat steps 1 and 2 twice for a total of three washes | | |
| 4. | Remove 50 ml DBPS wash solution | 50 | % |
| 5. | Add 50 µl of 0.5M EDTA solution | 0.5 | mM |
| 6. | Start agitation, CO2 and temperature controls | 100, 5, 37 | Rpm, %, ° C. |
| 7. | Time for detachment | 60 ± 10 | Min |

9.5 Rapid Bead to Bead Transfer Process Without Washing

Figure 23C:
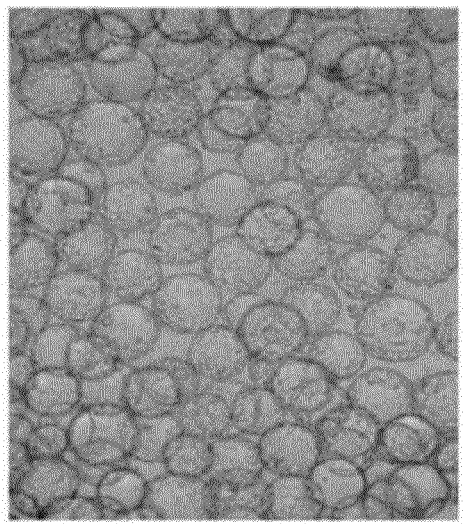
Figure 23F:
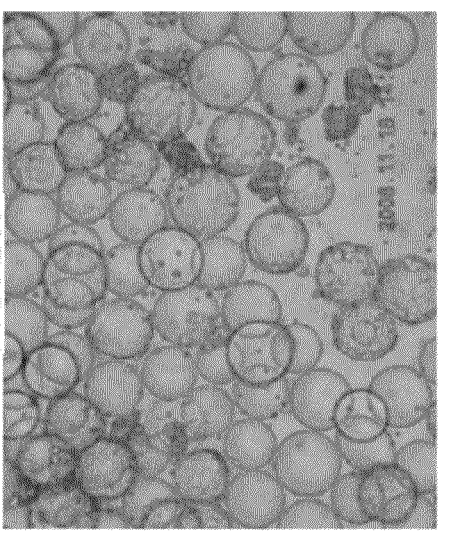
Figure 23B:
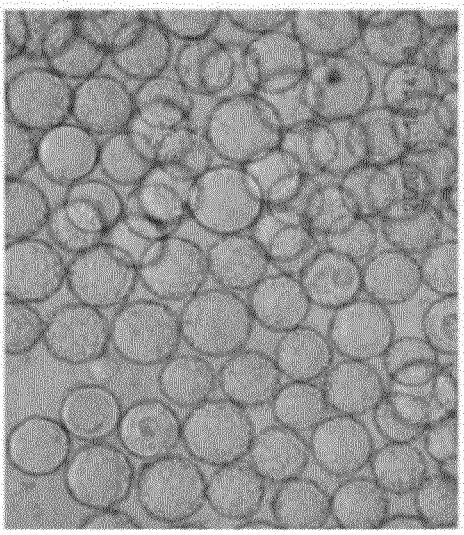
Figure 23E:
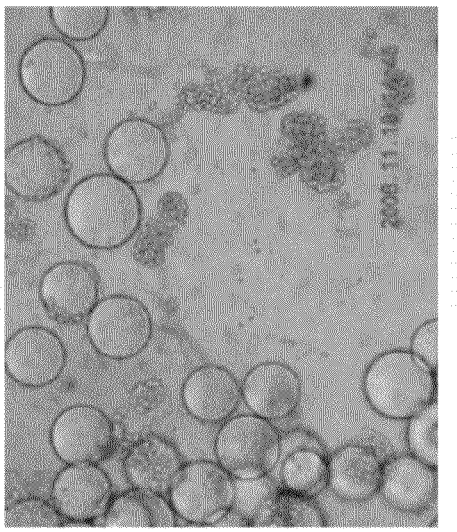
Figure 23A:
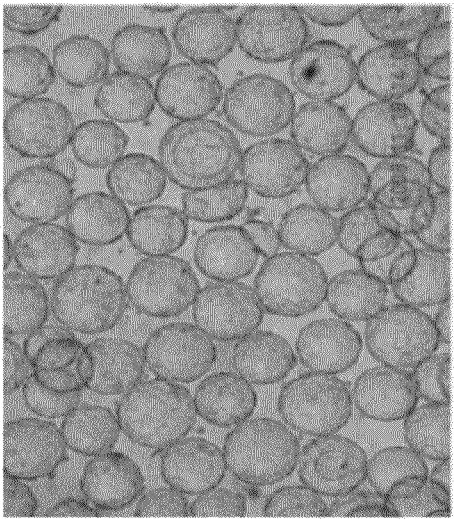
Figure 23D:
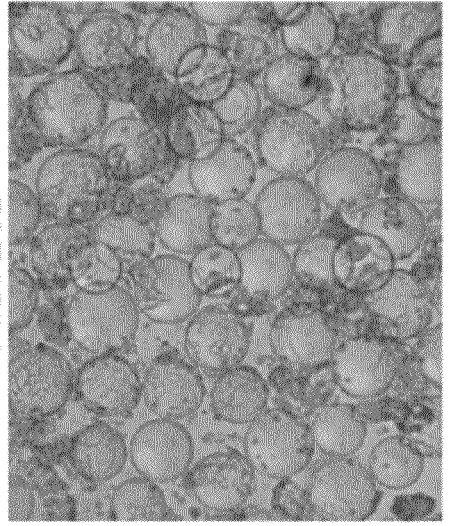
Figure 24C:
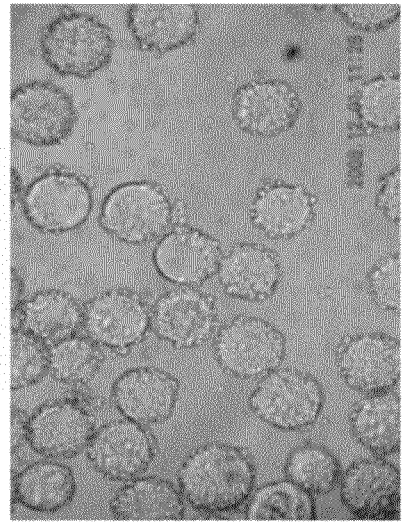
Figure 24F:
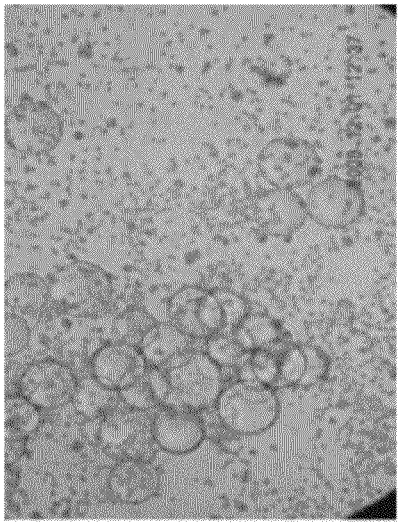
Figure 24B:
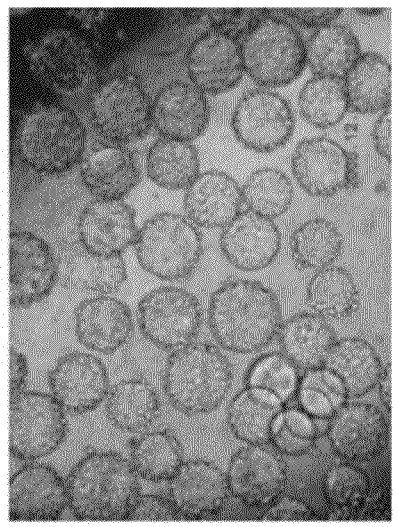
Figure 24E:
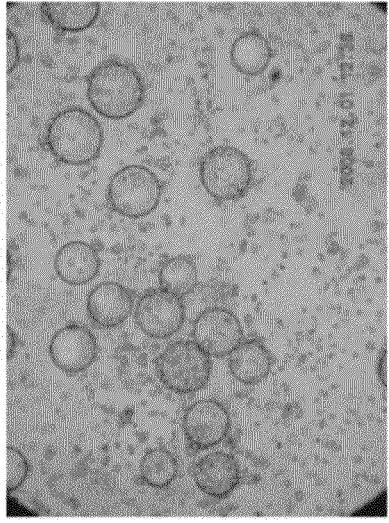
Figure 24A:
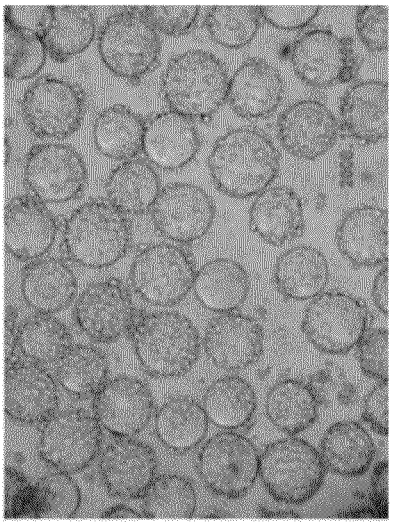
Figure 24D:
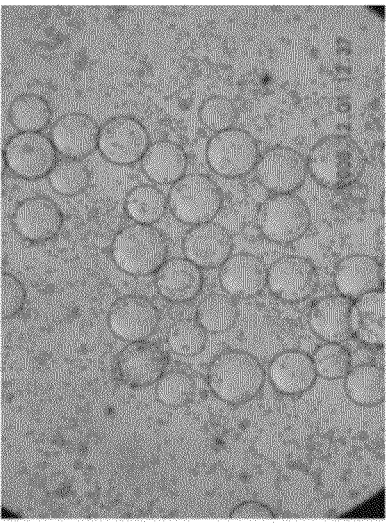

The presence of divalent cations in growth media can inhibit the action of proteases used to detach cells from microcarriers. As shown above, EDTA can be used to chelate these cations facilitating detachment of cells. A series of experiments were performed examine the effect of EDTA concentration on cell morphology and detachment. FIG. 23A shows untreated cells. They have a flattened morphology and are tightly adhered to the microcarriers. FIGS. 23B-F show the change in morphology seen after 60 minutes of exposure to increasing amounts of EDTA, 0.5, 1, 2, 5, and 10 mM, respectively. Some rounding is seen with the 0.5 and 1 mM treatments. Treatment with 2 mM and up results in additional rounding and detachment. Nearly all the cells detached from the microcarriers at the highest concentrations of EDTA. Based on these observations 1-2 mM EDTA can facilitate cell rounding.

A second series of experiments was performed to examine the effect of TrypLE concentration in the presence of 1 or 2 mM EDTA. After pre-treatment with 1 or 2 mM EDTA, TrypLE was added to the cell cultures at a final concentration of 0.0125×, 0.025× and 0.05× and detachment was monitored. FIG. 24 shows the detachment seen for the cells pre-treated with 2 mM EDTA using different concentrations of TrypLE over time. At time zero after TrypLE addition the cells showed a rounded morphology (FIGS. 24A, B, and C, 0.0125×, 0.025× and 0.05× TrypLE, respectively) with little detachment. At 60 minutes after TrypLE addition all the cultures showed some detachment. At the lower TrypLE concentrations (0.0125× and 0.025×) not all the cells were detached and some clumping was observed (FIGS. 24 E and E, respectively). At 0.05× TrypLE nearly all the cells were detached and little clumping was observed (FIG. 24 F). However, when these cells were transferred into a new production vessel supplemented with fresh growth medium they failed to reattach to the old and new microcarriers, likely due to chelation of the divalent cations in the fresh growth medium.

The addition of a matrix of CaCl2, MgCl2, MgSO4, and trace elements A, B, and C to the growth medium was examined for the ability to overcome the chelation effect on attachment and growth. Table 25 shows the percent of cell reattachment and spreading on day 4 post seeding with the addition of a matrix of concentrations of $CaCl_2$, $MgCl_2$, and $MgSO_4$ to MediV 105 SFM growth medium. Table 26 shows the cell counts on day 4 post seeding with the addition of a matrix of concentrations of $CaCl_2$, $MgCl_2$, $MgSO_4$, and Trace Elements A, B, and C, to MediV 105 SFM growth medium. As shown in Table 26, MDCK cells reached over 1E6 cells/mL and above 90% cell viability on Day 4 post bead to bead transfer when MediV 105 SFM was supplemented with 1.5 mM $CaCl_2$, 0.15 mM $MgCl_2$, 0.4 mM $MgSO_4$, and 2× of trace elements A, B, and C. Based on these studies additional experiments may be performed to further optimize these factors for example to determine the optimum growth conditions for additional cells types (e.g., VERO cells) and/or to make this process robust at any scale of virus production.

EDTA Concentration Studies:

MDCK cells grown in 850 $cm^2$ roller bottles were seeded to a 2 L-seed bioreactor (MediV 105SFM, 2 g microcarrier/L) at a density of 1.8.×105 cells/mL. The seed reactor was set at 7.4 of pH which was controlled by $CO_2$ and 1N NaOH; 50% of air saturation with the constant air of 20 mL/min; 37° C. temperature; and 175 rpm of agitation. On day 4, when fully confluent (1.2-1.6E6 cells/mL) 25 mL of microcarrier culture was transferred into 6×100 mL-flasks, and then EDTA was added to each flask to make different final concentration of 0.5, 1, 2, 5, 10, 20 mM. Subsequently, the flasks were incubated in orbital shaker at 37° C., 5% CO2, 200 rpm for 1 hour. Periodic microscopic examination of all flasks during the incubation period was performed to check the degree the cells become spherical in shape (rounding up) at different EDTA concentrations.

TrypLE Select Concentration in Combination with the Optimized Concentrations of EDTA:

MDCK cells grown in 850 cm2 roller bottles were seeded to 2×2 L-seed reactors (MediV 105 SFM, 2 g microcarrier/L) at a density of $1.8 \times 10^5$ cells/mL according to TR #348. The seed reactors were run for 4 days with the same bioreactor parameters described above. On day 4, 1 mM of EDTA was added to one bioreactor, and to the other with 2 mM EDTA. Both were agitated for 1 hour at 175 rpm. Then, pH of both bioreactors was adjusted to 8 before transferring cell suspensions from each bioreactor to 3×500 mL shaker flasks. From each set of culture, 10× TrypLE Select was added to each flask to make 0.05×, 0.025×, and 0.0125× final concentrations and were incubated at 37° C., 5% $CO_2$, 150 rpm in orbital shaker for 30 minutes. During the incubation period, samples from each set were taken periodically for microscopic examination to check for degree of cell detachment from the microcarriers. As per microscopic observation, when ≥90% of the cells have detached from the microcarriers an equal volume of Lima Bean Trypsin Inhibitor (LBTI) was added to stop the trypsin activity.

TABLE 25

Addition of $CaCl_2$, $MgCl_2$, and $MgSO_4$ to
MediV 105 SFM Post No Wash Cell Detachment

| Flask | $CaCl_2$(mM) | $MgCl_2$ (mM) | $MgSO_4$(mM) | Day 4 % Cell Reattachment |
|---|---|---|---|---|
| 1 | 1 | 0.15 | 0.1 | 75% |
| 2 | 1 | 0.2 | 0.8 | 80% |
| 3 | 1.5 | 0.2 | 0.2 | 85% |
| 4 | 1.5 | 0.2 | 0.1 | 90% |
| 5 | 1.5 | 0.15 | 0.2 | 75% |
| 6 | 1.5 | 0.15 | 0.8 | 90% |
| 7 | 1 | 0.1 | 0.4 | 60% |
| 8 | 1.25 | 0.15 | 0.45 | 80% |
| 9 | 1.25 | 0.15 | 0.45 | 95% |
| 10 | 1 | 0.15 | 0.4 | 30% |
| 11 | 1 | 0.15 | 0.2 | 30% |
| 12 | 1 | 0.2 | 0.4 | 25% |
| 13 | 1 | 0.15 | 0.8 | 30% |
| 14 | 1 | 0.1 | 0.8 | 55% |
| 15 | 1.5 | 0.1 | 0.4 | 75% |
| 16 | 1.5 | 0.1 | 0.2 | 80% |
| 17 | 1 | 0.1 | 0.2 | 40% |
| 18 | 1.5 | 0.1 | 0.8 | 75% |
| 19 | 1 | 0.2 | 0.1 | 60% |
| 20 | 1.5 | 0.15 | 0.4 | 80% |
| 21 | 1 | 0.1 | 0.1 | 65% |
| 22 | 1.5 | 0.2 | 0.4 | 85% |
| 23 | 1.5 | 0.1 | 0.1 | 80% |
| 24 | 1.5 | 0.15 | 0.1 | 85% |
| 25 | 1 | 0.2 | 0.2 | 75% |
| 26 | 1.5 | 0.2 | 0.8 | 60% |

TABLE 26

Addition of $CaCl_2$, $MgCl_2$, $MgSO_4$, and Trace Elements A,
B, and C, to MediV 105 SFM Post No Wash Cell Detachment

| Flask | $CaCl_2$(mM) | $MgCl_2$ (mM) | $MgSO_4$(mM) | TE ABC | Day 4 (cells/mL) |
|---|---|---|---|---|---|
| 1 | 1.5 | 0.1 | 0.8 | 1X | 4.71E+05 |
| 2 | 1 | 0.2 | 0.8 | 1X | 2.55E+05 |
| 3 | 1.5 | 0.2 | 0.2 | 1X | 4.41E+05 |
| 4 | 1.5 | 0.2 | 0.1 | 1X | 3.99E+05 |
| 5 | 1.5 | 0.15 | 0.8 | 1X | 3.63E+05 |
| 6 | 1.25 | 0.15 | 0.45 | 1X | 5.88E+05 |
| 7 | 1.5 | 0.1 | 0.2 | 1X | 3.27E+05 |
| 8 | 1.5 | 0.15 | 0.4 | 1X | 4.83E+05 |
| 9 | 1.5 | 0.2 | 0.4 | 1X | 4.65E+05 |
| 10 | 1.5 | 0.1 | 0.1 | 1X | 5.25E+05 |
| 11 | 1.5 | 0.15 | 0.1 | 1X | 5.49E+05 |
| 12 | 1.5 | 0.1 | 0.8 | A*BC* | 6.33E+05 |
| 13 | 1 | 0.2 | 0.8 | A*BC | 3.12E+05 |
| 14 | 1.5 | 0.2 | 0.2 | A*BC | 3.21E+05 |
| 15 | 1.5 | 0.2 | 0.1 | A*BC | 1.95E+05 |
| 16 | 1.5 | 0.15 | 0.8 | A*BC | 2.85E+05 |
| 17 | 1.25 | 0.15 | 0.45 | A*BC | 5.31E+05 |
| 18 | 1.5 | 0.1 | 0.2 | A*BC | 3.12E+05 |
| 19 | 1.5 | 0.15 | 0.4 | A*BC | 5.94E+05 |
| 20 | 1.5 | 0.2 | 0.4 | A*BC | 5.01E+05 |
| 21 | 1.5 | 0.1 | 0.1 | A*BC | 4.20E+05 |
| 22 | 1.5 | 0.15 | 0.1 | A*BC | 5.10E+05 |
| 23 | 1.5 | 0.1 | 0.8 | 2X | 5.64E+05 |
| 24 | 1 | 0.2 | 0.8 | 2X | 4.82E+05 |
| 25 | 1.5 | 0.2 | 0.2 | 2X | 4.26E+05 |
| 26 | 1.5 | 0.2 | 0.1 | 2X | 3.50E+05 |
| 27 | 1.5 | 0.15 | 0.6 | 2X | 2.37E+05 |
| 28 | 1.25 | 0.15 | 0.45 | 2X | 5.19E+05 |
| 29 | 1.5 | 0.1 | 0.2 | 2X | 1.01E+06 |
| 30 | 1.5 | 0.15 | 0.4 | 2X | 1.25E+06 |
| 31 | 1.5 | 0.2 | 0.4 | 2X | 6.39E+05 |
| 32 | 1.5 | 0.1 | 0.1 | 2X | 5.71E+05 |
| 33 | 1.5 | 0.15 | 0.1 | 2X | 7.98E+05 |

9.6 Purification Process for Cell Culture Produced Influenza

The development of a robust large scale purification process for influenza produced in cell culture required intensive development. An early stage process was developed where the viral harvest (60-65 hours post infection) was pumped into a bag, and 10× sucrose phosphate (SP) buffer was added to the viral harvest (VH) bag at 1/10 (v/v) dilution for viral stabilization. The stabilized viral harvest (SVH) was first treated with Benzonase at 50 Units/mL with 2 mM MgCl2 at 32° C. for 3 hours to remove MDCK host cell DNA (HCD) and the reaction was stopped by addition of 5 mM EDTA. Benzonase is an engineered recombinant endonuclease that degrades DNA into oligonucleotides in the presence of magnesium ions. The Benzonase treated viral harvest was then clarified by a 1.2 μm Polypropylene (PP) and 0.45 μm PVDF capsule filters. The clarified VH was conditioned by 5-fold (5×) ultrafiltration and 5-fold diafiltration with SP buffer on a 500 kDa molecular weight cut-off hollow fiber cartridge. Virus particles would be retained in the retentate side, while host cell protein (HCP), host cell DNA (HCD) and Benzonase would be diafiltered to the permeate side of the hollow fiber. The concentrated and diafiltered virus was purified using a Cellufine Sulfate (CS) chromatography column to further remove HCD, HCP and Benzonase impurities. CS is an affinity resin that binds virus on the column and the bound virus is eluted using a SP high salt buffer. The purified virus from column eluate would be diafiltered by five diavolumes of SP100 (200 mM sucrose and 100 mM potassium phosphate, pH 7.2) buffer on a 500 kDa molecular weight cut-off hollow fiber cartridge to remove the high salt elution buffer and formulate the purified virus. The diafiltered virus product is then stabilized by addition of cGAG in 1/9 (v/v) dilution and sterile-filtered using a 0.22 μm filter to make the final bulk product.

Substantial changes were implemented to the initial process that improved the scalability, the efficiency of the process and the final product quality. Changes made in the process were based on the evaluation of recovery and level of impurities (HCD, HCP and Benzonase) and were implemented into the original established process. In all, five process steps were implemented to address scalability and to improve the efficiency of process and final product quality. First, the viral harvest what changed to 48 hours post infection for cells infected using a viral input of 2000 FFU/mL, this time corresponds to the peak viral titer. Second, the HCD removal step was changed from batch-mode Benzonase treatment to on-column Benzonase treatment. These two steps together improve the final product quality by significantly lowering the HCD level of the starting material and final bulk. Third, the loading concentration of the CS resin was increased from 9.0 log 10 FFU/mL to 9.5 log 10 FFU/mL, this reduces the production column size from 4 L to 1.4 L and improves the process efficiency. Fourth, the second buffer exchange volume was increased from 5 to 8 diavolumes to enhance Benzonase clearance. Fifth, the final filter flux was decreased by half to an average of 25 L/m$^2$ to avoid any plugging during final filtration during in the CTM runs. The final method (detailed below) provides a process that gives an average overall recovery of 43.4%, with 0.72 ng/dose (by PicoGreen) and 0.1 ng/dose (by PCR) HCD, 0.21 µg/dose HCP, and 0.0035 ng/dose Benzonase, all of which are below the specifications required by regulatory agencies. FIG. 10 provides an overview of the initial and improved purification processes.

9.6.1 Materials and Methods

Materials, Reagent and Equipment: Other materials, equipment and reagents which perform similarly may be readily substituted.
1. 1.2 µm Polygard CN Opticap XL5 Filter (Millipore Corporation, Billerica, Mass., Cat. No. KN12A05HH1)
2. 0.45 µm Durapore Opticap XL4 Filter (Millipore Corporation, Billerica, Mass., Cat. No. KPHLA04HH3)
3. 50 L Bag (Hyclone, Ltd, Logan, Utah, Cat. No. SH30712.04)
4. 10 L Bag (Hyclone, Ltd, Logan, Utah, Cat. No. SH30712.12)
5. Hollow Fiber, 500 KD, 4,800 cm$^2$ (GE Healthcare, Uppsala, Sweden, Cat. No. UFP-500-C-6A)
6. Hollow Fiber, 500 KD, 290 cm$^2$ (GE Healthcare, Uppsala, Sweden, Cat. No. UFP-500-C-3×2MA)
7. Cellufine Sulfate Resin (Chisso Corporation, Tokyo, Japan, Cat. No. 19847)
8. Flange O-ring (GE Healthcare, Uppsala, Sweden, Cat. No. 18-8494-01)
9. Adaptor O-ring (GE Healthcare, Uppsala, Sweden, Cat. No. 18-8475-01)
10. Bed support, 23 µm, end piece (GE Healthcare, Uppsala, Sweden, Cat. No. 18-9252-01)
11. Bed support, 23 µm, adaptor (GE Healthcare, Uppsala, Sweden, Cat. No. 18-1103-08)
12. Gaskets 25 mm i d 6 mm, EPDM (GE Healthcare, Uppsala, Sweden, Cat. No. 18-0019-27)
13. 4-port-2-way valves (GE Healthcare, Uppsala, Sweden, Cat. No. 18-5757-01)
14. Sartopore2 300 filter capsule, 0.45 µm/0.22 µm, 300 cm2 (Satorius, Mass., Cat. No. 5441307H5-00-B)
15. Sartopore2 150 filter capsule, 0.45 µm/0.22 µm, 150 cm2 (Satorius, Mass., Cat. No. 5441307H4-00-B)
16. 1 L PETG bottles (Nalgene, Rochester, N.Y.U, Cat. No. 2019-1000)
17. 2 L PETG bottles (Nalgene, Rochester, N.Y.U, Cat. No. 2019-2000)
18. MasterFlex platinum-cured silicone tubing L/S size 24 (Cole Parmer, Vernon Hills, Ill., Cat. No. 96410-24)
19. MasterFlex platinum-cured silicone tubing L/S size 36 (Cole Parmer, Vernon Hills, Ill., Cat. No. 96410-36)
20. 1× Sucrose Phosphate buffer (Hyclone, Ltd, Logan, Utah, Cat. No. SH3A1577)-218 mM sucrose and 11 mM potassium phosphate, pH 7 buffer
21. 1×SP/1M NaCl buffer (Hyclone, Ltd, Logan, Utah, Cat. No. SH3A2034)
22. SP100 buffer (Hyclone, Ltd, Logan, Utah, Cat. No. SH3A1796)-200 mM sucrose and 100 mM potassium phosphate, pH 7.2 buffer
23. cGAG buffer (Hyclone, Ltd, Logan, Utah, Cat. No. SH3A1795)
24. Benzonase (EMD, Darmstadt, Germany, Cat. No. 1.01697.0002)
25. 1 M MgCl$_2$ (Sigma, St. Louis, Mo., Cat. No. M1028, lot #085K8920)
26. Quant-iT PicoGreen dsDNA kits (Invitrogen, Eugene, Oreg., Cat. No. P11496, lot #22987)
27. 0.5 N NaOH, diluted from 10 N NaOH (VWR, West Chester, Pa., Cat. No. VW3247-7)
28. Peristaltic Pump (Watson Marlow Inc., Wilmington, Mass., Models 520U, 520S and 520Di)
29. WaveMixer (GE Healthcare, Uppsala, Sweden, Cat. No. Mixer20/50EH)
30. AKTAprocess Chromatography Skid (GE Healthcare, Uppsala, Sweden, Cat. No. 28409334)
31. Uniflux10 Filtration Skid (GE Healthcare, Uppsala, Sweden, Cat. No. 28920799)
32. BPG 100 Chromatography Column (GE Healthcare, Uppsala, Sweden, Cat. No. 18-1103-01)
33. BPG 200 Chromatography Column (GE Healthcare, Uppsala, Sweden, Cat. No. 18-1103-11)
34. Flexstand (GE Healthcare, Uppsala, Sweden, Cat. No. 56-4107-54)

TABLE 27

Viral Harvest Lots from Single Use Bioreactors (with 67% media exchange)

| Strain (all ca reassortants) | Cell Culture Lot # | Purification Lots Run # | Harvest Hours post Infection |
|---|---|---|---|
| A/New Caledonia/20/99 | Sub 08012007-PP | 1 | 60-65 hr |
| A/Wisconsin67/05 | Sub 05012007-PD | 2 | 60-65 hr |
| A/Wisconsin67/05 | Sub 15012007-PP | 3 | 60-65 hr |
| A/New Caledonia/20/99 | Sub 19012007-PD | 4 | 60-65 hr |
| B/Malaysia2506/04 | Sub 22012007-PP | 5 | 60-65 hr |
| B/Malaysia2506/04 | Sub 26012007-PD | 6 | 60-65 hr |
| A/New Caledonia/20/99 | Sub 05022007-PP | 7 | 60-65 hr |
| A/Wisconsin67/05 | Sub 16022007-PD | 8 | 48 hr |
| B/Malaysia2506/04 | Sub 26022007-PP | 9 | 48 hr |

Cell Culture Viral Harvest (VH):
The detail of MDCK cell growth and virus production is described in International Patent Publication WO 08/105,931 (see in particular, Example 12). All the viral production runs were performed in a Single Use Bioreactor (SUB) with a ~67% media exchange process and the cells were infected using a viral input of 2000 FFU/mL. Virus was harvested at approximately 60-65 hrs (runs 1-7) or 48 hours (runs 8-9) post infection of MDCK cells. Microcarriers in the SUB were allowed to settle for no less than 45 minutes prior to viral harvest (VH). Approximately 18 L of virus was pumped into a 50 L bag at approximately 0.2 L/min, and 2 L of 10×SP buffer was pumped into the same bag for stabilization of virus harvest (SVH). After mixing, samples were taken at SVH stages to test for infectivity by FFA, HCD and HCP assays.

The following process may be utilized to directly couple the viral harvest step to the direct flow filtration step. The appropriate volume of 10×SP buffer is added to the bioreactor to obtain a stabilized viral harvest (SVH) comprising a final concentration of about 1×SP, the microcarriers may be allowed to settle and the viral harvest is coupled together with DFF and TFF steps using ATF. For example in an ATF/DFF/TFF coupling study, SVH was pumped directly from the bioreactor to the ATF system via the sample feed pump. Permeate of the ATF then passed through the inline DFF capsules and finally to the Uniflux process tank. Operation of ATF system is detailed in the ATF operational manual. The set points of the ATF system at pressure and exhaust cycles, specific to the height and head pressure of the bioreactor, were 3 L/min and 1.8 L/min respectively for 10 L and 20 L bioreactors. The flow rate of the Uniflux sample feed pump (ATF permeate flow rate) was set to match the specific TFF permeate flux per each experiment. The 5XUF5XDF process are detailed below. All 5XUF5XDF materials were further purified up to CS chromatography step, as detailed below.

Direct Flow Filtration 1 (DFF1):

A filter rig was prepared and autoclaved the day before viral harvest. The filter rig drawing showing the 1.2 μm Polygard CN polypropylene filter capsule and the 0.45 μm Durapore PVDF filter capsule is detailed in FIG. 9A, top panel. Approximately 20 L of SVH was pumped through the closed rig assembly at 1.5 Liter per Minute (LPM), and the filters were primed as the SVH passed through them. The total membrane surface area was 1800 $cm^2$ for the 1.2 μm Polygard CN polypropylene filter capsule and 1900 $cm^2$ for the 0.45 μm Durapore PVDF filter capsule. At a filtration flow rate of 1.5 LPM, the flux for the 1.2 μm and 0.45 μm filters were 500 Liter per $m^2$ area per hour (LMH) and 474 LMH, respectively. The actual loading for the 1.2 μm and 0.45 μm filters was 111 and 105 L/m2, respectively. The clarified filtrate was collected as DFF1 in a 20 L bag. The DFF1 filtrate was sampled and tested for infectivity by FFA, and for residual HCD and HCP.

Tangential Flow Filtration 1, 5× Ultrafiltration (UF)/5× DiaFiltration (DF) (TFF1):

Tubing rigs for the Uniflux skid were prepared and autoclaved the day prior to viral harvest. All the tubing rigs drawings are detailed in FIG. 9A, bottom panel. A Uniflux™ skid was used to perform the TFF1 step using the following operating parameters. The Uniflux skid is an automated membrane separations filtration system configured to operate hollow fiber cartridges. A 500 kDa of molecular weight cut-off (MWCO) hollow fiber with a 0.5 mm lumen size 4,800 $cm^2$ total membrane surface area and 60 cm path length was used. This process gives a final DFF1 loading of 41.7 L/$m^2$ membrane surface area which is in the optimal range of 40-150 L/m2 for the TFF1 process as previously evaluated. For runs 1-6, the same hollow fiber cartridge was cleaned post process and reused. For runs 7-9, a new hollow fiber was prepared and used for each run. New hollow fiber cartridges were prepared by rinsing with deionized (DI) water for 90 mins to remove the glycerol preservative, sanitized with 0.5 N NaOH for 1 hour and equilibrated with 1×SP buffer until the pH is 7.0 before each run. The entire 5XUF/5×DF process was operated using the Uniflux skid programmed at a constant shear rate of 16000 $s^{-1}$ and at a constant TMP of 20 psi.

The entire volume of DFF1 was processed through the Uniflux skid. Approximately 5 L of the DFF1 was first pumped into the Uniflux process tank. The permeate line was closed initially to establish a recirculation (retentate) flow rate of 8.6 L/min, which is equivalent to a shear rate of 16,000 $s^{-1}$. After 5 minutes of recirculation, the 5XUF process was started. The permeate line was opened to allow impurities smaller than 500 kDa such as HCP and DNA to pass through the membrane, while the retentate control valve gradually closed to achieve a transmembrane pressure (TMP) set point of 1.4 bar (20.3 psi). The remaining DFF1 filtrate was continuously pumped into the process tank to maintain a constant tank level of 5±0.1 L until the entire volume of DFF1 was fed into the tank. After all the DFF1 material was fed, the feed pump was stopped and the retentate continued to concentrate until the final retentate volume reached 4 L or 16 L of permeate was collected. The 4 L retentate (5XUF) was diafiltered by buffer exchange with 5× diavolumes of 1×SP buffer (20 L) and the process operated at the same shear rate and TMP as described above. The diafiltration buffer line was opened and the feed pump was started again to pump in 1× SP buffer. 5×DF process ended after 20 L of diafiltration permeate was collected. At the end of 5×DF, the retentate control valve was completely opened and the permeate line closed again to allow system recirculation to sweep off any recoverable virus that was weakly bound on the surface of the hollow fiber membrane during the process. The retentate, which contained the concentrated and diafiltered virus product, was drained and collected into a 10 L product bag. For the last two purification runs (8 and 9), an additional buffer rinse step was introduced after retentate collection. Approximately 1.5 L of 1×SP was pumped into the process tank and recirculated for another 5 minutes with the permeate line closed. This buffer rinse was also collected into the same 10 L product bag and the bag was labeled as 5XUF 5×DF TFF1 product and the total volume was approximately 5.5 L. The TFF1 product was sampled to test for infectivity by FFA, and HCD and HCP. The hollow fiber cartridge and Uniflux system were cleaned after each process run with 0.5 N NaOH for 1 hr using a recirculation flow rate of 8.6 L/min.

Packing of BPG 100/200 Cellufine Sulfate (CS) Column and Column Evaluation:

CS resin was stored in 20% ethanol at approximately 50% slurry. The amount of resin required to pack a BPG 100 or BPG 200 column was calculated using a compression ratio of 1.1. Both BPG100 and BPG200 columns were packed to the target bed height of 17.5 cm or target bed volume of 1.37 L and 5.50 L respectively. The amount of resin as calculated was prepared by performing a two times buffer exchange with 1×SP buffer, followed by one time buffer exchange with 1×SP/1M NaCl buffer.

The BPG 100 and BPG 200 columns were assembled according to the manufacturer's instructions. An empty column was prepared, sanitized with 0.5 N NaOH and rinsed with DI water before use. 1×SP buffer was used to flow-pack the CS resin into a BPG 100 column at 500 cm/hr to generate a column bed height of 15-20 cm (target 17.5 cm) using the AKTAprocess™ skid. The AKTAprocess is an automated liquid chromatography system.

The prepared resin slurry in 1×SP/1M NaCl buffer was poured along the side wall of the empty column and any residual resin remaining on the wall was rinsed off with water in a squirt bottle. The resin was allowed to settle to a resin bed height of at least 10 cm below the liquid level. The top adaptor was inserted in the column without disrupting the resin bed and then secured with retaining screws/nuts. A 4-port-2-way valve (4-2 valve) was installed at the column inlet. The four different ports were connected as follows:

1—AKTAprocess system column inlet
2—Column manual purge (connected to waste or recirculation line)
3—Spike test connector (a female lure lock used to inject high salt solutions for HETP test)
4—BPG 100/200 Column Inlet The BPG100 column bottom outlet was then connected to the AKTA system column outlet. Before lowering the column adaptor, the connections for the 4-2 valve, ports 3 and 4 were checked. The top adaptor was slowly lowered into the resin bed and a small volume of buffer was purged from port 3 of the 4-2 valve. This ensured that the inlet of the top adaptor was purged with buffer.

The 4-2 valve was then switched to connect ports 1 and 2. The 1×SP buffer was connected to the AKTA system inlet and flow was started at 500 cm/hr first to bypass the column at this point through the column purge port (port 2 on 4-2 valve). When the flow rate reached 500 cm/hr on the flow meter, the 4-2 valve was quickly adjusted so that ports 1 and 4 were connected. When the resin bed reached the target bed height, the adaptor closer was lower to resin bed. These steps were repeated until there was no change in resin bed height and the adaptor reached the resin bed. The adaptor was further lowered 1-3 mm to compress the resin bed to avoid any headspace between adaptor and resin bed.

Before the packing evaluation, the CS column was equilibrated with 1×SP to establish a stable conductivity baseline. Column packing was evaluated by injecting 1×SP/1M NaCl at 2% of the column volume (CV) using the spike test connector (port 3 to 4 on 4-2 valve). The column was equilibrated with 1×SP at flow rate of 50 cm/hr (port 1 to 4 on 4-2 valve). The conductivity peak appeared at approximately ½ the CV. The resulting conductivity peak on the Unicorn software was used to evaluate the column plate height (HETP) and peak asymmetry. Once the desired column HETP was reached, the column was sanitized and stored in 0.5 N NaOH before use.

Cellufine Sulfate Chromatography (CS):

Tubing rigs for the AKTA Process skid were prepared and autoclaved the day prior to viral harvest. All the tubing rigs drawings are detailed in FIG. 9B, top panel. The entire chromatography process was automated by programmed method.

All flow paths of AKTAprocess skid were manually equilibrated with 1×SP before each run. At the start of the process, the column was first equilibrated with 3 column volumes (CV) of 1×SP at a linear flow rate of 150 cm/hr. The entire volume of 5×UF 5×DF TFF1 was then loaded onto the column and unbounded material was collected as flow through. After loading, the column was washed with 1 CV of 1×SP at 150 cm/hr followed by 2.5 CV of 1×SP containing 50 U/mL Benzonase and 2 mM $MgCl_2$ (1×SPB) at 50 cm/hr for on-column Benzonase treatment. The decreased linear flow rate and calculated 1×SPB wash volume allowed the column resin to have a Benzonase contact time of 50 minutes. The column was then washed with 1 CV of 1×SP at 50 cm/hr to replace the last CV of 1×SPB on-column Benzonase treatment and an additional 1 CV of 1×SP at 150 cm/hr. The bound virus was eluted form the column with 3 CV of 1×SP/1M NaCl buffer. The CS eluate was collected in a 10 L bag and the collection of the elution peak was based on UV absorbance (A280 reading from 50 mAU to 50 mAU (0.1 O.D. to 0.1 O.D.) using 5 mm path length UV flow cell). The CS elution volume from BPG 100 column is approximately 0.6 to 0.9 L. The column and AKTAprocess system were sanitized with 0.5 N NaOH after each process run. The column load, flow through, wash and eluate were sampled to test for infectivity by FFA, Benzonase, HCD and HCP.

Tangential Flow Filtration 2, 8×DF (TFF2):

The setup and use of Flexstand was performed according to the manufacturer's directions. A 500 kDa MWCO hollow fiber with a 0.5 mm lumen size, 60 cm path length and 290 $cm^2$ total membrane surface area was used. With this size membrane area and the volume of CS elute described above, the final loading was in the range of 20-50 $L/m^2$ membrane surface area, which is the optimal range for the TFF2 process as previously evaluated. A new hollow fiber was setup on the Flexstand the day before viral harvest. The hollow fiber was rinsed with DI water for 90 minutes to remove the glycerol preservative, sanitized with 0.5 N NaOH for 1 hr and equilibrated with SP 100 buffer until the pH reached 7.2.

The entire volume of CS eluate was processed through the Flexstand system. The permeate line was closed initially to allow recirculation of the CS eluate at a feed flow rate of 0.5 L/min to generate a shear rate of 16,000 $s^{-1}$. After recirculation for 5 minutes, the permeate line was opened to start diafiltration. At the same time, SP100 buffer was pumped through the diafiltration line and the retentate control valve was gradually to obtain a transmembrane pressure (TMP) of 20-21 psi. The volume of the retentate reservoir was kept constant at a volume equal to the CS elution volume (range from 0.4-0.8 L) for the entire process by controlling the pump flow rate of the SP100 diafiltration line. Before run 8, the CS eluate was diafiltered with 5× diavolumes of SP 100 buffer. The CS eluate was buffer exchanged with the 8× diavolumes of SP100 buffer for purification runs 8-9. At the end of diafiltration, the retentate valve was completely opened and the permeate line closed again to allow for system recirculation for 5 minutes before product recovery. The diafiltered product was drained into a 10 L product bag. The diafiltered product was sampled to test for infectivity by FFA, Benzonase, HCD and HCP. The hollow fiber cartridge and system were cleaned with 0.5 N NaOH for 1 hr at a recirculation flow rate 0.5 L/min.

Direct Flow Filtration 2 (DFF2):

The filter rig was prepared and autoclaved the day before viral harvest. The filter rig drawing is detailed in FIG. 9B, bottom panel. The 0.22 μm polyether sulfone membrane capsule used had a total surface area of 150 $cm^2$ for runs 1-5 and 300 $cm^2$ for runs 6-9. The final sterile filtration DFF2 step was performed in the biosafety cabinet.

Concentrated Glutamate Arginine Gelatin (cGAG) was added to the 8×DF product at a 1:9 (v/v) dilution to make the final formulation of the purified virus. The formulated virus was pumped through the closed rig assembly at approximately 0.38 LPM for the 300 $cm^2$ capsule, and the filter was primed using the final product. The filtrate was collected in sterile 2 L bottles as the final bulk product. At a filtration flow rate of 0.38 LPM, the flux for the 300 $cm^2$ filters was 760 LMH. The formulated bulk loading to the membrane area was in the range of 20-150 $L/m^2$. The 0.22 μm filtered final bulk product was sampled to test for infectivity by FFA, Benzonase, HCD and HCP levels. The final bulk product was aliquoted into several 1-, 10- and 100-mL aliquots and flash frozen and stored in −80° C.

Sample Analysis and Calculations:

All the samples sent for analysis were flashing frozen and stored in −80° C. HCP assays were done essentially as described below. The HCD assay was done using the PicoGreen and PCR methods essentially as described below. HCD sizing was analyzed by direct label method of psoralen-biotin (blot) and direct staining in agarose gels. Benzonase quantification assay was essentially as described below. All values that are calculated ng or μg per dose are based on titer of 7 $\log_{10}$ FFU per dose (one dose is also commonly referred to as $10^7$ FFU).

Residual Host Cell DNA Determinations:

Residual MDCK host cell DNA is quantified using a microwell-format real-time PCR method. The target of the assay is a unique sequence within the cytochrome oxidase subunit I (Cox I) gene of dogs. Using a set of optimized oligonucleotide primers, a MDCK Cox I specific PCR product is generated from template and detected by the SYBR® Green dye. The microwell format accommodates DNA calibrators across a wide dynamic range (1000 to 0.1 ng/ml). Appropriate positive and negative controls are included in each assay. Test sample DNA are derived using a DNA extraction kit. Sample DNA quantities above the lower limit of quantification of 0.1 ng/ml will be calculated from the standard curve. Accuracy will be within 75 to 125% based on recovery of the spike control. The reported results will be the mean DNA quantity of the sample extraction replicates that yield spike recovery values of 50 to 150%. These analysis may be performed using commercially available kits, such as the Quant-iT PicoGreen kit (Invitrogen, Eugene, Oreg., Cat. No. P11496), following the procedure described in the kit.

Residual Host Cell Protein Determinations:

The residual host cell (MDCK) protein (HCP) are determined by an Enzyme-Linked Immunosorbent Assay (ELISA) using a primary biotinylated rabbit antibody produced against HCP (from an uninfected MDCK culture) and streptavidin-horse radish peroxidase (HRPO) conjugate. Antibodies against MDCK cell lysate are absorbed onto a polystyrene microplate. A blocking solution containing bovine serum albumin is added to saturate the excess binding sites. When a dilution of test article sample is added to the coated plate, the MDCK HCP, if present, will bind to the coated antibodies. A primary biotin-labeled antibody against MDCK lysate raised in rabbits is added to the plate, followed by horse radish peroxidase (HRPO) labeled streptavidin conjugate. Finally, the HRPO substrate is added and an ELISA plate reader is used to measure the intensity of the colored end product formed. The intensity of the color developed is proportional to the amount of MDCK HCP present in the test article. A standard curve is generated from the MDCK cell lysate calibrator of known protein concentration. From a standard curve, the protein concentration of MDCK cell lysate is determined.

Residual Benzonase Determinations:

The Benzonase activity is determined by its ability to cleave herring sperm DNA. The test article, in duplicate, is compared against a Benzonase standard curve, in which readings are measured with a spectrophotometer at 260 nm. The percent spike recovery (Benzonase activity) is calculated to determine the net Benzonase U/ml. The net Benzonase activity of a spiked reference standard should be between 1.1 and 1.9 U/ml, the coefficient of correlation should be ≥0.995, the activity in an unspiked sample dilution should be ≥0.7 U/ml for the activity to be quantifiable, and the percent spike recovery should be between 80 and 120%.

9.6.2 Results and Discussion

All the SUB runs showed harvest titer range from 8.0 to 8.6 $\log_{10}$ FFU/mL. The recovery, HCD and HCP results used to evaluate the performance of each purification runs are summarized in Table 28, Table 29, and Table 30. The following sections will summarize and discuss the changes made to improve the process efficiency and the final product quality. The process development for the initial and final purification schemes are summarized in FIG. 10, which shows the major changes from early purification runs to the last purification runs.

SVH—Change in Benzonase Treatment from SVH to On-Column Benzonase Treatment:

In the initial process, Benzonase treatment was performed at the SVH step to remove host cell DNA. This process step involved mixing 20 L of SVH with 50 U/mL Benzonase for three hours at 32° C. before performing the DFF1 step. In purification runs 1 to 4, Benzonase was added to SVH step while in purification runs 5 to 9, the Benzonase treatment was eliminated from the SVH step and performed as an on-column Benzonase treatment process during the CS chromatography step using a chromatography buffer that contained 50 U/mL of Benzonase and a resin contact time of 50 minutes. As shown in Table 29, purification runs 2 to 4, the HCD level was not reduced noticeably in terms of ng per dose between the SVH and DFF1; however, in purification runs 5 to 9, the HCD level was appreciably reduced after the Benzonase-on column CS chromatography step. The HCD level of final bulk product analyzed by both PCR and PicoGreen was found to be much lower for purification runs 5 to 9 (0.84-1.42 ng/dose) relative to purification runs 1 to 4 (3.25-40.49 ng/dose). This change not only improved the final product quality by lowering the final bulk HCD to a level less than or equal to 1 ng/dose but also increased the process efficiency by reducing the Benzonase treatment time and the total amount of Benzonase required. The impact of on-column Benzonase treatment will be further discussed in the CS chromatography section.

TABLE 28

Summary of Recovery for Purification Runs 1-9

| | Purification Run | | | | | | | | |
|---|---|---|---|---|---|---|---|---|---|
| | 1 | 2 | 3 | 4 | 5 | 6 | 7 | 8 | 9 |
| Strain | A/NC | A/Wis | A/Wis | A/NC | B/Mal | B/Mal | A/NC | A/Wis | B/Mal |
| Harvest (hr) | 60-65 | 60-65 | 60-65 | 60-65 | 60-65 | 60-65 | 60-65 | 48 | 48 |
| CS Column | BPG200 | BPG200 | BPG200 | BPG200 | BPG200 | BPG100 | BPG100 | BPG100 | BPG100 |
| CS Loading ($\log_{10}$/mL Gel) | N/A | 8.3 | 8.7 | 8.7 | 8.4 | 9.2 | 9.1 | 9.3 | 9.0 |
| Process* | 1a | 1a | 1a | 1a | 1b | 1b | 1b | 1b | 1b |
| Titer (VH-CC) | 8.3 | 8.4 | 8.4 | 8.4 | 8.3 | 8.6 | 8.4 | 8.6 | 8.0 |
| Titer (VH-P) | 7.9^ | 7.7^ | 8.4 | 8.6 | 8.1 | 8.3 | 8.3 | 8.4 | 7.9 |
| DFF1 | 99.1% | 154.6% | 79.4% | 52.7% | 124.1% | 124.3% | 124.2% | 78.3% | 123.1% |
| TFF1 | 107.2% | 73.8% | 50.9% | 53.4% | 30.3% | 42.2% | 74.5% | 80.0% | 76.1% |
| CS Eluate | N/A | 54.9% | 81.4% | 19.0% | 60.8% | 40.0% | 37.0% | 96.8% | 60.5% |
| TFF2 | N/A | 110.1% | 73.9% | 106.9%§ | 125.9%§ | 150.8% | 94.0% | 64.0%† | 92.0%† |

TABLE 28-continued

Summary of Recovery for Purification Runs 1-9

| | Purification Run | | | | | | | | |
|---|---|---|---|---|---|---|---|---|---|
| | 1 | 2 | 3 | 4 | 5 | 6 | 7 | 8 | 9 |
| DFF2 | N/A | 88.3%# | 111.1%# | 110.8%# | 88.3%# | 69.8% | 65.8% | 78.4% | 108.0% |
| Final Titer | N/A | 8.3 | 8.5 | 8.5 | 8.5 | 8.9 | 8.6 | 9.2 | 9.0 |
| Overall Yield | N/A | 60.9% | 27.0% | 6.3% | 25.4% | 22.0% | 21.2% | 30.4% | 56.3% |

VH-CCD: virus harvest cell culture,

VH-PD: virus harvest purification

*1a: Benzonase treatment in SVH bag; 1b: Benzonase treatment on column

^FFA assay based on Anti-NA instead of Anti-HA

§1400 cm2 hollow fiber (290 cm2 hollow fiber for the rest)

150 cm2 filter (300 cm2 filter for runs 6 through 9)

†8X DF (5X DF for the rest)

Several of the process changes are indicated in BOLD

TABLE 29

Summary of HCD for Purification Runs

| Run | 2 | | 3 | | 4 | | 5 | | 6 | |
|---|---|---|---|---|---|---|---|---|---|---|
| Strain | A/Wis | | A/Wis | | A/NC | | B/Mal | | B/Mal | |
| Harvest (hr) | 60-65 | | 60-65 | | 60-65 | | 60-65 | | 60-65 | |
| Column | BPG200 | | BPG200 | | BPG200 | | BPG200 | | BPG100 | |
| Process* | 1a | | 1a | | 1a | | 1b | | 1b | |
| DNA Level | ng/mL | ng/dose | ng/mL | ng/dose | ng/mL | ng/dose | ng/mL | ng/dose | ng/mL | ng/dose |
| SVH | 3228.8 | 644.2 | 7200 | 286.6 | 5480 | 137.7 | 3821 | 303.5 | 5720 | 286.7 |
| DFF1 | 2910 | 366.3 | 3920 | 196.5 | 1720 | 86.2 | 5328 | 336.2 | 4120 | 164 |
| TFF1 | 2520 | 126.3 | 1940 | 38.7 | 1610 | 32.1 | 14000 | 557.4 | 28200 | 562.7 |
| CS | 1204.9 | 47.97 | 537.4 | 10.72 | 146.1 | 14.6 | 37.8 | 1.2 | 135^ | 1.7^ |
| Eluate | | | | | | | | | 118.9 | 1.5 |
| TFF2 (5X) | 928.3 | 36.96 | 385.9 | 12.2 | 144 | 4.56 | 57.1 | 1.43 | 159.9 | 1.27 |
| TFF2 (8X) | | | | | | | | | | |
| DFF2 | 807.8 | 40.49 | 365.6 | 11.56 | 29^ | 0.92^ | 38.1 | 1.21 | 18.6^ | 0.23^ |
| | | | | | 102.9 | 3.25 | | | 69.9 | 0.88 |

| Run | 7 | | 8 | | 9 | |
|---|---|---|---|---|---|---|
| Strain | A/NC | | A/Wis | | B/Mal | |
| Harvest (hr) | 60-65 | | 48 | | 48 | |
| Column | BPG100 | | BPG100 | | BPG100 | |
| Process* | 1b | | 1b | | 1b | |
| DNA Level | ng/mL | ng/dose | ng/mL | ng/dose | ng/mL | ng/dose |
| SVH | 10800 | 541.3 | 3440 | 136.9 | 2070 | 260.6 |
| DFF1 | 4490 | 178.8 | 1440 | 72.17 | 1060 | 106 |
| TFF1 | 17100 | 171 | 3690 | 73.63 | 1690 | 67.28 |
| CS | 123^ | 1.55^ | 91.2 | 0.29 | 150.5 | 1.51 |
| Eluate | 82 | 1.03 | | | | |
| TFF2 (5X) | 72.1 | 1.14 | 135 | 0.54 | 190 | 1.9 |
| TFF2 (8X) | | | 16.8^ | 0.067^ | 34.8^ | 0.35^ |
| | | | 128.8 | 0.65 | 161.4 | 1.6 |
| DFF2 | 7.2^ | 0.18^ | 5 | 0.032^ | 16.4^ | 0.164^ |
| | 56.6 | 1.42 | 93.8 | 0.59 | 83.7 | 0.84 |

*1a: Benzonase treatment in bag; 1b: Benzonase treatment on column

^HCD assay based on real time PCR, The Picogreen assay was also performed for runs 2 thorough 9

Several of the process changes are indicated in BOLD

TABLE 30

Summary of HCP for Purification Runs 2-9

| Run | 2 | | 3 | | 4 | | 5 | | 6 | |
|---|---|---|---|---|---|---|---|---|---|---|
| Strain | A/Wis | | A/Wis | | A/NC | | B/Mal | | B/Mal | |
| Harvest (hr) | 60-65 | | 60-65 | | 60-65 | | 60-65 | | 60-65 | |
| Column | BPG200 | | BPG200 | | BPG200 | | BPG200 | | BPG100 | |
| Process* | 1a | | 1a | | 1a | | 1b | | 1b | |
| HCP Level | µg/mL | µg/dose | µg/mL | µg/dose | µg/mL | µg/dose | µg/mL | µg/dose | µg/mL | µg/dose |
| SVH | 278 | 55.5 | 392 | 15.6 | 269 | 6.76 | 231 | 18.35 | 250 | 12.53 |
| DFF1 | | | 369 | 18.5 | | | 329 | 20.76 | | |
| TFF1 | 82.3 | 4.12 | 382 | 7.62 | 68.2 | 1.36 | 345 | 13.73 | 108.7 | 2.17 |
| CS Eluate | 15.7 | 0.63 | 258 | 5.15 | 46.6 | 4.66 | 209 | 6.61 | 157 | 1.98 |
| TFF2 (5X) | 51 | 2.56 | 142 | 4.49 | 69.1 | 2.19 | 149 | 3.74 | 60.3 | 0.48 |
| TFF2 (8X) | | | | | | | | | | |
| DFF2 | 22 | 1.1 | 17.6 | 0.56 | 32.7 | 1.03 | 27.3 | 0.86 | 49.8 | 0.63 |

| Run | 7 | | 8 | | 9 | |
|---|---|---|---|---|---|---|
| Strain | A/NC | | A/Wis | | B/Mal | |
| Harvest (hr) | 60-65 | | 48 | | 48 | |
| Column | BPG100 | | BPG100 | | BPG100 | |
| Process* | 1b | | 1b | | 1b | |
| HCP Level | µg/mL | µg/dose | µg/mL | µg/dose | µg/mL | µg/dose |
| SVH | 233 | 11.68 | 135 | 5.37 | 174 | 21.9 |
| DFF1 | | | 83.7 | 4.19 | 140 | 14 |
| TFF1 | 86.8 | 0.87 | 24.3 | 0.48 | 27 | 1.07 |
| CS Eluate | 188 | 2.37 | 67.2 | 0.21 | 98.1 | 0.98 |
| TFF2 (5X) | 42.1 | 0.67 | 46.3 | 0.18 | 81.9 | 0.82 |
| TFF2 (8X) | | | 42.1 | 0.21 | 79 | 0.79 |
| DFF2 | 23.8 | 0.6 | 20.9 | 0.13 | 29.3 | 0.29 |

*1a: Benzonase treatment in bag; 1b: Benzonase treatment on column

TABLE 31

Overall DNA Clearance for Purification Runs 2-9

| Run # | Column Used | % DNA Remaining | Final Bulk DNA Level (ng/dose) | Vol. of 50 U/mL Benzonase |
|---|---|---|---|---|
| | | SVH Batch-mixed | | |
| 2 | BPG 200 | 3.36% | 40.49 | 20 L |
| 3 | BPG 200 | 1.09% | 11.56 | 20 L |
| 4 | BPG 200 | 0.15% | 3.25 | 20 L |
| | | CS On-Column | | |
| 5 | BPG 200 | 0.10% | 1.21 | 13 L |
| 6 | BPG 100 | 0.07% | 0.88 | 3.5 L |
| 7 | BPG 100 | 0.02% | 1.42 | 3.5 L |
| 8 | BPG 100 | 0.11% | 0.59 | 3.5 L |
| 9 | BPG 100 | 0.15% | 0.84 | 3.5 L |

TABLE 32

Summary of Residual Benzonase for Purification Runs 2-9

| Run | 2 | | 3 | | 4 | | 5 | | 6 | |
|---|---|---|---|---|---|---|---|---|---|---|
| Strain | A/Wis | | A/Wis | | A/NC | | B/Mal | | B/Mal | |
| Harvest (hr) | 60-65 | | 60-65 | | 60-65 | | 60-65 | | 60-65 | |
| Column | BPG200 | | BPG200 | | BPG200 | | BPG200 | | BPG100 | |
| Process* | 1a | | 1a | | 1a | | 1b | | 1b | |
| Benzonase Level | ng/mL | ng/dose | ng/mL | ng/dose | ng/mL | ng/dose | ng/mL | ng/dose | ng/mL | ng/dose |
| SVH | | | 0.35 | 0.014 | 0.06 | 0.002 | | | 0.18 | 0.009 |
| DFF1 | 70.9 | 8.926 | 50 | 2.506 | 46 | 2.306 | | | ND | |
| TFF1 | | | 2 | 0.04 | 9 | 0.18 | 0.07 | 0.003 | ND | |
| 1CV post SPB wash | | | | | | | 0.078 | | | |
| 2CV post SPB wash | | | | | | | 0.12 | | | |

TABLE 32-continued

Summary of Residual Benzonase for Purification Runs 2-9

| | | | | | | | | | | | |
|---|---|---|---|---|---|---|---|---|---|---|---|
| 3CV post SPB wash | | | | | | | 0.26 | | | | |
| 4CV post SPB wash | | | | | | | 0.28 | | | | |
| CS Eluate | | | | | 7.8 | 0.78 | 89 | 2.814 | >75 | >0.944 | |
| TFF2 (5X DF) | | 0.54 | 0.017 | 0.66 | 0.021 | 5.1 | 0.128 | 6.6 | 0.052 | |
| TFF2 (8X DF) | | | | | | | | | | | |
| DFF2 | 0.9 | 0.045 | 0.21 | 0.007 | 0.69 | 0.022 | 2.1 | 0.066 | 6.6 | 0.083 |

| | Run | 7 | 8 | 9 |
|---|---|---|---|---|
| | Strain | A/NC | A/Wis | B/Mal |
| | Harvest (hr) | 60-65 | 48 | 48 |
| | Column | BPG100 | BPG100 | BPG100 |
| | Process* | 1b | 1b | 1b |

| Benzonase Level | ng/mL | ng/dose | ng/mL | ng/dose | ng/mL | ng/dose |
|---|---|---|---|---|---|---|
| SVH | ND | | 0.12 | 0.005 | 0.14 | 0.0176 |
| DFF1 | ND | | 0.09 | 0.005 | 0.066 | 0.007 |
| TFF1 | ND | | 0.12 | 0.002 | 0.11 | 0.004 |
| 1CV post SPB wash | | | 0.15 | | 0.28 | |
| 2CV post SPB wash | | | 0.21 | | 0.15 | |
| 3CV post SPB wash | | | 0.33 | | 0.14 | |
| 4CV post SPB wash | | | | | 0.05 | |
| CS Eluate | 4.2 | 0.053 | 221.7 | 0.701 | 192 | 1.92 |
| TFF2 (5X DF) | 0.6 | 0.01 | 1.62 | 0.006 | 1.38 | 0.0138 |
| TFF2 (8X DF) | | | 0.36 | 0.002 | 0.45 | 0.005 |
| DFF2 | 3.6 | 0.09 | 0.27 | 0.002 | 0.52 | 0.005 |

*1a: Benzonase treatment in bag; 1b: Benzonase treatment on column
Several of the process changes are indicated in BOLD

TABLE 33

Summary of Process Attributes for all Purification Runs

| | Purification Run | | | | | | | |
|---|---|---|---|---|---|---|---|---|
| | 2 | 3 | 4 | 5 | 6 | 7 | 8 | 9 |
| Strain | A/Wis | A/Wis | A/NC | B/Mal | B/Mal | A/NC | A/Wis | B/Mal |
| Harvest (hr) | 60-65 | 60-65 | 60-65 | 60-65 | 60-65 | 60-65 | 48 | 48 |
| Column | BPG200 | BPG200 | BPG200 | BPG200 | BPG100 | BPG100 | BPG100 | BPG100 |
| Loading (log10 FFU/mL Gel) | 8.3 | 8.7 | 8.7 | 8.4 | 9.2 | 9.1 | 9.3 | 9 |
| Process* | 1a | 1a | 1a | 1b | –1b | 1b | 1b | 1b |
| VH Titer (CCD) | 8.4 | 8.4 | 8.4 | 8.3 | 8.6 | 8.4 | 8.6 | 8.0 |
| VH Titer (PD) | 7.7^ | 8.4 | 8.6 | 8.1 | 8.3 | 8.3 | 8.4 | 7.9 |
| Final Bulk Titer | 8.3 | 8.5 | 8.5 | 8.5 | 8.9 | 8.6 | 9.2 | 9.0 |
| Overall Yield§ | 60.9% | 27.0% | 6.3% | 25.4% | 22.0% | 21.2% | 30.4% | 56.3% |
| VH HCD (ng/mL) | 3229 | 7200 | 5480 | 3821 | 5720 | 10800 | 3440 | 2070 |
| Bulk HCD (ng/dose) PicoGreen | 40.49 | 11.56 | 3.25 | 1.21 | 0.88 | 1.42 | 0.59 | 0.84 |
| Bulk HCD (ng/dose) rtPCR | n/a | n/a | 0.92 | n/a | 0.23 | 0.18 | 0.032 | 0.164 |
| VH HCP (g/mL) | 278 | 392 | 269 | 231 | 250 | 233 | 135 | 174 |
| Bulk HCP (g/dose) | 1.1 | 0.56 | 1.03 | 0.86 | 0.63 | 0.6 | 0.13 | 0.29 |
| Benzonase (ng/dose) | 0.045 | 0.007 | 0.022 | 0.066 | 0.083 | 0.09 | 0.002 | 0.005 |

*1a: Benzonase treatment in bag; 1b: Benzonase treatment on column
^FFA assay based on Anti-NA instead of Anti-HA
§Based on VH-PD titer
Several of the process changes are indicated in BOLD

DFF1:

As shown in Table 28, the DFF1 step showed good recovery (78.3-154.6%) except for run 4 (52.7%). The DFF1 step removed the cells and cell debris and usually showed no loss in titer. This step also removed some amount of HCD (Table 29) but not HCP (Table 30). The membrane area of both filters (1.2- and 0.45-μm) used to filter 20 L of SVH was based on the capacity of both filters and was previously determined from a scale-down Vmax/Pmax studies using a safety factor of 2.6 and 1.5, respectively. For a filtration flow rate of 1.5 LPM, the flux for the 1.2 μm and 0.45 μm filters were 500 LMH and 474 LMH, respectively. The actual SVH loading for the 1.2 μm and 0.45 μm filters was 111 and 105 L/m$^2$, respectively.

TFF1—Changes in Setup and Recovery Method to Improve Step Recovery of TFF1:

The first six purification runs showed a gradual loss in potency recovery at the TFF1 step for each run from 107.2% to 30.3% (Table 28). For purification runs 1 to 6, the TFF1 hollow fiber cartridge was cleaned with 0.5 N NaOH and reused and after the process. It is unknown whether the cleaning efficiency of the hollow fiber cartridge was sufficient enough to completely remove the gel layers after each run and this could result in a decrease in virus recovery after this process step. To generate a more consistent step recovery, three major changes were implemented to the existing protocol beginning with purification run 7. First, a new hollow fiber was used for each run to eliminate the possibility of insufficient cleaning of the hollow fiber. Second, the concentrated retentate was recirculated in the hollow fiber cartridge for 5 minutes with retentate valve open and permeate valve closed before the TFF1 product was collected. This removed any potential gel layer that may have formed on the surface of membrane during the concentration and diafiltration process and allowed recovery. Third, an additional buffer rinse step was performed with the same recirculation flow rate and time (5 minutes) to recover residual virus in the hollow fiber cartridge and the buffer rinse was collected together with the product. After these implemented changes, the step recovery of TFF1 remained consistently high, approximately 75-80%, for purification runs 7 to 9 (Table 28). FIG. 11 shows a typical flux curve for the TFF1 process from performed at 16000 s$^{-1}$ shear rate and constant TMP at 20 psi (purification run 8). The flux decreased as the virus solution became more concentrated (5×UF) and it continued to decrease when the diafiltration step began but increased slightly toward the end of diafiltration step (5×DF). The flux ranged from 70-100 LMH for all purification runs and appeared to be related to the virus titer and the turbidity of the DFF1 filtrate. The slight increase in flux at the end of the diafiltration step was probably due to the additional removal of HCP and HCD impurities at the end of 5×DF. As shown in Table 30, the majority (80-90%) of the HCP impurities were removed at the 1$^{st}$ TFF (TFF1) step because any HCP smaller than 500 kDa should be removed in the permeate. The completion of the buffer exchange of virus harvest to the 1× was shown in the conductivity trace decreased from 12.5 mS/cm to 1 mS/cm at the end of 5×DF process (FIG. 11).

CS On-Column Benzonase Treatment to Increase HCD Removal:

The initial experiments were designed using a small scale CS column with bed height of 10 cm and a virus loading concentration of approximately 9.0 log$_{10}$ FFU per mL of resin. As the process was improved, the loading concentration of virus per mL of resin, the linear flow rate and the column bed height were linearly scaled. At a loading titer of 9.0 log$_{10}$ FFU/mL resin, a 4 L bed volume of CS would be required to process 20 L of stabilized virus harvest with a harvest titer of 8.3 log$_{10}$ FFU/mL. In development runs 1 to 5, 4 L of CS resin was packed into a BPG 200 column (20 cm inner diameter (i.d.)) to a final bed height of 12.5 cm. During the packing of the BPG 200 column at 200 cm/hr, the back pressure exceeded the recommended packing pressure of 2.5 bar pressure. (FIG. 12). A dynamic binding capacity study was performed and that showed that CS resin could actually bind up to approximately 9.7 log$_{10}$ FFU/mL resin under the packing conditions described above. As such, at a virus loading of 9.5 log$_{10}$ FFU/mL of resin, only 1.3 L of CS resin would be required to process 20 L of stabilized virus harvest with a harvest titer of 8.3 log$_{10}$ FFU/mL.

A BPG 200 column packed with 1.3 L of CS resin results in a final column bed height of 4.5 cm. A dramatic reduction in the column bed height gives a lower resolution compared to a packed column with a bed height of 15-20 cm (typical for large-scale processes). Starting from purification run 6, a BPG 100 column was packed to a target bed height of 17.5 cm+/−2.5 cm to give a CS column volume of 1.4 L. For the BPG 100 column, a packing flow rate of 500 cm/hr was used and the resultant packing pressure did not exceed the recommended packing pressure limit of the resin, which is different than packing pressure for the BPG 200 column (FIG. 12).

Comparing purification runs 6 to 9 (BPG 100) with purification runs 2 to 5 (BPG 200), a similar CS eluate step recovery averaging 54% and 59%, respectively, when the actual loading was increased from 8.4-8.9 log$_{10}$ FFU/mL resin (BPG 200 column) and 9-9.3 log$_{10}$ FFU/mL resin (BPG 100 column) (Table 28). In terms of column performance for HCD removal as performed using the on-column Benzonase treatment, purification runs 6 to 9 (BPG 100) showed comparable CS eluate HCD levels (0.3-1.5 ng/dose) as the CS eluate HCD level (1.2 ng/dose) in purification run 5 (BPG 200) (Table 29). Although the column performance was similar, the reduction of the column size improved the process efficiency by reducing the volume of CS eluate and buffer preparation when and will be important when moving to larger-scale manufacturing. FIG. 13 shows a typical chromatogram for the single virus peak eluted from the CS BPG 100 column (run 9).

As shown in Table 31, the overall HCD clearance for on-column Benzonase treatment (runs 5 to 9) was better than the batch-mode Benzonase treatment (runs 2 to 4). The percentage of HCD remaining after virus purification for Benzonase treatment ranged from 0.15-3.4% (runs 2 to 4), while the percentage of HCD remaining after virus purification for the on-column Benzonase treatment ranged from 0.02-0.15% (runs 5 to 9). The on-column Benzonase-treatment at the CS step was shown to have a higher overall HCD removal than the batch-mode Benzonase-treatment at SVH step, thus resulting in a lower DNA level of final bulk.

There are several advantages to using on-column Benzonase treatment compared to batch-mode Benzonase treatment. First, the process efficiency is increased by combining two process steps into one and replacing the 3 hours for Benzonase treatment at the SVH step with a 1 hour Benzonase treatment for the CS on-column step. Second, the total amount of Benzonase required in the purification process is reduced. Batch-mode Benzonase treatment requires one million units of Benzonase for a 20-L virus harvest, while the on-column Benzonase treatment only requires two hundred thousand units of Benzonase. Thus, the on-column Benzonase treatment reduces the total amount of Benzonase needed by five fold.

TFF2—Increase Diafiltration Volume on TFF2 to Increase Benzonase Clearance:

As shown in Table 28, the step recovery for TFF2 for all nine purification runs was consistently above 64% (64-150.8%). In run 3, the CS elution volume was 3.2 L. Using a 290 cm$^2$ hollow fiber, the CS eluate loading on the hollow fiber membrane increased to 110 L/m$^2$ and the total process time was 6 hours. A 1400 cm$^2$ hollow fiber membrane was used in the next two consecutive runs to avoid the long process time and to maintain the loading concentration at approximately 20-50 L/m$^2$ established in small-scale studies.

However, starting with run 6, the column size was changed from 4 L to 1.4 L, and the elution volume also decreased to no more than 0.9 L. This reduction in eluate volume was directly proportional to the column size. In runs 6 to 9, a 290 cm$^2$ hollow fiber cartridge was used to maintain the CS eluate loading concentration at 20-50 L/m$^2$. FIG. 14 shows a typical flux trace curve of the TFF2 process for purification run 8, which was performed at 16000 s$^{-1}$ shear rate and a constant TMP of 21 psi. The TFF2 flux was reasonably stable throughout the diafiltration process indicating that the operating conditions did not cause any fouling. The flux ranged from 80-110 LMH for all purification runs.

The TFF2 buffer exchange volume was also increased from 5 diavolumes to 8 diavolumes to enhance the clearance of Benzonase. As shown in Table 32, when the process changed to an on-column Benzonase treatment step (run 5), the Benzonase level of the CS eluate was >75 ng/mL indicating that Benzonase binds to CS column and co-eluted with the virus product. Benzonase binding to the CS column was also confirmed by evaluating the flow-through samples of 1 CV to 4 CV after the 1×SPB. The flow-through samples were shown to have low Benzonase levels (Table 32). Thus, the TFF2 buffer exchange volume was increased from 5 diavolumes to 8 diavolumes in purification runs 8 and 9 to increase the Benzonase clearance to a level below the limit of detection (LOD). As a result, the Benzonase level was decreased an additional 4-5 fold by increasing the diafiltration from 5×DF to 8×DF. This change reduced the Benzonase level in the final bulk to below the LOD, which is less than 0.1 ng/dose (Table 32).

DFF2—Increase the Filter Size for Final Sterile Filtration of Final Bulk:

As shown in Table 28, the average step recovery using a 150 cm$^2$ and 300 cm$^2$ 0.22 μm final filter are 88.3-111.1% and 65.8-108%, respectively. The 300 cm$^2$ filter was chosen as the final filter size to avoid any plugging of the feed stream during final sterile filtration in the CTM campaign runs. The membrane area used to filter 0.6-1 L of final bulk was based on the small-scale studies that previously established the loading to be in the range of 20-150 L/m2. The filtration flow rate was 0.38 LPM for the 300 cm$^2$ filters and the flux for the filters was 760 LMH. The actual loading for the filters was 20-33 L/m$^2$, which is within the range determined from the small-scale studies.

Upstream (SUB) Process Harvest Time Change from 3 dpi to 2 dpi:

Starting with purification run 8, the viral harvest time was changed from 3 dpi (60-65 hr harvest) to 2 dpi (48 hr harvest). The peak viral titer was observed at 48 hours dpi, when an viral input of 0.001 to 0.003 FFU/cell was used. The change in harvest time resulted in a reduction in the starting HCD and HCP levels as shown in the SVH step for purification runs 8 and 9 (Table 29 and Table 30). This change also resulted in a lower impurity level of HCD and HCP in the final bulk product (Table 29 and Table 30) and therefore improved the final product quality.

The Implemented Purification Process Yielded Good Viral Recovery and Purity:

The complete implemented process was demonstrated in purification runs 8 and 9. The average overall titer recovery of these two runs was 43.4%, with an average HCD impurity level of 0.72 ng/dose (by PicoGreen) and 0.1 ng/dose (by PCR), HCP impurity level of 0.21 μg/dose and Benzonase impurity level of 0.0035 ng/dose, all of which are below the purified bulk specifications.

In summary, several changes were made to the initial purification process to improve the process efficiency and final product quality including, 1) the viral harvest was changed from 3 dpi to 2 dpi to result in a lower HCD and HCP impurity level in SVH, 2) the HCD treatment step was changed from batch-mode Benzonase treatment at SVH to CS on-column Benzonase treatment to improve overall HCD degradation and removal, 3) the target loading concentration of the CS resin was increased from 9.0 log 10 FFA/mL to 9.5 log$_{10}$ FFA/mL, which reduces the column size from 4 L to 1.4 L, 4) the final formulation buffer exchange volume for TFF2 was increased from 5 diavolumes to 8 diavolumes to improve Benzonase removal, and 5) the final sterile filtration loading was decreased by half to an average of 25 L/m$^2$ to avoid any plugging during final filtration in the CTM runs.

The final purification process is shown in FIG. 10 and the data for all the purification runs are summarized in Table 33. The average overall virus recovery based on titer for the improved purification process was 43.4%, with an average impurity level of 0.0035 ng/dose for Benzonase, 0.72 ng/dose (PicoGreen) and 0.1 ng/dose (PCR) for HCD and 0.19 μg/dose for HCP. These impurity levels are below specifications. The final bulks for purification runs 6 to 9 were analyzed by DNA size analysis using a direct-label method (psoralen-biotin) blot and a direct staining method (agarose gel). The predominant signal in these analysis showed a DNA size distribution of 500 bp (data not shown).

9.6.3 Modified Purification Process for Cell Culture Produced Influenza

Figure 10B:
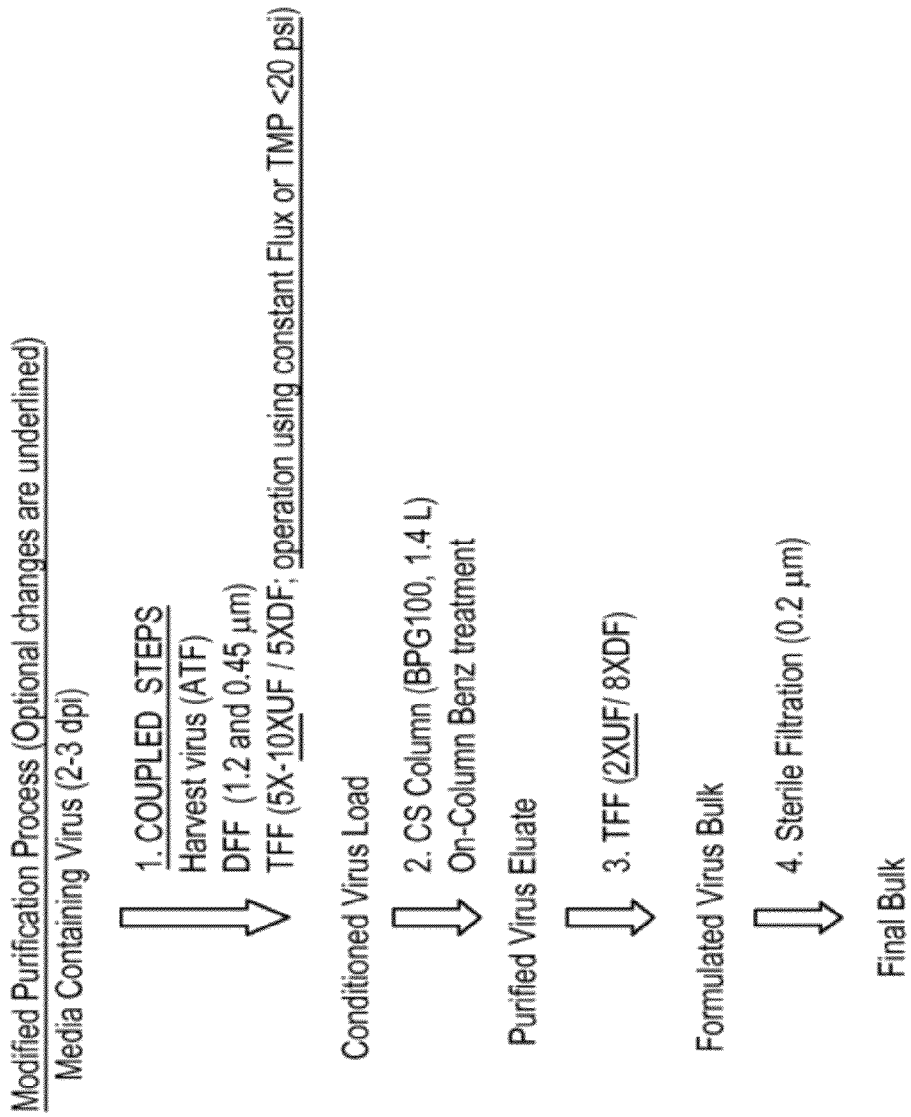

Additional modifications that can be made to the robust large scale purification process described in the Example provided in Section 0 are outlined in FIG. 10*b* and described in detail below. In particular, the harvest, clarification and TFF1 steps may be coupled to avoid the need for a harvest tank, reduce the number of manipulations and improve the overall processing time. For a smoother coupling operation TFF1 operation may be changed from constant TMP to constant Flux. Additionally, or alternatively, a lower TMP is utilized (lower than 20 psi, for example between about 10 psi (12,000 S$^{-1}$) to about 14.5 psi (16,000 S$^{-1}$)). A 2×UF step may be added to the TFF2 step to decrease the bulk volume. Optionally, a 10×UF in used in TFF1 to potentially double the loading on all subsequent purification steps.

Table 34 summarizes the parameter changes, recovery, and HCD for several purification runs. These runs utilized virus produced in MediV SFM 110 without media exchange essentially as described above (see the Example provided in Section 9.1). All purification runs were performed essentially as described for the 1b process (see the Example provided in Section 0) except as noted below. Runs #25, #27 and #30 were performed by coupling the harvest, DFF and TFF1 steps. For these runs the TFF1 was run at constant Flux (50 LMH, shear rate of 12,000 s$^{-1}$). Runs #24, #26 and #31 were performed without coupling the harvest, DFF and TFF1 steps. For these runs the TFF1 was run at a lower TMP (10 psi, shear rate of 16,000 s$^{-1}$). The conditioned viral load was divided for the CS step and processed either at 2 mM MgCl$_2$ or 10 mM MgCl$_2$. DNA analysis showed that increasing the MgCl$_2$ concentration did not reduce DNA size (data not shown). However, in one instance the yield was reduced (see Table 34).

Table 35 summarizes the parameter changes, recovery, and HCD for several purification runs of virus produced in MediV SFM 105 with media exchange. These runs utilized virus produced essentially as described in International Patent Publication WO 08/105,931 (see in particular, Example 12). All purification runs were performed essentially as described for the 1b process (see the Example provided in Section 0) except as noted below. Runs #40, #41 and #42 were performed by coupling the harvest, DFF and TFF1 steps. For these runs the TFF1 was run either at constant Flux (35 LMH, shear rate of 12,000 $s^{-1}$) or at constant TMP (10 psi, shear rate of 12,000 $s^{-1}$). The runs with constant flux were performed at small scale and were processed only to the CS step. Run #43 was performed without coupling the harvest, DFF and TFF1 steps.

Together these studies indicate that material from MediV SFM 110 (no MX) and MediV SFM 105 (with MX) process show similar Flux/TMP characteristics. The use of lower shear (12,000 $s^{-1}$), lower TMP (10 psi), and lower flux (35 LMH) does result in longer step TFF process time but the overall process time can be shorter when coupling of the harvest, DFF and TFF steps is implemented. The final concentration of HCD for these purification runs was seen to be between 0.01-0.6 ng/dose which is comparable to that obtained in the 1b process described above. The overall yields were generally above 30%.

TABLE 34

Summary of HCD and Yield for Additional Parameter Changes no MX

| | Run No. | | | | | |
|---|---|---|---|---|---|---|
| | #24 | #25 | #26 | #27 | #30 | #31 |
| Strain | B/Flo | B/Flo | A/SD | A/SD | A/Uru | A/Uru |
| SVH volume (L) | 14.5 | 10 | 12.5 | 15 | 11 | 14.5 |
| TFF coupling | No | Yes | No | Yes | Yes | No |
| TFF mode | TMP | Flux | TMP | Flux | Flux | TMP |
| TFF1 Parameter | 16k s−1, 10 psi | 12k s−1, 50 LMH | 16k s−1, 10 psi | 16k s−1, 50 LMH | 12k s−1, 50 LMH | 16k s−1, 10 psi |
| Titer (SVH) ($\log_{10}$ FFU/mL) | 8.5 | 8.5 | 8.9 | 8.9 | 8.8 | 9.1 |
| DNA (SVH) (ng/mL) | 277 | 2048 | 1672 | 2667 | 3649 | 1266 |
| Final BulkDNA (ng/dose) | 0.23 | 0.39 | 0.07 | 0.09 | 0.59 | 0.05 |
| Final Bulk DNA (ng/dose) (10 mM $MgCl_2$) | 0.18 | 0.31 | 0.07 | 0.07 | 0.57 | 0.04 |
| PB Titer (2 mM MgCl2) | 10 | 10 | 10 | 9.9 | 9.9 | 10.8 |
| PB Titer (10 mM MgCl2) | 10.1 | 10 | 9.9 | 10 | 9.8 | 10.6 |
| Overall Yield (%) (2 mM MgCl2) | 43 | 36 | 13 | 23 | 42 | 69 |
| Overall Yield (%) (10 mM MgCl2) | 46 | 40 | 8 | 21 | 15 | 59 |

TABLE 35

Summary of HCD and Yield for Additional Parameter Changes with MX

| Run No. | #40** | | #41 | | #42 | | #43 |
|---|---|---|---|---|---|---|---|
| Strain | A/UR | | A/SD | | A/UR | | A/UR |
| Harvest (dpi) | 3 | | 3 | | 3 | | 3 |
| ATF/DFF Coupling | Yes | | Yes | | Yes | | No |
| Constant Flux/TMP | TMP | Flux* | TMP | Flux* | TMP | Flux* | TMP |
| TFF1 parameter | 12k s−1, 10 psi | 12k s−1, 35 LMH | 12k s−1, 10 psi | 12k s−1, 35 LMH | 12k s−1, 10 psi | 12k s−1, 35 LMH | 12k s−1, 10 psi |
| CS loading ($\log_{10}$ FFU/mL) | 9.51 | 9.03 | 9.88 | 9.82 | 9.41 | 9.23 | 9.18 |
| Harvest titer ($\log_{10}$ FFU/mL) | 8.7 | 8.7 | 8.8 | 8.8 | 8.4 | 8.4 | 8.2 |
| Harvest DNA (ng/mL) | 395 | 395 | 1105 | 1105 | 2923 | 2923 | 2362 |
| Final Bulk DNA (ng/dose) | 0.2 | 0.41* | 0.12 | 0.21* | 0.2 | 0.77* | 0.4 |
| Final Bulk titer ($\log_{10}$ FFU/mL) | 9.7 | 9.0* | 10* | 10.0 | 9.7* | 9.4* | 9.5 |
| Overall Yield | 17% | 22%* | 26% | 45%* | 32% | 43%* | 40% |

*Runs at Constant Flux were performed at small scale and processed only to CS column step
**#40 was held after TFF1 over weekend due to Friday harvest

9.7 Evaluation of Resins for Influenza Virus Purification

Cellufine Sulfate (CS) is an affinity gel that binds the virus and the virus elutes from the column using a high-salt sucrose phosphate (SP) buffer. As described above Cellufine Sulfate gel may be used in the column chromatography step to further remove host cell DNA (HCD), host cell protein (HCP) impurities and Benzonase® contaminant introduced during the column wash step (on-column Benzonase treatment) for the degradation of host cell DNA during the manufacture of vaccine materials suitable for clinical trials. The binding capacity for the CS gel is 9.72 $\log_{10}$ FFU per mL gel determined by the dynamic binding capacity study with ca B/Malaysia/2506/04 virus strain (data not shown). Based on the binding capacity of the gel, the calculated column volumes for a 400-L and 1600-L trivalent vaccine cell culture based process are 25 L (40 cm×20 cm) and 100 L (80 cm×20 cm), respectively. With the consideration of 20-30% loss of the total infectious particles at the first direct flow filtration (DFF1) and tangential flow filtration (TFF1) steps prior to the CS column load, each target column size at each process scale would allow to purify the viral harvest titer up to 8.7 $\log_{10}$ FFU/mL without exceeding the capacity of the CS gel. However, identification of an alternative chromatography gel with higher virus binding capacity would provide for an increase overall production capacity without the need for any additional purification scale up.

The following example details the evaluation of six additional affinity resins (designated Resins A-F) using the purification process essentially as detailed above (see Example provided in Section 0). Briefly, using ca B/Malaysia 2506/04 as the model strain the sucrose-phosphate (SP) buffer stabilized viral harvest (VH) was clarified by a 1.2 µm polypropylene (PP) and 0.45 µm polyvinylidene difluoride (PVDF) capsule filters. The clarified VH was conditioned by 5-fold (5×) ultrafiltration (UF) and 5-fold (5×) diafiltration (DF) with sucrose-phosphate (SP) buffer using a 500 kDa molecular weight cut-off hollow fiber cartridge. The concentrated and diafiltered virus was then purified over the test chromatography columns to further remove host cell DNA (HCD), host cell protein (HCP) impurities and Benzonase® contaminant introduced during the column wash step (on-column Benzonase treatment) for the degradation of host cell DNA. Direct comparisons between the highest performing new resins and the CS gel currently utilize were also performed. Briefly, different viral harvest lots were used to evaluate the purification performance of test resins C and D compared to Cellufine Sulfate. The evaluation includes the step yield, binding capacity, and the impurity levels (e.g., HCD, HCP, and Benzonase®). Using this type of evaluation, the performance of new resins can be efficiently evaluated.

9.7.1 Materials and Methods

Materials, Reagent and Equipment:
Other materials, equipment and reagents which perform similarly may be readily substituted.

1. Virus harvest lots (ca B/Malaysia 2506/04, ca A/Wisconsin 67/05, ca A/Solomon Islands 03/06, ca A/Wisconsin67/05, ca A/South Dakota/6/2007) used in these studies were harvested at 48-68 hours post infection, the harvest titers were between 8.7-8.9 $\log_{10}$ FFU/mL. The clarified viral harvest was processed with 5× ultrafiltration (UF) and 5× diafiltration (DF) material by tangential flow filtration (TFF1) all performed essentially as detailed in Section 0 above, with final titers of 8.6-9.4 $\log_{10}$ FFU/mL as the column loads.
2. Quant-iT PicoGreen dsDNA kits (Invitrogen, Eugene, Oreg., Cat. No. P11496)
3. 1×SP buffer, pH 7.0 (Hyclone, Ltd, Logan, Utah, Cat. No. SH3A1577.03) or prepared with 6.5 mM potassium phosphate dibasic, 4.5 mM potassium phosphate monobasic, and 218 mM sucrose. For 1 L of 1×SP, 6.5 mL of 1 M potassium phosphate dibasic solution, 4.5 mL of 1 M potassium phosphate monobasic solution, 74.62 g of sucrose were mixed and dissolved in $H_2O$ to a final volume of 1 L. The pH was adjusted to 7.0 with 1 $NH_3PO_4$ or 1 N KOH if necessary
4. 1×SP, 1 M NaCl buffer was prepared with 9.5 mM potassium phosphate dibasic, 1.5 mM potassium phosphate monobasic, 218 mM sucrose, and 1 M NaCl. For 1 L of 1×SP, 1 M NaCl buffer, 9.5 mL of 1 M potassium phosphate dibasic solution, 1.5 mL of 1 M potassium phosphate monobasic solution, 74.62 g of sucrose, and 58.44 g of sodium chloride (NaCl) were mixed and dissolved in $H_2O$ to a final volume of 1 L. The pH was adjusted to 7.0 with 1 N 1 N $H_3PO_4$ or 1 N KOH if necessary
5. 1×SPB solution contains 2 mM MgCl2 and 50 U/mL Benzonase. To prepare 50 mL of 1×SPB, 100 µL of 1 M MgCl2 and 7.65 µL of Benzonase (327 U/mL) were added into 49.9 mL of 1×SP
6. Potassium Phosphate Dibasic, $K_2HPO_4$ (Sigma, St. Louis, Mo., Cat. No. P3786)
7. Potassium Phosphate Monobasic, $KH_2PO_4$ (Sigma, St. Louis, Mo., Cat. No. P5379)
8. 1 M $K_2HPO_4$ Potassium dibasic phosphate (174.18 g) was dissolved in $H_2O$ to final volume of 1 L
9. 1 M $KH_2PO_4$ Potassium monobasic phosphate (136.09 g) was dissolved in $H_2O$ to final volume of 1 L
10. Sucrose (EMD, Gibbstown, N.J., Cat. No. 1.07653.9012)
11. NaCl (EMD, Gibbstown, N.J., Cat. No. 7760)
12. 1 M $MgCl_2$ (Sigma, St. Louis, Mo., Cat. No. M1028)
13. Benzonase® (EMD, Darmstadt, Germany, Cat. No. 1.07653.9012, 353 U/µl)
14. 0.5 N NaOH, diluted from 10 N NaOH (VWR, West Chester, Pa., Cat. No. VW3247-7)
15. 0.22 µM Filters (Millipore, Billerica, Mass., Cat No. SCGPU11RE)
16. Polyethylene terephthalate glycol-modified (PETG) bottles (Nalgene, Rochester, N.Y.): 1 L (Cat. No. 2019-1000); 2 L (Cat. No. 2019-2000); 125 mL (Cat. No. 2019-0125); 250 mL (Cat. No. 2019-0250)
17. Conical Tubes (Corning, Corning, N.Y.): 15 mL (Cat. No. 430052); 50 mL (Cat. No. 630829);
18. 1.2 µm Polygard CN Opticap XL5 Filter (Millipore Corporation, Billerica, Mass., Cat. No. KN12A05HH1)
19. 0.45 µm Durapore Opticap XL4 Filter (Millipore Corporation, Billerica, Mass., Cat. No. KPHLA04HH3)
20. 20 L Bag (Hyclone, Ltd, Logan, Utah, Cat. No. SH30712.03)
21. 50 L Bag (Hyclone, Ltd, Logan, Utah, Cat. No. SH30712.04)
22. Hollow Fiber, 500 kDa, 4,800 $cm^2$ (GE Healthcare, Uppsala, Sweden, Model No. UFP-500-C-6A)
23. Hollow Fiber, 500 kDa, 1,400 $cm^2$ (GE Healthcare, Uppsala, Sweden, Model No. UFP-500-C-3×2 MA)
24. Omnifit columns (0.66 cm×20 cm and 1 cm×20 cm) (Bio-Chem Valve Inc. Coldhams Lane, Cambridge)
25. XK-16 column 16 mm×20 cm (GE Healthcare, Uppsala, Sweden)

26. Akta Explorer 100 (GE Healthcare, Uppsala, Sweden)
27. SpectraMax GEMINI EM microplater reader (Molecular Devices, Sunnyvale, Calif.)
28. Thermo Orion pH meter (Thermo Scientific, Waltham, Mass.)
29. CDM210 Conductivity meter (Radiometer Analytical, Lyon, France)

Preparation of Test Resins:

Resins were stored in 20% ethanol. The desired amount of (e.g., 42 mL) of a 50% resin slurry was pipetted into a 50 mL conical tube and spun at 1000 rpm for 10 minutes. The liquid was removed and the resin was resuspended with 21 mL of packing buffer (1×SP+1 M NaCl, pH 7.0). The exchange of the resin to the packing buffer was repeated three times.

Preparation of a XK-16 (16 mm×10 cm) Test or CS Resin Column:

All the parts of an empty column were cleaned with water and dried before packing. The column was assembled according to the manufacture's instructions. The column adaptor was inserted into the bottom of the column and the adaptor tubing was connected with a 30 mL of syringe. The column was positioned vertically and clamped on a stand. 10 mL of the packing buffer was filled into the column and the bottom syringe was pulled until 2 cm buffer was left in the column. The prepared Test Resin was poured into the column without introducing air bubbles and was settled by gravity. After the resin settled, the column was filled with the packing buffer. The top adaptor was carefully inserted into the column without introducing air bubbles. The column was then connected to the AKTA Explorer system and packed at 500 cm/hr (16.7 mL/min) for approximately 20 minutes with the packing buffer until the column bed height is not changed. The top adaptor was adjusted 1-2 mm down into the top of the gel. The final packed column bed height was 10 cm, which equals to 20 mL column volume. A smaller size Omnifit column (0.66 cm×17 cm), which equals to 5.8 mL of gel when packed was used for dynamic binding capacity studies with Test Resins and CS gels. The packed Test Resin column was sanitized with 1 N NaOH for 1 hour and re-equilibrated with 1×SP pH 7.0 buffer. The packed CS column was sanitized with 0.5 N NaOH for 1 hour and re-equilibrated with 1×SP pH 7.0 buffer.

Preparation of the 5× Ultrafiltration and 5× Diafiltration (5×UF/5×DF) Conditioned Virus Load for Test Resin and Cellufine Sulfate Columns:

15 or 20 L of the 1× stabilized virus harvest from a 15 L bioreactor or a 30 L SUB bioreactor (the details of MDCK cell growth and virus production are described in International Patent Publication WO 08/105,931, see in particular, Example 12) was filtered through a 1800 cm$^2$ 1.2 μm prefilter capsule and a 1900 cm$^2$ 0.45 μm filter capsule at a flow rate of 1.5 L/min and collected in a 20-L Hyclone bag. The direct flow filtration (DFF1) filtrate was then purified using tangential flow filtration (TFF1) by 5-fold ultrafiltration (5×UF) and 5-fold diafiltration (5×DF) with 1×SP buffer using the Flexstand system essentially as described for the improved process above (see Example provided in Section 0). The TFF1 step was performed at a constant shear rate of 16000 s$^{-1}$ and a TMP at 20 psi using a 1400 cm$^2$ or a 4800 cm$^2$ 500-kDa molecular weight cut-off hollow fiber cartridge for most of the lots. ca B/Malaysia viral harvest lot #1 was performed at a constant shear rate of 12000 s$^{-1}$ and TMP at 14.5 psi and ca B/Malaysia viral harvest lot #2 was performed at a constant shear rate of 12,000 s$^{-1}$ and constant flux of 70 LMH. The 5×UF/5×DF virus solution, was aliquoted at 100 mL per bottle. All the bottles were frozen in dry ice and stored at −80° C. as the Test Resin and CS column load material.

Test Resin and Cellufine Sulfate Column Running Conditions:

The operational parameters for the Test Resin column (16 mm×10 cm) runs were the essentially the same as detailed above for the BPG 100 column. Briefly, the column was first equilibrated with 3 column volumes (CV) of 1×SP and the desired amount of 5×UF/5×DF virus solution was loaded on the column at a flow rate of 150 cm/hr (5 mL/min for 1.6 cm×10 cm XK-16 column and 0.85 mL/min for 0.66 cm×17 cm Omnifit column). After 1 CV of 1×SP buffer wash, 1×SPB was loaded onto the column at 50 cm/hr (85 mL of 1×SPB with 1.7 mL/min for 1.6 cm×10 cm XK-16 column and 15 mL of 1×SPB with 0.3 mL/min for 0.66 cm×17 cm Omnifit column) for on-column Benzonase treatment with a contact time of 50 minutes. The column was then washed with the first 1 CV of 1×SP at 50 cm/hr and the second 1 CV of 1×SP at 150 cm/hr linear flow rate. The bound virus was eluted with 3 CV of 1×SP containing 1 M NaCl, pH 7.0 buffer at a linear flow rate of 150 cm/hr. The elution peak was collected from 20 mAU to 20 mAU (0.1 O.D. to 0.1 O.D.) at $A_{280}$ nm. The fractions were collected for Test Resin load, flow through, Benzonase wash, and eluate. All the samples were aliquoted, frozen in dry ice and stored at −80° C. for infectivity analysis by FFA (fluorescent focus assay) and DNA analysis by PicoGreen assay.

Test Resin Columns Purification Evaluation:

The packed Test Resin columns (16 mm×10 cm) were loaded individually with the ca B/Malaysia virus strain 5×UF/5×DF TFF1 material at the load concentration of 9.0 $\log_{10}$ FFU/mL. To avoid the loading of small volume, the 5×UF/5×DF virus load solution was prediluted 2.5 fold with 1×SP buffer from the titer of 9.4 $\log_{10}$ FFU/mL to 9.0 $\log_{10}$ FFU/mL before loading. 50 mL of the virus solution was loaded to target at 9.4 $\log_{10}$ FFU/mL gel for each column run. The calculation was based on the loading virus titer times the loading volume and divided by the CS column volume, log (10^(9.0 FFU/mL)×50 mL/20 mL column volume)=9.4 $\log_{10}$ FFU/mL gel. The virus load, flow through, Benzonase wash and eluate fractions were collected for each run. All the samples were aliquoted, frozen in dry ice and stored at −80° C. for infectivity analysis by FFA and for HCD, HCP and Benzonase quantitative analysis.

Test Resin Columns Binding Capacity Study:

The Test Resin columns (16 mm×10 cm) were loaded with the ca B/Malaysia virus strain 5×UF/5×DF TFF1 material at the load concentration of 9.0 $\log_{10}$ FFU/mL. The 5×UF/5×DF virus load solution was prediluted with 1×SP buffer from the titer of 9.4 $\log_{10}$ FFU/mL to 9.0 $\log_{10}$ FFU/mL before loading. Four different total virus loading ranges at 9.4, 9.9, 10.2 and 10.5 $\log_{10}$ FFU/mL gel were performed to evaluate the binding capacity of the Test Resins. For each run, the virus load, flow through and eluate samples were collected and analyzed for infectivity titer by Fluorescent Focus Assay (FFA) essentially as described above (see Example provided in Section 9.1) and for host cell DNA (HCD) analysis using the Quant-iT PicoGreen kit essentially following the procedure described in the kit. The column eluate HCD level in terms of ng per 10$^7$ titer dose was calculated as HCD (ng/mL)/(10^(CS eluate titer $\log_{10}$ FFU/mL-7.0 $\log_{10}$ FFU/dose))= HCD (ng/dose). The level of host cell protein (HCP) and Benzonase™ were also determined essentially as described above (see Example provided in Section 0).

Dynamic Binding Capacity Study of Cellufine Sulfate and Test Resins:

The TFF1 (5×UF/5×DF) material for different lots of ca B/Malaysia and ca A/Wisconsin strains were used to perform the column dynamic binding capacity studies to investigate the effect of the lot material on the performance and binding capacity of Test Resins in comparison with CS gel. The TFF1 (5×UF/5×DF) virus solution was loaded on the CS and Test Resin columns at 150 cm/hr. The amount of virus loading was targeted to 10.5 to 10.7 $\log_{10}$ FFU/mL of gel. The calculation was based on the loading virus titer times the loading volume and divided by the CS column volume, log(10^(TFF1 loading titer ($\log_{10}$ FFU/mL))×loading volume (mL)/column volume (mL))=target load at $\log_{10}$ FFU/mL gel. The flow through was collected as 1 column volume (CV) in each fraction tube. The flow-through fractions were assayed for titer by FFA. The breakthrough curve of the CS gel was plotted as the flow through volume versus the percentage of the virus titer concentration in the flow through relative to the loading titer concentration. The dynamic binding capacity was determined as the maximum amount of virus that can bind to the gel until reaching 10% of the loading virus concentration in the flow through. The volume (X) at 10% virus breakthrough was then used to calculate the binding capacity (Y) of the gel, which is the loading virus titer times the volume at 10% breakthrough and divided by the column volume, log(10^(loading titer ($\log_{10}$ FFU/mL))×(mL)/column volume (mL))=Y $\log_{10}$ FFU/mL of gel.

Loading Range Studies:

Three different lots of ca B/Malaysia TFF1 (5×UF/5×DF) material were used to perform the loading range studies to compare the effect of lot material on the performance of Test Resins C and D in comparison with CS gel. The target loading ranges for each individual lot and for each column gel are listed in Table 34. The column load, flow through and column eluate for each run were collected and analyzed using the FFA and HCD assays.

TABLE 36

Loading Range Studies of Cellufine Sulfate and Test Resin C and D Columns

| Gels | ca B/Malaysia lot #1 Virus Load ($\log_{10}$ FFU/mL gel) | ca B/Malaysia lot # 2 Virus Load ($\log_{10}$ FFU/mL gel) | ca B/Malaysia lot #3 Virus Load ($\log_{10}$ FFU/mL gel) |
|---|---|---|---|
| CS | 9.5 | 9.9 | 9.9 |
| | 9.7 | 10.1 | 10.2 |
| | 9.9 | 10.4 | 10.5 |
| | 10.2 | | |
| Test Resin C | 9.4 | 9.8 | NA |
| | 9.9 | 10.1 | NA |
| | 10.2 | 10.4 | NA |
| Test Resin D | 9.4 | 9.8 | 9.9 |
| | 10.2 | 10.1 | 10.2 |
| | | 10.4 | 10.5 |

Purification Step Yields:

Column purification step yield was calculated from the eluted virus titer times the elution volume divided by the loaded virus titer and the loaded volume, 10^(CS eluate titer FFU/mL)×elution volume/(10^(CS load titer FFU/mL)×load volume).

9.7.2 Results and Discussion

For the purification runs on the Test Resins A-D, each column was loaded with the ca B/Malaysia virus strain 5×UF/5×DF TFF1 material at the load concentration of 9.0 $\log_{10}$ FFU/mL. The target amount of virus load was 9.4 $\log_{10}$ FFU/mL gel for each run. The virus was eluted from the column using three column volumes (CV) of SP buffer with 1 M NaCl. The elution chromatogram for Test Resin A-D column runs is shown in FIG. 19, panels A-D, respectively. As shown in FIG. 19, Test Resins A and B appeared to show separated multiple elution peaks while Test Resins C and D showed a single peak with peak shoulders and heterogeneous features.

Table 37 summarizes the results of four purification runs comparing the step yields, column eluate impurity HCD, HCP and Benzonase contaminant levels. Test Resins C and D had higher step yields (103.5% and 76.5%) compared to Test Resins A and B and Test Resin B gave the lowest step yield (14.5%). In terms of the impurity HCD levels, ca B/Malaysia purified with Test Resins C and D had lower HCD levels (0.07 and 0.08 ng/dose) compared to Test Resins A and B (0.14 and 0.67 ng/dose). The HCP levels for ca B/Malaysia purified with Test Resin C (0.27 ng/dose) and Test Resin D (0.21 ng/dose) were similar to Test Resin A (0.26 ng/dose), but lower than Test Resin B (0.87 ng/dose). The Benzonase levels of ca B/Malaysia purified with Test Resins C and D (0.25 and 0.31 ng/dose) were lower than with Test Resins A and B (1.78 and 2.60 ng/dose).

TABLE 37

Comparison of Test Resin Step Yields, HCD, HCP and Benzonase Levels

| Test Resin | Eluate Titer ($\log_{10}$ FFU/mL) | Step Yield (%) | HCD ng/mL (ng/$10^7$dose) | HCP μg/mL (μg/$10^7$dose) | Benzonase ng/mL (ng/$10^7$dose) |
|---|---|---|---|---|---|
| A | 9.5 | 69.4 | 43.5 (0.14) | 41.2 (0.26) | 282.5 (1.78) |
| B | E1: 7.2 | 0.1 | 744 (469.4) | 10.3 (6.50) | 0.84 (0.53) |
| | E2: 8.6 (Major Eluate) | 14.5 | 25.8 (0.67) | 34.7 (0.87) | 103.3 (2.60) |
| C | 9.6 | 103.5 | 26.7 (0.07) | 107.5 (0.27) | 99.6 (0.25) |
| D | E1: 9.6 | 66.4 | 27.6 (0.07) | 71.5 (0.18) | 11.0 (0.03) |
| | E2: 9.2 | 10.1 | 22.4 (0.14) | 56.0 (0.35) | 322.9 (2.04) |
| | Total Eluate: 9.5 | 76.5 | 26.2 (0.08) | 67.2 (0.21) | 97.0 (0.31) |

In Table 38, the virus titer in the flow through for the four Test Resin runs showed either very low (2.2% of total infectious particles relative to the load for Test Resin C) or limit of detection (LOD) indicating that the virus was mostly bound to the gel at a loading of 9.4 $\log_{10}$ FFU/mL gel. Test Resin C had a higher amount of virus in the flow-through suggesting that Test Resin C may have a lower binding capacity compared to the other three Test Resins. The Benzonase wash fraction of these four runs also showed either non-detectable or a very low percentage of virus (1.2% for Test Resin C and 0.9% for Test Resin D). The initial screening results of the four purification runs with the Test Reins indicated that Test Resins C and D performed better relative to the other two gels in terms of the step yields and the eluate impurity and contaminant levels.

TABLE 38

Comparison of the Test Resins Flow-Through and Benzonase Wash Fractions

| Test Resins | Flow Through Fraction Titer ($\log_{10}$ FFU/mL) | Total Load in Flow Through (%) | Benzonase Wash Titer ($\log_{10}$ FFU/mL) | Total Load in Benzonase Wash (%) |
|---|---|---|---|---|
| A | LOD | LOD | LOD | LOD |
| B | LOD | LOD | LOD | LOD |
| C | 7.2 | 2.2 | 6.6 | 1.2 |
| D | LOD | LOD | 6.6 | 0.9 |

LOD—Limit of detection

The screening results of Test Resins A-D at a loading of 9.4 $\log_{10}$ FFU/mL of gel showed that the virus was mostly bound, thus a higher amount of virus load at loading levels of 9.4, 9.9, 10.2 and 10.5 $\log_{10}$ FFU/mL of gel were selected to evaluate the binding capacity of these resins. In addition, Test Resins E and F were also evaluated. The impact on the step yields and the HCD impurity levels at these loading levels were also evaluated. The binding capacity study results are summarized below. Table 39 lists the binding capacity results of Test Resins C and D. Table 40 lists binding capacity results of Test Resins A, B, E and F.

TABLE 39

Binding Capacity Study of Test Resins C and D (1M or 2M NaCl Elution)

| Test Resin | Loading ($\log_{10}$FFU/ mL gel) | NaCl Elution Conc NaCl | Eluate Infectivity ($\log_{10}$FFU/ mL) | DNA Level (ng/mL) | DNA (ng/$10^7$ dose) | Flow Through (% of the load) | Step Yield (%) |
|---|---|---|---|---|---|---|---|
| C | 9.4 | 1M | 9.6 | 26.7 | 0.07 | 2.8 | 103.5 |
| C | 9.4 | 2M | 9.7 | 100.5 | 0.20 | LOD | 90.2 |
| C | 9.9 | 2M | 9.9 | 1018.8 | 1.28 | 1.4 | 94.4 |
| C | 10.2 | 2M | 9.8 | 1381.3 | 2.19 | 14.4 | 79.4 |
| D | 9.4 | 1M | 9.5 | 26.2 | 0.08 | LOD | 76.5 |
| D | 9.4 | 2M | 9.6 | 44.0 | 0.11 | LOD | 59.7 |
| D | 10.2 | 2M | 9.8 | 617.8 | 0.98 | 1.4 | 75.7 |

LOD—Limit of detection

TABLE 40

Binding Capacity Study of Test Resins A, B, E and F (1M NaCl Elution)

| Test Resin | Loading ($\log_{10}$ FFU/mL of gel) | Eluate Infectivity ($\log_{10}$ FFU/mL) | DNA Level (ng/mL) | DNA (ng/$10^7$ dose) | Flow Through (% of the load) | Step Yield (%) |
|---|---|---|---|---|---|---|
| E | 9.4 | 9.5 | 234.4 | 0.74 | LOD | 82.0 |
| E | 9.9 | 9.7 | 2662.5 | 5.31 | LOD | 52.0 |
| E | 10.2 | 9.6 | 1997.7 | 5.87 | 8.3 | 47.8 |
| A | 9.4 | 9.5 | 43.5 | 0.14 | LOD | 69.4 |
| A | 9.9 | 9.6 | 1018.8 | 2.56 | LOD | 61.5 |
| A | 10.2 | 9.6 | 1367.4 | 3.43 | LOD | 62.6 |
| A | 10.5 | 9.6 | 2334.7 | 5.87 | 6.3 | 51.5 |
| B | 9.4 | 8.6 | 25.82 | 0.67 | LOD | 14.5 |
| B | 9.9 | 8.9 | 230.3 | 2.9 | LOD | 11.7 |
| F | 9.9 | 9.2 | 196.2 | 1.24 | LOD | 34.9 |

LOD—Limit of detection

In Table 39, the run results at 9.4 $\log_{10}$ FFU/mL of gel loading for Test Resins C and D were compared with SP buffer 1 M NaCl and 2 M NaCl elution, respectively. A 2 M NaCl elution was performed to evaluate whether the Test Resins C and D elution peaks would result in a single peak relative to the peaks observed with 1 M NaCl elution. As shown in FIG. 20, the elution peak was sharpened with 2 M NaCl elution for both gels without the heterogeneous features (compare FIG. 19B with 20A and FIG. 19D with 20B). As shown in Table 39, the 2 M NaCl elution doesn't affect the step yields significantly for both Test resin C and D considering the recovery based on titer from 103.5 to 90.2% for Test Resin C and from 76.5 to 59.7% for Test Resin D. The HCD levels of the eluate in terms of ng per dose were slightly increased for both gels when eluted with 2 M NaCl; increased from 0.07 to 0.2 ng/dose for Test Resin C and from 0.08 to 0.11 ng/dose for Test Resin D. For the assessment of impact on the HCD level at higher amount of virus load, as the load amount was increased from 9.4 to 9.9 $\log_{10}$ FFU/mL of gel, the eluate HCD level for Test Resin C increased from 0.2 to 1.26 ng/dose but the step yield was not affected (90.2% versus 94.4%). Further increasing the loading to 10.2 $\log_{10}$ FFU/mL of gel showed an increase in the amount of virus breakthrough (14.4%) in the flow through fraction thus resulting in a decreased yield (79.4%) and an increased HCD level in the eluate (2.19 ng/dose) for Test Resin C. Because the breakthrough curve was not yet evaluated for each gel, the binding capacity was estimated when no more than 2% of the virus appeared in the flow through for the corresponding amount of virus load. Thus, 9.9 $\log_{10}$ FFU/mL of gel was the estimated binding capacity of Test Resin C. As shown in Table 39, for Test Resin D, an increase in the virus load from 9.5 to 10.2 $\log_{10}$ FFU/mL of gel resulted in an increase in the HCD level from 0.11 ng/dose to 0.98 ng/dose but no major effect on the step yield (59.7% to 79.7%). This is because a small percentage of virus was detected in the flow-through (1.4%) even at a loading of 10.2 $\log_{10}$ FFU/mL gel. Thus, 10.2 $\log_{10}$ FFU/mL of gel was estimated to be the binding capacity of Test Resin D.

In summary, the estimated binding capacity for Test Resin C and D were 9.9 and 10.2 $\log_{10}$ FFU/mL of gel, respectively. Test Resin D had approximately two times higher binding capacity than Test Resin C in this set of studies with the ca B/Malaysia strain. When the amount of virus load was increased, the eluate HCD levels for both Test Resin C and D were also increased. Comparing the gels at the same loading level of 10.2 $\log_{10}$ FFU/mL of gel, the level HCD value per dose for Test Resin C (2.19 ng/dose) was higher than the Test Resin D (0.98 ng/dose) thus the impact on the HCD level for Test Resin C was more notable than Test Resin D at a higher virus load. In terms of the step yield comparing various amounts of virus load, Test Resin C gave slightly higher step yields than Test Resin D.

The initial screening results indicated that Test Resin C and D gave better purification results compared to Test Resin A and B when studies were performed at a loading of 9.4 $\log_{10}$ FFU/mL of gel. In order to evaluate whether Test Resin A and B as well as two additional Test Resins (E and F) could give even higher binding capacities than Test Resin C and D, binding capacity studies were performed with Test Resins A, B, E and F and evaluated for step yields. The results are summarized in Table 40. In this set of purification runs, the bound virus was eluted with SP buffer 1 M NaCl, which is the elution buffer condition used for the CS chromatography step described in the Example provided in Section 0.

As shown in Table 40, the estimated binding capacity for Test Resin E was between 9.9 to 10.2 $\log_{10}$ FFU/mL of gel because at these two loading ranges the percentage of virus in the flow through increased from not-detected to 8.3%. For Test Resin A, the estimated binding capacity was between 10.2 to 10.5 $\log_{10}$ FFU/mL of gel because the percentage of virus in the flow through increased from not-detected to 6.3% at these two loading ranges. The binding capacities for both Test Resin B and E were estimated to be at least >9.9 $\log_{10}$ FFU/mL of gel because there were no runs performed at higher loading ranges.

When evaluating the impact on the HCD levels at higher amounts of virus load, the HCD levels for Test Resins A, B, E, and F increased when the virus load was increased from 9.4 to 9.9 $\log_{10}$ FFU/mL of gel. Even higher HCD levels were observed for Test Resins A and E when loading was increased up to 10.2 and 10.5 $\log_{10}$ FFU/mL of gel. At the same amount of virus load (9.9 $\log_{10}$ FFU/mL of gel) with Test Resins C and D, higher HCD levels were observed in the elution fraction for several of the Test Resins (3.43 ng/dose for Test Resin A, 2.9 ng/dose for Test Resin B, 5.31 ng/dose for Test Resin E, and 1.24 ng/dose for Test Resin F) (Table 40). Thus, the impact on the HCD levels for the Test Resins A, B, E and F with the higher virus load was more remarkable than for Test Resins C and D.

61.5%) with the same amount of virus load (9.9 $\log_{10}$ FFU/mL of gel). The same trend was observed at a virus loading of 9.4 $\log_{10}$ FFU/mL of gel with higher step yields for Test Resin E (82%) and Test Resin A (69.4%) compared to Test Resin B (14.5%). Comparing the Test Resins, Test Resins C and D gave higher step yields than Test Resins A, B, E and F at different virus loading ranges. Test Resins C and D were further evaluated with different virus strains and harvest lots to compare the performance with the current CS gel.

Figure 21C:
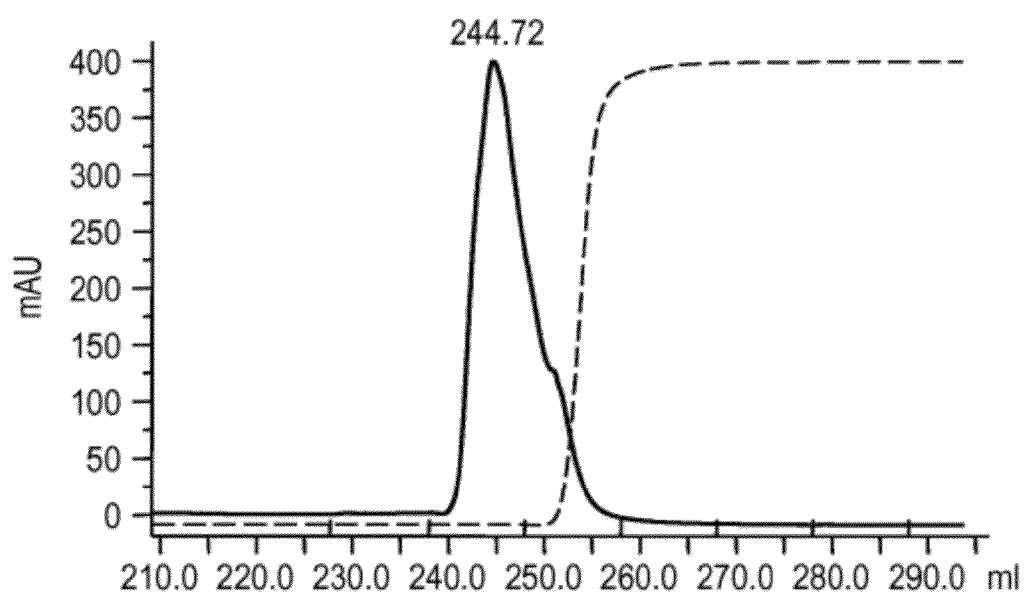

Test Resin C was used to evaluate the purification of other virus strains. FIGS. 21A and B show the elution peak chromatogram of the purification runs of ca A/Wisconsin and ca A/Solomon Islands, respectively, using a Test Resin C column. The peak profiles were fairly similar and consistent to the purification runs for ca B/Malaysia strain (FIG. 21C). Table 41 lists the step yields and HCD levels in the eluate for the purification of the ca B/Malaysia, ca A/Solomon Islands and ca A/Wisconsin strains. All the virus bound on the column and less than 1% of the total infectious virus particles relative to the load were observed in the flow through under the loading conditions at 9.4 to 10.0 FFU/mL gel. The step yields of the three strains ranged from 78.9 to 112.5%, which were relatively comparable for all three strains and were comparable to previous high yields for Test Resin C gel. Host cell DNA levels were still low when loading under 9.8 $\log_{10}$ FFU/mL gel, however, the DNA level in the eluate increased to 1.34 ng/dose when a high amount of virus load was applied (at 10 $\log_{10}$ FFU/mL of gel). A similar increase in HCD level was observed for the binding capacity study using Test Resin C gel with ca B/Malaysia strain in the previous study. The results indicated that Test Resins gave similar performance when purified with different strains.

TABLE 41

Purification Results Summary of the ca B/Malaysia, ca A/Wisconsin, and A/Solomon Islands Strains using Test Resin C Column

| Strain (ca) | Total Virus Load ($\log_{10}$FFU/mL gel) | Eluate Infectivity ($\log_{10}$FFU/mL) | DNA Level (ng/mL) | DNA (ng/$10^7$ dose) | Flow Through (%) | Step Yield (%) |
|---|---|---|---|---|---|---|
| B/Malaysia | 9.4 | 9.7 | 34.5 | 0.07 | 0.6 | 89.2 |
| A/Wisconsin | 10.0 | 9.9 | 1062.4 | 1.34 | 0.4 | 78.9 |
| A/Solomon Islands | 9.8 | 9.8 | 117.1 | 0.15 | 0.7 | 112.5 |

The step yield decreased from 82% to 47.8% for Test Resin E when the virus loading was increased from 9.4 to 10.2 $\log_{10}$ FFU/mL of gel (Table 40). For Test Resin A, the step yield also decreased (69.4% to 51.5%) when virus loading was increased from 9.4 to 10.5 $\log_{10}$ FFU/mL of gel. Both Test Resins B and F showed relative low step yields (11.7% and 34.9%) compared with the Test Resin E and A (52.0% and The purification of ca A/Wisconsin and ca B/Malaysia strains were evaluated using Test Resin D gel. FIGS. 22A and B show the elution peak chromatogram for virus elution. The peak elution profiles were similar for the two strains and the purification recovery for this step was high with an expected range (<2 ng/dose) of HCD levels for the eluate fraction for both strains (Table 42).

TABLE 42

Purification Results Summary of the ca B/Malaysia and ca A/Wisconsin Strains using Test Resin D Column

| Strain (ca) | Total Virus Load ($\log_{10}$FFU/mL of gel) | Eluate Infectivity ($\log_{10}$FFU/mL) | DNA Level (ng/mL) | DNA (ng/$10^7$ dose) | Flow Through (%) | Step Yield (%) |
|---|---|---|---|---|---|---|
| B/Malaysia | 9.9 | 10.0 | 202.8 | 0.20 | LOD | 98.1 |
| A/Wisconsin | 9.6 | 9.9 | 904.6 | 1.1 | LOD | 133 |

LOD—Limit of Detection

A dynamic binding capacity study was performed with the TFF 1 (5×UF 5×DF) material for ca B/Malaysia and ca A/Wisconsin, and three different lots of ca B/Malaysia with a total target virus load of 10.5 to 10.7 $\log_{10}$ FFU/mL of gel. In the beginning of the $A_{280}$ nm trace the virus load is relatively flat. After a certain load volume, the $A_{280}$ increased significantly and gradually reached a plateau indicating the column had exceeded the column capacity thereby allowing virus breakthrough. The percentage of virus in the flow through was calculated by dividing the virus titer of each flow through fraction by the loading titer and multiplying by 100. The breakthrough curve was plotted with the percentage of virus concentration in the flow through versus the loaded volume. The dynamic binding capacity of the gel is defined as the binding capacity per mL of gel when the flow through fraction reached 10% break through of the virus concentration relative to the loading concentration.

For the CS column, when 18 mL of the virus was loaded, 5% of the virus appeared in the flow through fraction. When a binding capacity at 10% break-through was reached, approximately 19 mL of virus solution was loaded. This represented a loading of 9.8 $\log_{10}$ FFU per mL of gel ($\log_{10}$ (10^ (9.3)×19 mL/5.8 mL)=9.8 $\log_{10}$ FFU per mL gel). Thus, 9.72 $\log_{10}$ FFU/mL of gel was determined to be the dynamic binding capacity for CS gel with ca B/Malaysia/2506/04 strain lot #2. Similarly, when 27 mL of virus was loaded on the Test Resin C column and 24 mL of virus was loaded on the Test Resin D column, 10% of the virus appeared in flow through fractions. The dynamic binding capacity of Test Resin C and D was determined to be 9.96 and 9.92 $\log_{10}$ FFU/mL of gel, respectively, with the same lot ca B/Malaysia. The dynamic binding capacities for the Test Resin C, D and CS column with several lots ca B/Malaysia and strains are summarized in Table 43. As shown in Table 43, the dynamic binding capacity varied and appeared to be dependent on the level of HCD and HCP in the loading material. The dynamic binding capacity of CS and Test Resin C and D columns were affected by the HCD level of the loading material; the higher of the HCD level of the loading material, the lower of the dynamic binding capacity of the gel. The dynamic binding capacity of the gel appears to be less affected by the HCP level of the loading material. It was hypothesized that some host cell DNA binds to the virus thus interfering with the kinetic binding of the virus to the gel surface ligand resulting in the lower binding capacity observed for virus lots with higher DNA levels. Among the four lots shown in Table 43, the dynamic binding capacity of the CS gel varied from 9.7 to 10.4 $\log_{10}$ FFU/mL of gel, binding capacity for Test Resin C ranged from 9.9 to 10.7 $\log_{10}$ FFU/mL of resin and binding capacity for Test Resin D ranged from 9.9 to above 10.7 $\log_{10}$ FFU/mL of gel. Overall, the dynamic binding capacity of Test Resin C and D gels were higher (~2 fold) compared to CS gel under the conditions evaluated. The dynamic binding capacity of Test Resin D gel was sometimes higher in some lots and at least comparable to Test Resin C gel.

TABLE 43

Summary of Dynamic Binding Capacity for Different Lots of Virus

| Strain (ca) | Loading Material Titer‡ | Loading Material DNA (ng/mL) | Loading Material DNA (ng/dose) | Loading Material HCP (μg/mL) | Loading Material HCP (μg/dose) | Estimated Dynamic Binding Capacity‡ |
|---|---|---|---|---|---|---|
| B/Malaysia Lot 1 | 9.3 | 7485.8 | 37.5 | NA | NA | CS: 9.7<br>TR C: 9.9<br>TR D: 10.2 |
| B/Malaysia Lot 2 | 9.3 | 21596.8 | 108.2 | 68.44 | 0.343 | CS: 9.8<br>TR C: 9.96<br>TRD: 9.92 |
| A/Wisconsin Lot 2 | 8.5 | 451.2 | 14.3 | 18.96 | 0.60 | CS: 10.4<br>TR C: 10.7<br>TR D: >10.7 |
| B/Malaysia Lot 3 | 9.1 | 9436.9 | 75.0 | 41.04 | 0.326 | CS: 10.2<br>TR D: 10.1 |

‡$\log_{10}$FFU/mL of gel

After comparing the dynamic binding capacity of CS to Test Resin C and D, individual runs were performed using three lots of ca B/Malaysia to evaluate the step yield and the removal of HCD for CS and Tes Resins using the same loading conditions. The target loading titer ranges for each lot were selected for study according to the dynamic binding capacity of the lot. Table 44 summarizes the purification step yield and HCD levels at various virus loading ranges for CS, Test Resin C and Test Resin D column purification of ca B/Malaysia lot 1. The estimated binding capacity for Test Resin C and D were 9.9 and 10.2 $\log_{10}$ FFU/mL of gel, respectively. Test Resin D had approximately two times higher binding capacity than Test Resin C in these studies. The binding capacity for CS was 9.7 $\log_{10}$ FFU/mL of gel[3] using the same lot of material. Both Test Resin C and D had a higher (2- and 4-fold) binding capacity than CS. When the amount of virus load was increased, the eluate HCD levels for both Test Resin C and D also increased. Comparing the gels at the same loading level of 10.2 $\log_{10}$ FFU/mL of gel, the HCD level per dose for Test Resin C (2.19 ng/dose) was higher than for Test Resin D (0.98 ng/dose). Thus, the increase in the eluate HCD level was similar for the Test Resin D and CS gel when the virus load was increased. However, for the Test Resin C gel, the increase in HCD level was more noteworthy compared to the CS gel. The step yield with various amounts of virus load was comparable or slightly with Test Resin C compared to Test Resin D. Compared to the CS column, Test Resin C and D columns gave higher step yields when virus purification was performed at a higher virus load condition. Overall, Test Resin D had a higher binding capacity and better purification performance compared to CS and Test Resin C.

TABLE 44

Comparison of CS and Test Resins
C and D with ca B/Malaysia Lot 1

| Gel | Total Virus Load‡ | Eluate Infectivity $\log_{10}$FFU/mL | Eluate DNA Level (ng/dose) | Flow Through (%) | Step Yield (%) |
|---|---|---|---|---|---|
| CS | 9.5 | 9.8 | 0.23 | 0.2 | 71.0 |
|  | 9.7 | 9.9 | 0.39 | 1.5 | 83.0 |
|  | 9.9 | 9.7 | 0.74 | 7.1 | 44.9 |
|  | 10.2 | 9.8 | 0.95 | 26.7 | 30.7 |
| Test Resin C | 9.4 | 9.7 | 0.2 | LOD | 90.2 |
|  | 9.9 | 9.9 | 1.28 | 1.4 | 94.4 |
|  | 10.2 | 9.8 | 2.19 | 14.4 | 79.4 |
| Test Resin D | 9.4 | 9.6 | 0.11 | LOD | 60.0 |
|  | 10.2 | 9.8 | 0.98 | 1.4 | 75.7 |

LOD—Limit of Detection
‡$\log_{10}$FFU/mL of gel

Table 45 summarizes the purification step yields and HCD levels at various virus loading ranges for the column purification with ca B/Malaysia lot 2 using CS, Test Resin C and Test Resin D. The binding capacities for Test Resin C and D and CS were 9.96, 9.92 and 9.80 $\log_{10}$ FFU/mL of gel, respectively. Test Resin C and D had a slightly higher binding capacity than CS gel. When the virus loading was close to the dynamic binding capacity, 9.8-9.9 $\log_{10}$ FFU/mL of gel, the step yields for all three gels were comparable at 47.5%-62.8%. At higher virus loading, 10.1 $\log_{10}$ FFU/mL of gel, the step yields for CS dramatically decreased to 25.2% and Test Resin C decreased to 50.2% while Test Resin D yield remained similar at 63.2%. When the loading was increased to 10.4 $\log_{10}$ FFU/mL of gel, the step yield of CS further decreased to 12.6% while the Test Resin C and D yields decreased to 49.8 and 39.5%, respectively. The step yields of Test Resin C and D were considerably higher than the CS gel.

TABLE 45

Comparison of CS and Test Resins
C and D with ca B/Malaysia Lot #2

| Gel | Total Virus Load‡ | Eluate Infectivity $\log_{10}$FFU/mL | Eluate DNA Level (ng/dose) | Flow Through (%) | Step Yield (%) |
|---|---|---|---|---|---|
| CS | 9.9 | 9.7 | 0.5 | 13.1 | 62.8 |
|  | 10.1 | 9.4 | 1.91 | 14.5 | 25.2 |
|  | 10.4 | 9.4 | 2.43 | 27 | 12.6 |
| Test Resin C | 9.8 | 9.6 | 0.97 | 6.5 | 59.9 |
|  | 10.1 | 9.7 | 2.51 | 17.9 | 50.2 |
|  | 10.4 | 9.9 | 2.93 | 19.6 | 49.8 |
| Test Resin D | 9.8 | 9.5 | LOD | N/A | 47.5 |
|  | 10.1 | 9.8 | 1.67 | 14.5 | 63.2 |
|  | 10.4 | 9.8 | 1.21 | 48.9 | 39.5 |

‡$\log_{10}$FFU/mL of gel

When the amount of virus load was increased, the eluate HCD levels for the CS, Test Resin C and D gels also increased. Comparison of the gels at the same amount of virus loading 9.8 to 10.4 $\log_{10}$ FFU/mL of gel, the level of HCD per dose for Test Resin C (0.97, 2.51, 2.93 ng/dose) was higher than the CS (0.5, 1.91, 2.43 ng/dose) and the HCD value for Test Resin D was the lowest (LOD, 1.67, 1.21 ng/dose). The increase in HCD level in virus purified using Test Resin C was greater than for the CS gel. The increase in the eluate HCD level was similar for the Test Resin D and CS gel, although less for Test Resin D. Overall, Test Resin D had higher binding capacity and better purification performance (step yield and HCD level) compared to CS and Test Resin C particularly when evaluated at a higher a virus load condition.

After assessing the overall purification performance of Test Resin C and D with CS column for the previous two lots of ca B/Malaysia, Test Resin D was chosen for purification studies to further compare the CS gel using B/Malaysia lot #3. The results are summarized in Table 46. For this lot, the dynamic binding capacity of CS and Test Resin D were comparable with 10.2 $\log_{10}$ FFU/mL of gel for CS and 10.1 $\log_{10}$ FFU/mL of gel for Test Resin D. When comparing performance with various amounts of virus load, the HCD levels were comparable between the CS and Test Resin D gel (all less than 1.1 ng/dose). For the step yields, especially at a higher virus load of 10.2 and 10.5 $\log_{10}$ FFU/mL of gel, Test Resin D gave slightly better step yields (52.8 and 65.8%) than CS gel (46.2 and 55.2%).

TABLE 46

Comparison of CS and Flu 4 with ca B/Malaysia Lot #3

| Gel | Total Virus Load‡ | Eluate Infectivity $\log_{10}$FFU/mL | Eluate DNA Level (ng/dose) | Flow Through (%) | Step Yield (%) |
|---|---|---|---|---|---|
| CS | 9.9 | 9.9 | 0.43 | LOD | 99.6 |
|  | 10.2 | 9.8 | 1.13 | 6.8 | 46.2 |
|  | 10.5 | 10.0 | 0.75 | 13.1 | 55.2 |
| FluSelect 4 | 9.9 | 9.8 | 0.79 | 0.7 | 79.1 |
|  | 10.2 | 9.8 | 0.81 | 8.6 | 52.8 |
|  | 10.5 | 10.1 | 1.08 | 20.7 | 65.8 |

‡$\log_{10}$FFU/mL of gel

To evaluate the scalability of the purification, Test Resin D gel was packed in a XK-50 column (5 cm×17 cm) to scale-up approximately 25-fold. A 10-L bioreactor viral harvest, TVCC-2 Lot #32 ca A/South Dakota strain, was processed after SP stabilization, DFF1 and TFF1 (5×UF and 5×DF) as described in the methods for the column load material. The TFF1 (5×UF 5×DF) material was loaded onto the Test Resin D and CS XK-50 column (5 cm×17 cm), respectively. The column running conditions and operational parameters including the loading and wash linear flow rate, on-column Benzonase treatment and the elution steps were the same as the TVCC-1 process (20-L scale) and the small scale run described in the methods section. FIG. 22C shows the elution peak chromatograms of Test Resin D at XK-50 column scale. The elution peak showed a small prepeak in the beginning of the elution followed by a main single peak without the multiple features of the elution peak as observed in the small scale elution chromatogram (FIGS. 22A and B). Table 47 summarizes the purification step yields and eluate HCD levels for the Test Resin D and CS column runs. At a total virus load of 10.0 $\log_{10}$ FFU/mL of gel, the Test Resin D pilot scale-up purification run gave a comparable step yield (75.6%) and low HCD levels (0.15 ng/dose) demonstrating the scalability of the Test Resin D gel. These results when compared to the CS XK-50 column run showed that the HCD level of the Test Resin D column eluate was two-fold lower than the CS column eluate.

TABLE 47

Comparison of CS and FluSelect 4 XK-50 Column Purification with ca A/South Dakota

| Gel | Loading Material Titer[‡] | Total Virus Load[‡] | Eluate Infectivity ($\log_{10}$FFU/mL) | Eluate DNA Level (ng/mL) | Eluate DNA Level (ng/dose) | Flow Through (%) | Step Yield (%) |
|---|---|---|---|---|---|---|---|
| CS | 9.4 | 10.0 | 10.0 | 330.5 | 0.33 | LOD | 68.8 |
| Test Resin D | 9.4 | 10.0 | 9.9 | 120.0 | 0.15 | LOD | 75.6 |

[‡]$\log_{10}$FFU/mL of gel

A total of six Test Resins were screened and evaluated for virus purification. The evaluation included assessment of the step yield, binding capacity, and the impurity level. Test Resins C and D had better binding capacities, higher step yields and lower impurity HCD levels relative to the other four Test Resins. The step yields of Test Resin B and F were too low to be considered for commercial scale preparations. The binding capacity of Test Resins A and E were slightly higher or comparable relative to Test Resin C and D; however, the step yields were not as high and the impurity HCD increased to much higher levels at higher amounts of virus load. Comparing Test Resins C and D, although slightly better step yields were observed for Test Resin C, Test Resin D appeared to have a higher binding capacity and less impact on the amount of HCD levels when a higher amount of virus was loaded. This suggested that Test Resins C and D are chromatography gels that could be considered for use in commercial scale purifications. Further performance assessment including the binding capacity, step yields and the host cell DNA level in the column eluate of the Test Resin C and D comparing with Cellufine Sulfate gels showed Test Resin D gel is better than Test Resin C thus selected as an alternative for CS for further scale-up evaluation. With the evaluation of four different virus lots, the dynamic binding capacity of Test Resin C and D was approximately 2-fold higher (in some lots) or at least comparable to the Cellufine Sulfate. Test Resin D had a similar or higher binding capacity than Test Resin C. In terms of the step yield and host cell DNA levels, Test Resin D had a similar yield compared to Test Resin C but generally higher yield than CS at the higher amount of virus loading condition. With an increased in virus load, the impact on the increase in the eluate HCD level was similar for the Test Resin D and CS gel but the impact on the increase in the eluate HCD level was more notable for the Test Resin C. The HCD level of Test Resin D eluate was comparable to CS for all the lots evaluated. Finally, the pilot scale-up evaluation of Test Resin D XK-50 column run showed a purification yield and low host DNA level in the eluate demonstrating scalability and the potential to be used as an alternative chromatography gel for cell culture based Flu process manufacturing.

9.8 Purification of RSV

Filters and Cartridges
1) 8-μm Sartopure PP2 nominal filter
2) 3-μm Sartopure PP2 nominal filter
3) 0.65-μm Sartopure PP2 nominal filter
4) 3.0/0.8-μm Sartoclean CA membrane filter
5) 0.45-μm Millipak 100 PVDF filter
6) UF/DF hollow fiber cartridge, 500 KDa membrane pore size, lumen i.d. can be either 0.5 mm or 1.0 mm, path length can vary from 30-60 cm Chemicals
1) Sucrose
2) Tris. Cl
3) KCl
4) $KH_2PO_4$
5) $K_2HPO_4$
6) NaCl
7) KCl
8) EDTA
9) Trehalose
10) SFM4MegaVir
11) Sodium Citrate
12) Potassium Citrate
13) Benzonase
14) NaOH
15) NaOCl Equipment
1) Wavemixer with heating unit (Wave Biotech Model #20/50EH
2) 10 L Stedim bags (Cat#FBP10381)
3) Carboys
4) Pipettes
5) Bottles (250 mL, 1 L Nalgene)
6) GE Flex Stand
7) Pumps (Watson Marlow 520 S, 620Di),
8) Balance (Sartorius, Model #EB60EDE-1; Sartorius Model #CP4202S)

Methodology
1) RSV (e.g., rA2 cp248/404/1030ΔSH) virus is grown in Vero cells. The current production platform uses a 10-L bioreactor. Virus harvest (VH) contains SFM4 MegaVir infection medium (Hyclone).
2) Viral harvest virus is pooled in a 10-L Stedim bag and filtered through a 8- or 3-μm filter at a feed pressure of 15 psi and with a load of 4-5 mL VH/cm$^2$ of the effective filtration area (EFA) for the 3-μm filter or 27 mL VH/cm$^2$ of the EFA for the 8-μm filter. The filtrate is collected and weighed in a 10-L Stedim bag.
3) The clarified viral harvest is treated with 50 U/mL of Benzonase at 32±3° C. for 3 hrs. The harvest is rocked at 30 rocks/min (rpm) and at a 3° angle.
4) The clarified, Benzonase-treated VH is filtered through a 0.65-μm Sartorius Sartopure PP2 filter with a load of 16-18 mL of clarified, Benzonase-treated VH/cm$^2$ of the EFA for the filter.
  a. The 0.65-μm filtrate is then stabilized with stabilization buffer comprising 36 mM TrisCl, 214 mM Sucrose and 150 mM NaCl or KCl.
5) The stabilized filtrate is stored overnight (16±3 hrs) and is used as the feed material for the ultrafiltration (concentration) step.
6) The ultrafiltration step is performed using a 500-kDa hollow fiber cartridge from GE Healthcare with the lumen i.d. of 0.5-1 mm. The stabilized 0.65-μm filtrate load on the cartridge is 10 mL per cm² of membrane area. The feed is concentrated 5-fold using an operational transmembrane pressure (TMP) of 15 psi and a shear rate of 12000 sec⁻¹.

7) The concentrated material is diafiltered with the diafiltration buffer (8-10-fold buffer exchange based on volume of the concentrate). The exchange buffer comprises Tris (5 mM); Sucrose (25% w/v); NaCl (150 mM); pH 7.2.

8) The diafiltered material is passed through a terminal filter (0.45-μm Millipak filter) with a load of 4-5 mL/cm². The filtrate is the final bulk (drug substance) and is aliquoted in bottles. All of the RSV viral drug substance aliquots are either flash frozen in a methanol-dry ice bath or using a control rate freezer.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In addition, the following United States provisional patent applications: 60/845,121 filed Sep. 16, 2006; 60/871,721 filed Dec. 22, 2006; 60/917,008 filed May 9, 2007; 60/951,813 filed Jul. 25, 2007; 61/099,749 filed Sep. 24, 2008; 61/104,933 filed Oct. 13, 2008; 61/122,456 filed Dec. 15, 2008; 61/187,721 filed Jun. 17, 2009, and U.S. patent application Ser. No. 11/855,769 filed Sep. 14, 2007 are incorporated by reference in their entirety.

We claim:

1. A method of purifying influenza viruses from cell culture comprising:
   (a) clarification of a viral harvest by direct flow filtration (DFF) through at least one membrane having a pore size of between about 1.2 micrometers to about 0.45 micrometers;
   (b) concentration by tangential flow filtration (TFF), which comprises ultrafiltration (UF) and buffer exchange by diafiltration (DF), using a membrane having 500 kDa molecular weight cut off (MWCO), wherein steps (a) and (b) are coupled, and wherein a viral harvest process is coupled to the clarification in step (a) and the concentration in step (b) using alternating tangential flow (ATF);
   (c) purification by affinity column chromatography following step (b);
   (d) concentration by UF and/or buffer exchange by DF following step (c) using a membrane having 500 kDa molecular weight cut off (MWCO); and
   (e) sterilization following step (d) by DFF through at least one membrane having a pore size of between about 0.45 micrometers to about 0.22 micrometers,
   wherein the overall recovery of purified viruses is at least 30%, and wherein the purified viruses comprise less than 0.1 ng host cell DNA (HCD), and less than 0.3 pg host cell protein (HCP) per $7.0\pm0.5$ $\log_{10}$ FFU of virus.

2. The method of claim 1, wherein sucrose and a phosphate buffer are added to the viral harvest to a final concentration, within a 10% concentration variation of each, of 218 mM sucrose, and 11 mM phosphate buffer pH 7.0-7.4, prior to step (a).

3. The method of claim 1, wherein the exchange buffer in step (b) comprises, within a 10% concentration variation of each, 218 mM sucrose, and 11 mM phosphate buffer pH 7.0-7.4.

4. The method of claim 1, wherein step (b) is performed at a transmembrane pressure (TMP) of between about 10 psi to about 20 psi and a flux rate of between about 35 liters per meter per hour (LMH) to about 50 LMH.

5. The method of claim 1, wherein step (b) results in a 5× concentration and least 5 diavolumes of buffer are exchanged.

6. The method of claim 1, wherein both concentration by UF and buffer exchange by DF occur in step (d) resulting in at least a 2× concentration and the exchange of at least 8 diavolumes of buffer.

7. The method of claim 1, wherein the exchange buffer in step (d) comprises, within a 10% concentration variation of each, 200 mM sucrose, and 100 mM phosphate buffer pH 7.0-7.4.

8. The method of claim 1, wherein between 8.0 $\log_{10}$ FFU to 11 $\log_{10}$ FFU of influenza viruses are loaded per mL of affinity media in step (c).

9. The method of claim 8, wherein 9.5 $\log_{10}$ FFU of influenza viruses are loaded per mL of affinity media in step (c).

10. The method of claim 1, wherein step (c) further comprises exposure to a non-specific endonuclease.

11. The method claim 10, wherein the purified viruses comprise less than 0.0050 ng non-specific endonuclease per $7.0\pm0.5$ $\log_{10}$ FFU of virus.

12. The method of claim 1, wherein the influenza viruses are harvested 48 hours post infection from cells infected with a viral input of 2000 FFU/mL.

13. The method of claim 1, wherein step (e) is performed at a flux rate of about 25 L/m².

* * * * *

UNITED STATES PATENT AND TRADEMARK OFFICE
CERTIFICATE OF CORRECTION

| | |
|---|---|
| PATENT NO. | : 9,085,753 B2 |
| APPLICATION NO. | : 13/473494 |
| DATED | : July 21, 2015 |
| INVENTOR(S) | : Jonathan Liu et al. |

It is certified that error appears in the above-identified patent and that said Letters Patent is hereby corrected as shown below:

In the claims,

Beginning in col. 123, lines 38-51, continuing to col. 124, line 12, Claim 1 should read as follows:

1. A method of purifying influenza viruses from cell culture comprising:
(a) clarification of a viral harvest by direct flow filtration (DFF) through at least one membrane having a pore size of between about 1.2 micrometers to about 0.45 micrometers;
(b) concentration by tangential flow filtration (TFF), which comprises ultrafiltration (UF) and buffer exchange by diafiltration (DF), using a membrane having 500 kDa molecular weight cut off (MWCO), wherein steps (a) and (b) are coupled, and wherein a viral harvest process is coupled to the clarification in step (a) and the concentration in step (b) using alternating tangential flow (ATF);
(c) purification by affinity column chromatography following step (b);
(d) concentration by UF and/or buffer exchange by DF following step (c) using a membrane having 500 kDa molecular weight cut off (MWCO); and
  (e) sterilization following step (d) by DFF through at least one membrane having a pore size of between about 0.45 micrometers to about 0.22 micrometers,
wherein the overall recovery of purified viruses is at least 30%, and wherein the purified viruses comprise less than 0.1 ng host cell DNA (HCD), and less than 0.3 μg host cell protein (HCP) per $7.0 \pm 0.5$ log10FFU of virus.

Signed and Sealed this
Twenty-third Day of August, 2016

*Michelle K. Lee*

Michelle K. Lee
*Director of the United States Patent and Trademark Office*